US010856547B2

(12) United States Patent
Wei et al.

(10) Patent No.: US 10,856,547 B2
(45) Date of Patent: *Dec. 8, 2020

(54) HYPERSENSITIVE RESPONSE ELICITOR PEPTIDES AND USE THEREOF

(71) Applicant: Plant Health Care, Inc., Raleigh, NC (US)

(72) Inventors: Zhongmin Wei, Kirkland, WA (US); Gregory A. Zornetzer, Seattle, WA (US)

(73) Assignee: PLANT HEALTH CARE, INC., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/244,748

(22) Filed: Aug. 23, 2016

(65) Prior Publication Data

US 2016/0360747 A1 Dec. 15, 2016

Related U.S. Application Data

(63) Continuation of application No. 14/872,298, filed on Oct. 1, 2015.

(60) Provisional application No. 62/140,789, filed on Mar. 31, 2015, provisional application No. 62/058,535, filed on Oct. 1, 2014.

(51) Int. Cl.
| | |
|---|---|
| *A01N 37/46* | (2006.01) |
| *C12N 15/82* | (2006.01) |
| *A01N 63/10* | (2020.01) |
| *C07K 14/00* | (2006.01) |
| *A01N 25/02* | (2006.01) |
| *A01N 25/12* | (2006.01) |
| *A01N 37/22* | (2006.01) |
| *A01N 43/36* | (2006.01) |
| *A01N 43/54* | (2006.01) |
| *A01N 43/90* | (2006.01) |
| *A01N 47/44* | (2006.01) |
| *A01N 51/00* | (2006.01) |
| *C07K 7/08* | (2006.01) |
| *C07K 14/415* | (2006.01) |
| *A01N 63/00* | (2020.01) |
| *C07K 14/195* | (2006.01) |
| *C07K 14/24* | (2006.01) |
| *C07K 14/27* | (2006.01) |

(52) U.S. Cl.
CPC ............ *A01N 37/46* (2013.01); *A01N 25/02* (2013.01); *A01N 25/12* (2013.01); *A01N 37/22* (2013.01); *A01N 43/36* (2013.01); *A01N 43/54* (2013.01); *A01N 43/90* (2013.01); *A01N 47/44* (2013.01); *A01N 51/00* (2013.01); *A01N 63/00* (2013.01); *A01N 63/10* (2020.01); *C07K 7/08* (2013.01); *C07K 14/001* (2013.01); *C07K 14/195* (2013.01); *C07K 14/24* (2013.01); *C07K 14/27* (2013.01); *C07K 14/415* (2013.01); *C12N 15/8279* (2013.01); *C12N 15/8283* (2013.01); *C07K 2319/00* (2013.01); *C07K 2319/20* (2013.01)

(58) Field of Classification Search
None
See application file for complete search history.

(56) References Cited

U.S. PATENT DOCUMENTS

| | | | |
|---|---|---|---|
| 5,473,039 | A | 12/1995 | Dyer et al. |
| 5,776,889 | A | 7/1998 | Wei et al. |
| 5,859,339 | A | 1/1999 | Ronald et al. |
| 5,977,060 | A | 11/1999 | Zitter et al. |
| 6,235,974 | B1 | 5/2001 | Qui et al. |
| 6,277,814 | B1 | 8/2001 | Qui et al. |
| 6,310,176 | B1 | 10/2001 | Barra et al. |
| 6,563,020 | B1 | 5/2003 | Simmons et al. |
| 6,624,139 | B1 | 9/2003 | Wei et al. |
| 6,858,707 | B1 | 2/2005 | Wei et al. |
| 7,132,393 | B2 | 11/2006 | Summerton |
| 7,132,525 | B2 | 11/2006 | Laby et al. |

(Continued)

FOREIGN PATENT DOCUMENTS

| | | |
|---|---|---|
| CN | 1793172 | 6/2006 |
| CN | 101284876 | 10/2008 |

(Continued)

OTHER PUBLICATIONS

Kim et al. "Mutational Analysis of Xanthamonas Harpin HpaG Identifies a Key Functional Region That Elicits the Hypersensitive Response in Nonhost Plants" J. Bacteriol. 186:6239-6247 (Year: 2004).*

(Continued)

*Primary Examiner* — Larry D Riggs, II
*Assistant Examiner* — Zachary J Miknis
(74) *Attorney, Agent, or Firm* — Troutman Pepper Hamilton Sanders LLP (Rochester)

(57) ABSTRACT

Disclosed are hypersensitive-response eliciting peptides that exhibit improved solubility, stability, resistance to chemical degradation, or a combination of these properties. Use of these peptides or fusion polypeptides, or DNA constructs encoding the same, for modulating plant biochemical signaling, imparting disease resistance to plants, enhancing plant growth, imparting tolerance to biotic stress, imparting tolerance and resistance to abiotic stress, imparting desiccation resistance to cuttings removed from ornamental plants, imparting post-harvest disease or post-harvest desiccation resistance to a fruit or vegetable, or enhancing the longevity of fruit or vegetable ripeness are also disclosed.

44 Claims, 13 Drawing Sheets
Specification includes a Sequence Listing.

(56) References Cited

U.S. PATENT DOCUMENTS

| | | |
|---|---|---|
| 8,440,881 B2 | 5/2013 | Park et al. |
| 2002/0007501 A1 | 1/2002 | Song et al. |
| 2002/0019337 A1 | 2/2002 | Wei et al. |
| 2002/0062500 A1 | 2/2002 | Fan et al. |
| 2002/0059658 A1 | 5/2002 | Wei et al. |
| 2003/0104979 A1 | 6/2003 | Wei et al. |
| 2004/0016029 A1 | 1/2004 | Wei et al. |
| 2004/0073977 A1 | 4/2004 | Misra et al. |
| 2005/0250699 A1 | 10/2005 | Kristensen et al. |
| 2006/0193774 A1 | 8/2006 | Summerton |
| 2006/0248617 A1 | 11/2006 | Imanaka et al. |
| 2009/0118134 A1 | 5/2009 | Vrijloeb et al. |
| 2010/0043095 A1 | 2/2010 | Wei |
| 2010/0064386 A1 | 3/2010 | Park et al. |
| 2011/0233469 A1 | 9/2011 | Petersen |
| 2012/0265513 A1 | 10/2012 | Fang et al. |
| 2013/0116119 A1 | 5/2013 | Rees et al. |
| 2013/0125258 A1 | 5/2013 | Emmanuel et al. |
| 2013/0150288 A1 | 6/2013 | Dobson |
| 2013/0172185 A1 | 7/2013 | Wei |
| 2013/0274104 A1 | 10/2013 | Reddig et al. |
| 2014/0227767 A2 | 8/2014 | Yeaman et al. |
| 2015/0218099 A1 | 8/2015 | Mann |
| 2016/0095314 A1 | 4/2016 | Wei et al. |
| 2016/0145310 A1* | 5/2016 | Wei ....................... A01N 37/46 504/335 |
| 2016/0353735 A1 | 12/2016 | Wei et al. |

FOREIGN PATENT DOCUMENTS

| | | | |
|---|---|---|---|
| CN | 101892244 | 11/2010 | |
| CN | 103103202 | 5/2013 | |
| CN | 1454989 | 11/2013 | |
| CN | 106831964 | 6/2017 | |
| EP | 1 930 025 A1 | 6/2008 | |
| EP | 1 997 502 A1 | 12/2008 | |
| EP | 2168592 | 3/2010 | |
| WO | 95/31564 | 11/1995 | |
| WO | 98/06748 | 2/1998 | |
| WO | 99/02655 | 7/1998 | |
| WO | 99/37664 | 7/1999 | |
| WO | WO-9937664 A1 * | 7/1999 | ............... C07K 7/08 |
| WO | 00/020452 A2 | 4/2000 | |
| WO | 00/28056 | 5/2000 | |
| WO | 01/055335 A2 | 8/2001 | |
| WO | 01/80639 | 11/2001 | |
| WO | 01/98501 A2 | 12/2001 | |
| WO | 2001/098501 | 12/2001 | |
| WO | 2002/022821 | 3/2002 | |
| WO | 2005/014639 A2 | 2/2005 | |
| WO | 2005/017158 | 2/2005 | |
| WO | 2005/115444 A2 | 12/2005 | |
| WO | 2006/077601 A2 | 7/2006 | |
| WO | 2008/104598 A2 | 9/2008 | |
| WO | 2010/019442 | 2/2010 | |
| WO | 2010/042654 A2 | 4/2010 | |
| WO | 2013/039857 A1 | 3/2013 | |
| WO | 2013/102189 | 7/2013 | |

OTHER PUBLICATIONS

Kim et al., "Mutational Analysis of Xanthomonas Harpin HpaG Identifies a Key Functional Region That Elicits the Hypersensitive Response in Nonhost Plants," J. Bacteriol. 186(18):6239-6247 (2004).
Ji et al., "Two Coiled-Coil Regions of Xanthomonas oryzae pv. Oryzae Harpin Differ in Oligomerization and Hypersensitive Response Induction," Amino Acids 40:381-392 (2011).
Haapalainen et al., "Functional Mapping of Harpin HrpZ of Pseudomonas syringae Reveals the Sites Responsible for Protein Oligomerization, Lipid Interactions, and Plant Defence Induction," Mol. Plant Pathol. 12(2):151-66 (2011).
Lilie et al, "Polyionic and Cysteine-Containing Fusion Peptides as Versatile Protein Tags," Biol. Chem. 394(8):995-1004 (2013).
Li et al., "Complete Regression of Well-Established Tumors Using a Novel Water-Soluble Poly(L-Glutamic Acid)-Paclitaxel Conjugate," Cancer Res. 58: 2404-2409 (1998).
International Search Report and Written Opinion for PCT/US2015/053387 dated Feb. 12, 2016.
Van Loon et al., "Systemic Resistance Induced by Rhizosphere Bacteria," Annu. Rev. Phytopathol. 36:453-83 (1998).
Oliveira et al., "Induced Resistance During the Interaction Pathogen x Plant and the Use of Resistance Inducers," Phytochemistry Letters 15:152-158 (2016).
Office Action for U.S. Appl. No. 15/016,768 (dated Feb. 1, 2017).
Office Action for U.S. Appl. No. 14/872,298 (dated Jan. 19, 2017).
Maget-Dana et al., "Amphiphilic Peptides as Models for Protein-Membrane Interactions: Interfacial Behaviour of Sequential Lys- and Leu-Based Peptides and Their Penetration Into Lipid Monolayers," Supramolecular Sci. 4:365-368 (1997).
Park et al., "Helix Stability Confers Salt Resistance Upon Helical Antimicrobial Peptides," J. Biol. Chem. 279:13896-13901 (2004).
Saito et al., "Synthesis of a Peptide Emulsifier With an Amphiphilic Structure," Bioscience, Biotechnology, and Biochemistry 59:388-392 (1995).
Inoue et al., "The HrpZ and HrpA Genes are Variable, and Useful for Grouping Pseudomonas syringae Bacteria," Journal of General Plant Pathology 72(1):26-33 (2006).
Shrestha et al., "The Hrp Gene Cluster in Erwinia Pyrifoliae and Determination of HR Active Domain in HrpNEp Protein," ISHS Acta Horticulturae 793: XI International Workshop on Fire Blight. (2008).
CAS RN 429026-68-6 (2002).
Wang et al., "Hpal is a Type III Translocator in Xanthomonas oryzae pv. Oryzae," BMC Microbiology (18):105 (2018).
Partial Supplementary European Search Report for Corresponding EP Patent Application No. 15847410.6 (dated Feb. 23, 2018).
Niv et al., "New Lytic Peptides Based on the D, L-Amphipathic Helix Motif Preferentially Kill Tumor Cells Compared to Normal Cells," Biochemistry, American Chemical Society 42(31):9346-9354 (2003).
Zeitler et al., "De-Novo Design of Antimicrobial Peptides for Plant Protection," Plos One 8(8):E71687 (2013).
Jung-Gun et al., "Mutational Analysis of Xanthomonas Harpin HpaG Identifies a Key Functional Region that Elicits the Hypersensitive Response in Nonhost Plants," Journal of Bacteriology, American Society for Microbiology 186(18):6239-6247 (2004).
Choi et al., "Harpins, Multifunctional Proteins Secreted by Gram-Negative Plant-Pathogenic Bacteria," Molecular Plant-Microbe Interactions 26(10):1115-1122 (2013).
Mur et al., "The Hypersensitive Response; The Centenary is Upon Us but How Much Do We Know?," Journal of Experimental Botany 59(3):501-520 (2007).
Gentilucci et al., "Chemical Modifications Designed to Improve Peptide Stability: Incorporation of Non-Natural Amino Acids, Pseudo-Peptide Bonds, and Cyclization," Current Pharmaceutical Design 16(28):3185-3203 (2010).
Trevino et al., "Measuring and Increasing Protein Solubility," Journal of Pharmaceutical Sciences 97 (10):4155-4166 (2008).
Colombian Office Action Patent Application No. NC2017/0003624 (dated Jun. 4, 2018) (With English Translation).
Office Action for U.S. Appl. No. 15/244,707 (dated Mar. 5, 2018).
Office Action for U.S. Appl. No. 14/872,298 (dated Oct. 17, 2017).
Olsen et al., "Trypsin Cleaves Exclusively C-Terminal to Arginine and Lysine Residues," Mol. and Cell. Proteomics 3.6 3:608-614 (2004).
Kim et al., "HrpW of Erwinia Amylovora, a New Harpin that Contains a domain Homologous to Pectate Lyases of a Distinct Class," J. Bacteriol 180(19):5203-5210 (1998).
CAS RN 208293-02-1 (2000).
Osusky et al., "Transgenic Potatoes Expressing a Novel Cationic Peptide are Resistant to Late Blight and Pink Rot," Transgenic Research 13(2):181-190 (2004).
Yevtushenko et al., "Comparison of Pathogen-Induced Expression and Efficacy of Two Amphibian Antimicrobial Peptides, MsrA2 and

(56) References Cited

OTHER PUBLICATIONS

Temporin A, for Engineering Wide-Spectrum Disease Resistance in Tobacco," Plant Biotechnology Journal 5(6):720-734 (2007).
Miao et al., "HpaXm from *Xanthomonas citri* Subsp. *malvacearum* is a Novel Harpin With Two Heptads for Hypersensitive Response," Journal of Microbiology and Biotechnology 20(1):54-62 (2010).
Chen et al., "Identification of Specific Fragments of HpaG Xooc, a Harpin for Xanthomonas Oryzae Pv. Oryzicola, That Induce Disease Resistance and Enhance Growth in Plants," Phytopathology 98(7):781-791 (2008).
Slechtova et al., "Insight into Trypsin Miscleavage: Comparison of Kinetic Constants of Problematic Peptide Sequences," Analytical Chemistry 87:7636-7643 (2015).
Office Action for U.S. Appl. No. 14/872,298 (dated Jul. 26, 2018).
Office Action for U.S. Appl. No. 15/016,768 (dated Sep. 7, 2018).
Colombian Office Action Patent Application No. NC2017/0003624 (dated Oct. 2, 2018) (With English Translation).
Chilean Office Action Patent Application No. 201700790 (dated Oct. 2, 2018) (With English Translation).
Colombian Office Action Patent Application No. NC2017/0003624 (dated Mar. 29, 2019) (With English Translation).
NCBI Reference No. WP_082338630 (Apr. 11, 2017).
NCBI Reference No. WP_014505138.1 (May 19, 2017).
Shenge et al., "Molecular Characterization of Pseudomonas Syringae pv. Tomato Isolates From Tanzania," Phytoparasitica 36(4):338-351 (2008).
Lee et al., "Relationship Between Antimicrobial Activity and Amphiphilic Property of Basic Model Peptides," Biochimica Biophysica Acta (BBA)-Biomembranes 862(1):211-219 (1986).
Examination Report European Patent Application No. 15847410.6 (dated Jan. 28, 2019).
Office Action for U.S. Appl. No. 15/244,707 (dated Dec. 17, 2018).
Office Action for U.S. Appl. No. 14/872,298 (dated Apr. 12, 2019).
STN File Registry RN 153512-20-0 (1994).
STN File Registry RN 220893-47-0 (1999).
STN File Registry RN 220922-27-0 (1999).
Examination Report European Patent Application No. 15845670.7 (dated Jun. 30, 2020).
Examination Report European Patent Application No. 15847410.6 (dated Jun. 30, 2020).

* cited by examiner

HYPERSENSITIVE RESPONSE ELICITOR PEPTIDES AND USE THEREOF

This application is a continuation of U.S. patent application Ser. No. 14/872,298, filed Oct. 1, 2015, which claims the priority benefit of U.S. Provisional Patent Application Ser. No. 62/058,535, filed Oct. 1, 2014, and U.S. Provisional Patent Application Ser. No. 62/140,789, filed Mar. 31, 2015, each of which is hereby incorporated by reference in its entirety.

FIELD OF THE INVENTION

The present invention relates to novel hypersensitive response elicitor peptides and their use for inducing active plant responses including, among others, growth enhancement, disease resistance, pest or insect resistance, and stress resistance.

BACKGROUND OF THE INVENTION

The identification and isolation of harpin proteins came from basic research at Cornell University attempting to understand how plant pathogenic bacteria interact with plants. A first line of defense is the hypersensitive response (HR), a localized plant cell death at the site of infection. Cell death creates a physical barrier to movement of the pathogen and in some plants dead cells can release compounds toxic to the invading pathogen. Research had indicated that pathogenic bacteria were likely to have a single factor that was responsible for triggering the HR. A basic aim of the Cornell research was to identify a specific bacterial protein responsible for eliciting the HR. The target protein was known to be encoded by one of a group of bacteria genes called the Hypersensitive Response and Pathogenicity (hrp) gene cluster. The hrp cluster in the bacterium *Erwinia amylovora* (Ea), which causes fire blight in pear and apple, was dissected and a single protein was identified that elicited HR in certain plants. This protein was given the name harpin (and, later, harpin$_{Ea}$) and the corresponding gene designated hrpN. This was the first example of such a protein and gene identified from any bacterial species.

A number of different harpin proteins have since been identified from *Erwinia, Pseudomonas, Ralstonia, Xanthomonas*, and *Pantoea* species, among others. Harpin proteins, while diverse at the primary amino acid sequence level, share common biochemical and biophysical characteristics as well as biological functions. Based on their unique properties, the harpin proteins are regarded in the literature as belonging to a single class of proteins.

Subsequent to their identification and isolation, it was thereafter discovered that harpins could elicit disease resistance in plants and increase plant growth. An important early finding was that application of purified harpin protein made a plant resistant to a subsequent pathogen attack, and in locations on the plant well away from the injection site. This meant that harpin proteins can trigger a Systemic Acquired Resistance (SAR), a plant defense mechanism that provides resistance to a variety of viral, bacterial, and fungal pathogens.

In crop protection, there is a continuous need for compositions that improve the health of plants. Healthier plants are desirable since they result in better yields and/or a better quality of the plants or crops. Healthier plants also better resist biotic and abiotic stress. A high resistance against biotic stresses in turn allows the growers to reduce the quantity of pesticides applied and consequently to slow down the development of resistances against the respective pesticides.

Harpin$_{\alpha\beta}$ is a fusion protein that is derived from several different harpins. Harpin$_{\alpha\beta}$ has been shown to suppress nematode egg production, enhance the growth, quality and yield of a plant, and increase a plant's vigor. Its amino acid and nucleotide sequences are described in detail in U.S. Application Publ. No. 2010/0043095.

To date, harpin and harpin$_{\alpha\beta}$ production and their use in agricultural and horticultural applications have been as a powdered solid coated on starch. This limits the use and versatility of the harpin proteins, because liquid suspensions of the powdered harpin proteins in water have an effective useful life of only 48-72 hours before significant degradation and loss of activity occurs. Another problem with harpin solutions is protein solubility and stability.

It would be desirable to identify synthetic and derivative harpin peptides that are readily soluble in aqueous solution, stable, resistant to chemical degradation, and effective in initiating the hypersensitive response in plants.

The present invention is directed to overcoming these and other limitations in the art.

SUMMARY OF THE INVENTION

A first aspect of the invention relates to an isolated peptide having the amino acid sequence of:

```
                                          (SEQ ID NO: 93)
(L/I/V/F)-X-X-(L/I/V/F)-(L/I)-X-X-(L/I/V/F)-

(L/I/V/A)-X-X-(L/I)-(L/I/V/F)
``` wherein the peptide is free of cysteine and methionine; each X at positions 2 and 6 is optional and, when present, is any amino acid; and each X at positions 3, 7, 10, and 11 is any amino acid. In one embodiment, X at only one of positions 2 and 6 is optional. In certain embodiments, SEQ ID NO: 93 may further include an additional amino acid residue between the hydrophobic doublets (two of L/I/V/F/A, as indicated). In certain embodiments, the isolated peptide further includes a hydrophilic amino acid sequence that is located N-terminal or C-terminal to SEQ ID NO: 93.

A second aspect of the invention relates to an isolated peptide having the amino acid sequence of:

```
                                          (SEQ ID NO: 93)
(L/I/V/F)-X-X-(L/I/V/F)-(L/I)-X-X-(L/I/V/F)-

(L/I/V/A)-X-X-(L/I)-(L/I/V/F)
``` wherein the peptide is free of cysteine and methionine; each X at positions 2, 6, and 10 is optional and, when present, is any amino acid; and each X at positions 3, 7, and 11 is any amino acid. In one embodiment, X at only one of positions 2, 6, and 10 is optional. In certain embodiments, SEQ ID NO: 93 may further include an additional amino acid residue between the hydrophobic doublets (two of L/I/V/F/A, as indicated). In certain embodiments, the isolated peptide further includes a hydrophilic amino acid sequence that is located N-terminal or C-terminal to SEQ ID NO: 93.

A third aspect of the invention relates to an isolated peptide having the amino acid sequence of:

```
             (SEQ ID NO: 1, P1/P4 consensus)
       XXGISEKXXXXXXXXXXXXXXXX,
``` wherein
- X at position 1 is optional and can be S, N, D, isoD, G, A, or S;
- X at position 2 is optional and can be Q, E, g-glutamate, G, A, or S;
- X at position 8 is Q, E, g-glutamate, G, A, or S;
- X at position 9 is L, I, F, or V;
- X at position 10 is optional and can be D or isoD;
- X at position 11 is Q, E, g-glutamate, G, A, or S;
- X at position 12 is M, L, I, or F;
- X at position 13 is M, L, or I;
- X at position 14 is optional and can be any hydrophilic amino acid, preferably C, S, T, A, D, isoD, K, or Q;
- X at position 15 is Q, E, g-glutamate, G, A, S, K, or I;
- X at position 16 is M, L, I, V, or F;
- X at position 17 is M, L, I, A, or V;
- X at position 18 is Q, E, g-glutamate, G, A, S, M, T, or K;
- X at position 19 is A, D, isoD, S, V, T, K, R, E, H, or G;
- X at position 20 is M, L, or I;
- X at position 21 is M, L, I, V, S, or F;
- X at position 22 is Q, E, g-glutamate, G, A, S;
- X at position 23 is P, Q, E, g-glutamate, G, A, or S; and wherein the isolated peptide comprises one or more mutations relative to a corresponding wildtype amino acid sequence. In certain embodiments, the one or more mutations improve the aqueous solubility, stability, or resistance to chemical degradation of the isolated peptide relative to a polypeptide comprising the corresponding wildtype amino acid sequence.

One exemplary family of peptides according to the third aspect of the invention have the amino acid sequence of:

```
                           (SEQ ID NO: 2, P4 consensus)
             SXGISEKXXDXXXXXXXXAXXXP,
``` wherein
- X at position 2 is Q, E, g-glutamate, G, A, or S;
- X at position 8 is Q, E, g-glutamate, G, A, or S;
- X at position 9 is L, A, D, isoD, I, V, or F;
- X at position 11 is Q, E, g-glutamate, G, A, or S;
- X at position 12 is L, D, isoD, I, or F;
- X at position 13 is L, I, V, or F;
- X at position 14 is any hydrophilic amino acid, preferably C, S, or T, S or T, or only S;
- X at position 15 is Q, E, g-glutamate, G, A, S, K, or I;
- X at position 16 is L, A, I, V, M, or F;
- X at position 17 is I, S, or F;
- X at position 18 is Q, E, g-glutamate, G, A, or S;
- X at position 20 is L, I, V, or F;
- X at position 21 is L or F; and
- X at position 22 is Q, E, g-glutamate, G, A, or S.

In certain embodiments, these peptides according to the third aspect of the invention also meet the structural features defining the peptides according to the first or second aspect of the invention.

Another exemplary family of peptides according to the third aspect of the invention have the amino acid sequence of:

```
                           (SEQ ID NO: 3, P1 consensus)
             XXGISEKXLDXLLTXLIXALLXX,
``` wherein
- X at position 1 is N, D, isoD, G, A, or S;
- X at position 2 is Q, E, g-glutamate, G, A, or S;
- X at position 8 is Q, E, g-glutamate, G, A, or S;
- X at position 11 is Q, E, g-glutamate, G, A, or S;
- X at position 15 is Q, E, g-glutamate, G, A, or S;
- X at position 18 is M, T, K, E, g-glutamate, G, A, or S;
- X at position 22 is Q, E, g-glutamate, G, A, or S; and
- X at position 23 is Q, E, g-glutamate, G, A, or S.

In certain embodiments, these peptides according to the third aspect of the invention also meet the structural features defining the peptides according to the first or second aspect of the invention.

A fourth aspect of the invention relates to an isolated peptide having the amino acid sequence of:

```
                           (SEQ ID NO: 47, P15b/P20 consensus)
          (i) KPXDSXSXIAKLISXLIXSLLX,
``` wherein
- X at position 3 is N, D, or isoD;
- X at position 6 is Q, E, g-glutamate, G, A, or S;
- X at position 8 is N, D, or isoD;
- X at position 15 is optional and can be any amino acid;
- X at position 18 is M, E, g-glutamate, G, A, S, T, or K; and
- X at position 22 is optional and can be Q, E, g-glutamate, G, A, or S; or

```
                           (SEQ ID NO: 12, P15/20 min consensus)
          (ii) IAKLISXLIXSLLX,
``` wherein
- X at position 7 is optional and can be any amino acid;
- X at position 10 is M, E, g-glutamate, G, A, S, T, or K; and
- X at position 14 is optional and can be Q, E, g-glutamate, G, A, or S.

In certain embodiments, the isolated peptide comprises one or more mutations relative to a corresponding wildtype amino acid sequence, and the one or more mutations improve the aqueous solubility, stability, or resistance to chemical degradation of the isolated peptide relative to a polypeptide comprising the corresponding wildtype amino acid sequence. In certain embodiments, the peptides according to the fourth aspect of the invention also meet the structural features defining the peptides according to the first or second aspect of the invention.

A fifth aspect of the invention relates to an isolated peptide having the amino acid sequence of:

```
                           (SEQ ID NO: 66, P6/6a consensus)
          (i) PSPXTXXLXXIVGXILXAXN,
``` wherein
- X at position 4 is F or Y;
- X at position 6 is Q, E, g-glutamate, G, A, or S;
- X at position 7 is optional and can be L, M, E, g-glutamate, G, A, S, T, or K;
- X at position 9 is M, E, g-glutamate, G, A, S, T, or K;
- X at position 10 is H or N;
- X at position 14 is E, g-glutamate, D, or isoD;
- X at position 17 is Q, E, g-glutamate, G, A, or S; and
- X at position 19 is Q, E, g-glutamate, G, A, or S; or

```
                           (SEQ ID NO: 135, P6/6a min consensus)
          (ii) XTXXLXXIVGXIL,
```

- X at position 1 is F or Y;
- X at position 3 is Q, E, g-glutamate, G, A, or S;
- X at position 4 is optional and, according to one embodiment, can be M, E, g-glutamate, G, A, S, T, or K; or according to another embodiment can be L;

X at position 6 is M, E, g-glutamate, G, A, S, T, or K;
X at position 7 is H or N; and
X at position 11 is E, g-glutamate, D, or isoD;
wherein the isolated peptide comprises one or more mutations relative to a corresponding wildtype amino acid sequence, and the one or more mutations improve the aqueous solubility, stability, or resistance to chemical degradation of the isolated peptide relative to a polypeptide comprising the corresponding wildtype amino acid sequence. In certain embodiments, the peptides according to the fifth aspect of the invention also meet the structural features defining the peptides according to the first or second aspect of the invention.

A sixth aspect of the invention relates to an isolated peptide having the amino acid sequence of:

(SEQ ID NO: 13, P14d consensus)
(i) XXXXXXLXXLLXXLVXLLK, wherein
X at position 1 can be: Q, N, D, E, g-glutamate, isoD, or S;
X at position 2 can be: D, E, g-glutamate, isoD;
X at position 3 can be: P, D, E, isoD, or g-glutamate;
X at position 4 can be M, A, S, D, E, isoD, or g-glutamate
X at position 5 can be Q, E, or g-glutamate;
X at position 6 can be A, E, or g-glutamate;
X at position 8 can be M, L, E, Q, D, N, G, A, S, isoD, or g-glutamate;
X at position 9 can be Q, N, E, D, G, A, S, isoD, or g-glutamate;
X at position 12 can be Q, N, E, D, G, A, S, isoD, or g-glutamate;
X at position 13 can be Q, N, E, D, G, A, S, isoD, or g-glutamate; and
X at position 16 can be K, Q, N, E, D, R, G, A, or S; or (SEQ ID NO: 14, P14d min consensus)
(ii) LXXLLXXLVXLLK, X at position 2 can be M, L, E, Q, D, N, G, A, S, isoD, or g-glutamate;
X at position 3 can be Q, N, E, D, G, A, S, isoD, or g-glutamate;
X at position 6 can be Q, N, E, D, G, A, S, isoD, or g-glutamate;
X at position 7 can be Q, N, E, D, G, A, S, isoD, or g-glutamate; and
X at position 10 can be K, Q, N, E, D, R, G, A, or S.

In certain embodiments, the isolated peptide comprises one or more mutations relative to a corresponding wildtype amino acid sequence, and the one or more mutations improve the aqueous solubility, stability, or resistance to chemical degradation of the isolated peptide relative to a polypeptide comprising the corresponding wildtype amino acid sequence. In certain embodiments, the peptides according to the sixth aspect of the invention also meet the structural features defining the peptides according to the first or second aspect of the invention.

A seventh aspect of the invention relates to an isolated peptide having the amino acid sequence of:

(SEQ ID NO: 16, P25 consensus)
(i) LXXL(L/M)XILXXLV, wherein
X at position 2 can be Q, N, E, g-glutamate, D, isoD, T, S, A, or G;
X at position 3 can be K, Q, N, E, g-glutamate, D, isoD, T, S, A, or G;
X at position 6 can be K, Q, N, E, g-glutamate, D, isoD, T, S, A, or G;
X at position 9 can be E, g-glutamate, D, isoD, Q, N, T, S, A, or G; and
X at position 10 can be A, G, S, T, E, g-glutamate, D, isoD, Q, or N; or (SEQ ID NO: 17, P25 consensus)
(ii) LXXVLXXL(L/M)XILXXLV, X at position 2 can be T, S, A, G, D, isoD, E, g-glutamate, Q, or N;
X at position 3 can be G, T, S, A, D, isoD, E, g-glutamate, Q, or N;
X at position 6 can be Q, N, E, g-glutamate, D, isoD, T, S, A, or G;
X at position 7 can be K, Q, N, E, g-glutamate, D, isoD, T, S, A, or G;
X at position 10 can be K, Q, N, E, g-glutamate, D, isoD, T, S, A, or G;
X at position 13 can be E, g-glutamate, D, isoD, Q, N, T, S, A, or G;
X at position 14 can be A, G, S, T, E, g-glutamate, D, isoD, Q, or N; and
V at position 16 is optional.

In certain embodiments, the isolated peptide comprises one or more mutations relative to a corresponding wildtype amino acid sequence, and the one or more mutations improve the aqueous solubility, stability, or resistance to chemical degradation of the isolated peptide relative to a polypeptide comprising the corresponding wildtype amino acid sequence. In certain embodiments, the peptides according to the seventh aspect of the invention also meet the structural features defining the peptides according to the first or second aspect of the invention.

An eighth aspect of the invention relates to an isolated peptide having the amino acid sequence of:

(SEQ ID NO: 21, P17/18)
(i) XXXXXXXXXXX(L/M)XXLLXXLLXXLXXX, wherein
X at position 1 can be any amino acid, but preferably Q, S, E, g-glutamate, A, T, G, D, isoD, N, K, or R;
X at position 2 can be any amino acid, but preferably Q, S, E, g-glutamate, A, T, G, D, isoD, N, K, or R;
X at position 3 can be any amino acid, but preferably P, Q, S, E, g-glutamate, A, T, G, D, isoD, N, K, or R;
X at position 4 can be any amino acid, but preferably I, Q, S, E, g-glutamate, A, T, G, D, N, isoD, K, or R;
X at position 5 can be any amino acid, but preferably D, isoD, S, E, g-glutamate, A, T, G, N, Q, K, or R;
X at position 6 can be any amino acid, but preferably R, Q, S, E, g-glutamate, A, T, G, D, isoD, N, or K;
X of position 7 can be any amino acid, but preferably Q, S, E, g-glutamate, A, T, G, D, isoD, N, K, or R;
X at position 8 can be any amino acid, but preferably T, Q, S, E, g-glutamate, A, G, D, isoD, N, K, or R;
X at position 9 can be any amino acid, but preferably I, Q, S, E, g-glutamate, A, T, G, D, isoD, N, K, or R;
X at position 10 can be any amino acid, but preferably E, g-glutamate, Q, S, A, T, G, D, isoD, N, K, or R;

X at position 11 can be any amino acid, but preferably Q, S, E, g-glutamate, A, T, G, D, isoD, N, K, or R;

X at position 13 can be any amino acid, but preferably A, S, T, G, D, isoD, E, g-glutamate, Q, N, K, or R;

X at position 14 can be any amino acid, but preferably Q, A, S, T, G, D, isoD, E, g-glutamate, N, K, or R;

X at position 17 can be any amino acid, but preferably A, S, T, G, D, isoD, E, g-glutamate, Q, N, K, or R;

X at position 18 can be any amino acid, but preferably Q, A, S, T, G, D, isoD, E, g-glutamate, N, K, or R;

X at position 21 can be any amino acid, but preferably K, A, S, T, G, D, isoD, E, g-glutamate, Q, N, or R;

X at position 22 can be any amino acid, but preferably S, A, T, G, D, isoD, E, g-glutamate, Q, N, K, or R;

X at position 25 can be any amino acid, but preferably S, A, T, G, D, isoD, E, g-glutamate, Q, N, K, or R;

X at position 26 can be any amino acid, but preferably P, S, A, T, G, D, isoD, E, g-glutamate, Q, N, K, or R; and X at position 27 can be any amino acid, but preferably Q, S, A, T, G, D, isoD, E, g-glutamate, N, K, or R; or (SEQ ID NO: 25, P17/18 min consensus)
(ii) (L/M)XXLLXXLLXXLL, wherein X at position 2 can be any amino acid, but preferably A, S, T, G, D, isoD, E, g-glutamate, Q, N, K, or R;

X at position 3 can be any amino acid, but preferably Q, A, S, T, G, D, isoD, E, g-glutamate, N, K, or R;

X at position 6 can be any amino acid, but preferably A, S, T, G, D, isoD, E, g-glutamate, Q, N, K, or R;

X at position 7 can be any amino acid, but preferably Q, A, S, T, G, D, isoD, E, g-glutamate, N, K, or R;

X at position 10 can be any amino acid, but preferably K, A, S, T, G, D, isoD, E, g-glutamate, Q, N, or R; and X at position 11 can be any amino acid, but preferably S, A, T, G, D, isoD, E, g-glutamate, Q, N, K, or R;

wherein the isolated peptide comprises one or more mutations relative to a corresponding wildtype amino acid sequence, and the one or more mutations improve the aqueous solubility, stability, or resistance to chemical degradation of the isolated peptide relative to a polypeptide comprising the corresponding wildtype amino acid sequence. In certain embodiments, the peptides according to the eighth aspect of the invention also meet the structural features defining the peptides according to the first or second aspect of the invention.

A ninth aspect of the invention relates to an isolated peptide having the amino acid sequence of:

(SEQ ID NO: 26, P19 consensus)
XLXX(L/M)LXLIXX(L/I/V/F/M)(L/I/V/F/M), wherein

X at position 1 is optional and can be L, I, V, F, or M;

X at position 3 can be any amino acid, but preferably K, A, S, T, G, D, isoD, E, g-glutamate, Q, N, or R;

X at position 4 can be any amino acid, but preferably A, S, T, G, D, isoD, E, g-glutamate, Q, N, K, or R;

X at position 7 can be any amino acid, but preferably K, A, S, T, G, D, isoD, E, g-glutamate, Q, N, or R;

X at position 10 can be any amino acid, but preferably A, S, T, G, D, isoD, E, g-glutamate, Q, N, K, or R; and X at position 11 can be any amino acid, but preferably R, A, S, T, G, D, isoD, E, g-glutamate, Q, N, or K.

In certain embodiments, the isolated peptide comprises one or more mutations relative to a corresponding wildtype amino acid sequence, and the one or more mutations improve the aqueous solubility, stability, or resistance to chemical degradation of the isolated peptide relative to a polypeptide comprising the corresponding wildtype amino acid sequence. In certain embodiments, the peptides according to the ninth aspect of the invention also meet the structural features defining the peptides according to the first or second aspect of the invention.

A tenth aspect of the invention relates to an isolated peptide that includes the amino acid sequence of (SEQ ID NO: 15, P3min consensus)
(L/M)XXLLX(L/M)FXXI(L/M)XX wherein X at position 2 can be Q, N, E, g-glutamate, D, isoD, T, S, A, or G;

X at position 3 can be Q, N, E, g-glutamate, D, isoD, T, S, A, or G;

X at position 6 can be K, Q, N, E, g-glutamate, D, isoD, T, S, A, or G;

X at position 9 can be E, g-glutamate, D, isoD, Q, N, T, S, A, or G;

X at position 10 can be A, G, S, T, E, g-glutamate, D, isoD, Q, or N;

X at position 13 can be Q, N, E, g-glutamate, D, isoD, T, S, A, or G; and

X at position 14 can be Q, N, E, g-glutamate, D, isoD, T, S, A, or G.

In certain embodiments, the isolated peptide comprises one or more mutations relative to a corresponding wildtype amino acid sequence, and the one or more mutations improve the aqueous solubility, stability, or resistance to chemical degradation of the isolated peptide relative to a polypeptide comprising the corresponding wildtype amino acid sequence. In certain embodiments, the peptides according to the tenth aspect of the invention also meet the structural features defining the peptides according to the first or second aspect of the invention.

An eleventh aspect of the invention relates to a fusion protein that includes one of the peptides of the first through eleventh aspects of the invention along with one or more of a purification tag, a solubility tag, or a second peptide according to one of the first through tenth aspects of the invention.

A twelfth aspect of the invention relates to a composition that includes one or more peptides according to the first, second, third, fourth, fifth, sixth, seventh, eighth, ninth, or tenth aspects of the invention, or a fusion protein according to the eleventh aspect of the invention, and a carrier.

A thirteenth aspect of the invention relates to a method of imparting disease resistance to plants. This method includes: applying an effective amount of an isolated peptide according to the first, second, third, fourth, fifth, sixth, seventh, eighth, ninth, or tenth aspects of the invention, a fusion protein according to the eleventh aspect of the invention, or a composition according to the twelfth aspect of the invention to a plant or plant seed or the locus where the plant is growing or is expected to grow, wherein said applying is effective to impart disease resistance.

A fourteenth aspect of the invention relates to a method of enhancing plant growth. This method includes: applying an effective amount of an isolated peptide according to the first, second, third, fourth, fifth, sixth, seventh, eighth, ninth, or tenth aspects of the invention, a fusion protein according to the eleventh aspect of the invention, or a composition according to the twelfth aspect of the invention to a plant or plant seed or the locus where the plant is growing or is expected to grow, wherein said applying is effective to enhance plant growth.

A fifteenth aspect of the invention relates to a method of increasing a plant's tolerance and resistance to biotic stressors. This method includes: applying an effective amount of an isolated peptide according to the first, second, third, fourth, fifth, sixth, seventh, eighth, ninth, or tenth aspects of the invention, a fusion protein according to the eleventh aspect of the invention, or a composition according to the twelfth aspect of the invention to a plant or plant seed or the locus where the plant is growing or is expected to grow, wherein said applying is effective to increase the plant's tolerance and resistance to biotic stress factors selected from the group consisting of pests such as insects, arachnids, nematodes, weeds, and combinations thereof.

A sixteenth aspect of the invention relates to a method of increasing a plant's tolerance to abiotic stress. This method includes: applying an effective amount of an isolated peptide according to the first, second, third, fourth, fifth, sixth, seventh, eighth, ninth, or tenth aspects of the invention, a fusion protein according to the eleventh aspect of the invention, or a composition according to the twelfth aspect of the invention to a plant or plant seed or the locus where the plant is growing or is expected to grow, wherein said applying is effective to increase the plant's tolerance to abiotic stress factors selected from the group consisting of salt stress, water stress (including drought and flooding), ozone stress, heavy metal stress, cold stress, heat stress, nutritional stress (phosphate, potassium, nitrogen deficiency), bleaching and light-induced stress, and combinations thereof.

A seventeenth aspect of the invention relates to a method imparting desiccation resistance to cuttings removed from ornamental plants. This method includes: applying an isolated peptide according to the first, second, third, fourth, fifth, sixth, seventh, eighth, ninth, or tenth aspects of the invention, a fusion protein according to the eleventh aspect of the invention, or a composition according to the twelfth aspect of the invention to a plant or the locus where the plant is growing, wherein said applying is effective to impart desiccation resistance to cuttings removed from the ornamental plant.

An eighteenth aspect of the invention relates to a method of imparting post-harvest disease or post-harvest desiccation resistance to a fruit or vegetable. This method includes: applying an effective amount of an isolated peptide according to the first, second, third, fourth, fifth, sixth, seventh, eighth, ninth, or tenth aspects of the invention, a fusion protein according to the eleventh aspect of the invention, or a composition according to the twelfth aspect of the invention to a plant containing a fruit or vegetable or the locus where the plant is growing; or applying an effective amount of the isolated peptide or the composition to a harvested fruit or vegetable, wherein said applying is effective to impart post-harvest disease resistance or desiccation resistance to the fruit or vegetable.

A nineteenth aspect of the invention relates to a method of enhancing the longevity of fruit or vegetable ripeness. This method includes: applying an effective amount of an isolated peptide according to the first, second, third, fourth, fifth, sixth, seventh, eighth, ninth, or tenth aspects of the invention, a fusion protein according to the eleventh aspect of the invention, or a composition according to the twelfth aspect of the invention to a plant containing a fruit or vegetable or the locus where the plant is growing; or applying an effective amount of the isolated peptide or the composition to a harvested fruit or vegetable, wherein said applying is effective to enhance the longevity of fruit or vegetable ripeness.

A twentieth aspect of the invention relates to a method of modulating one or more biological signaling processes of a plant. This method includes: applying an effective amount of an isolated peptide according to the first, second, third, fourth, fifth, sixth, seventh, eighth, ninth, or tenth aspects of the invention, a fusion protein according to the eleventh aspect of the invention, or a composition according to the twelfth aspect of the invention to a plant or the locus where the plant is growing, wherein said applying is effective in modulating one or more biochemical signaling processes.

A twenty-first aspect of the invention relates to a DNA construct including a first nucleic acid molecule encoding a polypeptide according to the first, second, third, fourth, fifth, sixth, seventh, eighth, ninth, or tenth aspects of the invention or a fusion protein according to the eleventh aspect of the invention; and a promoter-effective nucleic acid molecule operably coupled to the first nucleic acid molecule. This aspect of the invention also encompasses a recombinant expression vector containing the DNA construct, a recombinant host cell containing the DNA construct, as well as transgenic plants or plant seeds that include a recombinant plant cell of the invention (which contains the DNA construct).

A twenty-second aspect of the invention relates to a method of imparting disease resistance to plants, enhance plant growth, impart tolerance and resistance to biotic stressors, impart tolerance to abiotic stress, or modulating plant biochemical signaling. This method includes providing a transgenic plant transformed with a DNA construct according to the twenty-first aspect of the invention; and growing the plant under conditions effective to permit the DNA construct to express the peptide or the fusion polypeptide to impart disease resistance, enhance plant growth, impart tolerance to biotic stress, impart tolerance to abiotic stress, or modulate biochemical signaling to the transgenic plant.

A twenty-third aspect of the invention relates to a method of imparting desiccation resistance to cuttings removed from ornamental plants, imparting post-harvest disease or post-harvest desiccation resistance to a fruit or vegetable, or enhancing the longevity of fruit or vegetable ripeness. The method includes providing a transgenic plant transformed with a DNA construct including a first nucleic acid molecule encoding a polypeptide according to the first, second, third, fourth, fifth, sixth, seventh, eighth, ninth, or tenth aspects of the invention or a fusion protein according to the eleventh aspect of the invention; and growing the plant under conditions effective to permit the DNA construct to express the peptide or the fusion polypeptide to impart desiccation resistance to cuttings removed from a transgenic ornamental plant, impart post-harvest disease resistance or desiccation resistance to a fruit or vegetable removed from the transgenic plant, or enhance longevity of ripeness for a fruit or vegetable removed from the transgenic plant.

A twenty-fourth aspect of the invention relates to a method of imparting disease resistance to plants, enhancing plant growth, imparting tolerance and resistance to biotic stressors, imparting tolerance to abiotic stress, or modulating biochemical signaling. This method includes providing a transgenic plant seed transformed with a DNA construct according to the twenty-first aspect of the invention; planting the transgenic plant seed in soil; and propagating a transgenic plant from the transgenic plant seed to permit the DNA construct to express the peptide or the fusion polypeptide to impart disease resistance, enhance plant growth, impart tolerance to biotic stress, or impart tolerance to abiotic stress A twenty-fifth aspect of the invention relates to a method of imparting desiccation resistance to cuttings removed from ornamental plants, imparting post-harvest disease or post-harvest desiccation resistance to a fruit or vegetable, or enhancing the longevity of fruit or vegetable ripeness. The method includes providing a transgenic plant seed transformed with a DNA construct according to the twenty-first aspect of the invention; planting the transgenic plant seed in soil; and propagating a transgenic plant from the transgenic plant seed to permit the DNA construct to express the peptide or the fusion polypeptide to impart desiccation resistance to cuttings removed from a transgenic ornamental plant, impart post-harvest disease resistance or desiccation resistance to a fruit or vegetable removed from the transgenic plant, or enhance longevity of ripeness for a fruit or vegetable removed from the transgenic plant.

By providing HR-eliciting peptides that exhibit improved solubility, stability, resistance to chemical degradation, or a combination of these properties, it will afford growers with greater flexibility in preparing, handling, and delivering to plants in their fields or greenhouses effective amounts of compositions containing these HR-eliciting peptides. Simplifying the application process for growers will lead to greater compliance and, thus, improved results with respect to one or more of disease resistance, growth enhancement, tolerance and resistance to biotic stressors, tolerance to abiotic stress, desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. These and other benefits are described herein.

DETAILED DESCRIPTION OF THE INVENTION

Figure 1:
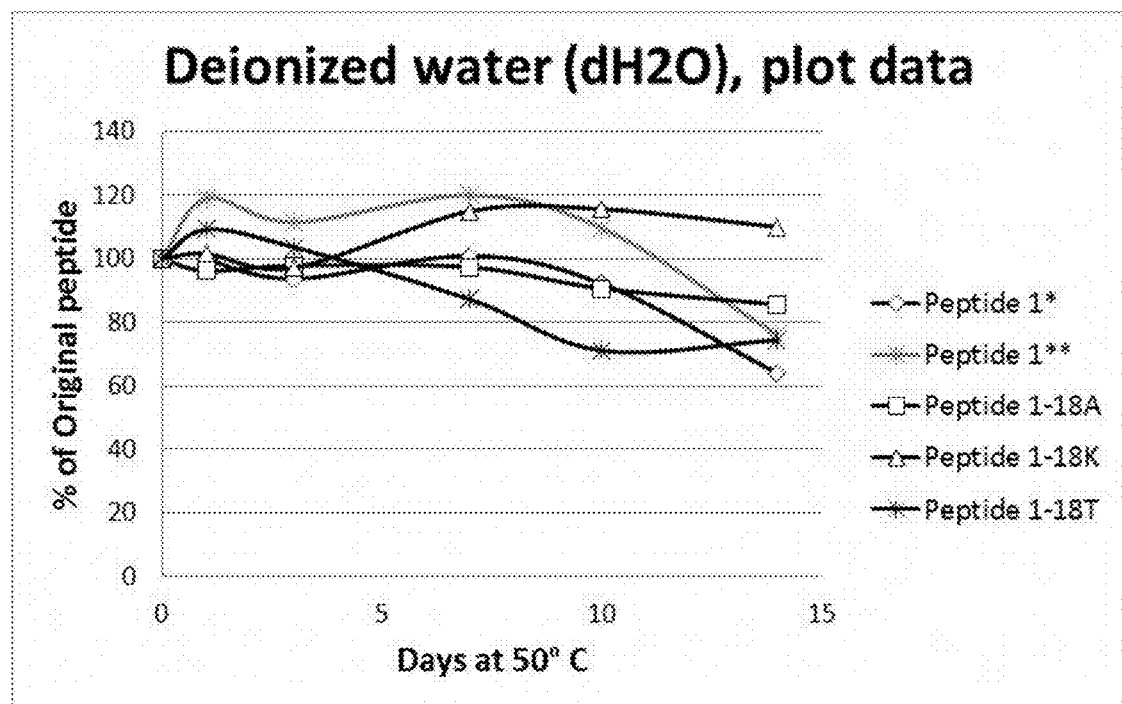
FIG. 1 shows a solubility and stability test of peptide P1 and P1 mutants dissolved in deionized water. The following peptides are shown: P1 (SEQ ID NO: 4); P1-18A (SEQ ID NO: 44); P1-18K (SEQ ID NO: 45); and P1-18T (SEQ ID NO: 42). The curve for 1* is normalized to 100% of P1 at the day 1 time point; 1** is the original P1 data.

One aspect of the invention relates to novel peptides that possess the ability to induce a hypersensitive response in plants and promote active plant responses that afford one or more of the following attributes: disease resistance, growth enhancement, tolerance and resistance to biotic stressors, tolerance to abiotic stress, desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants.

As used herein, naturally occurring amino acids are identified throughout by the conventional three-letter and/or one-letter abbreviations, corresponding to the trivial name of the amino acid, in accordance with the following list: Alanine (Ala, A), Arginine (Arg, R), Asparagine (Asn, N), Aspartic acid (Asp, D), Cysteine (Cys, C), Glutamic acid (Glu, E), Glutamine (Gln, Q), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). The abbreviations are accepted in the peptide art and are recommended by the IUPAC-IUB commission in biochemical nomenclature. Naturally occurring variations of amino acids include, without limitation, gamma-glutamate (g-Glu) and isoaspartate (iso-Asp or isoD).

The term "amino acid" further includes analogues, derivatives, and congeners of any specific amino acid referred to herein, as well as C-terminal or N-terminal protected amino acid derivatives (e.g., modified with an N-terminal, C-terminal, or side-chain protecting group, including but not limited to acetylation, formylation, methylation, amidation, esterification, PEGylation, and addition of lipids. Non-naturally occurring amino acids are well known and can be introduced into peptides of the present invention using solid phase synthesis as described below. Furthermore, the term "amino acid" includes both D- and L-amino acids. Hence, an amino acid which is identified herein by its name, three letter or one letter symbol and is not identified specifically as having the D or L configuration, is understood to assume any one of the D or L configurations. In one embodiment, a peptide comprises all L-amino acids.

In certain embodiments, peptides are identified to "consist of" a recited sequence, in which case the peptide includes only the recited amino acid sequence(s) without any extraneous amino acids at the N- or C-terminal ends thereof. To the extent that a recited sequence is in the form of a consensus sequence where one or more of the denoted X or Xaa residues can be any of one or more amino acids, then multiple peptide sequences are embraced by a peptide consisting of such a recited sequence.

In certain other embodiments, peptides are identified to "consist essentially of" a recited sequence, in which case the peptide includes the recited amino acid sequence(s) optionally with one or more extraneous amino acids at the N- and/or C-terminal ends thereof, which extraneous amino acids do not materially alter one or more of the following properties: (i) the ability of the peptide to induce a hypersensitive response in plants, (ii) solubility of the peptide in water or aqueous solutions, (iii) stability of the peptide dissolved in water or aqueous solution at 50° C. over a period of time (e.g., 3 weeks), and (iv) resistance of the peptide to chemical degradation in the presence of an aqueous buffered solution that includes a biocidal agent (e.g., Proxel® GXL) at 50° C. over a period of time (e.g., 3 weeks).

Briefly, the stability and resistance to chemical degradation of peptides can be assessed as follows using peptide samples having an initial purity of at least about 80%, at least about 82%, at least about 84%, at least about 86%, at least about 88%, at least about 90%, at least about 92%, at least about 94%, at least about 96%, or at least about 98%. For water stability, the peptide is dissolved directly in de-ionized water. For chemical degradation tests, the peptide is dissolved in an aqueous solution containing 50 mM pH buffer and 0.25% Proxel GXL. Exemplary pH buffers include, without limitation: (i) Citrate pH 5.6; (ii) MES pH 6.2; (iii) MOPS pH 6.5; (iv) imidazole pH 7.0; (v) Citrate pH 7.2; (vi) EDDS, pH 7.3; (vii) EDTA pH 8.0; (viii) sodium phosphate pH 8.0; or (ix) TES pH 8.0. Peptides are first dissolved in the aqueous solution at a concentration of 0.5 mg/ml. The samples are incubated at 50° C. to allow for accelerated degradation. An initial sample of the peptide is removed, diluted 10× with water, and analyzed by reverse-phase HPLC. Briefly, 20 µl of the sample is injected into the solvent flow of an HPLC instrument and analyzed on a C18 HPLC column (YMC ProPack C18, YMC, Japan, or C18 Stablebond, Agilent Technologies, USA) using either a triethylamine phosphate in water/acetonitrile gradient or a 0.1% TFA in water/0.1% TFA in acetonitrile gradient to separate different peptide species. Eluting peptides are monitored by UV absorbance at 218 nm and quantified based on the area under the peak. The area under the peak for the initial peptide sample is treated as the standard for relative quantification in subsequent runs. At regular intervals (e.g., 1, 3, 7, 10, 14, 17, and 21 days), each peptide sample is surveyed and analyzed by HPLC as described above. If necessary to observe degradation (i.e., where the peptide exhibits a high degree of chemical stability), this protocol can be extended by several weeks to observe degradation. The quantification of subsequent peptide runs is expressed as a percentage of the original (day 0) HPLC result.

A peptide that is at least partially soluble in water or aqueous solution exhibits a solubility of greater than 0.1 mg/ml, preferably at least about 1.0 mg/ml, at least about 2.0 mg/ml, at least about 3.0 mg/ml, or at least about 4.0 mg/ml. In certain embodiments, the peptide exhibits high solubility in water or aqueous solution, with a solubility of at least about 5.0 mg/ml, at least about 10.0 mg/ml, at least about 15.0 mg/ml, or at least about 20 mg/ml.

A peptide that is stable in water or aqueous solution exhibits at least about 66%, at least about 68%, at least about 70%, at least about 72%, at least about 74%, at least about 76%, at least about 78%, at least about 80%, at least about 82%, at least about 84%, at least about 86%, at least about 88%, or at least about 90% of the original peptide concentration over the designated period of time incubated at 50° C. In certain embodiments, the designated period of time is 3 days, 7 days, 14 days, 21 days, 28 days, one month, two months, or three months.

A peptide that is resistant to chemical degradation exhibits at least about 66%, at least about 68%, at least about 70%, at least about 72%, at least about 74%, at least about 76%, at least about 78%, at least about 80%, at least about 82%, at least about 84%, at least about 86%, at least about 88%, or at least about 90% of the original peptide concentration over the designated period of time incubated at 50° C. In certain embodiments, the designated period of time is 3 days, 7 days, 14 days, 21 days, 28 days, one month, two months, or three months.

A property of a peptide to elicit a hypersensitive response, or not, upon infiltration or application of the peptide to plant tissues can be measured by applying the peptide in dry powder form or in solution form to a plant, particularly though not exclusively a plant leaf. Application rates include 1-500 ug/ml for liquid solution and 0.0001-0.5% (w/w for powder application. Exemplary application of the peptide in solution form is described in the accompanying Examples. Plants are considered HR-positive ("HR+") if they exhibit wide-spread macroscopic cell death visible to the naked eye, accompanied by wilting and browning of the affected tissue within 48 hours. Plants are considered HR-negative ("HR-") if they exhibit no discernible wilting or tissue death observable by naked eye.

In certain embodiments, material alteration of the one or more properties is intended to mean that there is less than 20% variation, less than 15% variation, less than 10% variation, or less than 5% variation in a recited property when comparing a peptide possessing the one or more extraneous amino acids to an otherwise identical peptide lacking the one or more extraneous amino acids. In certain embodiments, the number of extraneous amino acids at the N- or C-terminal ends is up to 20 amino acids at one or both ends, up to 15 amino acids at one or both ends, up to 10 amino acids at one or both ends, up to 7 amino acids at one or both ends, up to 5 amino acids at one or both ends, or up to 3 amino acids at one or both ends. Further, to the extent that a recited sequence is in the form of a consensus sequence where one or more of the denoted X or Xaa residues can be any of one or more amino acids, then multiple peptide sequences are embraced by the peptide consisting essentially of such a recited sequence, without regard to additional variations of such sequences that are afforded by the presence of extraneous amino acids at the N- and/or C-terminal ends thereof.

In various embodiments of the invention, the disclosed peptides may include a hydrophilic amino acid sequence, e.g., at either the N-terminal or C-terminal end of a designated peptide sequence. The hydrophilic amino acid sequence is at least 3, at least 4, at least 5, at least 6, at least 7, at least 8, at least 9, or at least 10 amino acids in length, and includes amino acid residues that contribute to a hydrophilic property of the amino acid sequence that is adjacent to the amino acid sequence of the designated peptide (i.e., the peptide that induces an active plant response). Different methods have been used in the art to calculate the relative hydrophobicity/hydrophilicity of amino acid residues and proteins (Kyte et al., "A Simple Method for Displaying the Hydropathic Character of a Protein," *J. Mol. Biol.* 157: 105-32 (1982); Eisenberg D, "Three-dimensional Structure of Membrane and Surface Proteins," *Ann. Rev. Biochem.* 53: 595-623 (1984); Rose et al., "Hydrogen Bonding, Hydrophobicity, Packing, and Protein Folding," *Annu. Rev. Biomol. Struct.* 22: 381-415 (1993); Kauzmann, "Some Factors in the Interpretation of Protein Denaturation," *Adv. Protein Chem.* 14: 1-63 (1959), which are hereby incorporated by reference in their entirety). Any one of these hydrophobicity scales can be used for the purposes of the present invention; however, the Kyte-Doolittle hydrophobicity scale is perhaps the most often referenced scale. These hydropathy scales provide a ranking list for the relative hydrophobicity of amino acid residues. For example, amino acids that contribute to hydrophilicity include Arg (R), Lys (K), Asp (D), Glu (E), Gln (Q), Asn (N), and His (H) as well as, albeit to a lesser extent, Ser (S), Thr (T), Gly (G), Pro (P), Tyr (Y), and Trp (W). For example, polyglutamate sequences can be used to enhance solubility of proteins and other drug molecules (Lilie et al, *Biological Chemistry* 394(8):995-1004(2013); Li et al., *Cancer Research* 58: 2404-2409(1998)), each of which is hereby incorporated by reference in its entirety).

The "hydropathy index" of a protein or amino acid sequence is a number representing its average hydrophilic or hydrophobic properties. A negative hydropathy index defines the hydrophilicity of the amino acid sequence of interest. The hydropathy index is directly proportional to the hydrophilicity of the amino acid sequence of interest; thus, the more negative the index, the greater its hydrophilicity. In certain embodiments, the added hydrophilic amino acid sequence described above has a hydropathy index of less than 0, −0.4, −0.9, −1.3, −1.6, −3.5, −3.9, or −4.5. In certain embodiments, the resulting entire peptide will have a hydropathy index of less than 0.3, 0.2, 0.1, or 0.0, preferably less than −0.1, −0.2, −0.3, −0.4, more preferably less than −0.5, −0.6, −0.7, −0.8, −0.9, or −1.0.

In the peptides of the present invention, amino acids that contribute to a hydrophilic hydropathy index, for either the peptide as a whole or the added hydrophilic amino acid sequence, include Arg (R), Lys (K), Asp (D), Glu (E), Gln (Q), Asn (N), His (H), Ser (S), Thr (T), Gly (G), Pro (P), Tyr (Y), and Trp (W). Of these, Asp (D), Glu (E), Gln (Q), Asn (N) or their variants are preferred. Exemplary variants include g-glutamate for Glu and isoaspartic acid (or isoD) for Asp.

As used herein, in this and in other aspects of the invention, the term "hydrophobic amino acid" is intended to refer to an amino acid that contributes hydrophobicity to the hydropathy index of a designated amino acid sequence. Amino acids that contribute to a hydrophobic hydropathy index, for either the peptide as a whole or a particular amino acid sequence thereof, include Ile (I), Val (V), Leu (L), Phe (F), Cys (C), Met (M), and Ala (A). In certain embodiments, the term "hydrophobic amino acid" may refer to any one of Ile (I), Val (V), Leu (L), Phe (F), Cys (C), Met (M), and Ala (A); or, alternatively, to any one of Ile (I), Val (V), Leu (L), Phe (F), and Ala (A). In certain other embodiments, the term "hydrophobic amino acid" may refer to one of Ile (I), Val (V), Leu (L), and Phe (F).

As used herein, the term "non-hydrophobic amino acid" is intended to mean an amino acid that is hydrophilic (or not hydrophobic) on one of the above-identified hydrophobicity scales. This term generally refers to those amino acids that contribute to a hydrophilic hydropathy index for either the peptide as a whole or the added hydrophilic amino acid sequence.

In one aspect of the invention, the peptide includes the amino acid sequence of:

(SEQ ID NO: 93)
(L/I/V/F)-X-X-(L/I/V/F)-(L/I)-X-X-(L/I/V/F)-

(L/I/V/A)-X-X-(L/I)-(L/I/V/F)

wherein the peptide is free of cysteine and methionine; each X at positions 2 and 6 is optional and, when present, is any amino acid, including any naturally occurring amino acid; and each X at positions 3, 7, 10, and 11 is any amino acid, including any naturally occurring amino acid.

In a related aspect of the invention, the peptide includes the amino acid sequence of SEQ ID NO: 93 (shown above), wherein the peptide is free of cysteine and methionine; each X at positions 2, 6, and 10 is optional and, when present, is any amino acid, including any naturally occurring amino acid; and each X at positions 3, 7, and 11 is any amino acid, including any naturally occurring amino acid.

According to one embodiment, one or more of X at positions 2, 6, and 10 is not present (i.e., the gap between the first hydrophobic amino acid and the first hydrophobic amino acid doublet is reduced from two to one amino acid residue and/or the gap between the first and second hydrophobic amino acid doublets is reduced from two to one amino acid residue and/or the gap between the second and third hydrophobic amino acid doublets is reduced from two to one amino acid residue). In this embodiment, it is contemplated that these peptides exclude the amino acid at only one of positions 2, 6, and 10.

In an alternative embodiment, X at both of positions 2 and 6 is present (i.e., the gap between the hydrophobic amino acids is maintained at two amino acid residues at both locations).

In another embodiment, X at each of positions 2, 6, and 10 is present (i.e., the gap between the hydrophobic amino acids is maintained at two amino acid residues at each location).

In certain embodiments, SEQ ID NO: 93 may further include an additional amino acid residue between the hydrophobic doublets (two of L/I/V/F/A, as indicated) and these additional amino acid can be any amino acid. In these embodiments, the gap before the first hydrophobic doublet is three amino acids, the gap between the first and second hydrophobic doublets is three amino acids, the gap between the second and third hydrophobic doublet is three amino acids, or combinations thereof.

The peptide length in this embodiment is less than 100 amino acids, or alternatively less than 90 amino acids, less than 80 amino acids, less than 70 amino acids, less than 60 amino acids, or less than about 50 amino acids. In certain embodiments, the peptide length is between 13 and about 50 amino acids in length.

In the embodiments described above, where X at each of positions 2, 3, 6, 7, 10, and 11 (when present) of SEQ ID NO: 93 can be any amino acid, in certain embodiments these residues are hydrophilic in nature. As described above, these hydrophilic amino acids include Arg (R), Lys (K), Asp (D), Glu (E), Gln (Q), Asn (N), His (H), Ser (S), Thr (T), Gly (G), Pro (P), Tyr (Y), and Trp (W). Of these, Asp (D), Glu (E), Gln (Q), Asn (N) or their variants are preferred. Exemplary variants include g-glutamate for Glu and isoaspartic acid (or isoD) for Asp.

In this embodiment, the isolated peptide is stable when dissolved in water; resistant to chemical degradation in aqueous conditions in the presence of a pH buffer and a biocide, as described above; and/or has a solubility in an aqueous solution of at least about 1.0 mg/ml.

Another aspect of the invention relates to an isolated peptide having the amino acid sequence of:

(SEQ ID NO: 1, P1/P4 consensus)
XXGISEKXXXXXXXXXXXXXXXX, wherein
X at position 1 is optional and can be S, N, D, isoD, G, A, or S;
X at position 2 is optional and can be Q, E, g-glutamate, G, A, or S;
X at position 8 is Q, E, g-glutamate, G, A, or S;
X at position 9 is L, I, F, or V;
X at position 10 is optional and can be D or isoD;
X at position 11 is Q, E, g-glutamate, G, A, or S;
X at position 12 is M, L, I, or F;
X at position 13 is M, L, or I;
X at position 14 is optional and can be any hydrophilic amino acid, preferably C, S, T, A, D, isoD, K, or Q;
X at position 15 is Q, E, g-glutamate, G, A, S, K, or I;
X at position 16 is M, L, I, V, or F;
X at position 17 is M, L, I, A, or V;
X at position 18 is Q, E, g-glutamate, G, A, S, M, T, or K;
X at position 19 is A, D, isoD, S, V, T, K, R, E, g-glutamate, H, or G;
X at position 20 is M, L, or I;
X at position 21 is M, L, I, V, S, or F;
X at position 22 is Q, E, g-glutamate, G, A, S;
X at position 23 is P, Q, E, g-glutamate, G, A, or S; and
wherein the isolated peptide comprises one or more mutations relative to a corresponding wildtype amino acid sequence. In certain embodiments, the one or more mutations improve the aqueous solubility, stability, or resistance to chemical degradation of the isolated peptide relative to a polypeptide comprising the corresponding wildtype amino acid sequence.

In certain embodiments, these peptides according to the second aspect of the invention also meet the structural features defining the peptides of SEQ ID NO: 93, in which case methionine and cysteine residues are not present.

In this embodiment, the corresponding wildtype amino acid sequence, for purposes of comparing properties of the inventive peptide, is a polypeptide comprising or the peptide consisting of the amino acid sequence of NQGISEKQLDQLLTQLIMALLQQ (P1, SEQ ID NO: 4) or SQGISEKQLDQLLCQLIQALL (amino acids 1-21 of SEQ ID NO: 5, P4). P1 (SEQ ID NO: 4) is derived from the full length protein of *Xanthomonas* harpin HpaG (Kim et al., "Mutational Analysis of *Xanthomonas* Harpin HpaG Identifies a Key Functional Region That Elicits the Hypersensitive Response in Nonhost Plants," *J. Bacteriol.* 186(18): 6239-6247 (2004), which is hereby incorporated by reference in its entirety). P4 (SEQ ID NO: 5) is derived from the full length harpin of *Xanthomonas oryzae* pv. *oryzae* (Ji et al., "Two Coiled-Coil Regions of *Xanthomonas oryzae* pv. *Oryzae* Harpin Differ in Oligomerization and Hypersensitive Response Induction," *Amino Acids* 40:381-392 (2011), which is hereby incorporated by reference in its entirety).

In this embodiment, the isolated peptide is stable when dissolved in water; resistant to chemical degradation in aqueous conditions in the presence of a pH buffer and a biocide, as described above; and/or has a solubility in an aqueous solution of at least about 1.0 mg/ml.

The length of peptides according to this second aspect is preferably less than about 100 amino acids, or alternatively less than 90 amino acids, less than 80 amino acids, less than 70 amino acids, less than 60 amino acids, or less than about 50 amino acids. In certain embodiments, the peptide length is between 23 and about 50 amino acids in length.

One exemplary family of peptides according to the second aspect of the invention have the amino acid sequence of:

(SEQ ID NO: 2, P4 consensus)
SXGISEKXXDXXXXXXXXAXXXP, wherein
X at position 2 is Q, E, g-glutamate, G, A, or S;
X at position 8 is Q, E, g-glutamate, G, A, or S;
X at position 9 is L, A, D, isoD, I, V, or F;
X at position 11 is Q, E, g-glutamate, G, A, or S;
X at position 12 is L, D, isoD, I, or F;
X at position 13 is L, I, V, or F;
X at position 14 is any hydrophilic amino acid, preferably C, S, or T, S or T, or only S;
X at position 15 is Q, E, g-glutamate, G, A, S, K, or I
X at position 16 is L, A, I, V, M, or F
X at position 17 is I, S, or F
X at position 18 is Q, E, g-glutamate, G, A, or S;
X at position 20 is L, I, V, or F;
X at position 21 is L or F; and
X at position 22 is Q, E, g-glutamate, G, A, or S.

In certain embodiments, these peptides according to SEQ ID NO: 2 also meet the structural features defining the peptides of SEQ ID NO: 93, in which case methionine and cysteine residues are not present. Thus, in these embodiments, X at position 14 is S or T, preferably S.

Exemplary peptides that share the consensus structure with SEQ ID NO: 2, or are derived from SEQ ID NO: 2 and meet the consensus structure of SEQ ID NO: 93, are identified in Table 1 below:

TABLE 1

Peptide Variants of Peptide P4 (SEQ ID NO: 5)

| Peptide Name | Sequence | SEQ ID NO: |
|---|---|---|
| P4 | SQGISEKQLDQLLCQLIQALLQP | 5 |
| P4-14s | SQGISEKQLDQLLSQLIQALLQP | 6 |
| P4-14s-18e | SEGISEKQLDQLLSQLIEALLQP | 191 |
| P4-14s-18s | SQGISEKQLDQLLSQLISALLQP | 7 |
| P4-14s-2,18e | SEGISEKQLDQLLSQLIEALLQP | 8 |
| P4-2e-8e | SEGISEKELDQLLSQLIQALLQP | 9 |
| P4-2e-8e-15e | SEGISEKELDQLLSELIQALLQP | 10 |
| P4-allE | SEGISEKELDELLSELIEALLQP | 11 |
| P4-14s-9i | SQGISEKQIDQLLSQLIQALLQP | 196 |
| P4-14s-9v | SQGISEKQVDQLLSQLIQALLQP | 19 |
| P4-14s-9f | SQGISEKQFDQLLSQLIQALLQP | 20 |
| P4-14s-12i | SQGISEKQLDQILSQLIQALLQP | 22 |
| P4-14s-12f | SQGISEKQLDQFLSQLIQALLQP | 23 |

TABLE 1-continued

Peptide Variants of Peptide P4 (SEQ ID NO: 5)

| Peptide Name | Sequence | SEQ ID NO: |
|---|---|---|
| P4-14s-13i | SQGISEKQLDQLISQLIQALLQP | 24 |
| P4-14s-15a | SQGISEKQLDQLLSALIQALLQP | 27 |
| P4-14s-15k | SQGISEKQLDQLLSKLIQALLQP | 28 |
| P4-14s-15s | SQGISEKQLDQLLSSLIQALLQP | 29 |
| P4-14s-15i | SQGISEKQLDQLLSILIQALLQP | 30 |
| P4-14s-16i | SQGISEKQLDQLLSQIIQALLQP | 32 |
| P4-14s-16f | SQGISEKQLDQLLSQFIQALLQP | 34 |
| P4-14s-20i | SQGISEKQLDQLLSQLIQAILQP | 37 |
| P4-14s-21f | SQGISEKQLDQLLSQLIQALFQP | 40 |
| P4-14s-dN6 | KQLDQLLSQLIQALLQP | 94 |
| P4-14s-dN5 | EKQLDQLLSQLIQALLQP | 95 |
| P4-14s-dN4 | SEKQLDQLLSQLIQALLQP | 96 |
| P4-14s-dN2 | GISEKQLDQLLSQLIQALLQP | 97 |
| P4-14s-3E | SQEISEKQLDQLLSQLIQALLQP | 98 |
| P4-14S-4L | SQGLSEKQLDQLLSQLIQALLQP | 99 |
| P4-14S-4A | SQGASEKQLDQLLSQLIQALLQP | 100 |
| P4-14S-4D | SQGDSEKQLDQLLSQLIQALLQP | 101 |
| P4-14s-5V | SQGIVEKQLDQLLSQLIQALLQP | 102 |
| P4-14s-6R | SQGISRKQLDQLLSQLIQALLQP | 103 |
| P4-14s-6V | SQGISVKQLDQLLSQLIQALLQP | 104 |
| P4-14s-7D | SQGISEDQLDQLLSQLIQALLQP | 105 |
| P4-14s-7V | SQGISEVQLDQLLSQLIQALLQP | 106 |
| P4-14S-8V | SQGISEKVLDQLLSQLIQALLQP | 107 |
| P4-14S-8S | SQGISEKSLDQLLSQLIQALLQP | 108 |
| P4-14S-10V | SQGISEKQLVQLLSQLIQALLQP | 111 |
| P4-14S-11V | SQGISEKQLDVLLSQLIQALLQP | 112 |
| P4-14S-12V | SQGISEKQLDQVLSQLIQALLQP | 113 |
| P4-14S-12S | SQGISEKQLDQSLSQLIQALLQP | 114 |
| P4-14S-14V | SQGISEKQLDQLLVQLIQALLQP | 116 |
| P4-14S-15V | SQGISEKQLDQLLSVLIQALLQP | 117 |
| P4 | SQGISEKQLDQLLCQLIQALLQP | 5 |
| P4-14s-17L | SQGISEKQLDQLLSQLLQALLQP | 119 |
| P4-14s-17A | SQGISEKQLDQLLSQLAQALLQP | 120 |
| P4-14s-17V | SQGISEKQLDQLLSQLVQALLQP | 121 |
| P4-14s-18V | SQGISEKQLDQLLSQLIVALLQP | 122 |
| P4-14S-19V | SQGISEKQLDQLLSQLIQVLLQP | 123 |
| P4-14S-19D | SQGISEKQLDQLLSQLIQDLLQP | 124 |

TABLE 1-continued

Peptide Variants of Peptide P4 (SEQ ID NO: 5)

| Peptide Name | Sequence | SEQ ID NO: |
|---|---|---|
| P4-14S-19S | SQGISEKQLDQLLSQLIQSLLQP | 125 |
| P4-14S-21S | SQGISEKQLDQLLSQLIQALSQP | 127 |
| P4-14S-21I | SQGISEKQLDQLLSQLIQALIQP | 128 |
| P4-14S-21V | SQGISEKQLDQLLSQLIQALVQP | 129 |
| P4-14S-22V | SQGISEKQLDQLLSQLIQALLVP | 130 |
| P4-14S-dC2 | SQGISEKQLDQLLSQLIQALL | 131 |
| p4-d10 | SQGISEKQL_QLLSQLIQALLQP | 132 |
| p4-d14 | SQGISEKQLDQLL_QLIQALLQP | 133 |
| P4-14A | SQGISEKQLDQLLAQLIQALLQP | 136 |
| p4-14D | SQGISEKQLDQLLDQLIQALLQP | 137 |
| P4-14K | SQGISEKQLDQLLKQLIQALLQP | 138 |
| P4-14Q | SQGISEKQLDQLLQQLIQALLQP | 139 |
| p4-i9A | SQGISEKQALDQLLSQLIQALLQP | 140 |
| polyE-minp4 | *SEEEEE*LDQLLSQLIQALLQP | 232 |
| polyE-min2p4 | *SEEEEE*LDQLLSQLIQALLQ | 31 |
| polyE-min3P4 | *SEEEEE*LDQLLSQLIQALL | 33 |
| P4-NpolyR | *RRRRRGG*LDQLLSQLIQALLQP | 35 |
| P4-CpolyR | LDQLLSQLIQALLQP*GGRRRRR* | 36 |
| P4-NpolyK | *KKKKKGG*LDQLLSQLIQALLQP | 38 |
| P4-CpolyK | LDQLLSQLIQALLQP*GGKKKKK* | 39 |
| P4-7E-cR | SQGISE*E*QLDQLLSQLIQALLQPR | 194 |
| minp4-PolyE | LDQLLSQLIQALL*EEEEE* | 192 |
| SEE-minp4-EE | *SEE*LDQLLSQLIQALL*EE* | 193 |

Select peptides in Table 1 include solubility tags, indicated by italic print, including SEEEEE, SEE, EEEEE, EE, RRRRRGG, KKKKKGG, GGKKKKK, and GGRRRRR. Peptides comprising the sequences shown in Table 1 but lacking these specific solubility tags (or having a different solubility tag) are also contemplated herein.

As noted above, the peptide P4 (SEQ ID NO: 5) is derived from the harpin of *Xanthomonas oryzae* pv. *oryzae* (Ji et al., "Two Coiled-Coil Regions of *Xanthomonas oryzae* pv. *Oryzae* Harpin Differ in Oligomerization and Hypersensitive Response Induction," *Amino Acids* 40:381-392 (2011), which is hereby incorporated by reference in its entirety). Ji et al. discloses a fragment of this harpin having the amino acid sequence SQGISEKQLDQLLCQLIQALL (i.e., amino acids 1-21 of SEQ ID NO: 5). In certain embodiments, an isolated peptide comprising the amino acid sequence of SEQ ID NO: 5 is a peptide that has an overall length of less than about 100 amino acids (i.e., from 23 amino acids up to about 100 amino acids in length). In certain other embodiments, the isolated peptide consists essentially of SEQ ID NO: 5, whereas in another embodiment the isolated peptide consists of SEQ ID NO: 5.

Another exemplary family of peptides according to the second aspect of the invention have the amino acid sequence of:

```
                    (SEQ ID NO: 3, P1 consensus)
XXGISEKXLDXLLTXLIXALLXX,
``` wherein

X at position 1 is N, D, isoD, G, A, or S;
X at position 2 is Q, E, g-glutamate, G, A, or S;
X at position 8 is Q, E, g-glutamate, G, A, or S;
X at position 11 is Q, E, g-glutamate, G, A, or S;
X at position 15 is Q, E, g-glutamate, G, A, or S;
X at position 18 is M, T, K, E, g-glutamate, G, A, or S;
X at position 22 is Q, E, g-glutamate, G, A, or S; and
X at position 23 is Q, E, g-glutamate, G, A, or S.

In certain embodiments, these peptides according to SEQ ID NO: 3 also meet the structural features defining the peptides of SEQ ID NO: 93, in which case methionine and cysteine residues are not present. Thus, in those embodiments, X at position 18 is T, K, E, g-glutamate, G, A, or S.

In certain embodiments, the peptides sharing the structure of SEQ ID NO: 3 have at least one of the residues at positions 2, 8, 11, 15, 22, and 23 of SEQ ID NO: 3 being other than Gln (Q), i.e., being E, g-glutamate, G, A, or S. In certain embodiments, two or more of the residues at positions 2, 8, 11, 15, 22, and 23 of SEQ ID NO: 3 are other than Gln (Q), including three, four, five, or all six of these residues being other than Gln (Q).

Exemplary peptides that share the consensus structure with SEQ ID NO: 3, or are derived from SEQ ID NO: 3 and meet the consensus structure of SEQ ID NO: 93, are identified in Table 2 below:

TABLE 2

Peptide Variants of Peptide P1 (SEQ ID NO: 4)

| Peptide Name | Sequence | SEQ ID NO: |
|---|---|---|
| P1 | NQGISEKQLDQLLTQLIMALLQQ | 4 |
| P1-2E | NEGISEKQLDQLLTQLIMALLQQ | 41 |
| P1-18T | NQGISEKQLDQLLTQLITALLQQ | 42 |
| P1-18E | NQGISEKQLDQLLTQLIEALLQQ | 43 |
| P1-18A | NQGISEKQLDQLLTQLIAALLQQ | 44 |
| P1-18K | NQGISEKQLDQLLTQLIKALLQQ | 45 |
| P1-2E, 8E, 11E, 15E, 18E | NEGISEKELDELLTELIEALLQQ | 46 |
| P1-1S | SQGISEKQLDQLLTQLIMALLQQ | 109 |
| P1-14S | NQGISEKQLDQLLSQLIMALLQQ | 110 |
| P1-18Q | NQGISEKQLDQLLTQLIQALLQQ | 115 |
| P1-23P | NQGISEKQLDQLLTQLIMALLQP | 118 |
| polyE-minP1 | *SEEEEE*LDQLLTQLIEALLQQ | 126 |
| polyE-min2P1 | *SEEEEE*LDQLLTQLIEALLQ | 134 |
| polyE-min3P1 | *SEEEEE*LDQLLTQLIEALL | 141 |
| p1-allE-17A | NEGISEKELDELLTELAEALLQQ | 195 |

Select peptides in Table 2 include solubility tags, indicated by italic print, including SEEEEE. Peptides comprising the sequences shown in Table 2 but lacking this specific solubility tag (or having a different solubility tag) are also contemplated herein.

As noted above, the peptide of SEQ ID NO: 4 is derived from the harpin of *Xanthomonas oryzae* pv. *oryzae* (Ji et al., "Two Coiled-Coil Regions of *Xanthomonas oryzae* pv. *Oryzae* Harpin Differ in Oligomerization and Hypersensitive Response Induction," *Amino Acids* 40:381-392 (2011), which is hereby incorporated by reference in its entirety).

Yet another aspect of the invention relates to an isolated peptide having the amino acid sequence of:

```
                              (SEQ ID NO: 47, P15b/P20 consensus)
    (i) KPXDSXSXIAKLISXLIXSLLX,
``` wherein
X at position 3 is N, D, or isoD;
X at position 6 is Q, E, g-glutamate, G, A, or S;
X at position 8 is N, D, or isoD;
X at position 15 is optional and can be any amino acid;
X at position 18 is M, E, g-glutamate, G, A, S, T, or K; and
X at position 22 is optional and can be Q, E, g-glutamate, G, A, or S; or

```
                              (SEQ ID NO: 12, P15/20 min consensus)
    (ii) IAKLISXLIXSLLX,
``` wherein
X at position 7 is optional and can be any amino acid;
X at position 10 is M, E, g-glutamate, G, A, S, T, or K; and
X at position 14 is optional and can be Q, E, g-glutamate, G, A, or S.

In certain embodiments, these peptides according to SEQ ID NO: 47 or 12 also meet the structural features defining the peptides of SEQ ID NO: 93, in which case methionine and cysteine residues are not present. Thus, in those embodiments, X at position 15 of SEQ ID NO: 47 is other than M, and X at position 18 of SEQ ID NO: 47 is E, g-glutamate, G, A, S, T, or K. Similarly, X at position 7 of SEQ ID NO: 12 is other than M, and X at position 10 of SEQ ID NO: 47 is E, g-glutamate, G, A, S, T, or K.

The length of peptides according to this third aspect is preferably less than about 100 amino acids, or alternatively less than 90 amino acids, less than 80 amino acids, less than 70 amino acids, less than 60 amino acids, or less than about 50 amino acids. In certain embodiments, the peptide is between 20 and 44 amino acids in length.

In certain embodiments, the peptides sharing the structure of SEQ ID NO: 47 have at least one of the residues at positions 6 and 22 of SEQ ID NO: 47 being other than Gln (Q), i.e., being E, g-glutamate, G, A, or S. In certain embodiments, both the residues at positions 6 and 22 of SEQ ID NO: 47 are other than Gln (Q), or the residue at position 6 is other than Gln (Q) while the residue at position 22 is absent.

Exemplary peptides that share the consensus structure with SEQ ID NO: 47 or 12, or are derived from one of SEQ ID NOS: 47 and 12, and meet the consensus structure of SEQ ID NO: 93, are identified in Table 3 below:

TABLE 3

Peptide Variants of Peptide P15/1P20 Consensus
(SEQ ID NOS: 47 or 12)

| Peptide Name | Sequence | SEQ ID NO: |
|---|---|---|
| Wildtype | QKDVNFGTPDSTVQNPQDASKPNDSQSNIAKLISALIMSLLQMLT | 48 |
| P15b | KPNDSQSNIAKLISALIMSLLQ | 49 |
| P15b-8D-18E | KPNDSQSDIAKLISALIESLLQ | 50 |
| P15b-8D-18A | KPNDSQSDIAKLISALIASLLQ | 51 |
| P15b-8D-18S | KPNDSQSDIAKLISALISSLLQ | 52 |
| P15b-8D-18T | KPNDSQSDIAKLISALITSLLQ | 53 |
| P15b-8D-18K | KPNDSQSDIAKLISALIKSLLQ | 54 |
| P15b-8D-6,18E | KPNDSESDIAKLISALIESLLQ | 55 |
| P15b-3,8D | KPDDSQSDIAKLISALIMSLLQ | 56 |
| P15b-3,8D-6E | KPDDSESDIAKLISALIMSLLQ | 57 |
| P15b-3,8D-18E | KPDDSQSDIAKLISALIESLLQ | 58 |
| P15b-3,8D-6,18E | KPDDSESDIAKLISALIESLLQ | 59 |
| P15b-3,8D-allE | KPDDSESDIAKLISALIESLLE | 60 |
| P15b-8D-allE | KPNDSESDIAKLISALIESLLE | 61 |
| P15b-3D-allE | KPDDSESNIAKLISALIESLLE | 62 |
| P15a | NFGTPDSTVQNPQDASKPNDSQSNIAKLISALIMSLLQM | 63 |
| P15a-34Q-39P | NFGTPDSTVQNPQDASKPNDSQSNIAKLISALIQSLLQP | 142 |
| P15a-39P | NFGTPDSTVQNPQDASKPNDSQSNIAKLISALIMSLLQP | 143 |

TABLE 3-continued

Peptide Variants of Peptide P15/1P20 Consensus
(SEQ ID NOS: 47 or 12)

| Peptide Name | Sequence | SEQ ID NO: |
|---|---|---|
| P15a-34Q | NFGTPDSTVQNPQDASKPNDSQSNIAKLISALIQSLLQM | 144 |
| P15 | KPNDSQSNIAKLISALIMSLLQM | 64 |
| P15-59G | *SEEEEE*GGIAKLISALIESLLE | 149 |
| P15-59 | *SEEEEE*IAKLISALIESLLE | 150 |
| P15-dn4 | SQSNIAKLISALIMSLLQ | 227 |
| P20 | GTPDSTVQNPQDASKPNDSQSNIAKLIS_LIMSLL | 65 |
| P20-5 | KPNDSQSNIAKLIS_LIMSLL | 151 |
| P20-6 | KPNDSQSNIAKLIS_LIESLL | 152 |

Select peptides in Table 3 include solubility tags, indicated by italic print, including SEEEEE. Peptides comprising the sequences shown in Table 3 but lacking this specific solubility tag (or having a different solubility tag) are also contemplated herein.

In this embodiment, the corresponding wildtype amino acid sequence corresponds to amino acids 52 to 96 of the *Pseudomonas syringae* HrpW sequence identified in PCT Application WO 01/98501 to Fan et al., which is hereby incorporated by reference in its entirety. For purposes of comparing properties of the inventive peptides, it is intended that the polypeptide comprising or the peptide consisting of the amino acid sequence of SEQ ID NO: 48 is used as a reference.

In certain embodiments, the peptide includes one or more mutations relative to the corresponding wildtype amino acid sequence of SEQ ID NO: 48. These one or more mutations include deletions or substitutions relative to SEQ ID NO: 48. In certain embodiments, the one or more mutations improve the solubility in aqueous solution, stability, and/or resistance to chemical degradation of the isolated peptide relative to a polypeptide comprising or consisting of the corresponding wildtype amino acid sequence of SEQ ID NO: 48. In this embodiment, the isolated peptide is stable when dissolved in water; resistant to chemical degradation in aqueous conditions in the presence of a pH buffer and a biocide, as described above; and/or has a solubility in an aqueous solution of at least about 1.0 mg/ml.

In certain embodiments, an isolated peptide comprising the amino acid sequence of SEQ ID NO: 47 is a peptide that has an overall length between 20 and 36 amino acids, and consists essentially of SEQ ID NO: 49, SEQ ID NO: 63, or SEQ ID NO: 64, whereas in another embodiment the isolated peptide consists of SEQ ID NO: 49, SEQ ID NO: 63, or SEQ ID NO: 64.

In certain embodiments, an isolated peptide comprising the amino acid sequence of SEQ ID NO: 47 is a peptide that has an overall length of less than 100 amino acids and the amino acid sequence includes SEQ ID NO: 65. In certain embodiments the amino acid sequence of the peptide consists essentially of SEQ ID NO: 65, whereas in another embodiment the isolated peptide consists of SEQ ID NO: 65.

A further aspect of the invention relates to an isolated peptide having the amino acid sequence of:

(SEQ ID NO: 66, P6/6a consensus)
(i) PSPXTXXLXXIVGXILXAXN, wherein
X at position 4 is F or Y;
X at position 6 is Q, E, g-glutamate, G, A, or S;
X at position 7 is optional and, according to one embodiment, can be M, E, g-glutamate, G, A, S, T, or K; or according to another embodiment can be L;
X at position 9 is M, E, g-glutamate, G, A, S, T, or K;
X at position 10 is H or N;
X at position 14 is E, g-glutamate, D, or isoD;
X at position 17 is Q, E, g-glutamate, G, A, or S; and
X at position 19 is Q, E, g-glutamate, G, A, or S; or (SEQ ID NO: 135, P6/6a min consensus)
(ii) XTXXLXXIVGXIL, wherein
X at position 1 is F or Y;
X at position 3 is Q, E, g-glutamate, G, A, or S;
X at position 4 is optional and, according to one embodiment, can be M, E, g-glutamate, G, A, S, T, or K; or according to another embodiment can be L;
X at position 6 is M, E, g-glutamate, G, A, S, T, or K;
X at position 7 is H or N; and
X at position 11 is E, g-glutamate, D, or isoD;
wherein the isolated peptide comprises one or more mutations relative to a corresponding wildtype amino acid sequence. In certain embodiments, the one or more mutations improve the aqueous solubility, stability, or resistance to chemical degradation of the isolated peptide relative to a polypeptide comprising the corresponding wildtype amino acid sequence.

A comparative wildtype sequence corresponds to amino acids 85-105 of the full length harpin of *Xanthomonas oryzae* pv. *oryzae* (Ji et al., "Two Coiled-Coil Regions of *Xanthomonas oryzae* pv. *Oryzae* Harpin Differ in Oligomerization and Hypersensitive Response Induction," *Amino Acids* 40:381-392 (2011), which is hereby incorporated by reference in its entirety). This comparative wildtype sequence is the peptide consisting of the amino acid sequence PSPFTQMLMHIVGEILQAQNG (SEQ ID NO: 153).

In certain embodiments, the peptide according to this aspect does not consist of the amino acid sequence of PSPFTQMLMHIVGEILQAQN (P6a, SEQ ID NO: 67), which corresponds to amino acids 85-104 of the full length harpin of *Xanthomonas oryzae* pv. *oryzae* (Ji et al., "Two Coiled-Coil Regions of *Xanthomonas oryzae* pv. *Oryzae* Harpin Differ in Oligomerization and Hypersensitive Response Induction," *Amino Acids* 40:381-392 (2011), which is hereby incorporated by reference in its entirety).

In certain embodiments, the peptide of this aspect does not comprise the peptide sequence of motif 2 as described in U.S. Pat. No. 8,440,881, which is defined as (P/A/V)S(P/Q/A)(F/L/Y)TQ(M/A)LM(H/N/Q)IV(G/M)(E/D/Q), SEQ ID NO: 154. By way of example, peptides according to SEQ ID NO: 66 do not include peptides having M/A/T at position 7 when all other aligning residues match the sequence of motif 2; or peptides according to SEQ ID NO: 66 do not include peptides having H/N at position 10 when all other aligning residues match the sequence of motif 2; or peptides according to SEQ ID NO: 66 do not include peptides having E/D at position 14 when all other aligning residues match the sequence of motif 2. Similarly, peptides according to SEQ ID NO: 135 do not include peptides having M/A/T at position 4 when all other aligning residues match the sequence of motif 2; or peptides according to SEQ ID NO: 135 do not include peptides having H/N at position 7 when all other aligning residues match the sequence of motif 2; or peptides according to SEQ ID NO: 135 do not include peptides having E/D at position 11 when all other aligning residues match the sequence of motif 2.

In certain embodiments, the peptide includes one or more mutations relative to the corresponding wildtype amino acid sequence of SEQ ID NO: 153. These one or more mutations include deletions or substitutions relative to SEQ ID NO: 153. In certain embodiments, the one or more mutations improve the solubility in aqueous solution, stability, and/or resistance to chemical degradation of the isolated peptide relative to a polypeptide comprising or consisting of the corresponding wildtype amino acid sequence of SEQ ID NO: 153.

The length of peptides according to this aspect is preferably less than about 100 amino acids, or alternatively less than 90 amino acids, less than 80 amino acids, less than 70 amino acids, less than 60 amino acids, or less than about 50 amino acids. In certain embodiments, the peptide is between 19 and 50 amino acids in length.

In certain embodiments, the peptides according to SEQ ID NOS: 66 and 135 also meet the structural features defining the peptides of SEQ ID NO: 93, in which case methionine and cysteine residues are not present. For example, in peptides according to SEQ ID NO: 66 that are free of methionine amino acid residues, X at position 7, if present, is E, g-glutamate, G, A, S, T, K, or L; and X at position 9 is E, g-glutamate, G, A, S, T, or K. Similarly, for peptides according to SEQ ID NO: 135 that are free of methionine amino acid residues, X at position 4, if present, is E, g-glutamate, G, A, S, T, K, or L; and X at position 6 is E, g-glutamate, G, A, S, T, or K.

In certain embodiments, the peptides sharing the structure of SEQ ID NO: 66 have at least one of the residues at positions 6, 17, and 19 of SEQ ID NO: 66 being other than Gln (Q), i.e., being E, g-glutamate, G, A, or S. In certain embodiments, two or three of the residues at positions 6, 17, and 19 of SEQ ID NO: 66 are other than Gln (Q). Similarly, for peptides sharing the structure of SEQ ID NO: 135, according to one embodiment these peptides have the residue at positions 6 being other than Gln (Q), i.e., being E, g-glutamate, G, A, or S.

Exemplary peptides that share the consensus structure with SEQ ID NO: 66 or 135, or are derived from one of SEQ ID NOS: 66 and 135, and meet the consensus structure of SEQ ID NO: 93, are identified in Table 4 below:

TABLE 4

Peptide Variants of Peptide P6/P6b Consensus (SEQ ID NO: 66 or 135)

| Peptide Name | Sequence | SEQ ID NO: |
|---|---|---|
| wildtype | PSPFTQMLMHIVGEILQAQNG | 153 |
| P6a | PSPFTQMLMHIVGEILQAQN | 67 |
| P6 | PSPFTQ_LMHIVGEILQAQN | 68 |
| P6a-7A | PSPFTQALMHIVGEILQAQN | 69 |
| P6a-10N | PSPFTQMLMNIVGEILQAQN | 70 |
| P6a-4Y | PSPYTQMLMHIVGEILQAQN | 71 |
| P6a-14D | PSPFTQMLMHIVGDILQAQN | 72 |
| P6a-7,9A | PSPFTQALAHIVGEILQAQN | 73 |
| P6a-6E-7A | PSPFTEALMHIVGEILQAQN | 74 |
| P6a-6,17E-7A | PSPFTEALMHIVGEILEAQN | 75 |
| P6a-allE-7A | PSPFTEALMHIVGEILEAEN | 76 |
| P6a-allE-4Y-7A | PSPYTEALMHIVGEILEAEN | 77 |
| P6a-allE-7A-10N | PSPFTEALMNIVGEILEAEN | 78 |
| P6a-allE-7A-14D | PSPFTEALMHIVGDILEAEN | 79 |

TABLE 4-continued

Peptide Variants of Peptide P6/P6b Consensus
(SEQ ID NO: 66 or 135)

| Peptide Name | Sequence | SEQ ID NO: |
|---|---|---|
| P6a-allE-4Y-7A-10N-14D | PSPYTEALMNIVGDILEAEN | 80 |
| P6b | FTQMLMHIVGEILQAQN | 155 |
| P6c | PSPFTQMLMHIVGEIL | 156 |
| P6-7L | PSPFTQLLMHIVGEILQAQN | 157 |
| P6-9E | PSPFTQMLEHIVGEILQAQN | 158 |
| P6a-7L,9E | PSPFTQLLEHIVGEILQAQN | 159 |
| P6d | *SEEEEEF*TQMLMHIVGEIL | 160 |
| P6d-7L-9E | *SEEEEEF*TQLLEHIVGEIL | 161 |
| p6a-dN3-sol | *SEEF*TQMLMHIVGEILQAQN | 197 |
| p6a-dC4-sol | *SEEE*PSPFTQMLMHIVGEIL | 198 |

Select peptides in Table 4 include solubility tags, indicated by italic print, including SEE, SEEE, and SEEEEE. Peptides comprising the sequences shown in Table 4 but lacking these specific solubility tags (or having a different solubility tag) are also contemplated herein.

Another aspect of the invention relates to a peptide having the amino acid sequence of:

(SEQ ID NO: 18, P17/18)
(i) XXXXXXXXXXX(L/M)XXLLXXLLXXLLXXX, wherein
X at position 1 can be any amino acid, but preferably Q, S, E, g-glutamate, A, T, G, D, isoD, N, K, or R;
X at position 2 can be any amino acid, but preferably Q, S, E, g-glutamate, A, T, G, D, isoD, N, K, or R;
X at position 3 can be any amino acid, but preferably P, Q, S, E, g-glutamate, A, T, G, D, isoD, N, K, or R;
X at position 4 can be any amino acid, but preferably I, Q, S, E, g-glutamate, A, T, G, D, N, isoD, K, or R;
X at position 5 can be any amino acid, but preferably D, isoD, S, E, g-glutamate, A, T, G, N, Q, K, or R;
X at position 6 can be any amino acid, but preferably R, Q, S, E, g-glutamate, A, T, G, D, isoD, N, or K;
X of position 7 can be any amino acid, but preferably Q, S, E, g-glutamate, A, T, G, D, isoD, N, K, or R;
X at position 8 can be any amino acid, but preferably T, Q, S, E, g-glutamate, A, G, D, isoD, N, K, or R;
X at position 9 can be any amino acid, but preferably I, Q, S, E, g-glutamate, A, T, G, D, isoD, N, K, or R;
X at position 10 can be any amino acid, but preferably E, g-glutamate, Q, S, A, T, G, D, isoD, N, K, or R;
X at position 11 can be any amino acid, but preferably Q, S, E, g-glutamate, A, T, G, D, isoD, N, K, or R;
X at position 13 can be any amino acid, but preferably A, S, T, G, D, isoD, E, g-glutamate, Q, N, K, or R;
X at position 14 can be any amino acid, but preferably Q, A, S, T, G, D, isoD, E, g-glutamate, N, K, or R;
X at position 17 can be any amino acid, but preferably A, S, T, G, D, isoD, E, g-glutamate, Q, N, K, or R;
X at position 18 can be any amino acid, but preferably Q, A, S, T, G, D, isoD, E, g-glutamate, N, K, or R;
X at position 21 can be any amino acid, but preferably K, A, S, T, G, D, isoD, E, g-glutamate, Q, N, or R;
X at position 22 can be any amino acid, but preferably S, A, T, G, D, isoD, E, g-glutamate, Q, N, K, or R;
X at position 25 can be any amino acid, but preferably S, A, T, G, D, isoD, E, g-glutamate, Q, N, K, or R;
X at position 26 can be any amino acid, but preferably P, S, A, T, G, D, isoD, E, g-glutamate, Q, N, K, or R; and
X at position 27 can be any amino acid, but preferably Q, S, A, T, G, D, isoD, E, g-glutamate, N, K, or R; or (SEQ ID NO: 25, P17/18 min consensus)
(ii) (L/M)XXLLXXLLXXLL, wherein
X at position 2 can be any amino acid, but preferably A, S, T, G, D, isoD, E, g-glutamate, Q, N, K, or R;
X at position 3 can be any amino acid, but preferably Q, A, S, T, G, D, isoD, E, g-glutamate, N, K, or R;
X at position 6 can be any amino acid, but preferably A, S, T, G, D, isoD, E, g-glutamate, Q, N, K, or R;
X at position 7 can be any amino acid, but preferably Q, A, S, T, G, D, isoD, E, g-glutamate, N, K, or R;
X at position 10 can be any amino acid, but preferably K, A, S, T, G, D, isoD, E, g-glutamate, Q, N, or R; and
X at position 11 can be any amino acid, but preferably S, A, T, G, D, isoD, E, g-glutamate, Q, N, K, or R.

In certain embodiments, the peptide includes one or more mutations relative to a corresponding wildtype amino acid sequence of *Erwinia amylovora* HrpW. These one or more mutations include deletions or substitutions relative to the wildtype HrpW sequence. In certain embodiments, the one or more mutations improve the solubility in aqueous solution, stability, and/or resistance to chemical degradation of the isolated peptide relative to a polypeptide comprising or consisting of the corresponding wildtype amino acid sequence of *Erwinia amylovora* HrpW.

PCT Application WO 01/98501 to Fan et al., which is hereby incorporated by reference in its entirety, identifies two hypersensitive response eliciting domains of HrpW$_{Ea}$. The first extends from amino acid 5 to amino acid 64, particularly from amino acid 31 to amino acid 57 of Hrp- W$_{Ea}$. The second domain extends from amino acid 103 to amino acid 146, particularly from amino acid 116 to amino acid 140 of HrpW$_{Ea}$. Despite this description in Fan et al., the reference identifies only a single peptide fragment of HrpW$_{Ea}$, which is the peptide consisting of amino acids 10 to 59.

A comparative wildtype sequence corresponds to amino acids 10 to 59 of the full length *Erwinia amylovora* HrpW sequence identified in PCT Application WO 01/98501 to Fan et al., which is hereby incorporated by reference in its entirety. For purposes of comparing properties of the inventive peptides, it is intended that the peptide consisting of amino acids 10 to 59 of the *Erwinia amylovora* HrpW is used as a reference.

In certain embodiments, the peptide of this aspect does not consist of the amino acid sequence TSSSPGLFQSGGDNGLGGHNANSAL-GQQPIDRQTIEQMAQLLAELLKSLL (SEQ ID NO: 162), which corresponds to amino acids 10 to 59 of the full length *Erwinia amylovora* HrpW (PCT Application WO 01/98501 to Fan et al., which is hereby incorporated by reference in its entirety).

In certain embodiments, the peptide includes one or more mutations relative to the corresponding wildtype amino acid sequence of SEQ ID NO: 162. These one or more mutations include deletions or substitutions relative to SEQ ID NO: 162. In certain embodiments, the one or more mutations improve the solubility in aqueous solution, stability, and/or resistance to chemical degradation of the isolated peptide relative to a polypeptide comprising or consisting of the corresponding wildtype amino acid sequence of SEQ ID NO: 162.

The length of peptides according to this fourth aspect is preferably less than about 100 amino acids, or alternatively less than 90 amino acids, less than 80 amino acids, less than 70 amino acids, less than 60 amino acids, or less than about 50 amino acids. In certain embodiments, the peptide is between 13 and 50 amino acids in length, or even between 13 and 40 amino acids in length.

In certain embodiments, the peptides according to SEQ ID NOS: 18 and 25 also meet the structural features defining the peptides of SEQ ID NO: 93, in which case methionine and cysteine residues are not present. For example, when the peptide comprising SEQ ID NO: 18 is free of methionine amino acid residues, the amino acid at position 12 is L. Similarly, when the peptide comprising SEQ ID NO: 25 is free of methionine amino acid residues, the amino acid at position 1 is L.

In certain other embodiments, one or more of amino acids 1 to 11 and/or 25 to 27 is not present in the isolated peptide of SEQ ID NO: 18. For example, peptides lacking amino acids 25 to 27 exhibit improved stability relative to the wildtype sequence.

Exemplary peptides that share the consensus structure with SEQ ID NO: 18 or 25, or are derived from one of SEQ ID NOS: 18 and 25, or meet the consensus structure of SEQ ID NO: 93, are identified in Table 5 below:

TABLE 5

Peptide Variants of Peptides P17/P18 Consensus (SEQ ID NO: 18 or 25)

| Peptide Name | Sequence | SEQ ID NO: |
|---|---|---|
| wildtype | [*]QQPIDRQTIEQMAQLLAELLKSLL | 162 |
| P17 | [*]QQPIDRQTIEQMAQLLAQLLKSLL | 81 |
| P17a | [*]QQPIDRQTIEQLAQLLAQLLKSLL | 82 |
| P18 | QQPIDRQTIEQMAQLLAQLLKSLLSPQ | 83 |
| P18a | QQPIDRQTIEQLAQLLAQLLKSLLSPQ | 84 |
| P18b | IEQMAQLLAQLLKSLL | 85 |
| P18c | IEQLAQLLAQLLKSLL | 86 |
| P18d | DRQTIEQMAQLLAQLLKSLL | 87 |
| P18e | DRQTIEQLAQLLAQLLKSLL | 88 |
| P18-1 | QQPIDRQTIEQMAQLLAQLLKSLL | 163 |
| P18-3 | QQPIDRQTIEQLAQLLAQLLKSLLSP | 228 |
| P18-4 | DRQTIEQLAQLLAQLLKSLLSP | 164 |
| P18-5 | QTIEQLAQLLAQLLKSLLSP | 165 |
| P18-6 | *SEEEEE*IEQLAQLLAQLLKSLL | 166 |
| P18-7 | *SEEEEE*LAQLLAQLLKSLL | 167 |
| P18-10 | *SEEEEE*LAELLAELLKSLL | 231 |

In P17, P17a, and the wildtype sequence, [*] = TSSSPGLFQSGGDNGLGGHNANSALG

Select peptides in Table 5 include solubility tags, indicated by italic print, including SEEEEE. Peptides comprising the sequences shown in Table 5 but lacking these specific solubility tags (or having a different solubility tag) are also contemplated herein.

In this embodiment, the wildtype amino acid sequence corresponds to amino acids 10 to 59 of the *Erwinia amylovora* HrpW sequence identified in PCT Application WO 01/98501 to Fan et al., which is hereby incorporated by reference in its entirety. For purposes of comparing properties of the inventive peptides, it is intended that the peptide consisting of amino acids 10 to 59 of the *Erwinia amylovora* HrpW is used as a reference.

A further aspect of the invention relates to a peptide having the amino acid sequence of:

(SEQ ID NO: 26, P19 consensus)
XLXX(L/M)LXLIXX(L/I/V/F/M)(L/I/V/F/M), wherein

X at position 1 is optional and can be L, I, V, F, or M;

X at position 3 can be any amino acid, but preferably K, A, S, T, G, D, isoD, E, g-glutamate, Q, N, or R;

X at position 4 can be any amino acid, but preferably A, S, T, G, D, isoD, E, g-glutamate, Q, N, K, or R;

X at position 7 can be any amino acid, but preferably K, A, S, T, G, D, isoD, E, g-glutamate, Q, N, or R;

X at position 10 can be any amino acid, but preferably A, S, T, G, D, isoD, E, g-glutamate, Q, N, K, or R; and X at position 11 can be any amino acid, but preferably R, A, S, T, G, D, isoD, E, g-glutamate, Q, N, or K.

As noted above, PCT Application WO 01/98501 to Fan et al., which is hereby incorporated by reference in its entirety, identifies two hypersensitive response eliciting domains of HrpW$_{Ea}$, one of which extends from amino acid 103 to amino acid 146, particularly from amino acid 116 to amino acid 140 of HrpW$_{Ea}$. Despite this description in Fan et al., this reference does not identify a peptide fragment of HrpW$_{Ea}$ containing this domain.

A comparative wildtype sequence corresponds to amino acids 116 to 140 of the full length *Erwinia amylovora* HrpW sequence identified in PCT Application WO 01/98501 to Fan et al., which is hereby incorporated by reference in its entirety. For purposes of comparing properties of the inventive peptides, it is intended that the peptide consisting of amino acids 116 to 140 of the *Erwinia amylovora* HrpW is used as a reference.

In certain embodiments, the peptide of this aspect does not consist of the amino acid sequence ITPDGQGGGQI-GDNPLLKAMLKLIA (SEQ ID NO: 89), which corresponds to amino acids 116 to 140 of the full length *Erwinia amylovora* HrpW (PCT Application WO 01/98501 to Fan et al., which is hereby incorporated by reference in its entirety).

In certain embodiments, the peptide includes one or more mutations relative to the corresponding wildtype amino acid sequence of SEQ ID NO: 89. These one or more mutations include deletions or substitutions relative to SEQ ID NO: 89. In certain embodiments, the one or more mutations improve the solubility in aqueous solution, stability, and/or resistance to chemical degradation of the isolated peptide relative to a polypeptide comprising or consisting of the corresponding wildtype amino acid sequence of SEQ ID NO: 89.

The length of peptides according to this aspect is preferably less than about 100 amino acids, or alternatively less than 90 amino acids, less than 80 amino acids, less than 70 amino acids, less than 60 amino acids, or less than about 50 amino acids. In certain embodiments, the peptide is between 18 and 50 amino acids in length.

Exemplary peptides that share the consensus structure with SEQ ID NO: 26, or are derived from SEQ ID NO: 26 and meet the consensus structure of SEQ ID NO: 93, are identified in Table 6 below:

TABLE 6

Peptide Variants of Peptide P19 Consensus
(SEQ ID NO: 26)

| Peptide Name | Sequence | SEQ ID NO: |
|---|---|---|
| P19 | ITPDGQGGGQIGDNPLLKAMLKLIA | 89 |
| P19-20L | ITPDGQGGGQIGDNPLLKALLKLIA | 90 |
| P19a | ITPDGQGGGQIGDNPLLKAMLKLIARMMDG | 91 |
| P19a-allL | ITPDGQGGGQIGDNPLLKALLKLIARLLDG | 92 |
| P19-4 | QGGGQIGDNPLLKAMLKLIARMMDG | 226 |
| P19-5 | *SEEEEE*IGDNPLLKALLKLIARLLDG | 168 |
| P19-5a | *SEEEEE*IGDDELLKALLKLIARLLDG | 169 |
| P19-6 | *SEEEEE*LLKALLKLIARLLDG | 170 |
| P19-11 | *SEEEEE*IGDNPLLKALLKLIARLL | 171 |
| P19-7 | *SEEEEE*LLKALLKLIARLL | 172 |
| P19-8 | *SEEEEE*LKALLKLIARLL | 173 |

Select peptides in Table 6 include solubility tags, indicated by italic print, including SEEEEE. Peptides comprising the sequences shown in Table 6 but lacking this specific solubility tag (or having a different solubility tag) are also contemplated herein.

Certain peptides in Table 6 also meet the structural features defining the peptides of SEQ ID NO: 93, in which case methionine and cysteine residues are not present. When these peptides also meet the limitations of SEQ ID NO: 93, amino acid residue 1 of SEQ ID NO: 26, when present, is L, I, V, or F; amino acid 5 of SEQ ID NO: 26 is L; and amino acids 12 and 13 of SEQ ID NO: 26 are independently L, I, V, or F.

Still another aspect of the invention relates to a peptide having the amino acid sequence:

(SEQ ID NO: 13, P14d consensus)
(i) XXXXXXLXXLLXXLVXLLK, wherein
X at position 1 can be: Q, N, D, E, g-glutamate, isoD, or S;
X at position 2 can be: D, E, g-glutamate, isoD;
X at position 3 can be: P, D, E, isoD, or g-glutamate;
X at position 4 can be M, A, S, D, E, isoD, or g-glutamate
X at position 5 can be Q, E, or g-glutamate;
X at position 6 can be A, E, or g-glutamate;
X at position 8 can be M, L, E, Q, D, N, G, A, S, isoD, or g-glutamate;
X at position 9 can be Q, N, E, D, G, A, S, isoD, or g-glutamate;
X at position 12 can be Q, N, E, D, G, A, S, isoD, or g-glutamate;
X at position 13 can be Q, N, E, D, G, A, S, isoD, or g-glutamate; and
X at position 16 can be K, Q, N, E, D, R, G, A, or S; or (SEQ ID NO: 14, P14d min consensus)
(ii) LXXLLXXLVXLLK, X at position 2 can be M, L, E, Q, D, N, G, A, S, isoD, or g-glutamate;
X at position 3 can be Q, N, E, D, G, A, S, isoD, or g-glutamate;
X at position 6 can be Q, N, E, D, G, A, S, isoD, or g-glutamate;
X at position 7 can be Q, N, E, D, G, A, S, isoD, or g-glutamate; and
X at position 10 can be K, Q, N, E, D, R, G, A, or S.

In certain embodiments, the peptide includes one or more mutations relative to the corresponding wildtype amino acid sequence of *Ralstonia solanacearum* (previously *Pseudomonas solanacearum*) PopA. These one or more mutations include deletions or substitutions relative to the wildtype PopA sequence. In certain embodiments, the one or more mutations improve the solubility in aqueous solution, stability, and/or resistance to chemical degradation of the isolated peptide relative to a polypeptide comprising or consisting of the corresponding wildtype amino acid sequence of *Ralstonia solanacearum* PopA.

A comparative wildtype sequence corresponds to amino acids 92 to 125 of the *Ralstonia solanacearum* (previously *Pseudomonas solanacearum*) PopA sequence identified in PCT Application WO 01/98501 to Fan et al., which is hereby incorporated by reference in its entirety. For purposes of comparing properties of the inventive peptides, it is intended that the wildtype peptide of Fan et al., consisting of amino acids 92 to 125 of the *Ralstonia solanacearum* PopA, is used as a reference.

In certain embodiments, the peptide of this aspect does not consist of the amino acid sequence of QAPQSANKT-GNVDDANNQDPMQALMQLLEDLVKL (SEQ ID NO: 174), which corresponds to amino acids 92 to 125 of the *Ralstonia solanacearum* PopA (see PCT Application WO 01/98501 to Fan et al., which is hereby incorporated by reference in its entirety).

The length of peptides according to this aspect is preferably less than about 100 amino acids, or alternatively less than 90 amino acids, less than 80 amino acids, less than 70 amino acids, less than 60 amino acids, or less than about 50 amino acids. In certain embodiments, the peptide is between 12 and 50 amino acids in length.

Exemplary peptides that share the consensus structure with SEQ ID NOS: 13 or 14, or are derived from SEQ ID NO: 13 and meet the consensus structure of SEQ ID NO: 93, are identified in Table 7 below:

TABLE 7

Peptide Variants of Peptide P14d (SEQ ID NO: 13)

| Peptide Name | Sequence | SEQ ID NO: |
|---|---|---|
| wildtype | QAPQSANKTGNVDDANNQDPMQALMQLLEDLVKL | 174 |
| P14d | QDPMQALMQLLEDLVKLLK | 175 |
| P14e | QDPAQALLQLLEDLVKLLK | 176 |
| P14f | QDPAQALEQLLEDLVKLLK | 177 |
| P14-30 | *SEEEEE*ALEQLLEDLVKLLK | 178 |
| P14c | QAGPQSANKTGNVDDANNQDPMQALMQLLEDLVKLLK | 199 |

Select peptides in Table 7 include solubility tags, indicated by italic print, including SEEEEE. Peptides comprising the sequences shown in Table 7 but lacking this specific solubility tag (or having a different solubility tag) are also contemplated herein.

It is notable that a C-terminal lysine residue seems to be necessary for HR elicitation by p14d variants. This is a slight deviation from the canonical sequence of SEQ ID NO: 93. Without being bound by belief, it is believed that the C-terminal lysine may be necessary due to the single hydrophilic amino acid between 2 hydrophobic doublet sequences within the p14d variants (LVKLL).

Certain peptides according to this aspect also meet the structural features defining the peptides of SEQ ID NO: 93, in which case methionine and cysteine residues are not present. For example, for peptides comprising SEQ ID NO: 13, amino acid residue 4 of SEQ ID NO: 13 is A, S, D, isoD, E, or g-glutamate, and amino acid residue 8 of SEQ ID NO: 13 is L, E, g-glutamate, Q, D, isoD, N, G, A, or S. Similarly, for peptides comprising SEQ ID NO: 14 the amino acid residue at position 2 is L, E, g-glutamate, Q, D, isoD, N, G, A, or S.

Yet another aspect of the invention relates to a peptide having the amino acid sequence:

(SEQ ID NO: 16, P25 consensus)
(i) LXXL(L/M)XILXXLV wherein
X at position 2 can be Q, N, E, g-glutamate, D, isoD, T, S, A, or G;

X at position 3 can be K, Q, N, E, g-glutamate, D, isoD, T, S, A, or G;
X at position 6 can be K, Q, N, E, g-glutamate, D, isoD, T, S, A, or G;
X at position 9 can be E, g-glutamate, D, isoD, Q, N, T, S, A, or G; and
X at position 10 can be A, G, S, T, E, g-glutamate, D, isoD, Q, or N; or (SEQ ID NO: 17, P25 consensus)
(ii) LXXVLXXL(L/M)XILXXLV wherein
X at position 2 can be T, S, A, G, D, isoD, E, g-glutamate, Q, or N;
X at position 3 can be G, T, S, A, D, isoD, E, g-glutamate, Q, or N;
X at position 6 can be Q, N, E, g-glutamate, D, isoD, T, S, A, or G;
X at position 7 can be K, Q, N, E, g-glutamate, D, isoD, T, S, A, or G;
X at position 10 can be K, Q, N, E, g-glutamate, D, isoD, T, S, A, or G;
X at position 13 can be E, g-glutamate, D, isoD, Q, N, T, S, A, or G;
X at position 14 can be A, G, S, T, E, g-glutamate, D, isoD, Q, or N; and
V at position 16 is optional.

In certain embodiments, the peptide includes one or more mutations relative to a corresponding wildtype amino acid sequence of *Ralstonia solanacearum* (previously *Pseudomonas solanacearum*) PopA. These one or more mutations include deletions or substitutions relative to the wildtype PopA sequence. In certain embodiments, the one or more mutations improve the solubility in aqueous solution, stability, and/or resistance to chemical degradation of the isolated peptide relative to a polypeptide comprising or consisting of the corresponding wildtype amino acid sequence of *Ralstonia solanacearum* PopA.

A comparative wildtype sequence corresponds to amino acids 206 to 260 of the *Ralstonia solanacearum* (previously *Pseudomonas solanacearum*) PopA sequence, which is identified in PCT Application WO 01/98501 to Fan et al., which is hereby incorporated by reference in its entirety, as a hypersensitive response domain. For purposes of comparing properties of the inventive peptides, it is intended that the wildtype peptide of Fan et al., consisting of amino acids 206 to 260 of the *Ralstonia solanacearum* PopA, is used as a reference.

In certain embodiments, the peptide of this aspect does not consist of the amino acid sequence of NGADGGNGVNGNQANGPQNAGDVNGANGAD-DGSEDQGGLTGVLQK LMKILNALVQ (SEQ ID NO: 179), which corresponds to amino acids 206 to 260 of the *Ralstonia solanacearum* PopA (see PCT Application WO 01/98501 to Fan et al., which is hereby incorporated by reference in its entirety).

The length of peptides according to this aspect is preferably less than about 100 amino acids, or alternatively less than 90 amino acids, less than 80 amino acids, less than 70 amino acids, less than 60 amino acids, or less than about 50 amino acids. In certain embodiments, the peptide is between 12 and 50 amino acids in length.

Exemplary peptides that share the consensus structure with one of SEQ ID NOS: 16 or 17, or are derived from one of SEQ ID NOS: 16 or 17 and meet the consensus structure of SEQ ID NO: 93, are identified in Table 8 below:

TABLE 8

Peptide Variants of Peptides P2 (SEQ ID NO: 180) and P25 (SEQ ID NO: 182)

| Peptide Name | Sequence | SEQ ID NO: |
|---|---|---|
| wildtype | [*]ANGADDGSEDQGG__LTGVLQKLMKILNALVQ | 179 |
| P2 | ANGADDGSEDQGGLTLTGVLQKLMKILNALVQ | 180 |
| P25-4 | EDQGGLTLTGVLQKLMKILNALVQ | 181 |
| P25 | GGLTLTGVLQKLMKILNAL | 182 |
| P25s | EDQGGLTLTGVLQKLMKILNAL | 183 |
| P25-7 | EDQGGLTLTGVLQKLLKILNAL | 184 |
| P25-8 | EDQGGLTLTGVLQELMEILNAL | 185 |
| P25-20E | EDQGGLTLTGVLQKLLKILEALVQ | 186 |
| P25-10 | S*EEEE*LTLTGVLQKLLKILEAL | 187 |
| P25-11 | S*EEEEE*LTGVLQKLLKILEAL | 188 |
| P25-15 | S*EEEEE*LTLTGVLQKLLKILEA | 200 |
| P25-16 | S*EEEEE*VLQKLLKILEALV | 201 |
| P25-17 | S*EEEEE*LQKLLKILEALVQ | 202 |

[*] = N-terminal sequence NGADGGNGVNGNQANGPQNAGDVNG

Select peptides in Table 8 include solubility tags, indicated by italic print, including SEEEEE. Peptides comprising the sequences shown in Table 8 but lacking these specific solubility tags (or having a different solubility tag) are also contemplated herein.

Notably, a number of these derivative peptides in Table 8 include a repeated LT sequence not observed in the wildtype sequence. However, one should note that these sequences require a larger hydrophobic sequence to cause a hypersensitive response as compared with SEQ ID NO: 93. Without being bound by belief, it is believed that this may be due to the presence of the amino acid valine in the sequence rather than leucine as well as the presence of only a single hydrophilic amino acid between the hydrophobic doublets (LLKIL). Although these changes are deleterious to HR, their effect can be reversed by the addition of additional hydrophobic residues at the C-terminus of the peptide ( . . . KIL versus . . . KILEALV or . . . KILNALV).

Certain peptides according to this aspect also meet the structural features defining the peptides of SEQ ID NO: 93, in which case methionine and cysteine residues are not present. For example, for peptides comprising SEQ ID NO: 16, amino acid residue 5 is L; and for peptides comprising SEQ ID NO: 17, amino acid residue 9 is L.

Yet another aspect of the invention relates to a peptide having the amino acid sequence:

(i)
                (SEQ ID NO: 15, P3min consensus)
(L/M)XXLLX(L/M)FXXI(L/M)XX wherein
  X at position 2 can be Q, N, E, g-glutamate, D, isoD, T, S, A, or G;
  X at position 3 can be Q, N, E, g-glutamate, D, isoD, T, S, A, or G;
  X at position 6 can be K, Q, N, E, g-glutamate, D, isoD, T, S, A, or G;
  X at position 9 can be E, g-glutamate, D, isoD, Q, N, T, S, A, or G;
  X at position 10 can be A, G, S, T, E, g-glutamate, D, isoD, Q, or N;
  X at position 13 can be Q, N, E, g-glutamate, D, isoD, T, S, A, or G; and
  X at position 14 can be Q, N, E, g-glutamate, D, isoD, T, S, A, or G.

In certain embodiments, the peptide includes one or more mutations relative to a corresponding wildtype amino acid sequence of *Erwinia amylovora* HrpN. These one or more mutations include deletions or substitutions relative to the wildtype HrpN sequence. In certain embodiments, the one or more mutations improve the solubility in aqueous solution, stability, and/or resistance to chemical degradation of the isolated peptide relative to a polypeptide comprising or consisting of the corresponding wildtype amino acid sequence of *Erwinia amylovora* HrpN.

A comparative wildtype sequence corresponds to amino acids 137 to 180 or 150 to 180 of the *Erwinia amylovora*

HrpN sequence, which are identified in U.S. Pat. No. 7,132, 525 to Wei et al., which is hereby incorporated by reference in its entirety. The HrpN peptide containing aa 137 to 180 was identified as a hypersensitive response-eliciting fragment, whereas the HrpN peptide containing aa 150 to 180 could not be expressed and tested. For purposes of comparing properties of the inventive peptides, it is intended that the wildtype peptide of Wei et al., consisting of either amino acids 137 to 180 or 150 to 180 of the *Erwinia amylovora* HrpN, is used as a reference.

In certain embodiments, the peptide of this aspect does not consist of the amino acid sequence of $S_{137}$TSQNDDSTSGTDS$_{150}$TSDSSDPMQQLLKMFSEI-MQSLFGDGQDGT$_{180}$ (SEQ ID NO: 230), which corresponds to amino acids 137 to 180 of the *Erwinia amylovora* HrpN (see U.S. Pat. No. 7,132,525 to Wei et al., which is hereby incorporated by reference in its entirety), or the 31-amino acid peptide corresponding to aa 150 to 180 thereof.

The length of peptides according to this aspect is preferably less than about 100 amino acids, or alternatively less than 90 amino acids, less than 80 amino acids, less than 70 amino acids, less than 60 amino acids, less than about 50 amino acids, less than about 40 amino acids, or less than 30 amino acids. In certain embodiments, the peptide is between 12 and 30 amino acids in length.

Exemplary peptides that share the consensus structure with SEQ ID NOS: 15, or are derived from SEQ ID NOS: 15 and meet the consensus structure of SEQ ID NO: 93, are identified in Table 9 below:

TABLE 9

Peptide Variants of Peptide P3 Consensus (SEQ ID NO: 15)

| Peptide Name | Sequence | SEQ ID NO: |
|---|---|---|
| wildtype | STSQNDDSTSGTDSTSDSSDPMQQLLKMFSEIMQSLFGDGQDGT | 203 |
| P3 | QNDDSTSGTDSTSDSSDPMQQLLKMFSEIMQSLFGDGQDGT | 204 |
| P3-3 | SDPMQQLLKMFSEIMQSLF | 205 |
| P3-4 | S*EEE*LQQLLK*L*FSEIL*QSL*F | 206 |
| P3-6 | S*EEEE*LQQLLKLFSEILQSL | 207 |
| P3-7 | S*EEEE*LQQLLKLFSEILQS | 208 |
| P3-11 | LQQLLKLFSEILQSLF*EEEE* | 209 |

Select peptides in Table 9 include solubility tags, indicated by italic print, including SEEE, SEEEEE, and EEEE. Peptides comprising the sequences shown in Table 9 but lacking these specific solubility tags (or having a different solubility tag) are also contemplated herein.

It is notable that the minimal P3 sequence requires a longer sequence than the minimal HR-box sequence of SEQ ID NO: 93. Without being bound by belief, it is believed that this may be due to the presence of two phenylalanine residues within the hydrophobic sequence.

Certain peptides according to this aspect also meet the structural features defining the peptides of SEQ ID NO: 93, in which case methionine and cysteine residues are not present. For example, for peptides comprising SEQ ID NO: 15, amino acid residues 1, 7, and 12 are L.

Based on the disclosed consensus sequence (SEQ ID NO: 93), it is possible to generate novel peptide sequences with predicted HR activity that deviate significantly from bacterial protein sequences. These peptides can contain hydrophilic residues optimized for maximum solubility and chemical stability. In a preferred embodiment, these hydrophilic residues are glutamate. Lysine and arginine are also possible choices, however a large number of these residues will cause a toxic response in the plant.

In addition to the foregoing peptides that are modeled (and modified) based on naturally occurring sequences within larger HR-eliciting proteins, the present invention also contemplates entirely synthetic peptides that meet the consensus of SEQ ID NO: 93. Ideally, these synthetic peptides include a number of strongly hydrophilic amino acids spanning between the hydrophobic residues specified by SEQ ID NO: 93. Exemplary synthetic peptides are listed in Table 10 below. These peptides contain the necessary hydrophobic peptides associated with HR elicitation. The intervening hydrophilic residues are chosen for maximum solubility, preferably with charged amino acids. It is possible to use uncharged amino acids, but larger proportions of uncharged amino acids may cause the resulting peptide to aggregate in solution and form a precipitate or gel. Glutamate is preferred for chemical stability over aspartate. Although lysine and arginine have even superior solubility characteristics, poly-cations produced a toxic response in the tested plants. As a result, arginine-rich sequences such as P30-1 (SEQ ID NO: 211) should be avoided.

TABLE 10

Other HR-box peptides

| Peptide Name | Sequence | SEQ ID NO: |
|---|---|---|
| P30-2 | *SEE*LEELLEELIEELL | 189 |
| P30-3 | LEELLEELIEELL*EE* | 190 |
| P30-4 | LEELLEELIEELL | 210 |
| P30-1 | *R*LRRLLRRLIRRLL*RP* | 211 |
| P30-5 | LDDLLDDLIDDLL*DD* | 212 |
| P18-13 | LEELLEELLEELL*EE* | 213 |
| P14-54 | LEQLLEDLVKLLK_EE_ | 214 |
| P14-55 | LEQLLEDLVELLE_EE_ | 215 |

TABLE 10-continued Other HR-box peptides

| Peptide Name | Sequence | SEQ ID NO: |
|---|---|---|
| P14-56 | LEELLEDLVELL*EE* | 216 |
| P14-57 | LEELLEELVELL*EE* | 217 |
| P3-12 | LEELLELFEEILEELF*EE* | 218 |
| P3-13 | LEELLKLFEEILEELF*EE* | 219 |
| P20-50a | IEELIELIEELL*EE* | 220 |
| P15-67 | IEELIEELIEELL*EE* | 221 |
| P19-54c | LEELLKLIERLL*EE* | 222 |
| P19-54b | LEELLELIERLL*EE* | 223 |
| P19-54a | LEELLKLIE*E*LL*EE* | 224 |
| P19-54 | LEELLELIE*E*LL*EE* | 225 |

Select peptides in Table 10 include solubility tags, indicated by italic print, including SEE, EE, DD, or EEE. Peptides comprising the sequences shown in Table 10 but lacking these specific solubility tags (or having different solubility tags) are also contemplated herein.

The isolated peptides of the invention can also be presented in the form of a fusion peptide that includes, in addition, a second amino acid sequence coupled to the inventive peptides via peptide bond. The second amino acid sequence can be a purification tag, such as poly-histidine (His$_6$-), a glutathione-S-transferase (GST-), or maltose-binding protein (MBP-), which assists in the purification but can later be removed, i.e., cleaved from the peptide following recovery. Protease-specific cleavage sites or chemical-specific cleavage sites (i.e., in a cleavable linker sequence) can be introduced between the purification tag and the desired peptide. Protease-specific cleavage sites are well known in the literature and include, without limitation, the enterokinase specific cleavage site (Asp)$_4$-Lys, which is cleaved after lysine; the factor Xa specific cleavage site Ile-(Glu or Asp)-Gly-Arg, which is cleaved after arginine; the trypsin specific cleavage site, which cleaves after Lys and Arg; and the Genenase™ I specific cleavage site Pro-Gly-Ala-Ala-His-Tyr. Chemicals and their specific cleavage sites include, without limitation, cyanogen bromide (CNBr), which cleaves at methionine (Met) residues; BNPS-skatole, which cleaves at tryptophan (Trp) residues; formic acid, which cleaves at aspartic acid-proline (Asp-Pro) peptide bonds; hydroxylamine, which cleaves at asparagine-glycine (Asn-Gly) peptide bonds; and 2-nitro-5-thiocyanobenzoic acid (NTCB), which cleaves at cysteine (Cys) residues (see Crimmins et al., "Chemical Cleavage of Proteins in Solution," *Curr. Protocol. Protein Sci.*, Chapter 11: Unit 11.4 (2005), which is hereby incorporated by reference in its entirety). In order to use one of these cleavage methods, it may be necessary to remove unwanted cleavage sites from within the desired peptide sequences by mutation. For example, p4-7E-cR (SEQ ID NO: 40) has been mutated for compatibility with trypsin: the lysine residue at position 7 is mutated to a glutamate and a C-terminal arginine is added to represent the product of a theoretical trypsin cleavage. Likewise, p19-5 (SEQ ID NO: 168) contains the sequence 'NP' which can be cleaved under acidic conditions. Mutation of these residues to 'DE' in p19-5a (SEQ ID NO: 169) prevents this particular cleavage mechanism. The desired peptide product can be purified further to remove the cleaved purification tags.

The isolated peptides of the invention can also be presented in the form of a fusion peptide that includes multiple peptide sequences of the present invention linked together by a linker sequence, which may or may not take the form of a cleavable amino acid sequence of the type described above. Such multimeric fusion proteins may or may not include purification tags. In one embodiment, each monomeric sequence can include a purification tag linked to a peptide of the invention by a first cleavable peptide sequence; and the several monomeric sequences can be linked to adjacent monomeric sequences by a second cleavable peptide sequence. Consequently, upon expression of the multimeric fusion protein, i.e., in a host cell, the recovered fusion protein can be treated with a protease or chemical that is effective to cleave the second cleavable peptide sequence, thereby releasing individual monomeric peptide sequences containing purification tags. Upon affinity purification, the recovered monomeric peptide sequences can be treated with a protease or chemical that is effective to cleave the first cleavable peptide sequence and thereby release the purification tag from the peptide of interest. The latter can be further purified using gel filtration and/or HPLC as described infra.

According to one approach, the peptides of the present invention can be synthesized by standard peptide synthesis operations. These include both FMOC (9-fluorenylmethyl-oxy-carbonyl) and tBoc (tert-butyloxy-carbonyl) synthesis protocols that can be carried out on automated solid phase peptide synthesis instruments including, without limitation, the Applied Biosystems 431 A, 433 A synthesizers and Peptide Technologies Symphony or large scale Sonata or CEM Liberty automated solid phase peptide synthesizers. The use of alternative peptide synthesis instruments is also contemplated. Peptides prepared using solid phase synthesis are recovered in a substantially pure form.

The peptides of the present invention may be also prepared by using recombinant expression systems followed by separation and purification of the recombinantly prepared peptides. Generally, this involves inserting an encoding nucleic acid molecule into an expression system to which the molecule is heterologous (i.e., not normally present). One or more desired nucleic acid molecules encoding a peptide of the invention may be inserted into the vector. The heterologous nucleic acid molecule is inserted into the expression system or vector in proper sense (5'-3') orientation and correct reading frame relative to the promoter and any other 5' and 3' regulatory molecules.

Representative nucleotide sequences for expression in bacteria and plant hosts are included in Table 11 below:

TABLE 11

| Peptide & Optimized Host | Nucleotide Sequence | SEQ ID NO: |
|---|---|---|
| P4-14s<br>*A. thaliana* | TCTCAAGGAATTTCTGAAAAGCAACTTGATCAACTTC<br>TTTCTCAACTTATTCAAGCTCTTCTTCAACCT | 145 |

TABLE 11-continued

| Peptide & Optimized Host | Nucleotide Sequence | SEQ ID NO: |
|---|---|---|
| P4-14s<br>E. coli | AGCCAGGGTATTAGCGAAAAACAGCTGGATCAGCTGC<br>TGAGCCAGCTGATTCAGGCACTGCTGCAGCCG | 146 |
| P1-2E,8E,11E,15E,18E<br>A. thaliana | AATGAAGGAATTTCTGAAAAGGAACTTGATGAACTTC<br>TTACTGAACTTATTGAAGCTCTTCTTCAACAA | 147 |
| P1-2E,8E,11E,15E,18E<br>E. coli | AATGAAGGTATTAGCGAAAAAGAACTGGATGAACTGC<br>TGACCGAACTGATTGAAGCACTGCTGCAGCAG | 148 |

With knowledge of the encoded amino acid sequence listed herein and the desired transgenic organism, additional codon-optimized DNA sequences and RNA sequences can be generated with nothing more than routine skill.

Expression (including transcription and translation) of a peptide or fusion polypeptide of the invention by the DNA construct may be regulated with respect to the level of expression, the tissue type(s) where expression takes place and/or developmental stage of expression. A number of heterologous regulatory sequences (e.g., promoters and enhancers) are available for controlling the expression of the DNA construct. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394, each of which is hereby incorporated by reference in its entirety), the nopaline synthase (NOS) promoter (Ebert et al., *Proc. Natl. Acad. Sci. (U.S.A.)* 84:5745-5749 (1987), which is hereby incorporated by reference in its entirety), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987), which is hereby incorporated by reference in its entirety) and the CaMV 35S promoter (Odell et al., *Nature* 313:810-812 (1985), which is hereby incorporated by reference in its entirety), the figwort mosaic virus 35S-promoter (U.S. Pat. No. 5,378,619, which is hereby incorporated by reference in its entirety), the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624-6628 (1987), which is hereby incorporated by reference in its entirety), the sucrose synthase promoter (Yang et al., *Proc. Natl. Acad. Sci. (U.S.A.)* 87:4144-4148 (1990), which is hereby incorporated by reference in its entirety), the R gene complex promoter (Chandler et al., *Plant Cell* 1:1175-1183 (1989), which is hereby incorporated by reference in its entirety), the chlorophyll a/b binding protein gene promoter, the CsVMV promoter (Verdaguer et al., *Plant Mol Biol.*, 37:1055-1067 (1998), which is hereby incorporated by reference in its entirety), and the melon actin promoter (PCT Publ. No. WO00/56863, which is hereby incorporated by reference in its entirety). Exemplary tissue-specific promoters include the tomato E4 and E8 promoters (U.S. Pat. No. 5,859,330, which is hereby incorporated by reference in its entirety) and the tomato 2AII gene promoter (Van Haaren et al., *Plant Mol Bio.*, 21:625-640 (1993), which is hereby incorporated by reference in its entirety).

In one preferred embodiment, expression of the DNA construct is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219 (1991), which is hereby incorporated by reference in its entirety), globulin (Belanger and Kriz, *Genet.* 129: 863-872 (1991), GenBank Accession No. L22295, each of which is hereby incorporated by reference in its entirety), gamma zein Z 27 (Lopes et al., *Mol Gen Genet.* 247:603-613 (1995), which is hereby incorporated by reference in its entirety), L3 oleosin promoter (U.S. Pat. No. 6,433,252, which is hereby incorporated by reference in its entirety), phaseolin (Bustos et al., *Plant Cell* 1(9):839-853 (1989), which is hereby incorporated by reference in its entirety), arcelin5 (U.S. Application Publ. No. 2003/0046727, which is hereby incorporated by reference in its entirety), a soybean 7S promoter, a 7Sa promoter (U.S. Application Publ. No. 2003/0093828, which is hereby incorporated by reference in its entirety), the soybean 7Sαβ conglycinin promoter, a 7Sα promoter (Beachy et al., *EMBO J.* 4:3047 (1985); Schuler et al., *Nucleic Acid Res.* 10(24):8225-8244 (1982), each of which is hereby incorporated by reference in its entirety), soybean trypsin inhibitor (Riggs et al., *Plant Cell* 1(6):609-621 (1989), which is hereby incorporated by reference in its entirety), ACP (Baerson et al., *Plant Mol. Biol.*, 22(2):255-267 (1993), which is hereby incorporated by reference in its entirety), stearoyl-ACP desaturase (Slocombe et al., *Plant Physiol.* 104(4):167-176 (1994), which is hereby incorporated by reference in its entirety), soybean a' subunit of β-conglycinin (Chen et al., *Proc. Natl. Acad. Sci.* 83:8560-8564 (1986), which is hereby incorporated by reference in its entirety), *Vicia faba* USP (U.S. Application Publ. No. 2003/229918, which is hereby incorporated by reference in its entirety) and *Zea mays* L3 oleosin promoter (Hong et al., *Plant Mol. Biol.*, 34(3):549-555 (1997), which is hereby incorporated by reference in its entirety).

Nucleic acid molecules encoding the peptides of the present invention can be prepared via solid-phase synthesis using, e.g., the phosphoramidite method and phosphoramidite building blocks derived from protected 2'-deoxynucleosides. To obtain the desired oligonucleotide, the building blocks are sequentially coupled to the growing oligonucleotide chain in the order required by the sequence of the product. Upon the completion of the chain assembly, the product is released from the solid phase to solution, deprotected, collected, and typically purified using HPLC. The limits of solid phase synthesis are suitable for preparing oligonucleotides up to about 200 nt in length, which encodes peptides on the order of about 65 amino acids or less. The ends of the synthetized oligonucleotide can be designed to include specific restriction enzyme cleavage site to facilitate ligation of the synthesized oligonucleotide into an expression vector.

For longer peptides, oligonucleotides can be prepared via solid phase synthesis and then the synthetic oligonucleotide sequences ligated together using various techniques. Recombinant techniques for the fabrication of whole synthetic genes are reviewed, for example, in Hughes et al., "Chapter Twelve—Gene Synthesis: Methods and Applications," *Methods in Enzymology* 498:277-309 (2011), which is hereby incorporated by reference in its entirety.

Once a suitable expression vector is selected, the desired nucleic acid sequences are cloned into the vector using standard cloning procedures in the art, as described by Sambrook et al., Molecular Cloning: A Laboratory Manual, Cold Springs Laboratory, Cold Springs Harbor, N.Y. (1989), or U.S. Pat. No. 4,237,224 to Cohen and Boyer, which are hereby incorporated by reference in their entirety. The vector is then introduced to a suitable host.

A variety of host-vector systems may be utilized to recombinantly express the peptides of the present invention. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by *Agrobacterium*. The expression elements of these vectors vary in their strength and specificities. Depending upon the host-vector system utilized, any one of a number of suitable transcription and translation elements can be used to carry out this and other aspects of the present invention.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Alternatively, if the peptide of interest of interest is not secreted, it can be isolated from the recombinant cells using standard isolation and purification schemes. This includes disrupting the cells (e.g., by sonication, freezing, French press, etc.) and then recovering the peptide from the cellular debris. Purification can be achieved using the centrifugation, precipitation, and purification procedures described above. The use of purification tags, described above, can simplify this process.

In certain embodiments, purification is not required. Where purification is not performed, cell-free lysates can be recovered following centrifugation for removal of cellular debris. The resulting cell-free lysate can be treated with heat for a sufficient amount of time to deactivate any native proteases in the recovered fraction, e.g., 10 min at 100° C. If desired, one or more biocidal agents, protease inhibitors, and non-ionic surfactants can be introduced to such a cell-free preparation (see U.S. Application Publ. No. 20100043095 to Wei, which is hereby incorporated by reference in its entirety).

Once the peptides of the present invention are recovered, they can be used to prepare a composition that includes a carrier, and one or more additives selected from the group consisting of a bacteriocidal or biocidal agent, a protease inhibitor, a non-ionic surfactant, a fertilizer, an herbicide, an insecticide, a fungicide, a nematicide, biological inoculants, plant regulators, and mixtures thereof.

In certain embodiments, the compositions include greater than about 1 nM of the peptide, greater than about 10 nM of the peptide, greater than about 20 nM of the peptide, greater than about 30 nM of the peptide, greater than about 40 nM of the peptide, greater than about 50 nM of the peptide, greater than about 60 nM of the peptide, greater than about 70 nM of the peptide, greater than 80 about nM of the peptide, greater than about 90 nM of the peptide, greater than about 100 nM of the peptide, greater than about 150 nM of the peptide, greater than about 200 nM of the peptide, or greater than about 250 nM of the peptide. In certain embodiments, the compositions include less than about 1 nM of the peptide. For example, certain peptides can be present at a concentration of less than about 2 ng/ml, less than about 1.75 ng/ml, less than about 1.5 ng/ml, less than about 1.25 ng/ml, less than about 1.0 ng/ml, less than about 0.75 ng/ml, less than about 0.5 ng/ml, less than about 0.25 ng/ml, or even less than about 0.1 ng/ml.

Suitable carriers include water, aqueous solutions optionally containing one or more co-solvents, slurries, and solid carrier particles. Exemplary solid carriers include mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, and products of vegetable origin, such as cereal meal, tree bark meal, wood meal and nutshell meal, cellulose powders, starches and starch derivatives, as well as other mono-, di-, and poly-saccharides.

Suitable fertilizers include, without limitation, ammonium sulfate, ammonium phosphate, ammonium nitrate, ureas, and combinations thereof.

Suitable insecticides include, without limitation, members of the neonicotinoid class such as imidicloprid, clothianidin, and thiamethoxam; members of the organophosphate class such as chlorpyrifos and malathion; members of the pyrethroid class such as permethrin; other natural insecticides such as nicotine, nornicotine, and pyrethrins; members of the carbamate class such as aldicarb, carbofuran, and carbaryl; members of the macrocyclic lactone class such as various abamectin, avermectin, and ivermectin products; members of the diamide class such as chlorantraniliprole, cyantraniliprole, and flubendiamide; chitin synthesis inhibitors, particularly those of the benzoylurea class such as lufenuron and diflubenzuron; and any combination thereof, including combinations of two or more, three or more, or four or more insecticides. Additional insecticides are listed in the Compendium of Pesticide Common Names, which is database operated by Alan Wood and available in electronic form at the alanwood.net internet site.

Suitable fungicides include, without limitation, members of the strobilurin class such as azoxystrobin, pyraclostrobin, trifloxystrobin, picoxystrobin, and fluoxastrobin; members of the triazole class such as ipconazole, metconazole, tebuconazole, triticonazole, tetraconazole, difenoconazole, flutriafol, propiconazole and prothioconazole; members of the succinate dehydrogenase class such as carboxin, fluxapyroxad, boscalid and sedaxane: members of the phenylamide class such as metalaxyl, mefenoxam, benalaxyl, and oxadixyl; members of the phenylpyrrole class such as fludioxonil; members of the phthalimide class such as captan; members of the dithiocarbamate class such as mancozeb and thiram; members of the benzimidazole class such as thiabendazole; and any combination thereof, including combinations of two or more, three or more, or four or more fungicides. Additional fungicides are listed in the Compendium of Pesticide Common Names, which is a database operated by Alan Wood and available in electronic form at the alanwood.net internet site.

Suitable nematicides include, without limitation, chemicals of the carbamate class such as aldicarb, aldoxycarb, oxamyl, carbofuran, and cleothocarb; and chemicals of the organophosphate class such as thionazin, ethoprophos, fenamiphos, fensulfothion, terbufos, isazofos, and ebufos. Additional nematicides are listed in the Compendium of Pesticide Common Names, which is a database operated by Alan Wood and available in electronic form at the alanwood.net internet site.

Suitable bactericides include, without limitation, those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie; Proxel® GXL from ICI). Additional bactericides are listed in the Compendium of Pesticide Common Names, which is a database operated by Alan Wood and available in electronic form at the alanwood.net internet site.

Suitable inoculants include, without limitation, *Bradyrhizobium* spp., particularly *Bradyrhizobium japonicum* (BASF Vault® products), *Bacillus subtilis*, *Bacillus firmus*, *Bacillus pumilis*, *Streptomyces lydicus*, *Trichoderma* spp., *Pasteuria* spp., other cultures of rhizobial cells (BASF Nodulator® and Rhizo-Flo®), and any combination thereof, including combinations of two or more, three or more, or four or more inoculants.

Plant regulators are chemical substances, either natural or synthetic, that either stimulate or inhibit plant biochemical signaling. These are usually, but not exclusively, recognized by receptors on the surface of the cell, causing a cascade of reactions in the cell. Suitable plant regulators include, without limitation, ethephon; ethylene; salicylic acid; acetylsalicylic acid; jasmonic acid; methyl jasmonate; methyl dihydrojasmonate; chitin; chitosan; abscisic acid; any auxin compound or inhibitor, including but not limited to (4-chlorophenoxy)acetic acid, (2,4-dichlorophenoxy)acetic acid, and 2,3,5-triiodobenzoic acid; any cytokinin, including but not limited to kinetin and zeatin; gibberellins; brassinolide; and any combination thereof, including combinations of two or more, three or more, or four or more regulators.

Other suitable additives include buffering agents, wetting agents, coating agents, and abrading agents. These materials can be used to facilitate application of the compositions in accordance with the present invention. In addition, the compositions can be applied to plant seeds with other conventional seed formulation and treatment materials, including clays and polysaccharides.

Compositions or systems use for plant seed treatment include: one or more of the peptides of the present invention, preferably though not exclusively one of P1, P4-14S, P6a, P14d, P15a, P18, P19, or P25, in combination with one or more insecticides, nematicides, fungicides, other inoculants, or other plant regulators, including combinations of multiple insecticides, or multiple nematicides, multiple fungicides, multiple other inoculants, or multiple plant regulators. Suitable insecticides, nematicides, fungicides, inoculants, and plant regulators for these combination treatments include those identified above. These compositions are presented in the form of a single composition at the time of seed treatment. In contrast, a system used for seed treatment may involve multiple treatments, e.g., a composition containing the peptides is used in one treatment and a composition containing the one or more insecticides, nematicides, fungicides, plant regulators and/or bactericides, is used in a separate treatment. In the latter embodiment, both of these treatments are carried out at about the same time, i.e., before planting or at about the time of planting.

One such example includes one or more of peptides of the present invention, including (without limitation) one of P1, P4-14S, P6a, P14d, P15a, P18, P19, or P25, in combination with Poncho™ (clothianidin) available from Bayer Crop Science, Poncho™ VOTiVO (clothianidin and *Bacillus firmus* biological nematicide) available from Bayer Crop Science, and Gaucho™ (imidicloprid) available from Bayer Crop Science.

Another example includes one or more of peptides of the present invention, including (without limitation) one of P1, P4-14S, P6a, P14d, P15a, P18, P19, or P25, in combination with Cruiser™ (thiamethoxam) available from Syngenta, CruiserMaxx™ (thiamethoxam, mefenoxam, and fludioxynil) available from Syngenta, Cruiser Extreme™ (thiamethoxam, mefenoxam, fludioxynil, and azoxystrobin) available from Syngenta, Avicta™ (thiamethoxam and abamectin) available from Syngenta, and Avicta™ Complete (thiamethoxam, abamectin, and Clariva Complete™ which contains the *Pasteuria nishizawae*—Pn1 biological inoculant) available from Syngenta, and Avicta Complete™ Corn (thiamethoxam, mefenoxam, fludioxynil, azoxystrobin, thiabendazole and abamectin) available from Syngenta.

Another example includes one or more of peptides of the present invention, including (without limitation) one of P1, P4-14S, P6a, P14d, P15a, P18, P19, or P25, in combination with Vault Liquid plus Integral (*Bradyrhizobium* species and *Bacillus subtilis* strain MBI 600 inoculants) available from BASF, Vault NP (*Bradyrhizobium japonicum* inoculant) available from BASF, and Subtilex NG (*Bacillus subtilis* biological inoculant) available from BASF.

The present invention further relates to methods of imparting disease resistance to plants, enhancing plant growth, effecting pest control, imparting biotic or abiotic stress tolerance to plants, and/or modulating plant biochemical signaling. These methods involve applying an effective amount of an isolated peptide of the invention, or a composition of the invention to a plant or plant seed or the locus where the plant is growing or is expected to grow. As a consequence of such application, the peptide contacts cells of the plant or plant seed, and induces in the plant or a plant grown from the plant seed disease resistance, growth enhancement, tolerance to biotic stress, tolerance to abiotic stress, or altered biochemical signaling. Alternatively, the peptide or composition of the invention can be applied to plants such that seeds recovered from such plants themselves are able to impart disease resistance in plants, to enhance plant growth, to affect insect control, to impart tolerance to biotic or abiotic stress, and/or to modulate biochemical signaling, to modulate maturation.

In these embodiments, it is also possible to select plants or plant seeds or the locus to which the isolated peptide or composition of the invention is applied. For example, for fields known to contain a high nematode content, the plants or plant seeds to be grown in such fields, or the fields (locus), can be selectively treated by applying the isolated peptide or composition of the invention as described herein; whereas no such treatment may be necessary for plants or plant seeds grown in fields containing low nematode content. Similarly, for fields having reduced irrigation, the plants or plant seeds to be grown in such fields, or the fields (locus), can be selectively treated by applying the isolated peptide or composition of the invention as described herein; whereas no such treatment may be necessary for plants or plant seeds grown in fields having adequate irrigation. Likewise, for fields prone to flooding, the plants or plant seeds to be grown in such fields, or the fields (locus), can be selectively treated by applying the isolated peptide or composition of the invention as described herein; whereas no such treatment may be necessary for plants or plant seeds grown in fields that are not prone to flooding. As yet another example of such selection, for fields prone to insect attack at certain times of the growing season, the plants or plant seeds to be grown in such fields, or the fields (locus), can be selectively treated by applying the isolated peptide or composition of the invention as described herein; whereas the same field may not be treated at ineffective times of the growing season or other fields that are not prone to such attack may go untreated. Such selection steps can be carried out when practicing each of the methods of use described herein, i.e., imparting disease resistance to plants, enhancing plant growth, effecting pest control (including insects and nematodes), imparting biotic or abiotic stress tolerance to plants, and/or modulating plant biochemical signaling.

As an alternative to applying an isolated peptide or a composition containing the same to plants or plant seeds in order to impart disease resistance in plants, to effect plant growth, to control insects, to impart stress resistance and/or modulated biochemical signaling to the plants or plants grown from the seeds, transgenic plants or plant seeds can be utilized. When utilizing transgenic plants, this involves providing a transgenic plant transformed with a DNA molecule encoding a peptide of the invention and growing the plant under conditions effective to permit that DNA molecule to impart disease resistance to plants, to enhance plant growth, to control insects, to impart tolerance to biotic or abiotic stress, and/or to modulate biochemical signaling. Alternatively, a transgenic plant seed transformed with a DNA molecule encoding a peptide of the invention can be provided and planted in soil. A plant is then propagated from the planted seed under conditions effective to permit that DNA molecule to express the peptide and thereby impart disease resistance to the transgenic plant, to enhance plant growth, to control insects, to impart tolerance to biotic or abiotic stress, and/or to modulate biochemical signaling.

The present invention further relates to methods of improving desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. These methods involve applying an effective amount of an isolated peptide of the present invention or a composition according to the present invention to a plant or the locus where the plant is growing. As a consequence of such application, the peptide contacts cells of the plant or plant seed, and induces desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. Alternatively, an effective amount of an isolated peptide of the present invention or a composition according to the present invention can be applied to a harvested fruit or vegetable. As a consequence of such application, the peptide contacts cells of the harvested fruit or vegetable, and induces post-harvest disease resistance or desiccation resistance to the treated fruit or vegetables, and/or improved longevity of fruit or vegetable ripeness for the treated fruit or vegetables.

As an alternative to applying an isolated peptide or a composition containing the same to plants or plant seeds in order to induce desiccation resistance to cuttings removed from ornamental plants, post-harvest disease resistance or desiccation resistance to fruit or vegetables harvested from plants, and/or improved longevity of fruit or vegetable ripeness for fruit or vegetables harvested from plants, transgenic plants or plant seeds can be utilized. When utilizing transgenic plants, this involves providing a transgenic plant transformed with a DNA molecule encoding a peptide of the invention and growing the plant under conditions effective to permit that DNA molecule to induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants. Alternatively, a transgenic plant seed transformed with a DNA molecule encoding a peptide of the invention can be provided and planted in soil. A plant is then propagated from the planted seed under conditions effective to permit that DNA molecule to express the peptide and thereby induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants.

In these embodiments, it is also possible to select transgenic plants or plant seeds for carrying out the present invention. For example, for fields known to contain a high nematode content, the transgenic plants or plant seeds can be selectively grown in such fields; whereas non-transgenic plants or plant seeds can be grown in fields containing low nematode content. Similarly, for fields having reduced irrigation, the transgenic plants or plant seeds can be selectively grown in such fields; whereas non-transgenic plants or plant seeds can be grown in fields having adequate irrigation. Likewise, for fields prone to flooding, the transgenic plants or plant seeds can be grown in such fields; whereas non-transgenic plants or plant seeds can be grown in fields that are not prone to flooding. As yet another example of such selection, for fields prone to insect attack at certain times of the growing season, the transgenic plants or plant seeds can be selectively grown in such fields; whereas non-transgenic plants or plant seeds can be grown in fields that are not prone to such insect attack. Such selection steps can be carried out when practicing each of the methods of use described herein, i.e., imparting disease resistance to plants, enhancing plant growth, effecting pest control (including insects and nematodes), imparting biotic or abiotic stress tolerance to plants, and/or modulating plant biochemical signaling.

The present invention further relates to methods of improving desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. These methods involve applying an effective amount of an isolated peptide of the present invention or a composition according to the present invention to a plant or the locus where the plant is growing. As a consequence of such application, the peptide contacts cells of the plant or plant seed, and induces desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. Alternatively, an effective amount of an isolated peptide of the present invention or a composition according to the present invention can be applied to a harvested fruit or vegetable. As a consequence of such application, the peptide contacts cells of the harvested fruit or vegetable, and induces post-harvest disease resistance or desiccation resistance to the treated fruit or vegetables, and/or improved longevity of fruit or vegetable ripeness for the treated fruit or vegetables.

In these embodiments, it is also possible to select plants, cuttings, fruits, vegetables, or the locus to which the isolated peptide or composition of the invention is applied. For example, for harvested cuttings or fruit or vegetables that are being shipped great distances or stored for long periods of time, then these can be selectively treated by applying the isolated peptide or composition of the invention as described herein; whereas harvested cuttings or fruit or vegetables that are being shipped locally and intended to be consumed without substantially periods of storage can be excluded from such treatment.

As an alternative to applying an isolated peptide or a composition containing the same to plants or plant seeds in order to induce desiccation resistance to cuttings removed from ornamental plants, post-harvest disease resistance or desiccation resistance to fruit or vegetables harvested from plants, and/or improved longevity of fruit or vegetable ripeness for fruit or vegetables harvested from plants, transgenic plants or plant seeds can be utilized. When utilizing transgenic plants, this involves providing a transgenic plant transformed with a DNA molecule encoding a peptide of the invention and growing the plant under conditions effective to permit that DNA molecule to induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants. Alternatively, a transgenic plant seed transformed with a DNA molecule encoding a peptide of the invention can be provided and planted in soil. A plant is then propagated from the planted seed under conditions effective to permit that DNA molecule to express the peptide and thereby induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants.

In these embodiments, it is also possible to select transgenic plants or plant seeds for carrying out the present invention. For example, transgenic plants or plant seeds can be selected for growing when it is known that harvested cuttings or fruit or vegetables are intended to be shipped great distances or stored for long periods of time post-harvest; whereas non-transgenic plants or plant seeds can be selected for growing when it is known that harvested cuttings or fruit or vegetables are intended to be shipped locally and/or consumed without substantially periods of storage.

Suitable plants include dicots and monocots, including agricultural, silvicultural, ornamental and horticultural plants, whether in a natural or genetically modified form. Exemplary plants include, without limitation, alfalfa, apple, apricot, asparagus, avocados, bananas, barley, beans, beech (*Fagus* spec.), begonia, birch, blackberry, blueberry, cabbage, camphor, canola, carrot, castor oil plant, cherry, cinnamon, citrus, cocoa bean, coffee, corn, cotton, cucumber, cucurbit, eucalyptus, fir, flax, fodder beet, fuchsia, garlic, geranium, grapes, ground nut, hemp, hop, juneberry, juncea (*Brassica juncea*), jute, lentil, lettuce, linseed, melon, mustard, nectarine, oak, oats, oil palm, oil-seed rape, olive, onion, paprika, pea, peach, pear, pelargonium, peppers, petunia, pine (*Pinus* spec.), plum, poplar (*Populus* spec.), pome fruit, potato, rape, raspberry, rice, rubber tree, rye, sorghum, soybean, spinach, spruce, squash, strawberry, sugar beet, sugar cane, sunflower, tea, teak, tobacco, tomato, triticale, turf, watermelon, wheat and willow (*Salix* spec.), *Arabidopsis thaliana*, Saintpaulia, poinsettia, chrysanthemum, carnation, and zinnia.

With respect to modified biochemical signaling, this includes both enhancement of certain plant biochemical pathways and diminishment of certain other plant biochemical pathways. Biochemical signaling pathways that can be altered in accordance with the present invention include gene expression and protein production, production of metabolites, and production of signaling molecules/secondary metabolites. Exemplary biochemical signaling pathways and their modifications include, without limitation, induction of nitric oxide production, peroxide production, and other secondary metabolites; agonist of the ethylene signaling pathway and induction of ethylene-responsive gene expression (see Dong et al., *Plant Phys.* 136:3628-3638 (2004); Li et al., *Planta* 239:831-46 (2014); Chang et al., *PLoS One* 10, e0125498 (2015), each of which is hereby incorporated by reference in its entirety); agonist of the salicylic acid signaling pathway and induction of salicylic acid-responsive gene expression (see Dong et al., *Plant J.* 20:207-215 (1999), which is hereby incorporated by reference in its entirety); agonist of the abscisic acid pathway and induction of abscisic acid-responsive gene expression (see Dong et al., *Planta* 221: 313-327 (2005), which is hereby incorporated by reference in its entirety); agonist of the gibberellin signaling pathway and induction of gibberellin-responsive gene expression (see Li et al., *Planta* 239:831-46 (2014), which is hereby incorporated by reference in its entirety); antagonist of jasmonic acid signaling and inhibiting expression of jasmonic acid-responsive genes (see Dong et al., *Plant Phys.* 136:3628-3638 (2004), which is hereby incorporated by reference in its entirety); inducing protease inhibitor expression (see Laluk and Mengiste, *Plant J.* 68:480-494 (2011); Xia et al., *Chin. Sci. Bull* 56: 2351-2358 (2011), each of which is hereby incorporated by reference in its entirety); inducing reactive oxygen species production in plant tissues; inducing immune-related and antimicrobial peptide production, such as, without limitation, peroxidase, superoxide dismutase, chitinase, and β-1,3-glucanase (Wang et al., *J. Agric. Food Chem.* 59:12527-12533 (2011), which is hereby incorporated by reference in its entirety); and inducing expansin gene expression and production (see Li et al., *Planta* 239:831-46 (2014), which is hereby incorporated by reference in its entirety).

With respect to disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus and Tomato mosaic virus. Resistance, inter alia, to the following bacteria can also be imparted to plants in accordance with present invention: pathogenic *Pseudomonas* spp., pathogenic *Erwinia* spp., pathogenic *Xanthomonas* spp., and pathogenic *Ralstonia* spp. Plants can be made resistant, inter alia, to the following fungi by use of the method of the present invention: *Fusarium* spp. and *Phytophthora* spp.

With regard to the use of the peptides or compositions of the present invention to enhance plant growth, various forms of plant growth enhancement or promotion can be achieved. This can occur as early as when plant growth begins from seeds or later in the life of a plant. For example, plant growth according to the present invention encompasses greater yield, increased plant vigor, increased vigor of seedlings (i.e., post-germination), increased plant weight, increased biomass, increased number of flowers per plant, higher grain and/or fruit yield, increased quantity of seeds produced, increased percentage of seeds germinated, increased speed of germination, increased plant size, decreased plant height (for wheat), greater biomass, more and bigger fruit, earlier fruit coloration, earlier bud, fruit and plant maturation, more tillers or side shoots, larger leaves, delayed leaf senescence, increased shoot growth, increased root growth, altered root/shoot allocation, increased protein content, increased oil content, increased carbohydrate content, increased pigment content, increased chlorophyll content, increased total photosynthesis, increased photosynthesis efficiency, reduced respiration (lower $O_2$ usage), compensation for yield-reducing treatments, increased durability of stems (and resistance to stem lodging), increased durability of roots (and resistance to root lodging), better plant growth in low light conditions, and combinations thereof. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

With regard to the use of the peptides or compositions of the present invention to control pests (including but not limited to insects and nematodes, which are biotic stressors), such pest control encompasses preventing pests from contacting plants to which the peptide or composition of the invention has been applied, preventing direct damage to plants by feeding injury, causing pests to depart from such plants, killing pests proximate to such plants, interfering with insect larval feeding on such plants, preventing pests from colonizing host plants, preventing colonizing insects from releasing phytotoxins, interfering with egg deposition on host plants, etc. The present invention also prevents subsequent disease damage to plants resulting from pest infection.

The present invention is effective against a wide variety of insects (biotic stressors). European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, and tomato pinworm. Collectively, this group of insect pests represents the most economically important group of pests for vegetable production worldwide. The present invention is also effective against nematodes, another class of economically important biotic stressors. Soybean Cyst Nematode (*Heterodera glycines*) is a major pest of soybeans. Reniform Nematode (*Rotylenchulus reniformis*) is a major pest of cotton as can parasitize additional crop species, notably soy and corn. Additional nematode pests include the root knot nematodes of the genus *Meloidogyne* (particularly in cotton, wheat, and barley), cereal cyst nematodes of the genus *Heterodera* (particularly in soy, wheat, and barley), root lesion nematodes of the genus *Pratylenchus*, seed gall nematodes of the genus *Anguina* (particularly in wheat, barley, and rye), and stem nematodes of the genus *Ditylenchus*. Other biotic stressors include arachnids, weeds, and combinations thereof.

With regard to the use of the peptides or compositions of the present invention to impart abiotic stress resistance to plants, such abiotic stress encompasses any environmental factor having an adverse effect on plant physiology and development. Examples of such environmental stress include climate-related stress (e.g., drought, flood, frost, cold temperature, high temperature, excessive light, and insufficient light), air pollution stress (e.g., carbon dioxide, carbon monoxide, sulfur dioxide, $NO_x$, hydrocarbons, ozone, ultraviolet radiation, acidic rain), chemical (e.g., insecticides, fungicides, herbicides, heavy metals), nutritional stress (e.g., over- or under-abundance of fertilizer, micronutrients, macronutrients, particularly potassium, nitrogen derivatives, and phosphorus derivatives), and improved healing response to wounding. Use of peptides of the present invention imparts resistance to plants against such forms of environmental stress.

A further aspect of the present invention relates to the use of the peptides of the present invention as a safener in combination with one or more of the active agents (i.e., in a composition or in separate compositions) for the control of aquatic weeds in a body of water as described in U.S. Publ. No. 20150218099 to Mann, which is hereby incorporated by reference in its entirety.

Yet another aspect of the present invention relates to the use of the peptides of the present invention as a plant strengthener in a composition for application to plants grown under conditions of reduced water irrigation, which composition also includes at least one antioxidant and at least one radiation manager, and optionally at least one plant growth regulator, as described in U.S. Publ. No. 20130116119 to Rees et al., which is hereby incorporated by reference in its entirety.

The methods of the present invention involving application of the peptide or composition can be carried out through a variety of procedures when all or part of the plant is treated, including leaves, stems, roots, propagules (e.g., cuttings), fruit, etc. This may (but need not) involve infiltration of the peptide into the plant. Suitable application methods include high or low pressure spraying, injection, and leaf abrasion proximate to when peptide application takes place. When treating plant seeds, in accordance with the application embodiment of the present invention, the hypersensitive response elicitor protein or polypeptide can be applied by low or high pressure spraying, coating, immersion (e.g., soaking), or injection. Other suitable application procedures can be envisioned by those skilled in the art provided they are able to effect contact of the hypersensitive response elicitor polypeptide or protein with cells of the plant or plant seed. Once treated with the peptides or compositions of the present invention, the seeds can be planted in natural or artificial soil and cultivated using conventional procedures to produce plants. After plants have been propagated from seeds treated in accordance with the present invention, the plants may be treated with one or more applications of the peptides or compositions of the invention to impart disease resistance to plants, to enhance plant growth, to control insects on the plants, to impart biotic or abiotic stress tolerance, to improve desiccation resistance of removed cuttings, to impart post-harvest disease resistance or desiccation resistance to harvested fruit or vegetables, and/or improved longevity of fruit or vegetable ripeness for harvested fruit or vegetables.

The peptides or compositions of the invention can be applied to plants or plant seeds in accordance with the present invention alone or in a mixture with other materials. Alternatively, the peptides or compositions can be applied separately to plants with other materials being applied at different times.

In the alternative embodiment of the present invention involving the use of transgenic plants and transgenic seeds, a peptide of the invention need not be applied topically to the plants or seeds. Instead, transgenic plants transformed with a DNA molecule encoding a peptide of the invention are produced according to procedures well known in the art. A vector suitable for expression in plants (i.e., containing translation and transcription control sequences operable in plants) can be microinjected directly into plant cells by use of micropipettes to transfer mechanically the recombinant DNA. Crossway, *Mol. Gen. Genetics,* 202:179-85 (1985), which is hereby incorporated by reference in its entirety. The genetic material may also be transferred into the plant cell using polyethylene glycol. Krens, et al., *Nature,* 296:72-74 (1982), which is hereby incorporated by reference in its entirety.

Another approach to transforming plant cells with a gene encoding the peptide of the invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies. Fraley, et al., *Proc. Natl. Acad. Sci. USA,* 79:1859-63 (1982), which is hereby incorporated by reference in its entirety. The DNA molecule may also be introduced into the plant cells by electroporation. Fromm et al., *Proc. Natl. Acad. Sci. USA,* 82:5824 (1985), which is hereby incorporated by reference in its entirety. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25-28° C. *Agrobacterium* is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue. Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. J. Schell, *Science,* 237:1176-83 (1987), which is hereby incorporated by reference in its entirety.

After transformation, the transformed plant cells must be regenerated. Plant regeneration from cultured protoplasts is described in Evans et al., *Handbook of Plant Cell Cultures*, Vol. 1: (MacMillan Publishing Co., New York, 1983); and Nasil I. R. (ed.), *Cell Culture and Somatic Cell Genetics of Plants*, Acad. Press, Orlando, Vol. 1, 1984, and Vol. III (1986), which are hereby incorporated by reference in their entirety.

It is known that practically all plants can be regenerated from cultured cells or tissues. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the hypersensitive response elicitor resulting in disease resistance, enhanced plant growth, control of insects on the plant, abiotic or biotic stress tolerance, improved desiccation resistance of removed cuttings, post-harvest disease resistance or desiccation resistance in harvested fruit or vegetables, and/or improved longevity of fruit or vegetable ripeness for harvested fruit or vegetables.

Alternatively, transgenic seeds are recovered from the transgenic plants. These seeds can then be planted in the soil and cultivated using conventional procedures to produce transgenic plants. The transgenic plants are propagated from the planted transgenic seeds under conditions effective to impart disease resistance to plants, to enhance plant growth, to control insects, to impart abiotic or biotic stress tolerance, to improve desiccation resistance of removed cuttings, to impart post-harvest disease resistance or desiccation resistance in harvested fruit or vegetables, and/or to impart improved longevity of fruit or vegetable ripeness for harvested fruit or vegetables.

When transgenic plants and plant seeds are used in accordance with the present invention, they additionally can be treated with the same materials as are used to treat the plants and seeds to which a peptide of the invention or composition of the invention is applied. These other materials, including peptides or composition of the invention, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the peptides or compositions of the invention to impart disease resistance, enhance growth, control insects, abiotic or biotic stress tolerance, desiccation resistance of removed cuttings, post-harvest disease resistance or desiccation resistance in harvested fruit or vegetables, and/or improved longevity of fruit or vegetable ripeness for harvested fruit or vegetables.

Such transgenic plants may also be treated with conventional plant treatment agents, e.g., bacteriocidal or biocidal agents, protease inhibitors, non-ionic surfactants, fertilizers, herbicides, insecticides, fungicides, nematicides, biological inoculants, plant regulators, and mixtures thereof, as described above.

EXAMPLES

The following examples are provided to illustrate embodiments of the present invention but are by no means intended to limit its scope.

Example 1

Development of "HR Box" Peptides of SEQ ID NO: 93

The HR box was originally developed based on examination of a number of Hypersensitive Response-Inducing sequences (P1, SEQ ID NO: 4; P4, SEQ ID NO: 5; and P15, SEQ ID NO: 64, among others). A repeating sequence of leucine and isoleucine residues was identified. P4 was chosen as a representative sequence as the basis for mutational studies that would reveal the sequence determinants of HR elicitation. HR in tobacco was tested as described in Wei, *Science* 257:85-88 (1992), which is hereby incorporated by reference in its entirety. Briefly, peptides were dissolved at a concentration of 500 µg/ml in aqueous solution. Four serial dilutions were performed with an equal volume of water, yielding peptide samples at 500, 250, 125, 62.5, 31.25 µg/ml peptide solutions. *Nicotiana tabacum* cultivar xanthi plants were used at 5-7 weeks old (preflowering). Leaves were lightly punctured with a toothpick in a middle leaf panel. Peptide solutions were then infused via needle-less syringe into the wound, filling the panel. Each peptide sample was infused into a leaf of 2 different plants. The leaves were observed and scored over the next 48 hours for withering and browning, lesions typical of programmed cell death. These mutational studies had three main goals: (1) increase the solution stability of the peptides; (2) make disruptive mutations to verify the residues which are most important for HR elicitation; and (3) make conservative mutations to identify the degree of specificity for particular amino acids.

Peptides were assessed for one or more of solubility, stability against chemical degradation, effect of bulking agents on solution stability, oxidation protection, and solution stability studies.

Solubility was assessed by creating 0.2% AI (active ingredient) solutions of pure, chemically synthesized peptide in deionized water, and observing the solution for evidence of precipitation over 48 hours at room temperature. P1 (SEQ ID NO: 4) was largely insoluble in water. However, the mutant with several glutamine residues replacing glutamate residues (P1-2E,8E,11E,15E,18E, SEQ ID NO: 46) was soluble. P4 (SEQ ID NO: 5) and P4-14S (SEQ ID NO: 6) were also completely soluble.

Subsequent experiments were run to better quantify peptide solubility. 20-50 mg of pure peptide were mixed with 0.25 ml of water and increasing amounts of water were added until the peptide dissolved. These experiments estimate the solubility of P1 (SEQ ID NO: 4) at <1 mg/ml, the solubility of P4 (SEQ ID NO: 5) at 100 mg/ml, and the solubility of P1-18K (SEQ ID NO: 45) at 20 mg/ml.

Stability against chemical degradation was assessed in various pH buffers by creating 0.2% AI solutions of pure, chemically synthesized peptide in deionized water, 0.25% weight to volume of Proxel® GXL (biocide), and 50 millimolar (mM) of eight buffers (separately) as follows: IVIES pH 5.6, MOPS pH 6.5, Citrate pH 7.2, EDDS pH 7.3, EDTA pH 8, Phosphate pH 8, Imidazole pH 8, and TES pH 8. The solutions were observed on HPLC for evidence of degradation (% loss of the peptide signal over time, relative to the time 0 sample) over a period of weeks at elevated temperature (50° C.). P1-2E, -8E, -11E, -15E, -18E (SEQ ID NO: 46) was more stable than P1 (SEQ ID NO: 4) (40 days vs 20 days over 80%), and P4-14S (SEQ ID NO: 6) was significantly more stable than P4 (SEQ ID NO: 5) (35 days vs 3 days over 80%). The best buffers for P1 and P4-14S are TES pH 8 and Citrate pH 7.2, in that order. Precipitation of P1 was observed after several days. Other peptides (P1-2E, -8E, -11E, -15E, -18E; P4, and P4-14s) remained in solution.

Effect of bulking agents on the chemical degradation of P1 and P1-2E, -8E, -11E, -15E, -18E was assessed by creating 0.2% AI solutions of pure, chemically synthesized peptide in a solution of 50 mM TES pH 8.0 in water and 20% weight to volume (of solution) of the bulking agents trehalose, maltrin, sucrose or talc (separate formulas). These solutions were observed on HPLC for evidence of degradation (% loss of the peptide signal over time, relative to the time 0 sample) over time at elevated temperature (50° C.). The concentration of P1 in all mixtures dropped to less than 60% of the original peptide concentration after 6 days of incubation. In contrast, the concentration of p1-2E, -8E, -11E, -15E, -18E in all samples remained above 80% of the original concentration for at least 14 days. The best bulking agent for P1-2E, -8E, -11E, -15E, -18E is talc powder (44 days above 80%).

Solution stability studies were carried out by creating 0.2% AI solutions of pure, chemically synthesized peptide in deionized water, 50 mM of TES buffer, 0.25% Proxel GXL, and 30% isopropanol. Peptides solutions were analyzed by HPLC for % loss of the peptide signal over time, relative to the time 0 sample. Maximum lifetime of P1-2E, -8E, -11E, -15E, -18E is 45 days over 80%. Maximum lifetime of P4-14S is 140 days over 80%.

Solution stability mutations: Solution stability was increased by choosing a peptide sequence (P4, SEQ ID NO: 5) which did not contain methionine residues. However, this peptide contained a cysteine residue, leading to very poor stability. Mutation of this cysteine to the conservative replacement serine (sulfur to oxygen change in chemical structure) generated P4-14s (SEQ ID NO: 6), which retained its ability to elicit the HR. It was subsequently shown (as noted above) that P4-14s is a highly stable peptide. Additional studies replaced one or more glutamine residues with glutamate residues to reduce the chance of deamidation in solution. In particular, a variant of P1, termed P1-2E, 8E, 11E, 15E, 18E (SEQ ID NO: 46), contained these mutations at positions 2, 8, 11, 15, and 18. This peptide exhibited both improved solubility and stability when compared with P1.

Based on the P4-14s stable backbone (SEQ ID NO: 6), disruptive single mutations were introduced at specific residues within the sequence. In the case of Leucine residues, these were mutated to alanine (smaller and less hydrophobic sidechain, a moderately disruptive mutation) and/or aspartic acid (negatively charged sidechain, a highly disruptive mutation). The intervening sequences, depending on the identity of the amino acid in question, were mutated to have a negative charge (aspartic acid or glutamic acid), have a hydrophobic sidechain (valine), a minimal sidechain (alanine), or a small polar sidechain (serine). These mutant peptides were tested for elicitation of the hypersensitive response. Additional mutations were chosen based on the initial HR results. In addition, the spacing between the leucine/isoleucine residues was evaluated by either deleting a single residue between the leucine repeats (denoted with 'del') or by inserting an alanine residue between the leucine repeats (denoted with iA).

For those amino acids that were important for HR elicitation, more conservative mutations were chosen to determine the specificity of interactions. The leucine residues were mutated to isoleucine, valine, phenylalanine or tyrosine, with the latter 2 residues being less conservative. As above, these mutants were tested for HR elicitation.

The results of these mutation studies are summarized in Table 12 below:

In Table 12, the sequence of P4-14s is shown along with all mutations tested at each position. Those mutations that did not interfere with the hypersensitive response are listed in the labeled "HR Positive Mutations". Those mutations that caused a reduction in the severity of the hypersensitive response are shown in the row labeled "Weak HR Mutations". Mutations that eliminated the hypersensitive response are shown in the red row labeled "HR Negative Mutations". The notation dN2 and dN4 denote a deletion of 2 or 4 residues, respectively, from the beginning of the peptide; dC2 denotes a deletion of 2 residues from the end of the peptide; del denotes a deletion of the residue at that position; and iA represents the insertion of an alanine residue before that position.

Example 2

Solubility and Stability of P1 and Mutant Peptides

Figure 2:
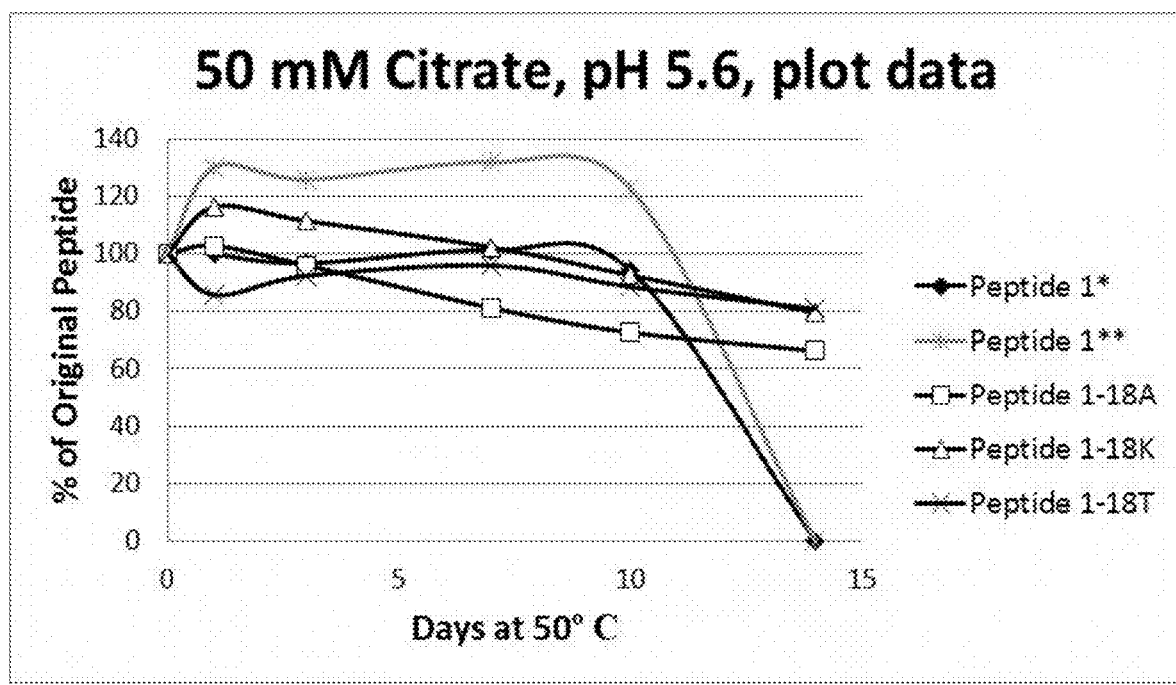
FIG. 2 shows a solubility and stability test of peptide P1 and P1 mutants dissolved in 50 mM citrate, pH 5.6. The following peptides are shown: P1, P1-18A, P1-18K, and P1-18T. The curve for 1* is normalized to 100% of P1 at the day 1 time point; 1** is the original P1 data.
Figure 3:
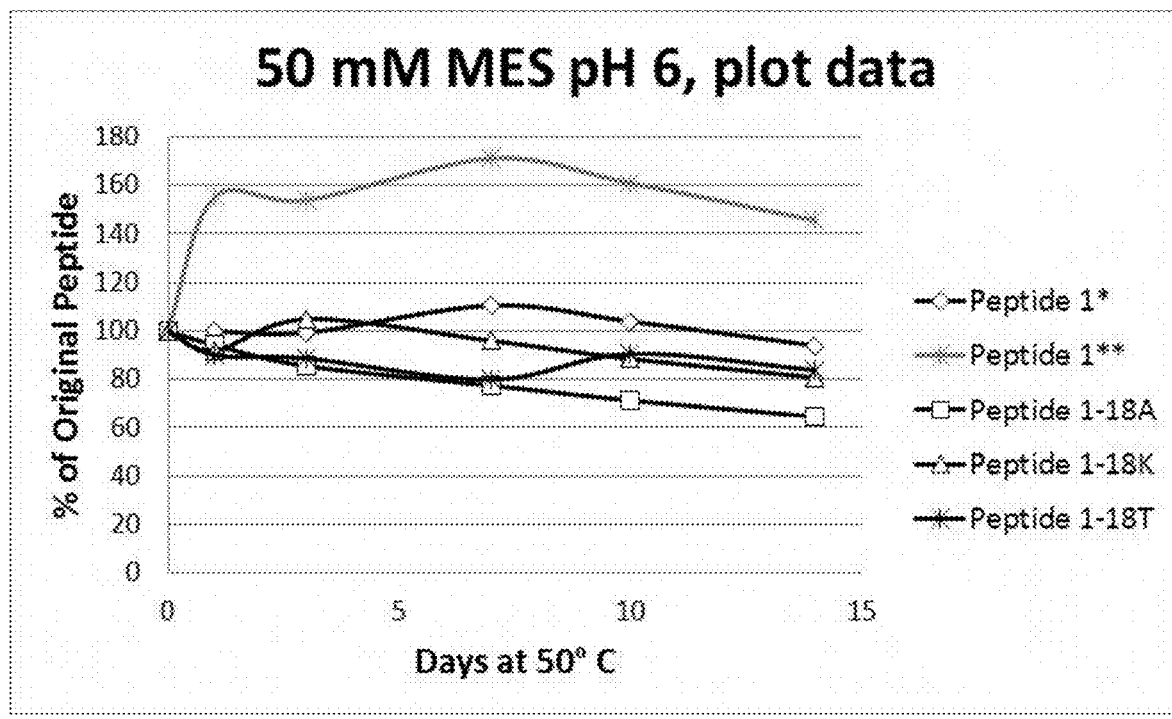
FIG. 3 shows a solubility and stability test of peptide P1 and P1 mutants dissolved in 50 mM MES, pH 6. The following peptides are shown: P1, P1-18A, P1-18K, and P1-18T. The curve for 1* is normalized to 100% of P1 at the day 1 time point; 1** is the original P1 data.
Figure 4:
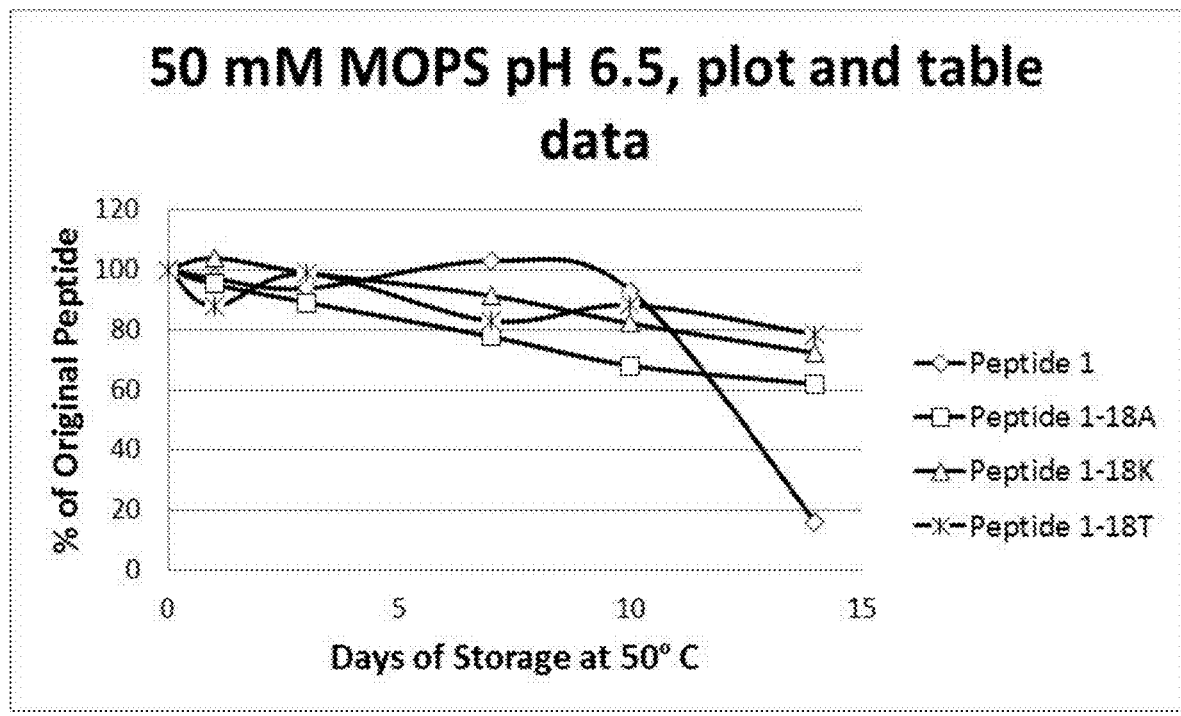
FIG. 4 shows a solubility and stability test of peptide P1 and P1 mutants dissolved in 50 mM MOPS, pH 6.5. The following peptides are shown: P1, P1-18A, P1-18K, and P1-18T.
Figure 5:
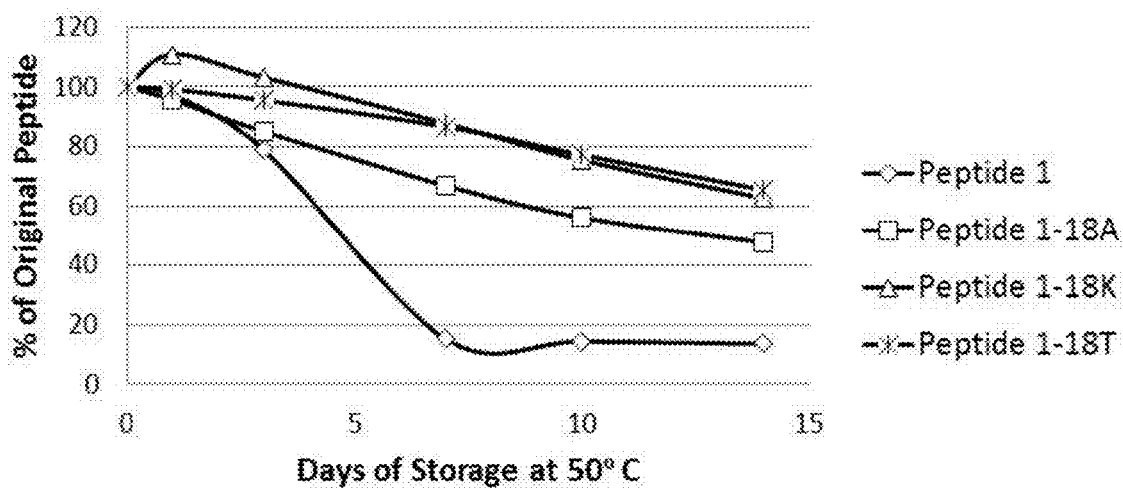
FIG. 5 shows a solubility and stability test of peptide P1 and P1 mutants dissolved in 50 mM citrate, pH 7.2. The following peptides are shown: P1, P1-18A, P1-18K, and P1-18T.

As described above, P1 and P1-derived sequences mutated at position 18 (methionine replaced with alanine, threonine, or lysine) were assessed for solution stability and chemical compatibility for 14 days. Notably, P1 exhibited solubility problems at lower pH (in deionized water solution, in 50 mM citrate pH 5.6, and in 50 mM MES pH 6.0). In these cases, the peptide concentration increased after 24-hour incubation at 50° C. Notably, the mutant peptides generally did not exhibit this issue. As shown in FIGS. 1-3, data were normalized to 100% peptide at the day 1 time point (shown as peptide 1* in the legend and the original peptide 1 data is marked with a double asterisk **). In a stability test dissolved in water (FIG. 1), peptide 1 was modestly stable, but exhibited solubility issues. The 18K and 18A mutants exhibited slightly higher stability (10-25% after 14 days). Dissolved in a slightly acidic citrate buffer (FIG. 2), P1 exhibited both solubility and stability issues. It was not detected by HPLC after 14 days in solution. By contrast the 18T and 18K mutants retained 80% of the original concentration, and the 18A mutant retained ~60% of the original concentration. As shown in FIG. 3, in 50 mM MES pH 6.0, P1 exhibited stronger solubility problems, with a 50% increase in soluble concentration after 24 hour incubation at 50° C. However, it exhibited better stability than the mutants (10-30% after 14 days). In citrate pH 7.2

TABLE 12

Summary of Mutations and HR Elicitation Results

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| P4-14S | S | Q | G | I | S | E | K | Q | L | D | Q | L | L | S | Q | L | I | Q | A | L | L | Q | P |
| HR Positive Mutations | E<br>dN2 | | E<br>A<br>D | L<br>dN4 | V<br>dN5 | R<br>dN6 | V | D<br>V<br>S | E<br>I<br>V | iA<br>V | del<br>V<br>F | V<br>M | I<br>M | I<br>T<br>A<br>V<br>D<br>K<br>Q<br>del | S<br>A<br>I<br>K | E<br>M<br>F | I<br>V<br>L | M<br>S<br>M<br>T<br>K<br>V | E<br>S | D<br>M<br>V | I<br>I<br>M | F<br>dC2 | V |
| Weak HR Mutations | | | | | | | | | | | F<br>S | | | | | V | A | A | | | V<br>S | | |
| HR Negative Mutations | | | | | | | | | A | iA | D<br>D<br>Y<br>S | iA | D<br>D<br>V<br>F<br>Q | A | iA | A<br>S<br>F | D<br>S | del<br>iA<br>F | S<br>V | D<br>V<br>F | | | |

Figure 6:
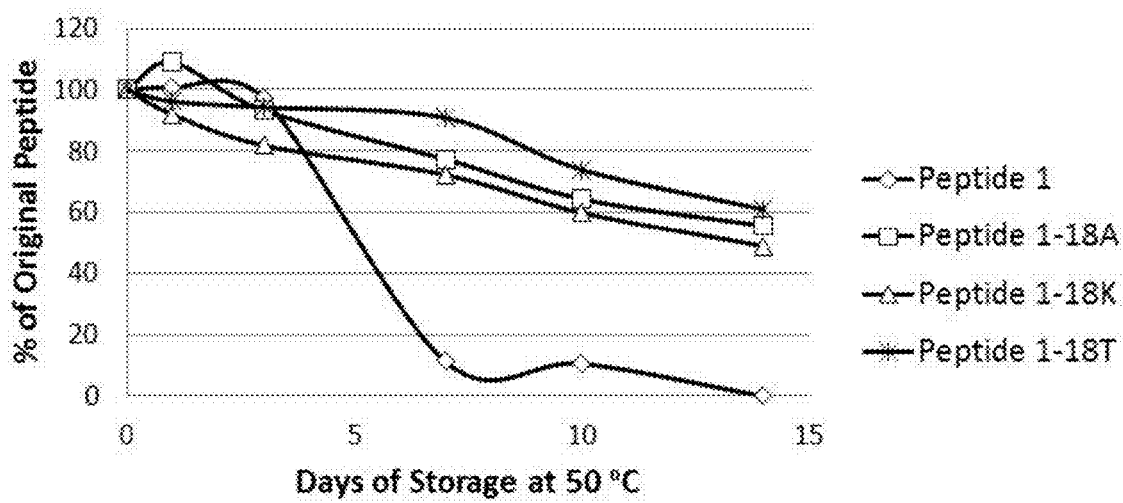
FIG. 6 shows a solubility and stability test of peptide P1 and P1 mutants dissolved in 50 mM EDDS, pH 7.3. The following peptides are shown: P1, P1-18A, P1-18K, and P1-18T.
Figure 7:
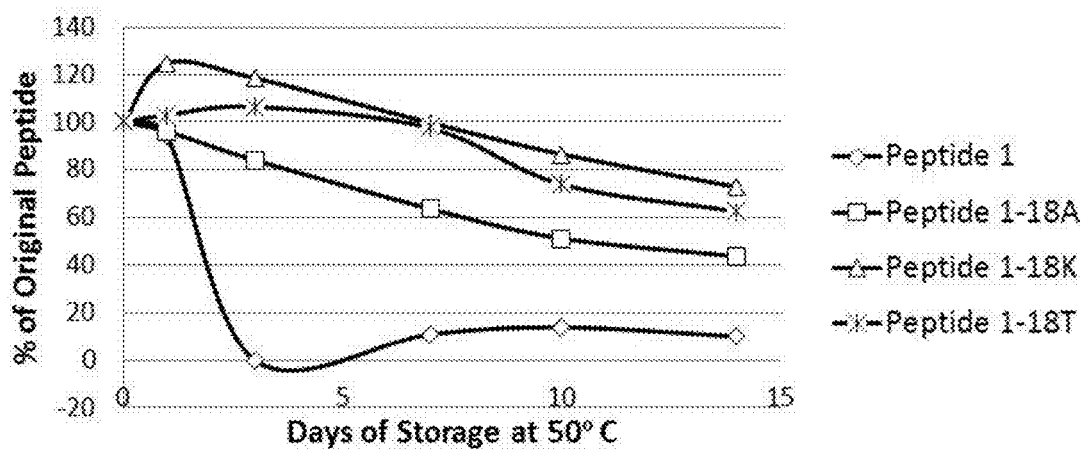
FIG. 7 shows a solubility and stability test of peptide P1 and P1 mutants dissolved in 50 mM imidazole, pH 7.5. The following peptides are shown: P1, P1-18A, P1-18K, and P1-18T.
Figure 8:
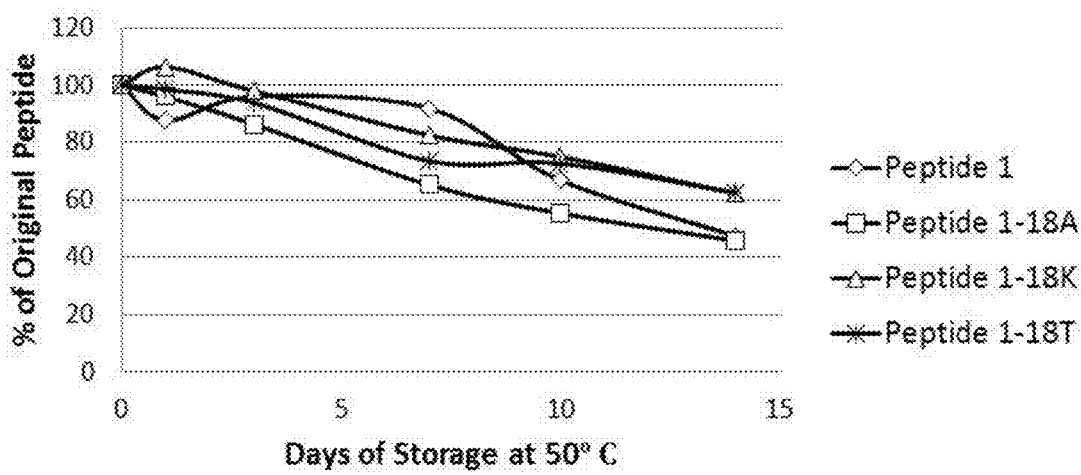
FIG. 8 shows a solubility and stability test of peptide P1 and P1 mutants dissolved in 50 mM EDTA, pH 8. The following peptides are shown: P1, P1-18A, P1-18K, and P1-18T.
Figure 9:
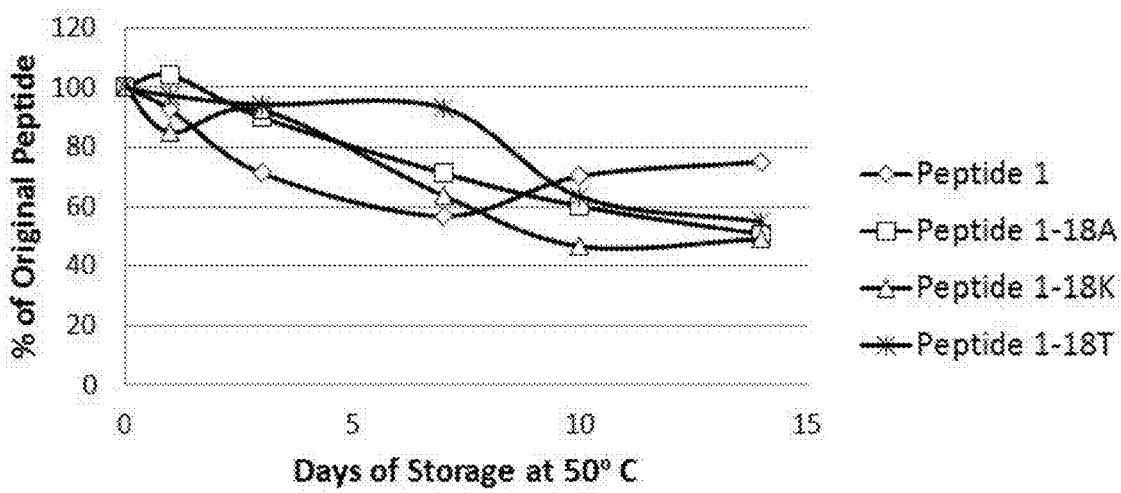
FIG. 9 shows a solubility and stability test of peptide P1 and P1 mutants dissolved in phosphate, pH 8.0. The following peptides are shown: P1, P1-18A, P1-18K, and P1-18T.
Figure 10:
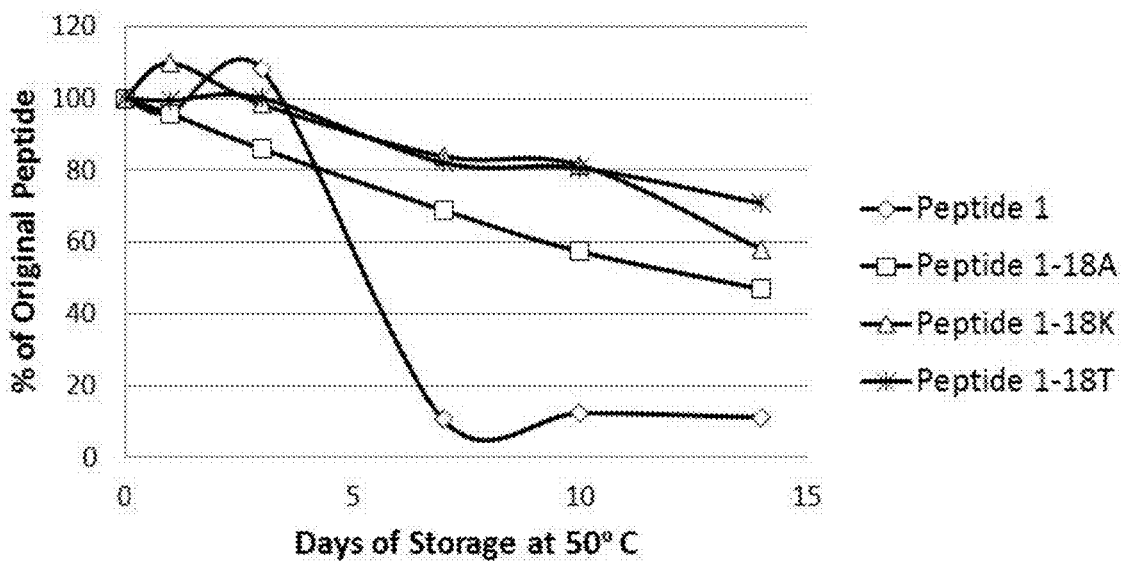
FIG. 10 shows a solubility and stability test of peptide P1 and P1 mutants dissolved in 50 mM TES, pH 8.0. The following peptides are shown: P1, P1-18A, P1-18K, and P1-18T.
Figure 11:
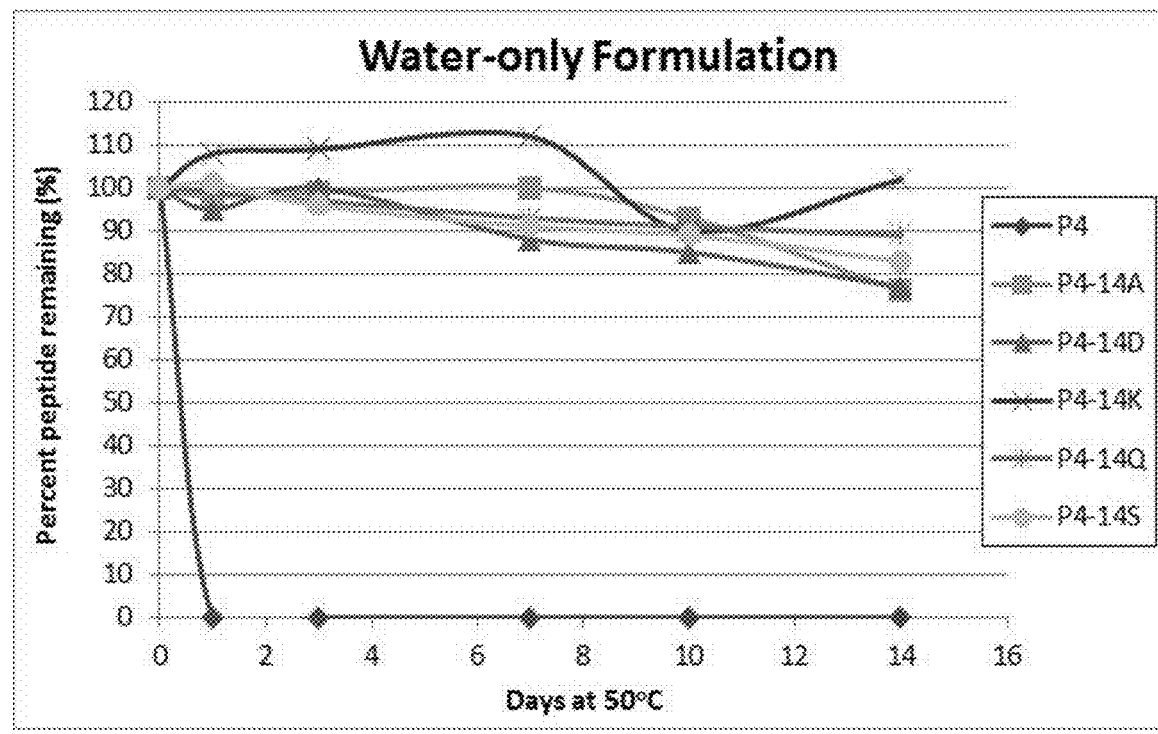
FIG. 11 shows a solubility and stability test of peptide P4 and P4 mutants dissolved in deionized water. The following peptides are shown: P1, P1-18A, P1-18K, and P1-18T.
Figure 12:
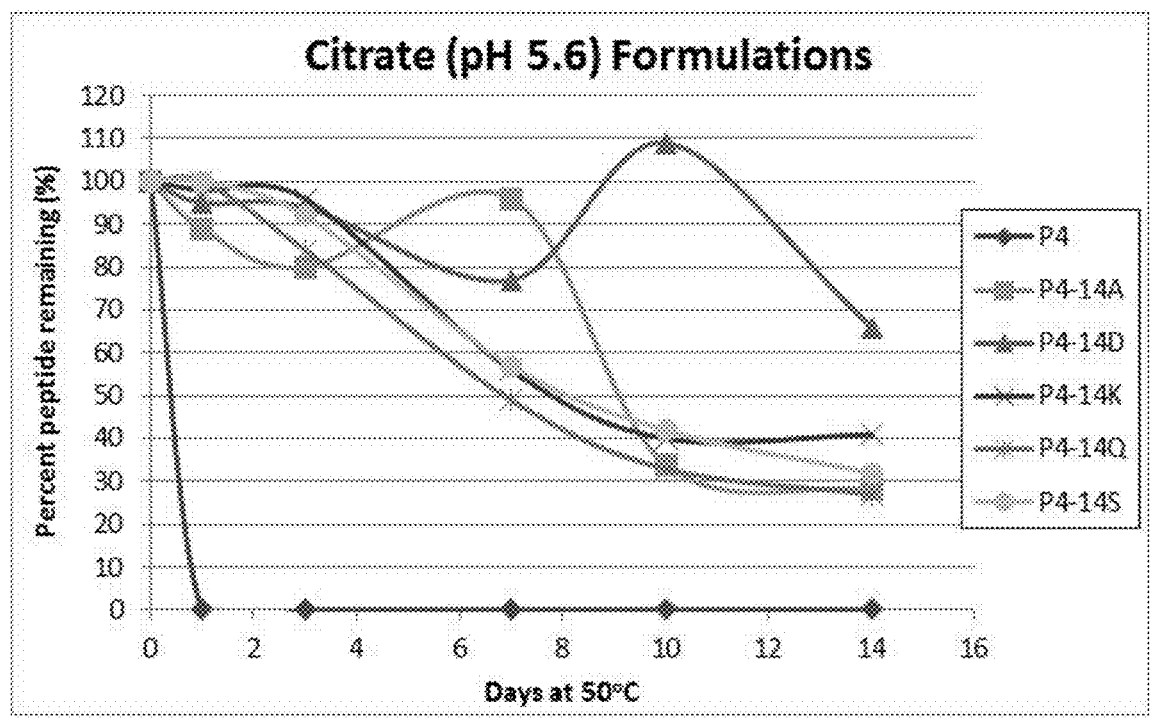
FIG. 12 shows a solubility and stability test of peptide P4 and P4 mutants dissolved in 50 mM citrate, pH 5.6. The following peptides are shown: P4 (SEQ ID NO: 5); P4-14A (SEQ ID NO: 136); P4-14D (SEQ ID NO: 137); P4-14K (SEQ ID NO: 138); P4-14Q (SEQ ID NO: 139); and P4-14S (SEQ ID NO: 6).
Figure 13:
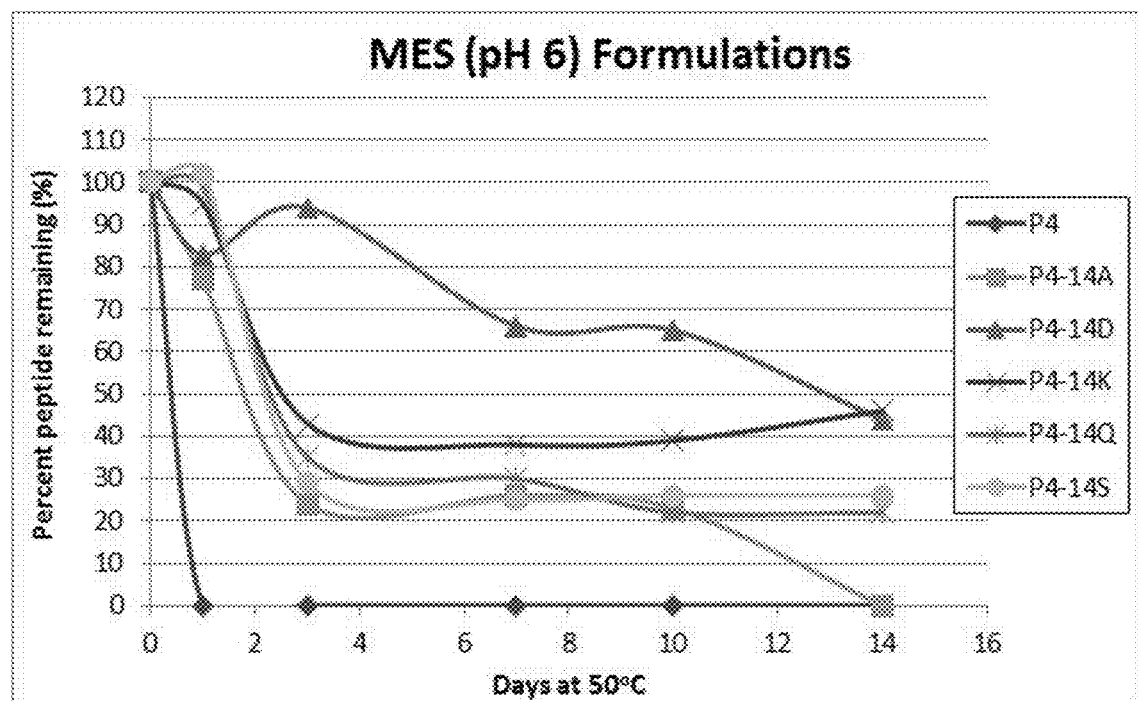
FIG. 13 shows a solubility and stability test of peptide P4 and P4 mutants dissolved in 50 mM IVIES, pH 6. The following peptides are shown: P4, P4-14A, P4-14D, P4-14K, P4-14Q, and P4-14S.
Figure 14:
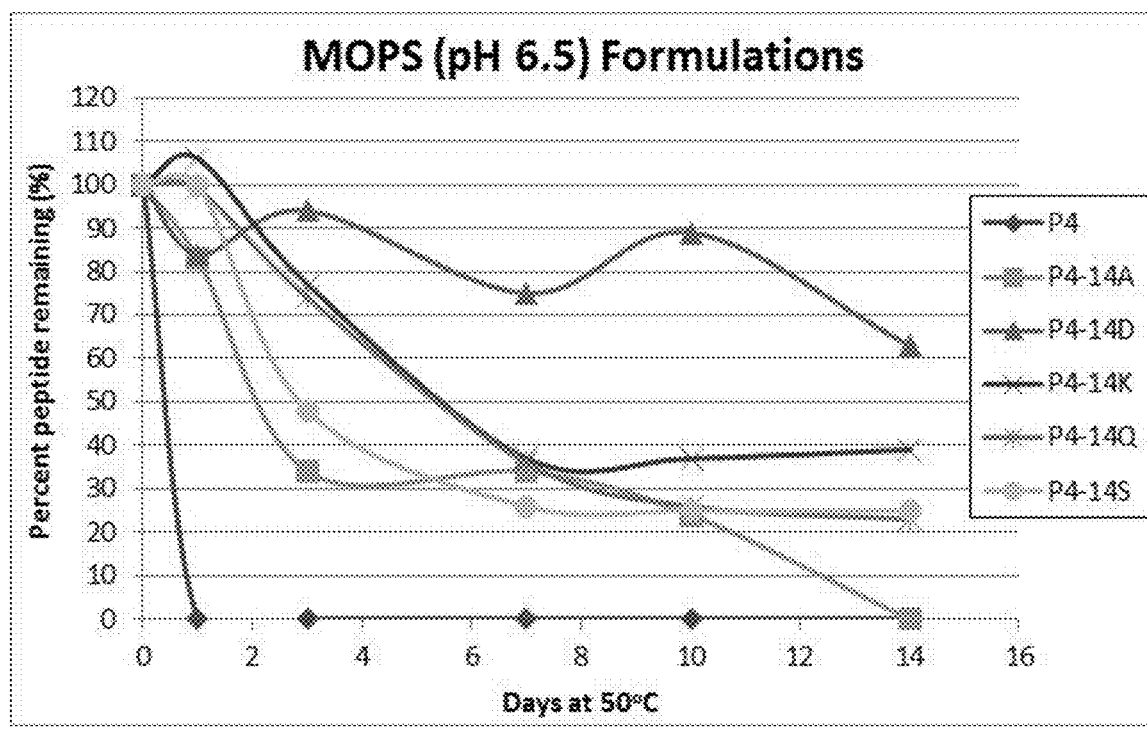
FIG. 14 shows a solubility and stability test of peptide P4 and P4 mutants dissolved in 50 mM MOPS, pH 6.5. The following peptides are shown: P4, P4-14A, P4-14D, P4-14K, P4-14Q, and P4-14S.
Figure 15:
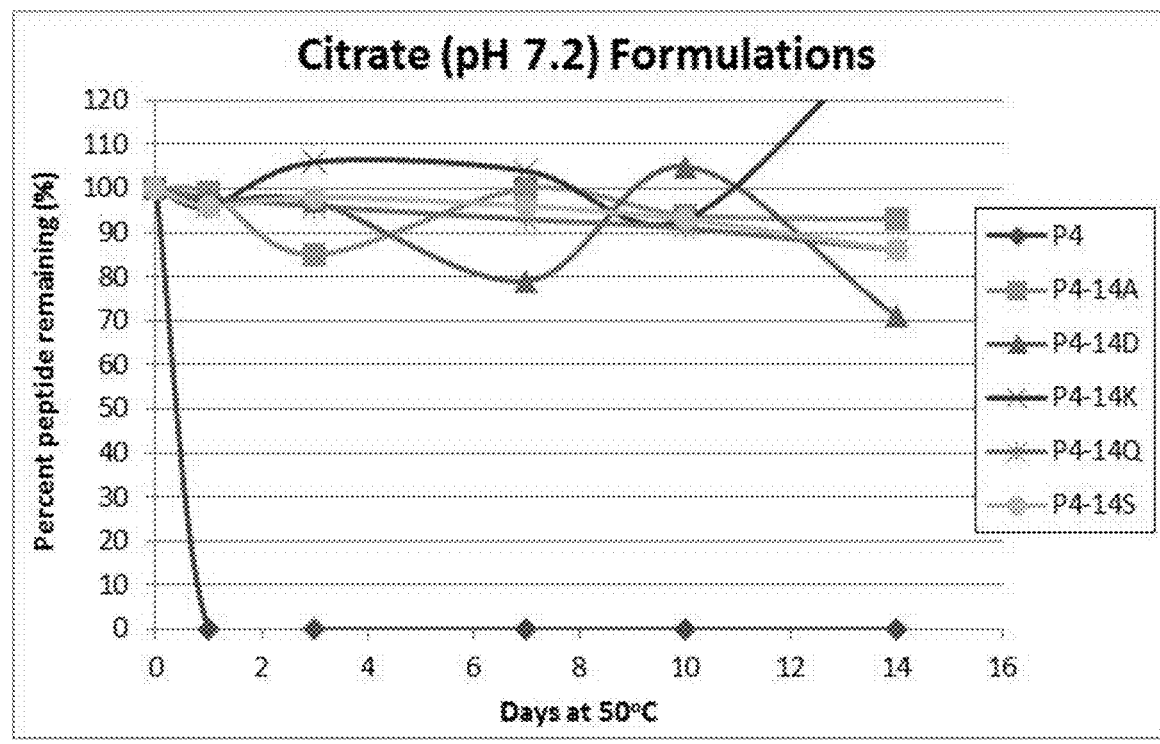
FIG. 15 shows a solubility and stability test of peptide P4 and P4 mutants dissolved in 50 mM citrate, pH 7.2. The following peptides are shown: P4, P4-14A, P4-14D, P4-14K, P4-14Q, and P4-14S.
Figure 16:
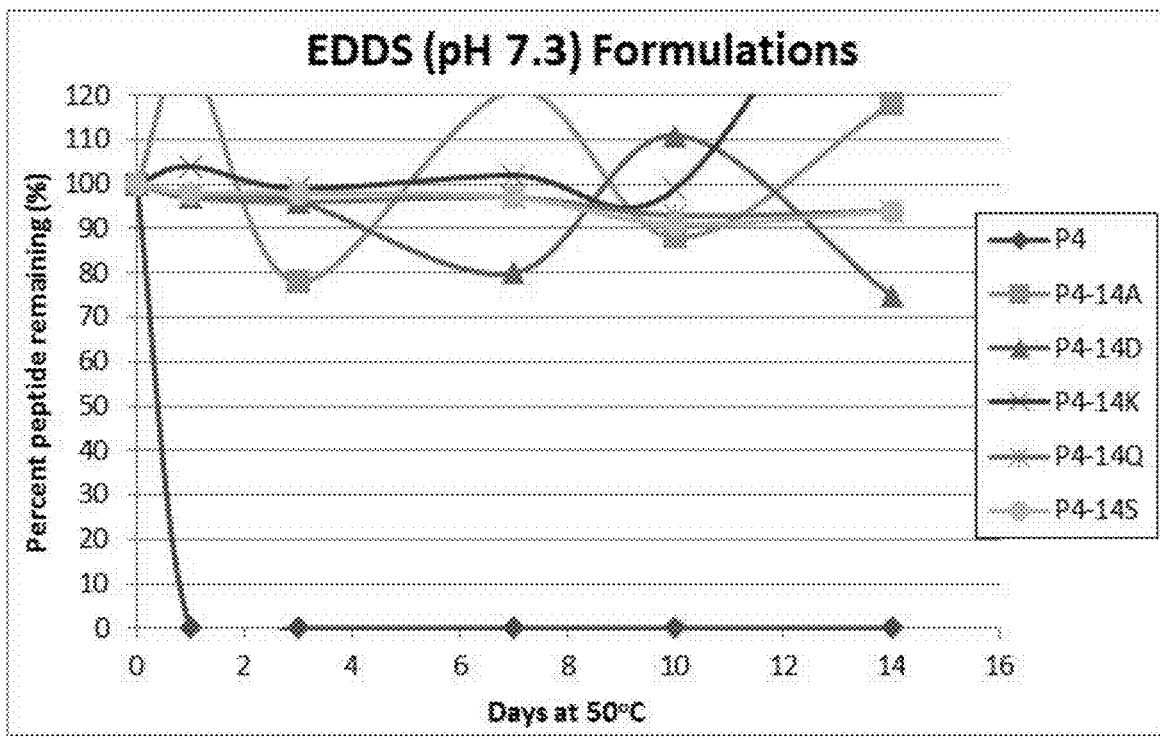
FIG. 16 shows a solubility and stability test of peptide P4 and P4 mutants dissolved in 50 mM EDDS, pH 7.3. The following peptides are shown: P4, P4-14A, P4-14D, P4-14K, P4-14Q, and P4-14S.
Figure 17:
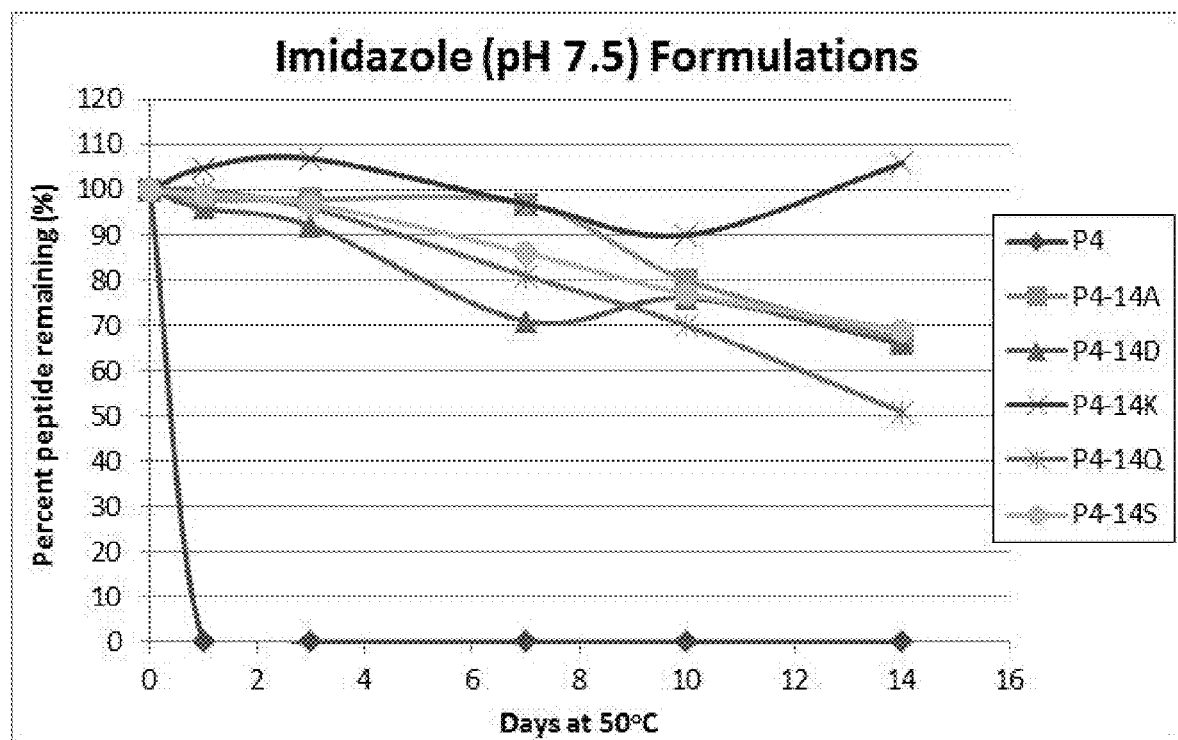
FIG. 17 shows a solubility and stability test of peptide P4 and P4 mutants dissolved in 50 mM imidazole, pH 7.5. The following peptides are shown: P4, P4-14A, P4-14D, P4-14K, P4-14Q, and P4-14S.
Figure 18:
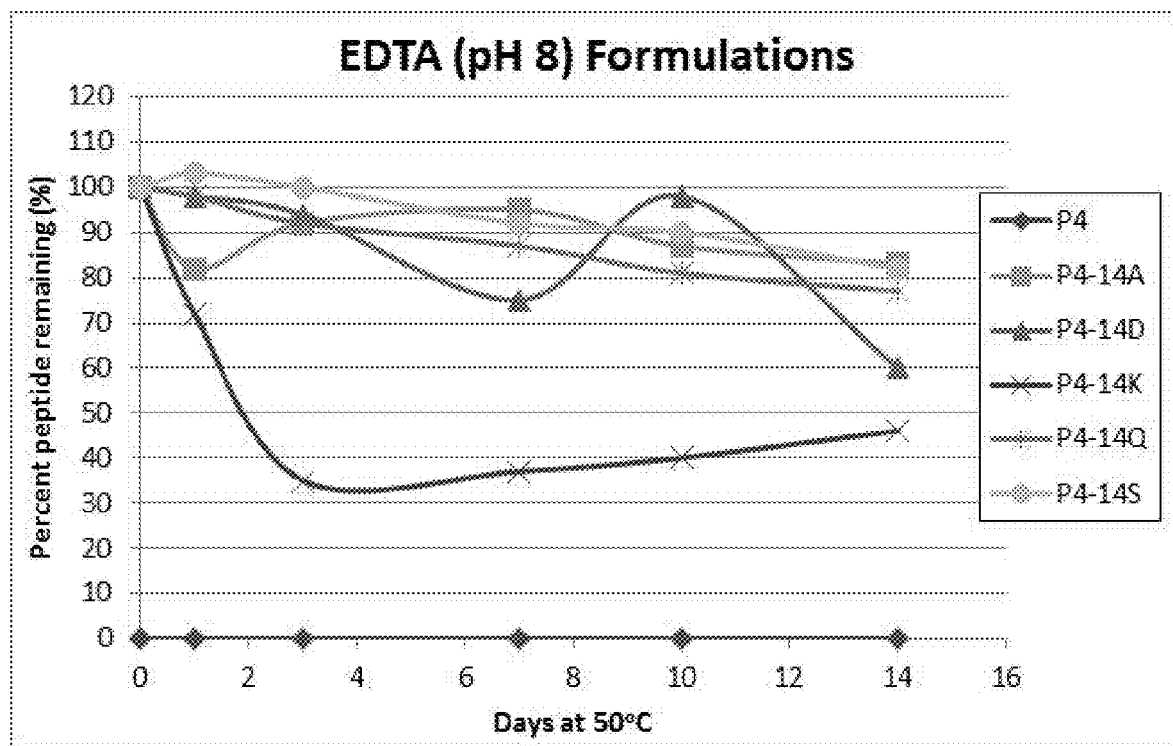
FIG. 18 shows a solubility and stability test of peptide P4 and P4 mutants dissolved in 50 mM EDTA, pH 8. The following peptides are shown: P4, P4-14A, P4-14D, P4-14K, P4-14Q, and P4-14S.
Figure 19:
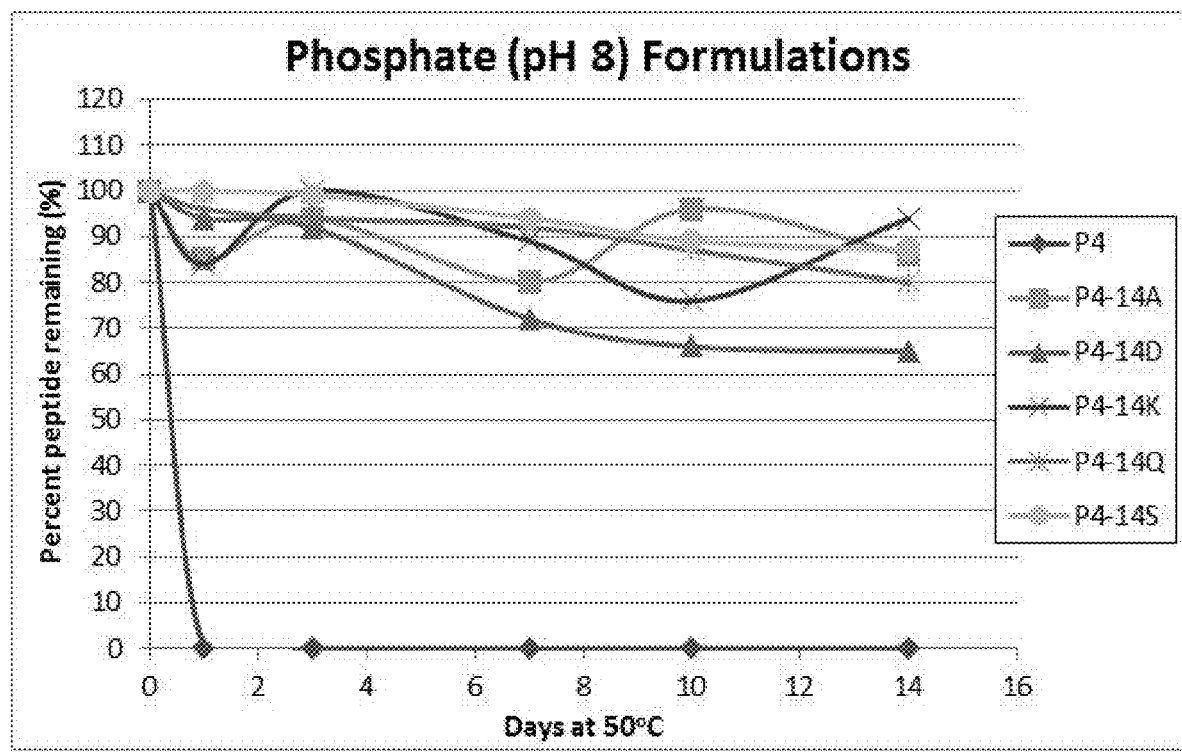
FIG. 19 shows a solubility and stability test of peptide P4 and P4 mutants dissolved in phosphate, pH 8. The following peptides are shown: P4, P4-14A, P4-14D, P4-14K, P4-14Q, and P4-14S.
Figure 20:
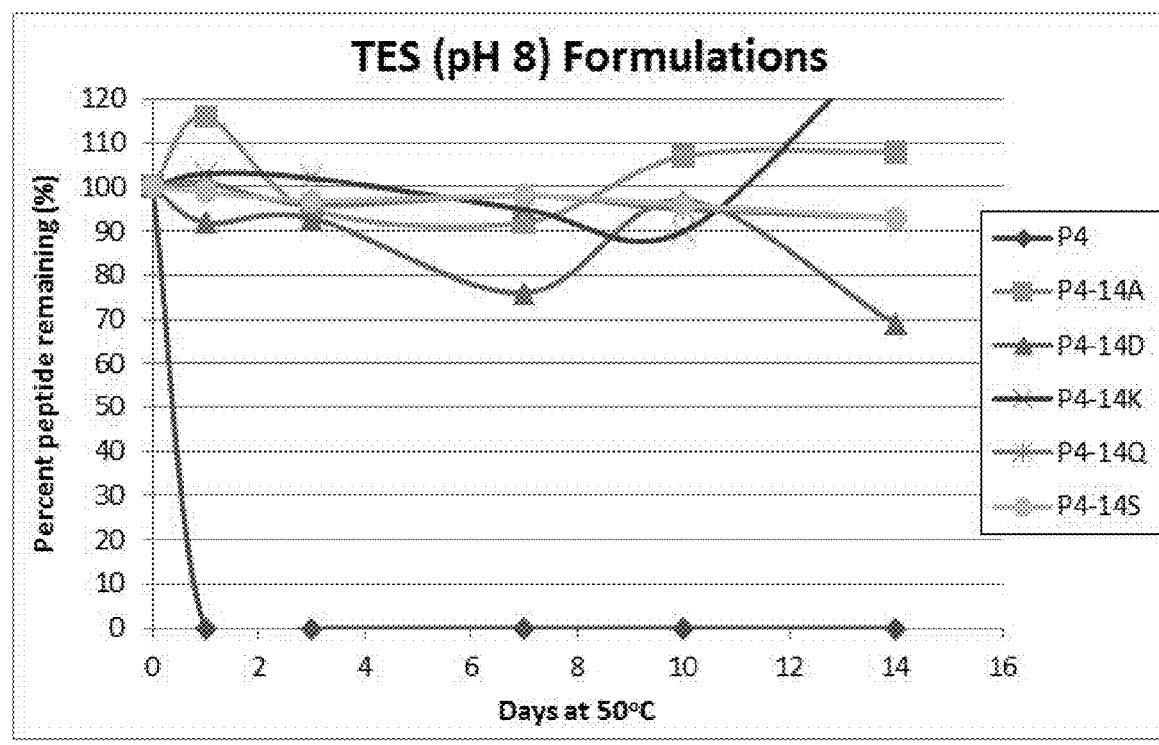
FIG. 20 shows a solubility and stability test of peptide P4 and P4 mutants dissolved in 50 mM TES, pH 8. The following peptides are shown: P4, P4-14A, P4-14D, P4-14K, P4-14Q, and P4-14S.
Figure 21:
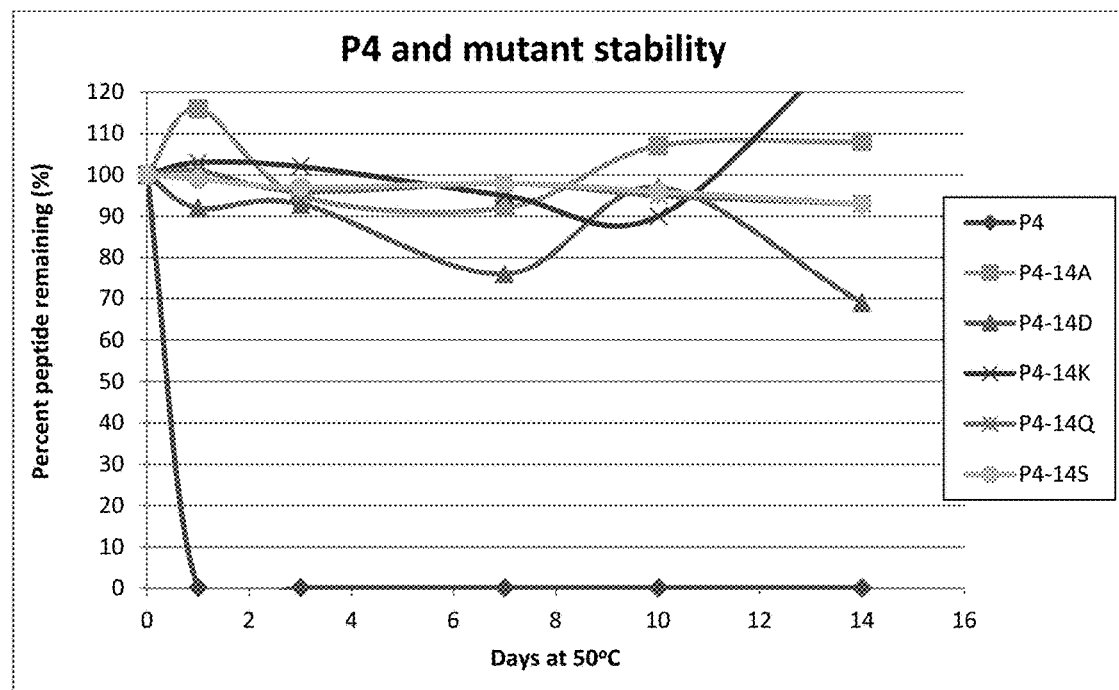
FIG. 21 shows a comparison of the stability of peptide P4 and P4 mutants dissolved in 30% isopropanol, 5 mM DTPA, 0.5% sodium thiosulfate, and 50 mM TES pH 8. The following peptides are shown: P4, P4-14A, P4-14D, P4-14K, P4-14Q, P4-14S
Figure 22:
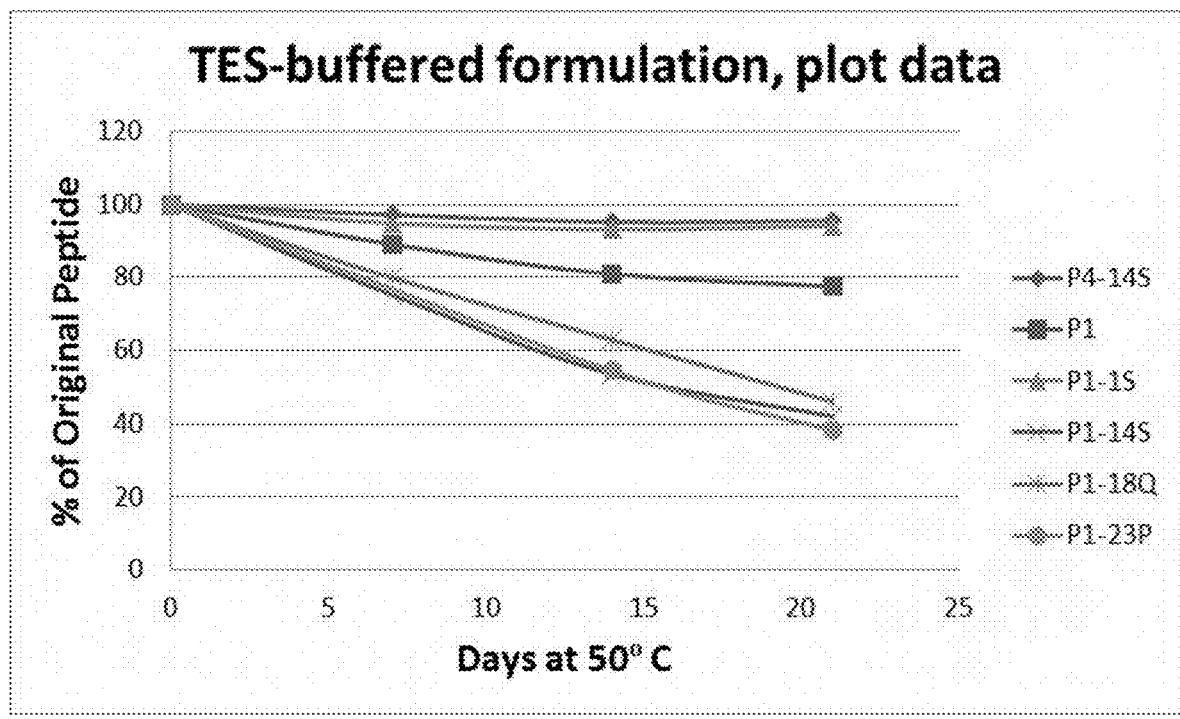
FIG. 22 shows a comparison of the stability of various peptides dissolved in 50 mM TES pH 8. The following peptides are shown: P1 (SEQ ID NO: 4); P4-14S (SEQ ID NO: 6); P1-15 (SEQ ID NO: 109); P1-14S (SEQ ID NO: 110); P1-18Q (SEQ ID NO: 115); and P1-23P (SEQ ID NO:118).
Figure 23:
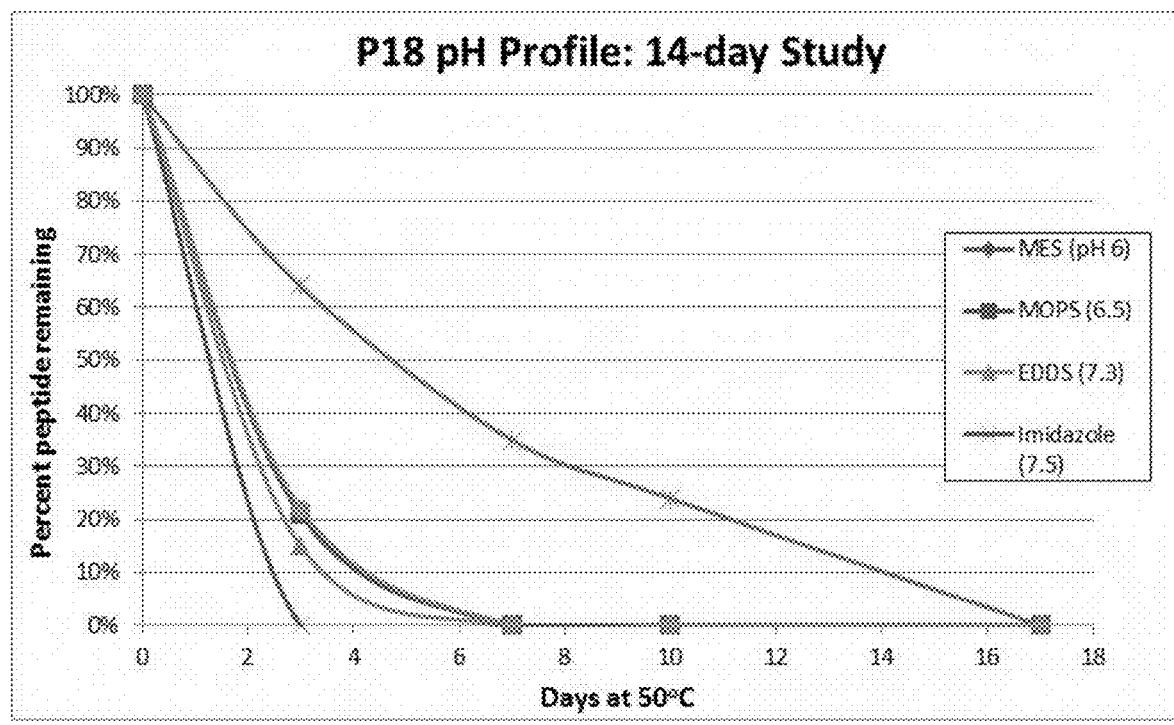
FIG. 23 shows a solubility and stability test of peptide P18 (SEQ ID NO: 83) dissolved in either IVIES pH 6, MOPS pH 6.5, EDDS pH 7.3, imidazole pH 7.5, or EDTA pH 8.

(FIG. 6), P1 did not exhibit solubility problems, but did exhibit poor stability (20% of original concentration after 7 days at 50° C. By contrast, the 18K and 18T mutants exhibited >60% stability after 14 days. In 50 mM EDDS, pH 7.3 (FIG. 7), Peptide 1 exhibited poor stability, with only 10% of the material remaining after 7 days. By comparison, the mutants retained at least 50% of starting material after 14 days. In 50 mM imidazole, pH 8.0 (FIG. 8), Peptide 1 exhibited particularly poor stability, reduced to less that 10% of the original concentration after only 3 days. By comparison, all mutants exhibited greater stability, with 18K and 18T mutants retaining 60-75% of the original material after 14 days. Peptide 1 exhibited better stability in a solution of 50 mM EDTA, pH 8.0 (FIG. 9), matching the performance of the 18A mutant. However, the 18K and 18T mutants exhibited better tability after 14 days incubated at 50° C. (15-20% improvement). When dissolved in phosphate, pH 8.0 (FIG. 10), Peptide 1 appears to outperform the stability of the mutants, although it does exhibit solubility problems (some cloudiness in solution). In a solution of 50 mM TES, pH 8.0 (FIG. 11), Peptide 1 is more than 90% degraded after 1 week of incubation at 80° C. By comparison, 18T, 18K, and 18A mutants exhibit better performance (71%, 58%, and 47% remaining after 14 days incubation at 50° C.).

In general, Peptide 1 either exhibits solubility problems or poor stability in a wide variety of buffered solutions. This is addressed by mutation of methionine to other residues. Bulkier residues (threonine and lysine) generally seem preferred over alanine for stability.

Example 3

Solubility and Stability of P4 and Mutant Peptides

As described above, P4 and P4-derived sequences mutated at position 14 (cysteine replaced with alanine/A, aspartic acid/D, lysine/K, glutamine/Q, and serine/S) were assessed for solution stability and chemical compatibility for 14 days. In general, peptide 4 exhibited very poor stability due to the presence of cysteine (FIGS. 12-21). After less than 1 day, the original P4 HPLC peak was not detected in the samples. By comparison, all mutants exhibited better stability. Most of these retained at least 50% of the original material for 14 days at 50° C. In general, peptide 4 mutants exhibit better stability at higher pH values (>7.0). Notably, p4-14s can regularly exhibit stability of 90% after 14 days, depending on conditions. All of the mutant peptides exhibited the hypersensitive response when infiltrated into tobacco leaves (as in example 1).

Example 4

Comparison of Peptide 1 and Peptide 4 Stability

Although peptide 1 and peptide 4 exhibit a high degree of sequence similarity, the stabilized mutants of peptide 4 are more stable than the p1 mutants. A series of mutations of p1 were made to confer stability similar to p4-14s. These are: p1-1S (SEQ ID NO: 109, Table 1), p1-14S (SEQ ID NO: 110, Table 1), p1-18Q (SEQ ID NO: 115, Table 1), p1-23P (SEQ ID NO: 118, Table 1). These peptides, along with p1 and p4-14s, were dissolved in 30% isopropanol, 5 mM DTPA, and 50 mM TES pH 8.0 and tested for stability at 50 C. Similar stability was observed for p4-14S and p1-1S, indicating that the N-terminal amino acid exhibits a strong effect on peptide stability.

Example 5

Solubility for P15b and Mutants

Initial results suggest that p15b has solubility problems. It has a relatively high hydrophobicity (0.19). At 0.2% w/v, it was partially soluble in water, insoluble in 50 mM of each of citrate pH ~5.2, citrate pH 7.0, phosphate pH 7.0 (check), TES pH 8.0, EDTA pH 8.0, and EDDS pH 7.0. It was at least partially soluble in 50 mM IVIES pH 6.0, and MOPS pH 6.5. However, P15a dissolves more easily in aqueous solutions. Its solubility is >10 mg/ml in 50 mM TES pH 8.0. Additional p15 variants were synthesized that included poly-glutamate solubility tags (p15-59G and p15-59, SEQ ID NOS: 149 and 150, respectively). When p15-59 was dissolved in 50 mM TES, pH 8.0, it exhibited solubility >10 mg/ml (1% w/v).

Example 6

Stability of P17/P18 & Variants

Figure 24:
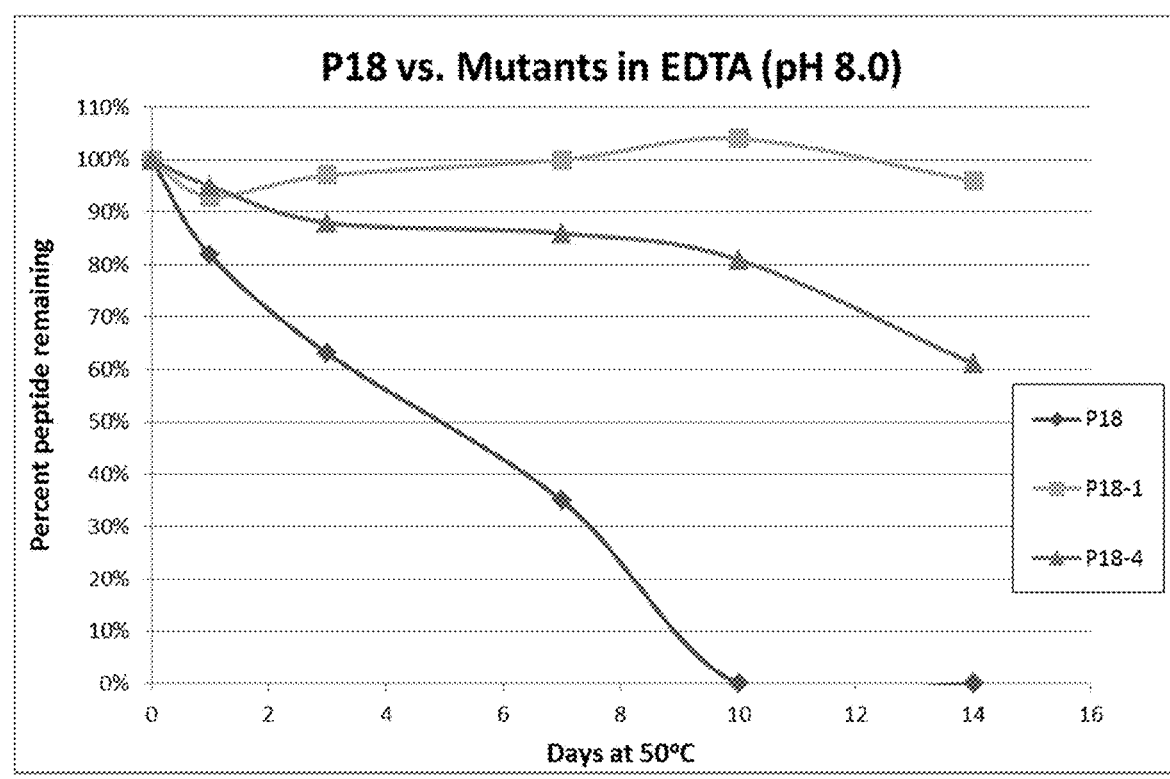
FIG. 24 shows a solubility and stability test of peptide P18 and P18 mutants dissolved in 50 mM EDTA, pH 8. The following peptides are shown: P18 (SEQ ID NO: 83), P18-1 (SEQ ID NO: 163), and P18-4 (SEQ ID NO: 164).

As described above, P18 (SEQ ID NO: 83) was tested for stability and chemical compatibility with different pH buffers. P18 exhibits relatively poor stability in aqueous buffer solutions at 50° C. Most samples degraded to 20% of original concentration in 3 days. One exception is a 50 mM EDTA solution, which degrades to 35% after 7 days (FIG. 24). Mutation of the methionine at position 12 to leucine (in P18-4, SEQ ID NO: 164) causes moderate stabilization: 60% stability after 14 days. Notably, truncation of the last 3 amino acids from the C-terminus (P18-1, SEQ ID NO: 163) also leads to dramatically increased stability (>90% stability over the 14-day trial).

Example 7

Stability of P19 & Variants

Figure 25:
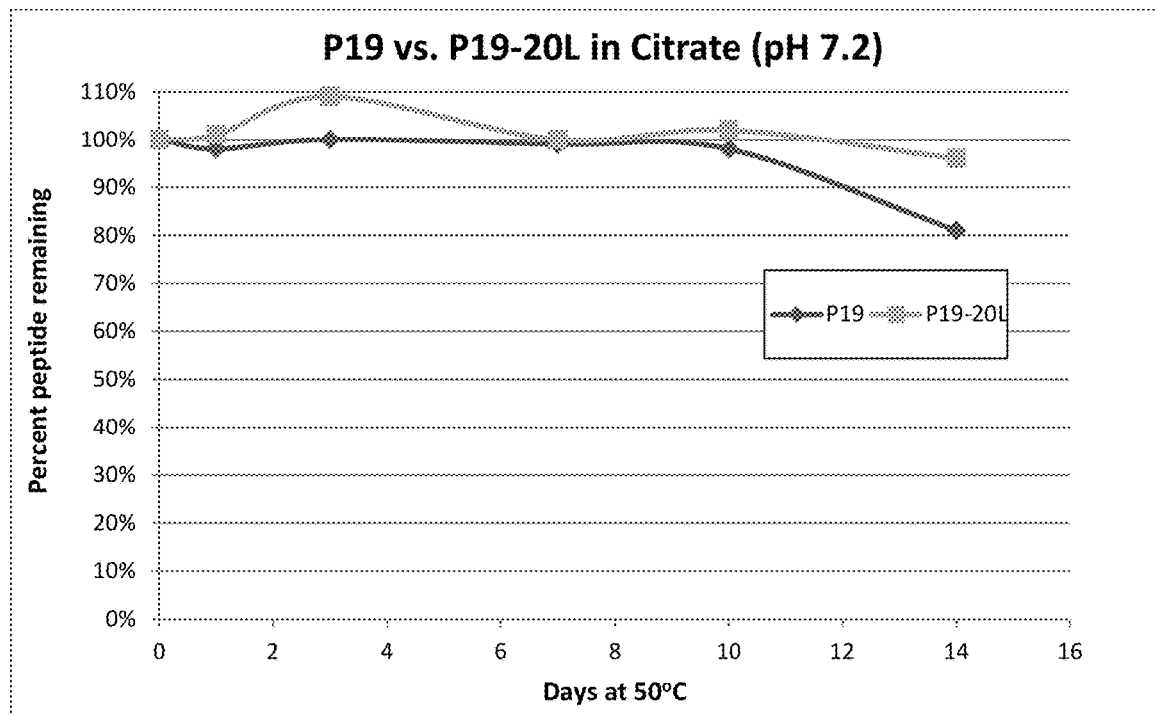
FIG. 25 shows a stability test of peptide P19 (SEQ ID NO: 89) and P19-20L (SEQ ID NO: 90) mutant dissolved in 50 mM citrate, pH 7.2.
Figure 26:
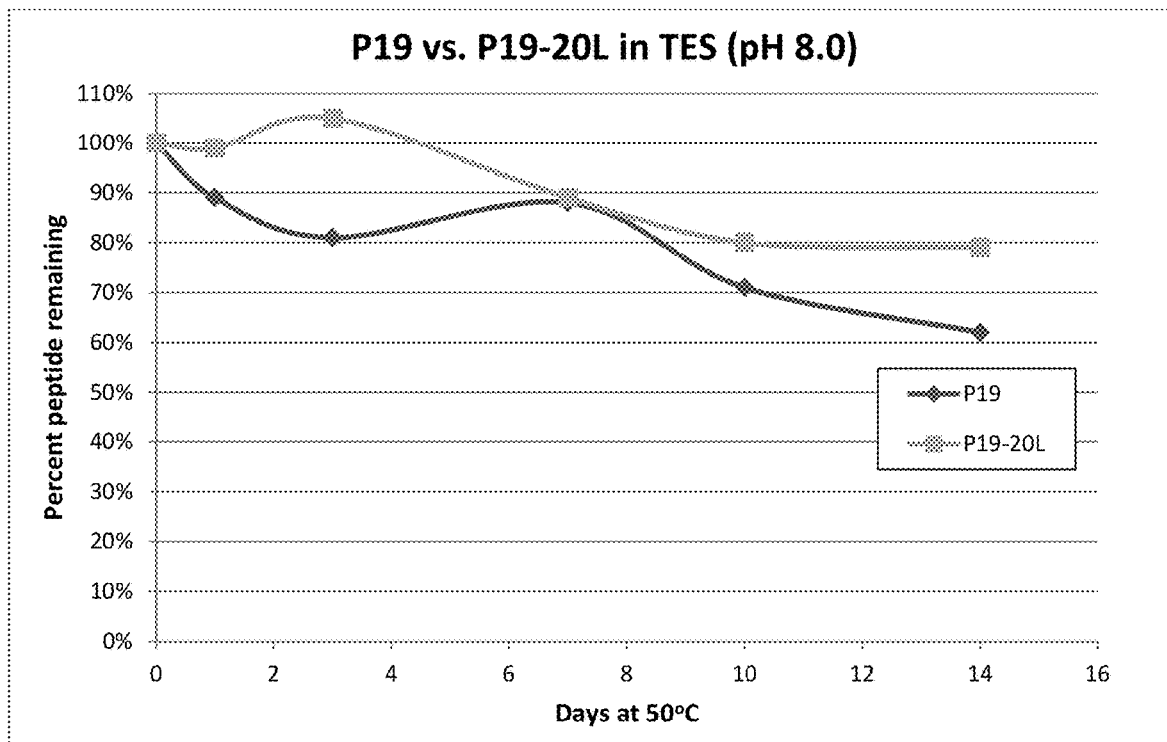
FIG. 26 shows a stability test of peptide P19 (SEQ ID NO: 89) and P19-20L (SEQ ID NO: 90) mutant dissolved in 50 mM TES, pH 8.0.

In general, P19 (SEQ ID NO: 89) exhibits relatively high stability, >80% stability over 14 days at 50° C. under a variety of conditions. The exceptions were peptide dissolved in water alone (52%) or 50 mM TES pH 8.0 (62%). Mutation of its one methionine residue at position 12 to leucine (P19-20L, SEQ ID NO: 90) leads to a modest increase in stability when dissolved in 50 mM citrate pH 7.2 or 50 mM TES, pH 8.0 (FIGS. 25 and 26). When using buffers at lower pH (5.5-7.0), the performance of P19 and P19-20L was observed to be similar; more than 80% peptide was retained for 14 days.

Example 8

P14d, P14e, P14f Stability

P14d sequence (SEQ ID NO: 175) is derived from the popA sequence of *Ralstonia solanacearum*. It conforms to the HR-box motif and causes HR in tobacco leaves. Mutation of the methionine residues generated the stabilized peptides P14e (SEQ ID NO: 176) and P14f (SEQ ID NO: 177). The mutated peptides exhibit >85% stability for >50 days at 50° C. (in 50 mM TES, pH 8.0 and 30% isopropanol). During the same period of time, P14d exhibits around 50% chemical stability.

Example 9

Growth Tests

For growth tests, corn and soy seeds were planted in flats with 2 seeds per cell within the flat at a greenhouse facility. The seeds were allowed to germinate and the smaller plant is culled, leaving one plant per cell. Once the first true leaves are fully expanded and the second leaves are beginning to expand, the plants were initially measured for height. This was performed by stretching the highest leaf upward and measuring the distance to the soil. Peptides were dissolved in water at the indicated concentrations (below). The plants were then treated with a foliar spray using widely available spray bottles until liquid was dripping from the leaves. 4 flats of 14 plants each were treated per condition (peptide or control). Corn and soy were treated as indicated in Table 13 and compared with matched water-treated control plants. The plants were allowed to grow for 14 days. The height of the plants was again measured and compared to the original height to quantify growth. In some cases, the plants were allowed to grow without watering for 2-4 days until the onset of wilting and drought stress. At this time, the above-ground portions of the plants were harvested and weighed to determine the fresh mass. Finally, the above-ground material was dried at 70° C. for 48 hours and weighed to determine dry biomass. The results of these growth trials are shown in Table 13. Growth, dry biomass, and fresh mass are calculated as the % increase over the water-treated control.

TABLE 13

Growth Trial Results

| Peptide | SEQ ID NO: | Rate | Host | Growth (% difference) | Dry biomass (% difference) | Fresh mass (% difference) |
|---|---|---|---|---|---|---|
| P15a | 63 | 0.2 | Corn | 6.0 | 5.0 | N.D. |
| P15b | 49 | 0.2 | Corn | 0.9 | 2.0 | 13.9 |
| P18 | 83 | 0.2 | Corn | 15.0 | 9.0 | N.D. |
| P18 | 83 | 0.2 | Soy | 18.0 | 15.0 | N.D. |
| P19 | 89 | 0.2 | Soy | 18.0 | 12.6 | N.D. |
| P25 | 182 | 5.0 | Corn | 7.0 | 11.0 | N.D. |
| P25 | 182 | 0.2 | Soy | 10.0 | 2.0 | N.D. |
| P4-14s-18E | 191 | 2.0 | Soy | 9.0 | 0.8 | N.D. |
| P30-3 | 190 | 0.2 | Corn | 8.7 | 8.0 | 13.4 |
| P25-11 | 188 | 0.2 | Corn | 4.1 | 4.7 | 1.6 |
| P25-11 | 188 | 5 | Corn | 1.0 | 6.2 | 10.9 |

N.D. = Not determined.

Several of the tested peptides exhibit growth and/or biomass increases in corn and soy. Notably, although P15b did not cause an overt growth or dry biomass phenotype, it did cause an increase in fresh biomass, which is suggestive of increased water uptake or retention. This is an indication of drought tolerance in those treated plants. Another peptide, P30-3, was observed to cause an increase in growth, fresh mass, and dry biomass.

Example 10

Minimal Sequences Required for HR Response

After determining the residues most critical for hypersensitive response elicitation, we designed additional mutants to verify the smallest peptide sequence responsible for this behavior. Due to the hydrophobic nature of the core HR sequence (containing 7 leucine or isoleucine residues in 13 residues total), it was recognized that solubility would be a problem for the minimal peptide. As a result, hydrophilic sequences were added to many peptides to bring the hydrophobicity on the Kyte-Doolittle scale to around −0.2 for the peptides.

Initially, a poly-lysine or poly-arginine sequence was used, i.e., P4 having an N-linked polyR or polyK sequence, or a C-linked polyR or polyK sequence (SEQ ID NOS: 35, 36, 38, 39). However, when infiltrated into tobacco leaves, these peptides caused necrotic lesions not typical of HR. This led to the hypothesis that poly-cationic sequences cause a toxic response when infiltrated into tobacco leaves. When poly-lysine and poly-arginine alone was infiltrated into the leaf, a similar necrotic lesion was observed. As a result, testing of peptides containing cationic solubility enhancing sequences was discontinued. Notably, HR+ peptides can contain at least one or two cationic amino acids, but larger numbers of positive charges appear to be detrimental. As a substitute for cationic peptides, polyanions were considered, specifically poly-glutamate. Poly-glutamate was chosen since aspartate has a greater chance of isomerizing to iso-aspartate, and serine was added at the N-terminus to eliminate the formation of pyroglutamic acid at the N-terminus of the peptide. It is also reasonable to add glutamate residues at the C-terminal end of the peptide.

The hypersensitive response test was run as described in example #1. For P4, the smallest variant peptide that elicited HR was P4-polyE-min3 (SEQ ID NO: 33). For P1, the smallest variant peptide that elicited HR was P1-polyE-min3 (SEQ ID NO: 141). For P18, the smallest variant peptide that elicited HR was P18-7 (SEQ ID NO: 167). For P19, the smallest variant peptide that elicited HR was P19-8 (SEQ ID NO: 173). For P15, the smallest variant peptide that elicited HR was P15-59 (SEQ ID NO: 150). For P14d, the smallest variant peptide that elicited HR was P14-30 (SEQ ID NO: 178). For P25, the smallest variant peptide that elicited HR was P25-11 (SEQ ID NO: 188). In addition, minimal peptide sequences were generated incorporating the leucine repeat sequence characteristic of the HR-box and glutamic acid residues in the variable positions to increase solubility. These sequences are: P30-2 (SEELEELLEELIEELL, SEQ ID NO: 189), P30-3 (LEELLEELIEELLEE, SEQ ID NO: 190), and P30-4 (LEELLEELIEELL, SEQ ID NO: 210). These minimal HR-box sequences were soluble >5 mg/ml in 50 mM TES and produced an HR response when infiltrated into tobacco leaves.

Likewise, additional peptides were developed for enhanced solubility based on the hydrophobic backbone sequences of P3, P25, P14, P15, and P19. These are listed in Table 10, supra.

Based on the previously described behavior of harpins and HR+ peptides, it is expected that these new peptides will have wide-ranging bioactivity including inducing resistance to TMV, resistance to nematodes, increased stress and drought resistance, increased growth, and increased yield as described in PCT Application WO 01/98501 to Fan et al., which is hereby incorporated by reference in its entirety.

Example 11

Derivatives of Peptide P1 that Cause HR Response in Tobacco

HR tests (described in Example 1) were run on variants of P1 to determine the minimal sequence required for HR and to identify residues of importance. The following peptides of Table 14 were determined to be positive for HR:

TABLE 14

| Peptide Name | Sequence | SEQ ID NO: |
|---|---|---|
| P1 | NQGISEKQLDQLLTQLIMALLQQ | 4 |
| P1-allE, | NEGISEKELDELLTELIEALLQQ | 46 |
| P1-18T | NQGISEKQLDQLLTQLITALLQQ | 42 |
| P1-18E | NQGISEKQLDQLLTQLIEALLQQ | 43 |
| P1-18A | NQGISEKQLDQLLTQLIAALLQQ | 44 |
| P1-18K | NQGISEKQLDQLLTQLIKALLQQ | 45 |
| P1-1S | SQGISEKQLDQLLTQLIMALLQQ | 109 |
| P1-14S | NQGISEKQLDQLLSQLIMALLQQ | 110 |
| P1-18Q | NQGISEKQLDQLLTQLIQALLQQ | 115 |
| P1-23P | NQGISEKQLDQLLTQLIMALLQP | 118 |
| polyE-min3p1 | SEEEEELDQLLTQLIEALL | 141 |

Example 12

Derivatives of Peptide P3 that Cause HR Response in Tobacco

HR tests (described in Example 1) were run on variants of P3 to determine the minimal sequence required for HR and to identify residues of importance. The following peptides of Table 15 were determined to be positive for HR.

TABLE 15

| Peptide Name | Sequence | SEQ ID NO: |
|---|---|---|
| P3 | QNDDSTSGTDSTSDSSDPMQQLLKMFSEIMQSLFGDGQDGT | 204 |
| P3-3 | SDPMQQLLKMFSEIMQSLF | 205 |
| P3-4 | SEEELQQLLKLFSEILQSLF | 206 |
| P3-6 | SEEEEELQQLLKLFSEILQSL | 207 |
| P3-7 | SEEEEELQQLLKLFSEILQS | 208 |

It is notable that P3 seems to require a longer sequence than the minimal HR-box repeat for efficient HR elicitation. This may be due to the sub-optimal phenylalanine residues and the presence of only a single K residue to separate the hydrophobic residues (LLKLF in P3 and its variants) present in this sequence. However, it is important to note that additional hydrophobic residues are not strictly necessary, considering that P3-6 and P3-7 cause HR.

Example 13

Derivatives of Peptide P25 that Cause HR Response in Tobacco

HR tests (described in Example 1) were run on variants of P25 to determine the minimal sequence required for HR and to identify residues of importance. The following peptides of Table 16 were determined to be positive for HR.

TABLE 16

| Peptide Name | Sequence | SEQ ID NO: |
|---|---|---|
| P25 | GGLTLTGVLQKLMKILNAL | 182 |
| P25s | EDQGGLTLTGVLQKLMKILNAL | 183 |
| P25-4 | EDQGGLTLTGVLQKLMKILNALVQ | 181 |
| P25-10 | SEEEEELTLTGVLQKLLKILEAL | 187 |
| P25-11 | SEEEEELTGVLQKLLKILEAL | 188 |
| P25-15 | SEEEEELTLTGVLQKLLKILEA | 200 |
| P25-16 | SEEEEEVLQKLLKILEALV | 201 |
| P25-17 | SEEEEELQKLLKILEALVQ | 202 |

It is important to note that P25 variants seem to require more sequence than the minimal HR consensus (SEQ ID NO:93) to HR elicitation. This may be due to the presence of valine residues where leucine is preferred or due to the presence of a single hydrophilic residue between the hydrophobic repeats (LLKIL). Although we include P25-15, P25-16, and P25-17 as HR+, they exhibited a very weak hypersensitive response that only occurred in some tobacco plants at the highest application rate. Notably, the additional sequence content does not seem to require leucine/isoleucine/valine residues, as suggested by the biological response to P25-15.

Example 14

Derivatives of Peptide P14d that Cause HR Response in Tobacco

HR tests (described in Example 1) were run on variants of P14 to determine the minimal sequence required for HR and to identify residues of importance. The following peptides of Table 17 were determined to be positive for HR.

TABLE 17

| Peptide Name | Sequence | SEQ ID NO: |
|---|---|---|
| P14d | QDPMQALMQLLEDLVKLLK | 175 |
| P14e | QDPAQALLQLLEDLVKLLK | 176 |
| P14f | QDPAQALEQLLEDLVKLLK | 177 |
| P14c | QAGPQSANKTGNVDDANNQDPMQALMQLLEDLVKLLK | 199 |
| P14-30 | SEEEEEALEQLLEDLVKLLK | 178 |

It is important to note that P14d variants seem to require more sequence than the minimal HR consensus (SEQ ID NO: 93) to HR elicitation. In particular, the additional C-terminal lysine residue seems to be required for activity. This may be due to the presence of a single hydrophilic residue between the hydrophobic repeats (LVKLL).

Example 15

Derivatives of Peptides P15/P20 that Cause HR Response in Tobacco

HR tests (described in Example 1) were run on variants of P15/P20 to determine the minimal sequence required for HR and to identify residues of importance. The following peptides of Table 18 were determined to be positive for HR.

TABLE 18

| Peptide name | Sequence | SEQ ID NO: |
|---|---|---|
| P15a | NFGTPDSTVQNPQDASKPNDSQSNIAKLISALIMSLLQM | 63 |
| P15b | KPNDSQSNIAKLISALIMSLLQ | 49 |
| P20 | GTPDSTVQNPQDASKPNDSQSNIAKLIS_LIMSLL | 65 |
| P15-8D-18E | KPNDSQSDIAKLISALIESLLQ | 50 |
| P15-dN4 | SQSNIAKLISALIMSLLQ | 227 |
| P15a-39P | NFGTPDSTVQNPQDASKPNDSQSNIAKLISALIMSLLP | 143 |
| P15a-34Q | NFGTPDSTVQNPQDASKPNDSQSNIAKLISALIQSLLM | 144 |
| p15-59 | SEEEEEEIAKLISALIESLLE | 150 |

Example 16

Derivatives of Peptides P17/P18 that Cause HR Response in Tobacco

HR tests (described in Example 1) were run on variants of P17 and P18 to determine the minimal sequence required for HR and to identify residues of importance. The following peptides of Table 19 were determined to be positive for HR.

TABLE 19

| Peptide Name | Sequence | SEQ ID NO: |
|---|---|---|
| P17 | [*]QQPIDRQTIEQMAQLLAQLLKSLL | 81 |
| P18 | QQPIDRQTIEQMAQLLAQLLKSLLSPQ | 83 |
| P18-1 | QQPIDRQTIEQMAQLLAQLLKSLL | 163 |

TABLE 19-continued

| Peptide Name | Sequence | SEQ ID NO: |
|---|---|---|
| P18-2 | QQPIDRQTIEQLAQLLAQLLKSLL | 229 |
| P18-3 | QQPIDRQTIEQLAQLLAQLLKSLLSP | 228 |
| P18-4 | DRQTIEQLAQLLAQLLKSLLSP | 164 |
| P18-5 | QTIEQLAQLLAQLLKSLLSP | 165 |
| P18-6 | SEEEEEIEQLAQLLAQLLKSLL | 166 |

TABLE 19-continued

| Peptide Name | Sequence | SEQ ID NO: |
|---|---|---|
| P18-7 | SEEEEELAQLLAQLLKSLL | 167 |
| P18-10 | SEEEEELAELLAELLKSLL | 231 |

[*] = N-terminal sequence of TSSSPGLFQSGGDNGLGGHNANSALG

Example 17

Derivatives of Peptides P19 that Cause HR Response in Tobacco

HR tests (described in Example 1) were run on variants of P19 to determine the minimal sequence required for HR and to identify residues of importance. The following peptides of Table 20 were determined to be positive for HR.

TABLE 20

| Peptide Name | Sequence | SEQ ID NO: |
|---|---|---|
| P19 | ITPDGQGGGQIGDNPLLKAMLKLIA | 89 |
| P19-20L | ITPDGQGGGQIGDNPLLKALLKLIA | 90 |
| P19a | ITPDGQGGGQIGDNPLLKAMLKLIARMMDG | 91 |
| P19a-allL | ITPDGQGGGQIGDNPLLKALLKLIARLLDG | 92 |
| P19-4 | QGGGQIGDNPLLKAMLKLIARMMDG | 226 |
| P19-7 | SEEEEELLKALLKLIARLL | 172 |
| P19-8 | SEEEELKALLKLIARLL | 173 |
| P19-11 | SEEEEEIGDNPLLKALLKLIARLL | 171 |

It is important to note that although P19 and P19-1 exhibit HR, they do not completely conform to the consensus HR-box sequence (SEQ ID NO: 93). However, the addition of context sequence in P19-2 and P19-3 leads to a sequence that does conform to the consensus. It is likely that the additional isoleucine residues in P19, and P19-1 (N-terminal isoleucine and the IGDN sequence) increase the propensity for HR elicitation.

Example 18

Induced Resistance of Tobacco to Infection with Tobacco Mosaic Virus

Peptides were tested for the induction of resistance to tobacco mosaic virus (TMV) in tobacco. Briefly, three tobacco plants at 6-8 weeks old were selected per group (samples and controls). The bottom-most leaf of the plant was covered and the plant was sprayed with a solution of water (negative control), peptide, or Proact (positive control). The spray was applied until the leaves were fully wetted, indicated by liquid dripping from the leaves. The plants were then allowed to dry and the leaf covering was removed.

Three days post-treatment, the previously-covered leaf and a leaf on the opposite side of the plant were then lightly dusted with diatomaceous earth and 20 ul of a 1.7 ug/ml solution of purified tobacco mosaic virus was applied. The TMV solution was then spread across the leaf surface by lightly rubbing solution and the diatomaceous earth across the surface of the leaves. Two minutes after inoculation, the diatomaceous earth was rinsed off the leaves with water. 3 days after TMV inoculation, the leaves were scored based on the number of TMV lesions observed. The leaf was also scored for signs of the hypersensitive response, including yellowing and wilting of the affected leaves.

Effectiveness described in Table 21 refers to the % decline in TMV lesions on treated vs UTC plants. A reduction of TMV on covered leaves indicates a systemic immune response in the plant while reduction on uncovered leaves indicates a local response. Asterisks indicate that the P-value derived from a T-test was <0.05.

TABLE 21

Summary of TMV Resistance

| Peptide | SEQ ID NO: | Concentration (ug/ml) | Effectiveness Uncovered (%) | Effectiveness Covered (%) |
|---|---|---|---|---|
| P1 | 4 | 20 | 100* | 91* |
| P1-allE | 46 | 5 | 74* | 66* |
| polyE-min3p1 | 141 | 10 | 92* | 79* |
| P4 | 5 | 20 | 88* | 89* |
| P4-14S | 6 | 20 | 80* | 97* |
| polyE-min3p4 | 33 | 10 | 88* | 86* |
| P6 | 68 | 20 | 99* | 93* |
| P6a | 67 | 20 | 72* | 58 |
| P14d | 175 | 5 | 93* | 96* |
| P14e | 176 | 10 | 90 | 79* |
| P14f | 177 | 10 | 72 | 86* |
| P14-30 | 178 | 10 | 74 | 25 |
| P15 | 64 | 10 | 95* | 72* |
| P15a | 63 | 10 | 88 | 55 |
| P18 | 83 | 5 | 63* | 80* |
| P18-6 | 166 | 10 | 69* | 86* |
| P18-7 | 167 | 20 | 15* | 30* |
| P18-10 | 231 | 20 | 84* | 87* |
| P19 | 89 | 5 | 79* | 90* |
| P19-7 | 172 | 10 | 88* | 82* |
| P19-8 | 173 | 20 | 74* | 77* |
| P25 | 182 | 20 | 94* | 94* |
| P25-11 | 188 | 10 | 100* | 97* |
| P30-2 | 189 | 10 | 94* | 65* |
| P30-3 | 190 | 10 | 95* | 95* |

In general, peptides that elicit a hypersensitive response in tobacco also confer a strong resistance to TMV. The peptides provided resistance in the leaves that received the treatment. However, the peptides also caused "system acquired resistance" whereby an immune response in one part of a plant triggers signaling that increases immunity in other parts of the plant. This was shown by the reduced TMV infection in covered leaves that did not directly receive the peptide treatment. Peptides that caused particularly strong immune responses included some of the minimal HR box peptide sequences: P14d, P25-11, and P30-3.

Example 19

Effect of Peptide Seed Treatment on Root and Shoot Growth

Peptides were tested for biological effects on the allocation of growth resources to the shoot (above ground) and root (below ground). Peptides were dissolved at 0.2, 2, or 5 μg/ml in a total volume of 100 ml deionized water. Corn or soybean seeds were then soaked for one hour in the peptide solution. Untreated control (UTC) plants were soaked in deionized water. Clear plastic 300 ml beverage cups (Solo®, Dart Container Corporation) were prepared for planting by marking the bottom with a cross, dividing the bottom into four equal quadrants. The cups were then filled with Sunshine Mix #1 soil (SunGro Horticulture) sieved to ¼". 100 ml of water was added to the soil. Treated seeds were then planted by pressing the seed lightly into the top of the soil. The seeds were then covered with an additional 50 ml of loose soil. Seeds were allowed to germinate and grow for 12-14 days.

The length of the shoot was measured as the distance from the soil to the lightly stretched tip of the highest leaf for each plant. Plants that failed to germinate or exhibited stunted growth were removed from the trial. Stunting was defined as lacking a fully expanded true leaf at time of data collection or having an expanded true leaf judged by eye to be <½ the average leaf area of the treatment group. Generally, 30 seeds were planted per treatment group and 15-25 plants were used for data collection.

Root growth was estimated by counting the number of times that a primary root crosses the quadrant marks on the bottom of the cup. These were often observed along the bottom circumference of the cup, although some were visible along the side of the container and were counted as if crossing a vertical extension of the quadrant line. This number was divided by 4 to produce a root growth index. This index was found to correlate ~90% with measured total primary root length (sum of lengths of all primary roots after rinsing soil from roots and measuring directly).

TABLE 22

Summary of Root & Shoot Growth

| Peptide (Host) | SEQ ID NO: | Rate (µg/ml) | Root (%) | Shoot (%) |
|---|---|---|---|---|
| P4-14s (soy) | 6 | 0.2 | 13.5* | −0.1 |
| P14c (soy) | 199 | 5.0 | 14.4* | 9.0* |
| P15a (corn) | 63 | 0.2 | 14.2* | −4.5 |
| P15b (soy) | 49 | 5.0 | 34* | 15.6* |
| P18 (corn) | 83 | 2.0 | 7.7 | −2.0 |
| P30-3 (corn) | 190 | 0.2 | 15.4* | −0.7 |

TABLE 22-continued

Summary of Root & Shoot Growth

| Peptide (Host) | SEQ ID NO: | Rate (µg/ml) | Root (%) | Shoot (%) |
|---|---|---|---|---|
| P30-3 (soy) | 190 | 2.0 | −17.9* | 11.4* |
| P30-3 (soy) | 190 | 0.2 | 4.2 | 8.8* |
| P15-59 (corn) | 150 | 0.2 | 7.6 | −8.6* |
| P19-8 (corn) | 89 | 5.0 | 4.1 | −2.7 |

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed:

1. An isolated peptide that consists essentially of the amino acid sequence of
(L/M)XXLLXXLLXXLL (SEQ ID NO: 25), wherein
X at position 2 can be A, S, T, G, D, isoD, E, γ-glutamate, Q, N, K, or R;
X at position 3 can be Q, A, S, T, G, D, isoD, E, γ-glutamate, N, K, or R;
X at position 6 can be A, S, T, G, D, isoD, E, γ-glutamate, Q, N, K, or R;
X at position 7 can be Q, A, S, T, G, D, isoD, E, γ-glutamate, N, K, or R;
X at position 10 can be K, A, S, T, G, D, isoD, E, γ-glutamate, Q, N, or R; and
X at position 11 can be S, A, T, G, D, isoD, E, γ-glutamate, Q, N, K, or R;
wherein the isolated peptide does not comprise the amino acid sequence of LEELLEELLEELLEE (SEQ ID NO: 213) or TSSSPGLFQSGGDNGLGGHNANSALGQ-QPIDRQTIEQMAQLLAELLKSLL (SEQ ID NO: 162);
wherein the isolated peptide does not contain more than two cationic amino acid residues; and
wherein the isolated peptide, when introduced onto mechanically wounded plant leaf tissue, induces a hypersensitive response.

2. The isolated peptide according to claim 1, wherein the isolated peptide is either (i) more stable than the polypeptide of SEQ ID NO: 162 when dissolved in water or aqueous solution; or (ii) more resistant to chemical degradation than the polypeptide of SEQ ID NO: 162 when dissolved in an aqueous buffer solution containing a biocide.

3. The isolated peptide according to claim 1, wherein the peptide is at least 90% pure.

4. The isolated peptide according to claim 1, wherein the peptide is a fusion polypeptide comprising a second amino acid sequence coupled via peptide bond to the amino acid sequence.

5. The isolated peptide according to claim 4, wherein the second amino acid sequence includes a purification tag.

6. The isolated peptide according to claim 5, wherein the second amino acid sequence further includes a cleavable linker sequence between the purification tag and the amino acid sequence.

7. The isolated peptide according to claim 4, wherein the peptide is a fusion polypeptide comprising a first amino acid sequence for said peptide linked to a second amino acid sequence for said peptide.

8. A fusion polypeptide comprising a plurality of amino acid sequences linked together in series, one of the plurality of amino acid sequences consisting essentially of the peptide according to claim 1.

9. A composition comprising one or more peptides according to claim 1 and a carrier.

10. The composition according to claim 9, wherein the composition is a clarified cell extract.

11. The composition according to claim 9 further comprising an additive selected from the group consisting of fertilizer, herbicide, insecticide, fungicide, nematicide, a bactericidal agent, a biological inoculant, a plant regulator, and mixtures thereof.

12. The composition according to claim 11, wherein the additive comprises either:
(i) clothianidin, a combination of clothianidin and *Bacillus firmus*, imidicloprid, or a combination of imidicloprid and *Bacillus firmus*; or
(ii) thiamethoxam; a combination of thiamethoxam, mefenoxam, and fludioxynil; a combination of thiamethoxam, mefenoxam, fludioxynil and azoxystrobin; a combination of thiamethoxam and abamectin; a combination of thiamethoxam, abamectin, and a Pasteuria nematicide; or a combination of thiamethoxam, mefenoxam, fludioxynil, azoxystrobin, thiabendazole, and abamectin; or (iii) a biological inoculant comprising a *Bradyrhizobium* spp., a *Bacillus* spp., or a combination of a *Bradyrhizobium* spp. and a *Bacillus* spp.

13. The composition according to claim 9, wherein the carrier is an aqueous carrier.

14. The composition according to claim 13, wherein the aqueous carrier further comprises one or more of a biocidal agent, a protease inhibitor, a non-ionic surfactant, or a combination thereof.

15. The composition according to claim 9, wherein the carrier is a solid carrier in particulate form.

16. The composition according to claim 15, wherein the solid carrier is a dry powder.

17. The isolated peptide according to claim 1 further comprising an arginine residue at the C-terminal end.

18. The isolated peptide according to claim 1, wherein
X at position 2 is A, S, T, G, D, isoD, E, γ-glutamate, Q, or N;
X at position 3 is Q, A, S, T, G, D, isoD, E, γ-glutamate, or N;
X at position 6 is A, S, T, G, D, isoD, E, γ-glutamate, Q, or N;
X at position 7 is Q, A, S, T, G, D, isoD, E, γ-glutamate, or N;
X at position 10 is A, S, T, G, D, isoD, E, γ-glutamate, Q, or N; and
X at position 11 is S, A, T, G, D, isoD, E, g-glutamate, Q, or N.

19. A method of imparting disease resistance to plants comprising:
applying an effective amount of an isolated peptide according to claim 1 to a plant or plant seed or the locus where the plant is growing or is expected to grow, wherein said applying is effective to impart disease resistance.

20. A method of enhancing plant growth comprising:
applying an effective amount of an isolated peptide according to claim 1 to a plant or plant seed or the locus where the plant is growing or is expected to grow, wherein said applying is effective to enhance plant growth.

21. A method of increasing a plant's tolerance to biotic stress comprising:
applying an effective amount of an isolated peptide according to claim 1 to a plant or plant seed or the locus where the plant is growing or is expected to grow, wherein said applying is effective to increase the plant's tolerance to biotic stress factors selected from the group consisting of insects, arachnids, nematodes, weeds, and combinations thereof.

22. A method of increasing a plant's tolerance to abiotic stress comprising:
applying an effective amount of an isolated peptide according to claim 1 to a plant or plant seed or the locus where the plant is growing or is expected to grow, wherein said applying is effective to increase the plant's tolerance to abiotic stress factors selected from the group consisting of salt stress, water stress, ozone stress, heavy metal stress, cold stress, heat stress, nutritional stress, and combinations thereof.

23. An isolated peptide that consists essentially of the amino acid sequence of (L/M)XXLLXXLLXXLL (SEQ ID NO: 25) wherein
X at positions 2, 3, 6, 7, 10, and 11 are independently selected from the group consisting of A, S, T, G, D, isoD, E, γ-glutamate, Q, N, K, and R;
the peptide further comprises a solubility tag sequence, located N- or C-terminal of SEQ ID NO: 25, whereby the peptide has an average Kyte-Doolittle hydropathy index of less than 0.3;
the isolated peptide does not contain more than two cationic amino acid residues;
the isolated peptide does not comprise the amino acid sequence of LEELLEELLEELLEE (SEQ ID NO: 213); and
wherein the isolated peptide, when introduced onto mechanically wounded plant leaf tissue, induces a hypersensitive response.

24. The isolated peptide according to claim 23, wherein X at positions 2, 3, 6, 7, 10, and 11 are independently selected from the group consisting of A, S, T, G, D, isoD, E, γ-glutamate, Q, and N.

25. The isolated peptide according to claim 24, wherein the isolated peptide further comprises a C-terminal Arg or Lys residue.

26. An isolated peptide selected from the group consisting of:
(i) a peptide that is up to 50 amino acids in length and comprises the amino acid sequence of one of SEQ ID NOS: 81-88, 119, 163-167, 228, 229, and 231 and
(ii) a peptide that comprises the amino acid sequence of one of SEQ ID NOs: 81-88, 119, 163-167, 228, 229, and 231, except that (i) any lysine or arginine residues are changed to glutamate and (ii) an arginine residue is introduced at the C-terminal end of the peptide.

27. The isolated peptide according to claim 26, wherein the isolated peptide comprises the amino acid sequence of QQPIDRQTIEQMAQLLAQLLKSLLSPQ (SEQ ID NO: 83).

28. The isolated peptide according to claim 27, wherein the isolated peptide comprises the amino acid sequence of QQPIDRQTIEQMAQLLAQLLKSLLSPQ (SEQ ID NO: 83) except that the Arg residue at position 6 and the Lys residue at position 21 are changed to Glu, and an Arg residue is introduced at the C-terminal end.

29. The isolated peptide according to claim 26, wherein the isolated peptide comprises the amino acid sequence of one of SEQ ID NOS: 81-88, 119, 163-167, 228, 229, and 231.

30. The isolated peptide according to claim 1, wherein the peptide has an average Kyte-Doolittle hydropathy index of less than 0.3.

31. The isolated peptide according to claim 1, wherein the peptide has an average Kyte-Doolittle hydropathy index of less than 0.1.

32. The isolated peptide according to claim 23, wherein the peptide has an average Kyte-Doolittle hydropathy index of less than 0.1.

33. A fusion polypeptide comprising a plurality of amino acid sequences linked together in series, one of the plurality of amino acid sequences comprising the peptide according to claim 23.

34. A composition comprising one or more peptides according to claim 23 and a carrier.

35. A method of imparting disease resistance to plants comprising: applying an effective amount of an isolated peptide according to claim 23 to a plant or plant seed or the locus where the plant is growing or is expected to grow, wherein said applying is effective to impart disease resistance.

36. A method of enhancing plant growth comprising: applying an effective amount of an isolated peptide according to claim 23 to a plant or plant seed or the locus where the plant is growing or is expected to grow, wherein said applying is effective to enhance plant growth.

37. A method of increasing a plant's tolerance to biotic stress comprising:
applying an effective amount of an isolated peptide according to claim 23 to a plant or plant seed or the locus where the plant is growing or is expected to grow, wherein said applying is effective to increase the plant's tolerance to biotic stress factors selected from the group consisting of insects, arachnids, nematodes, weeds, and combinations thereof.

38. A method of increasing a plant's tolerance to abiotic stress comprising:
applying an effective amount of an isolated peptide according to claim 23 to a plant or plant seed or the locus where the plant is growing or is expected to grow, wherein said applying is effective to increase the plant's tolerance to abiotic stress factors selected from the group consisting of salt stress, water stress, ozone stress, heavy metal stress, cold stress, heat stress, nutritional stress, and combinations thereof.

39. A fusion polypeptide comprising a plurality of amino acid sequences linked together in series, one of the plurality of amino acid sequences comprising the peptide according to claim 26.

40. A composition comprising one or more peptides according to claim 26 and a carrier.

41. A method of imparting disease resistance to plants comprising: applying an effective amount of an isolated peptide according to claim 26 to a plant or plant seed or the locus where the plant is growing or is expected to grow, wherein said applying is effective to impart disease resistance.

42. A method of enhancing plant growth comprising: applying an effective amount of an isolated peptide according to claim 26 to a plant or plant seed or the locus where the plant is growing or is expected to grow, wherein said applying is effective to enhance plant growth.

43. A method of increasing a plant's tolerance to biotic stress comprising:
applying an effective amount of an isolated peptide according to claim 26 to a plant or plant seed or the locus where the plant is growing or is expected to grow, wherein said applying is effective to increase the plant's tolerance to biotic stress factors selected from the group consisting of insects, arachnids, nematodes, weeds, and combinations thereof.

44. A method of increasing a plant's tolerance to abiotic stress comprising:
applying an effective amount of an isolated peptide according to claim 26 to a plant or plant seed or the locus where the plant is growing or is expected to grow, wherein said applying is effective to increase the plant's tolerance to abiotic stress factors selected from the group consisting of salt stress, water stress, ozone stress, heavy metal stress, cold stress, heat stress, nutritional stress, and combinations thereof.

* * * * *

SEQUENCE LISTING

```
<160> NUMBER OF SEQ ID NOS: 232

<210> SEQ ID NO 1
<211> LENGTH: 23
<212> TYPE: PRT
<213> ORGANISM: Artificial
<220> FEATURE:
<223> OTHER INFORMATION: P1/P4 consensus
<220> FEATURE:
<221> NAME/KEY: MISC_FEATURE
<222> LOCATION: (1)..(1)
<223> OTHER INFORMATION: X at position 1 is optional, S, N, D, isoD, G,
      A, or S
<220> FEATURE:
<221> NAME/KEY: MISC_FEATURE
<222> LOCATION: (2)..(2)
<223> OTHER INFORMATION: X at position 2 is optional, Q, E, g-glutamate,
      G, A, or S
<220> FEATURE:
<221> NAME/KEY: MISC_FEATURE
<222> LOCATION: (8)..(8)
<223> OTHER INFORMATION: X at position 8 is Q, E, g-glutamate, G, A, or
      S
<220> FEATURE:
<221> NAME/KEY: MISC_FEATURE
<222> LOCATION: (9)..(9)
<223> OTHER INFORMATION: X at position 9 is L, I, F, or V
<220> FEATURE:
<221> NAME/KEY: MISC_FEATURE
<222> LOCATION: (10)..(10)
<223> OTHER INFORMATION: X at position 10 is optional, D or isoD
<220> FEATURE:
<221> NAME/KEY: MISC_FEATURE
<222> LOCATION: (11)..(11)
<223> OTHER INFORMATION: X at position 11 is Q, E, g-glutamate, G, A, or
      S
<220> FEATURE:
<221> NAME/KEY: MISC_FEATURE
<222> LOCATION: (12)..(12)
<223> OTHER INFORMATION: X at position 12 is M, L, I, or F
<220> FEATURE:
<221> NAME/KEY: MISC_FEATURE
<222> LOCATION: (13)..(13)
<223> OTHER INFORMATION: X at position 13 is M, L, I
<220> FEATURE:
```

```
<221> NAME/KEY: MISC_FEATURE
<222> LOCATION: (14)..(14)
<223> OTHER INFORMATION: X at position 14 is optional, any hydrophilic
      amino acid, preferably C, S, T, A, D, isoD, K, or Q
<220> FEATURE:
<221> NAME/KEY: MISC_FEATURE
<222> LOCATION: (15)..(15)
<223> OTHER INFORMATION: X at position 15 is Q, E, g-glutamate, G, A, S,
      K, or I
<220> FEATURE:
<221> NAME/KEY: MISC_FEATURE
<222> LOCATION: (16)..(16)
<223> OTHER INFORMATION: X at position 16 is M, L, I, V, F
<220> FEATURE:
<221> NAME/KEY: MISC_FEATURE
<222> LOCATION: (17)..(17)
<223> OTHER INFORMATION: X at position 17 is M, L, I, A, or V
<220> FEATURE:
<221> NAME/KEY: MISC_FEATURE
<222> LOCATION: (18)..(18)
<223> OTHER INFORMATION: X at position 18 is Q, E, g-glutamate, G, A, S,
      M, T, or K
<220> FEATURE:
<221> NAME/KEY: MISC_FEATURE
<222> LOCATION: (19)..(19)
<223> OTHER INFORMATION: X at position 19 is A, D, isoD, S, V, T, K, R,
      E, H, or G
<220> FEATURE:
<221> NAME/KEY: MISC_FEATURE
<222> LOCATION: (20)..(20)
<223> OTHER INFORMATION: X at position 20 is M, L, or I
<220> FEATURE:
<221> NAME/KEY: MISC_FEATURE
<222> LOCATION: (21)..(21)
<223> OTHER INFORMATION: X at position 21 is M, L, I, V, S, or F
<220> FEATURE:
<221> NAME/KEY: MISC_FEATURE
<222> LOCATION: (22)..(22)
<223> OTHER INFORMATION: X at position 22 is Q, E, g-glutamate, G, A, or
      S
<220> FEATURE:
<221> NAME/KEY: MISC_FEATURE
<222> LOCATION: (23)..(23)
<223> OTHER INFORMATION: X at position 23 is P, Q, E, g-glutamate, G, A,
      or S

<400> SEQUENCE: 1

Xaa Xaa Gly Ile Ser Glu Lys Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 2
<211> LENGTH: 23
<212> TYPE: PRT
<213> ORGANISM: Artificial
<220> FEATURE:
<223> OTHER INFORMATION: P4 consensus
<220> FEATURE:
<221> NAME/KEY: MISC_FEATURE
<222> LOCATION: (2)..(2)
<223> OTHER INFORMATION: X at position 2 is Q, E, g-glutamate, G, A, or
      S
<220> FEATURE:
<221> NAME/KEY: MISC_FEATURE
<222> LOCATION: (8)..(8)
<223> OTHER INFORMATION: X at position 8 is Q, E, g-glutamate, G, A, or
      S
<220> FEATURE:
<221> NAME/KEY: MISC_FEATURE
<222> LOCATION: (9)..(9)
<223> OTHER INFORMATION: X at position 9 is L, A, D, isoD, I, F, or V
<220> FEATURE:
<221> NAME/KEY: MISC_FEATURE
<222> LOCATION: (11)..(11)
<223> OTHER INFORMATION: X at position 11 is Q, E, g-glutamate, G, A, or
```

```
                                                S
<220> FEATURE:
<221> NAME/KEY: MISC_FEATURE
<222> LOCATION: (12)..(12)
<223> OTHER INFORMATION: X at position 12 is L, D, isoD, I, or F
<220> FEATURE:
<221> NAME/KEY: MISC_FEATURE
<222> LOCATION: (13)..(13)
<223> OTHER INFORMATION: X at position 13 is L, I, V, or F
<220> FEATURE:
<221> NAME/KEY: MISC_FEATURE
<222> LOCATION: (14)..(14)
<223> OTHER INFORMATION: X at position 14 is any hydrophilic amino acid,
      preferably C, S, or T
<220> FEATURE:
<221> NAME/KEY: MISC_FEATURE
<222> LOCATION: (15)..(15)
<223> OTHER INFORMATION: X at position 15 is Q, E, g-glutamate, G, A, S,
      K, or I
<220> FEATURE:
<221> NAME/KEY: MISC_FEATURE
<222> LOCATION: (16)..(16)
<223> OTHER INFORMATION: X at position 16 is L, A, I, V, M, or F
<220> FEATURE:
<221> NAME/KEY: MISC_FEATURE
<222> LOCATION: (17)..(17)
<223> OTHER INFORMATION: X at position 17 is I, S, or F
<220> FEATURE:
<221> NAME/KEY: MISC_FEATURE
<222> LOCATION: (18)..(18)
<223> OTHER INFORMATION: X at position 18 is Q, E, g-glutamate, G, A, S
<220> FEATURE:
<221> NAME/KEY: MISC_FEATURE
<222> LOCATION: (20)..(20)
<223> OTHER INFORMATION: X at position 20 is L, I, V, F
<220> FEATURE:
<221> NAME/KEY: MISC_FEATURE
<222> LOCATION: (21)..(21)
<223> OTHER INFORMATION: X at position 21 is L or F
<220> FEATURE:
<221> NAME/KEY: MISC_FEATURE
<222> LOCATION: (22)..(22)
<223> OTHER INFORMATION: X at position 22 is Q, E, g-glutamate, G, A, or
      S

<400> SEQUENCE: 2

Ser Xaa Gly Ile Ser Glu Lys Xaa Xaa Asp Xaa Xaa Xaa Xaa Xaa Xaa
1               5                   10                  15

Xaa Xaa Ala Xaa Xaa Xaa Pro
            20

<210> SEQ ID NO 3
<211> LENGTH: 23
<212> TYPE: PRT
<213> ORGANISM: Artificial
<220> FEATURE:
<223> OTHER INFORMATION: P1 consensus
<220> FEATURE:
<221> NAME/KEY: MISC_FEATURE
<222> LOCATION: (1)..(1)
<223> OTHER INFORMATION: X at position 1 is N, D, isoD, G, A, or S
<220> FEATURE:
<221> NAME/KEY: MISC_FEATURE
<222> LOCATION: (2)..(2)
<223> OTHER INFORMATION: X at position 2 is Q, E, g-glutamate, G, A, or
      S
<220> FEATURE:
<221> NAME/KEY: MISC_FEATURE
<222> LOCATION: (8)..(8)
<223> OTHER INFORMATION: X at position 8 is Q, E, g-glutamate, G, A, or
      S
<220> FEATURE:
<221> NAME/KEY: MISC_FEATURE
<222> LOCATION: (11)..(11)
<223> OTHER INFORMATION: X at position 11 is Q, E, g-glutamate, G, A, or
      S
```

```
<220> FEATURE:
<221> NAME/KEY: MISC_FEATURE
<222> LOCATION: (15)..(15)
<223> OTHER INFORMATION: X at position 15 is Q, E, g-glutamate, G, A, S
<220> FEATURE:
<221> NAME/KEY: MISC_FEATURE
<222> LOCATION: (18)..(18)
<223> OTHER INFORMATION: X at position 18 is M, T, K, E, g-glutamate, G,
      A, or S
<220> FEATURE:
<221> NAME/KEY: MISC_FEATURE
<222> LOCATION: (22)..(22)
<223> OTHER INFORMATION: X at position 22 is Q, E, g-glutamate, G, A, or
      S
<220> FEATURE:
<221> NAME/KEY: MISC_FEATURE
<222> LOCATION: (23)..(23)
<223> OTHER INFORMATION: X at position 23 is Q, E, g-glutamate, G, A, or
      S

<400> SEQUENCE: 3

Xaa Xaa Gly Ile Ser Glu Lys Xaa Leu Asp Xaa Leu Leu Thr Xaa Leu
1               5                   10                  15

Ile Xaa Ala Leu Leu Xaa Xaa
            20

<210> SEQ ID NO 4
<211> LENGTH: 23
<212> TYPE: PRT
<213> ORGANISM: Artificial
<220> FEATURE:
<223> OTHER INFORMATION: synthetic peptide

<400> SEQUENCE: 4

Asn Gln Gly Ile Ser Glu Lys Gln Leu Asp Gln Leu Leu Thr Gln Leu
1               5                   10                  15

Ile Met Ala Leu Leu Gln Gln
            20

<210> SEQ ID NO 5
<211> LENGTH: 23
<212> TYPE: PRT
<213> ORGANISM: Artificial
<220> FEATURE:
<223> OTHER INFORMATION: synthetic peptide

<400> SEQUENCE: 5

Ser Gln Gly Ile Ser Glu Lys Gln Leu Asp Gln Leu Leu Cys Gln Leu
1               5                   10                  15

Ile Gln Ala Leu Leu Gln Pro
            20

<210> SEQ ID NO 6
<211> LENGTH: 23
<212> TYPE: PRT
<213> ORGANISM: Artificial
<220> FEATURE:
<223> OTHER INFORMATION: synthetic peptide

<400> SEQUENCE: 6

Ser Gln Gly Ile Ser Glu Lys Gln Leu Asp Gln Leu Leu Ser Gln Leu
1               5                   10                  15

Ile Gln Ala Leu Leu Gln Pro
            20

<210> SEQ ID NO 7
<211> LENGTH: 23
```

```
<212> TYPE: PRT
<213> ORGANISM: Artificial
<220> FEATURE:
<223> OTHER INFORMATION: synthetic peptide

<400> SEQUENCE: 7

Ser Gln Gly Ile Ser Glu Lys Gln Leu Asp Gln Leu Leu Ser Gln Leu
1               5                   10                  15

Ile Ser Ala Leu Leu Gln Pro
            20

<210> SEQ ID NO 8
<211> LENGTH: 23
<212> TYPE: PRT
<213> ORGANISM: Artificial
<220> FEATURE:
<223> OTHER INFORMATION: synthetic peptide

<400> SEQUENCE: 8

Ser Glu Gly Ile Ser Glu Lys Gln Leu Asp Gln Leu Leu Ser Gln Leu
1               5                   10                  15

Ile Glu Ala Leu Leu Gln Pro
            20

<210> SEQ ID NO 9
<211> LENGTH: 23
<212> TYPE: PRT
<213> ORGANISM: Artificial
<220> FEATURE:
<223> OTHER INFORMATION: synthetic peptide

<400> SEQUENCE: 9

Ser Glu Gly Ile Ser Glu Lys Glu Leu Asp Gln Leu Leu Ser Gln Leu
1               5                   10                  15

Ile Gln Ala Leu Leu Gln Pro
            20

<210> SEQ ID NO 10
<211> LENGTH: 23
<212> TYPE: PRT
<213> ORGANISM: Artificial
<220> FEATURE:
<223> OTHER INFORMATION: synthetic peptide

<400> SEQUENCE: 10

Ser Glu Gly Ile Ser Glu Lys Glu Leu Asp Gln Leu Leu Ser Glu Leu
1               5                   10                  15

Ile Gln Ala Leu Leu Gln Pro
            20

<210> SEQ ID NO 11
<211> LENGTH: 23
<212> TYPE: PRT
<213> ORGANISM: Artificial
<220> FEATURE:
<223> OTHER INFORMATION: synthetic peptide

<400> SEQUENCE: 11

Ser Glu Gly Ile Ser Glu Lys Glu Leu Asp Glu Leu Leu Ser Glu Leu
1               5                   10                  15

Ile Glu Ala Leu Leu Gln Pro
            20

<210> SEQ ID NO 12
```

```
<211> LENGTH: 14
<212> TYPE: PRT
<213> ORGANISM: Artificial
<220> FEATURE:
<223> OTHER INFORMATION: P15/20 min consensus
<220> FEATURE:
<221> NAME/KEY: MISC_FEATURE
<222> LOCATION: (7)..(7)
<223> OTHER INFORMATION: X of position 7 is optional, any amino acid
<220> FEATURE:
<221> NAME/KEY: MISC_FEATURE
<222> LOCATION: (10)..(10)
<223> OTHER INFORMATION: X at position 10 is M, E, g-glutamate, G, A, S,
      T, or K
<220> FEATURE:
<221> NAME/KEY: MISC_FEATURE
<222> LOCATION: (14)..(14)
<223> OTHER INFORMATION: X at position 14 is optional, Q, E,
      g-glutamate, G, A, S

<400> SEQUENCE: 12

Ile Ala Lys Leu Ile Ser Xaa Leu Ile Xaa Ser Leu Leu Xaa
1               5                   10

<210> SEQ ID NO 13
<211> LENGTH: 19
<212> TYPE: PRT
<213> ORGANISM: Artificial
<220> FEATURE:
<223> OTHER INFORMATION: P14d consensus
<220> FEATURE:
<221> NAME/KEY: MISC_FEATURE
<222> LOCATION: (1)..(1)
<223> OTHER INFORMATION: X at position 1 is Q,N, D, E, g-glutamate,
      isoD, or S
<220> FEATURE:
<221> NAME/KEY: MISC_FEATURE
<222> LOCATION: (2)..(2)
<223> OTHER INFORMATION: X at position 2 can be D, E, g-glutamate, isoD
<220> FEATURE:
<221> NAME/KEY: MISC_FEATURE
<222> LOCATION: (3)..(3)
<223> OTHER INFORMATION: X at position 3 can be P, D, E, isoD, or
      g-glutamate
<220> FEATURE:
<221> NAME/KEY: MISC_FEATURE
<222> LOCATION: (4)..(4)
<223> OTHER INFORMATION: X at position 4 can be M, A, S, D, E, isoD, or
      g-glutamate
<220> FEATURE:
<221> NAME/KEY: MISC_FEATURE
<222> LOCATION: (5)..(5)
<223> OTHER INFORMATION: X at position 5 can be Q, E, or g-glutamate
<220> FEATURE:
<221> NAME/KEY: MISC_FEATURE
<222> LOCATION: (6)..(6)
<223> OTHER INFORMATION: X at position 6 can be A, E, or g-glutamate
<220> FEATURE:
<221> NAME/KEY: MISC_FEATURE
<222> LOCATION: (8)..(8)
<223> OTHER INFORMATION: X at position 8 can be M, L, E, Q, D, N, G, A,
      S, isoD, or g-glutamate
<220> FEATURE:
<221> NAME/KEY: MISC_FEATURE
<222> LOCATION: (9)..(9)
<223> OTHER INFORMATION: X at position 9 can be Q, N, E, D, G, A, S,
      isoD or, g-glutamate
<220> FEATURE:
<221> NAME/KEY: MISC_FEATURE
<222> LOCATION: (12)..(12)
<223> OTHER INFORMATION: X at position 12 can be Q, N, E, D, G, A, S,
      isoD or, g-glutamate
<220> FEATURE:
<221> NAME/KEY: MISC_FEATURE
<222> LOCATION: (13)..(13)
<223> OTHER INFORMATION: X at position 13 can be Q, N, E, D, G, A, S,
      isoD or, g-glutamate
```

-continued

```
<220> FEATURE:
<221> NAME/KEY: MISC_FEATURE
<222> LOCATION: (16)..(16)
<223> OTHER INFORMATION: X at position 16 can be K, Q, N, E, D, R, G, A,
      or S

<400> SEQUENCE: 13

Xaa Xaa Xaa Xaa Xaa Xaa Leu Xaa Xaa Leu Leu Xaa Xaa Leu Val Xaa
1               5                   10                  15

Leu Leu Lys

<210> SEQ ID NO 14
<211> LENGTH: 13
<212> TYPE: PRT
<213> ORGANISM: Artificial
<220> FEATURE:
<223> OTHER INFORMATION: P14d min consensus
<220> FEATURE:
<221> NAME/KEY: MISC_FEATURE
<222> LOCATION: (2)..(2)
<223> OTHER INFORMATION: X at position 2 can be M, L, E, Q, D, N, G, A,
      S, isoD, or g-glutamate
<220> FEATURE:
<221> NAME/KEY: MISC_FEATURE
<222> LOCATION: (3)..(3)
<223> OTHER INFORMATION: X at position 3 can be Q, N, E, D, G, A, S,
      isoD or, g-glutamate
<220> FEATURE:
<221> NAME/KEY: MISC_FEATURE
<222> LOCATION: (6)..(6)
<223> OTHER INFORMATION: X at position 6 is Q, N, E, D, G, A, S, isoD
      or, g-glutamate
<220> FEATURE:
<221> NAME/KEY: MISC_FEATURE
<222> LOCATION: (7)..(7)
<223> OTHER INFORMATION: X at position 7 can be Q, N, E, D, G, A, S,
      isoD or, g-glutamate
<220> FEATURE:
<221> NAME/KEY: MISC_FEATURE
<222> LOCATION: (10)..(10)
<223> OTHER INFORMATION: X at position 10 can be K, Q, N, E, D, R, G, A,
      or S

<400> SEQUENCE: 14

Leu Xaa Xaa Leu Leu Xaa Xaa Leu Val Xaa Leu Leu Lys
1               5                   10

<210> SEQ ID NO 15
<211> LENGTH: 14
<212> TYPE: PRT
<213> ORGANISM: Artificial
<220> FEATURE:
<223> OTHER INFORMATION: P3min consensus
<220> FEATURE:
<221> NAME/KEY: MISC_FEATURE
<222> LOCATION: (1)..(1)
<223> OTHER INFORMATION: X at position 1 is L or M
<220> FEATURE:
<221> NAME/KEY: MISC_FEATURE
<222> LOCATION: (2)..(2)
<223> OTHER INFORMATION: X at position 2 can be Q, N, E, g-glutamate, D,
      isoD, T, S, A, or G
<220> FEATURE:
<221> NAME/KEY: MISC_FEATURE
<222> LOCATION: (3)..(3)
<223> OTHER INFORMATION: X at position 3 can be Q, N, E, g-glutamate, D,
      isoD, T, S, A, or G
<220> FEATURE:
<221> NAME/KEY: MISC_FEATURE
<222> LOCATION: (6)..(6)
<223> OTHER INFORMATION: X at position 6 can be K, Q, N, E, g-glutamate,
      D, isoD, T, S, A, or G
<220> FEATURE:
<221> NAME/KEY: MISC_FEATURE
```

```
<222> LOCATION: (7)..(7)
<223> OTHER INFORMATION: X at position 7 is L or M
<220> FEATURE:
<221> NAME/KEY: MISC_FEATURE
<222> LOCATION: (9)..(9)
<223> OTHER INFORMATION: X at position 9 can be E, g-glutamate, D, isoD,
      Q, N, T, S, A, or G
<220> FEATURE:
<221> NAME/KEY: MISC_FEATURE
<222> LOCATION: (10)..(10)
<223> OTHER INFORMATION: X at position 10 can be A, G, S, T, E,
      g-glutamate, D, isoD, Q, or N
<220> FEATURE:
<221> NAME/KEY: MISC_FEATURE
<222> LOCATION: (12)..(12)
<223> OTHER INFORMATION: X at position 12 is L or M
<220> FEATURE:
<221> NAME/KEY: MISC_FEATURE
<222> LOCATION: (13)..(13)
<223> OTHER INFORMATION: X at position 13 can be Q, N, E, g-glutamate,
      D, isoD, T, S, A, or G
<220> FEATURE:
<221> NAME/KEY: MISC_FEATURE
<222> LOCATION: (14)..(14)
<223> OTHER INFORMATION: X at position 14 can be Q, N, E, g-glutamate,
      D, isoD, T, S, A, or G

<400> SEQUENCE: 15

Xaa Xaa Xaa Leu Leu Xaa Xaa Phe Xaa Xaa Ile Xaa Xaa Xaa
1               5                   10

<210> SEQ ID NO 16
<211> LENGTH: 12
<212> TYPE: PRT
<213> ORGANISM: Artificial
<220> FEATURE:
<223> OTHER INFORMATION: P25 consensus
<220> FEATURE:
<221> NAME/KEY: MISC_FEATURE
<222> LOCATION: (2)..(2)
<223> OTHER INFORMATION: X at position 2 can be Q, N, E, g-glutamate, D,
      isoD, T, S, A, or G
<220> FEATURE:
<221> NAME/KEY: MISC_FEATURE
<222> LOCATION: (3)..(3)
<223> OTHER INFORMATION: X at position 3 can be K, Q, N, E, g-glutamate,
      D, isoD, T, S, A, or G
<220> FEATURE:
<221> NAME/KEY: MISC_FEATURE
<222> LOCATION: (5)..(5)
<223> OTHER INFORMATION: X at position 5 can be L or M
<220> FEATURE:
<221> NAME/KEY: MISC_FEATURE
<222> LOCATION: (6)..(6)
<223> OTHER INFORMATION: X at position 6 can be K, Q, N, E, g-glutamate,
      D, isoD, T, S, A, or G
<220> FEATURE:
<221> NAME/KEY: MISC_FEATURE
<222> LOCATION: (9)..(9)
<223> OTHER INFORMATION: X at position 9 can be E, g-glutamate, D, isoD,
      Q, N, T, S, A, or G
<220> FEATURE:
<221> NAME/KEY: MISC_FEATURE
<222> LOCATION: (10)..(10)
<223> OTHER INFORMATION: X at position 10 can be A, G, S, T, E,
      g-glutamate, D, isoD, Q, or N

<400> SEQUENCE: 16

Leu Xaa Xaa Leu Xaa Xaa Ile Leu Xaa Xaa Leu Val
1               5                   10

<210> SEQ ID NO 17
<211> LENGTH: 16
<212> TYPE: PRT
<213> ORGANISM: Artificial
```

```
<220> FEATURE:
<223> OTHER INFORMATION: P25 consensus
<220> FEATURE:
<221> NAME/KEY: MISC_FEATURE
<222> LOCATION: (2)..(2)
<223> OTHER INFORMATION: X at position 2 can be T, S, A, G, D, isoD, E,
      g-glutamate, Q, or N
<220> FEATURE:
<221> NAME/KEY: MISC_FEATURE
<222> LOCATION: (3)..(3)
<223> OTHER INFORMATION: X at position 3 can be G, T, S, A, D, isoD, E,
      g-glutamate, Q, or N
<220> FEATURE:
<221> NAME/KEY: MISC_FEATURE
<222> LOCATION: (6)..(6)
<223> OTHER INFORMATION: X at position 6 can be Q, N, E, g-glutamate, D,
      isoD, T, S, A, or G
<220> FEATURE:
<221> NAME/KEY: MISC_FEATURE
<222> LOCATION: (7)..(7)
<223> OTHER INFORMATION: X at position 7 can be K, Q, N, E, g-glutamate,
      D, isoD, T, S, A, or G
<220> FEATURE:
<221> NAME/KEY: MISC_FEATURE
<222> LOCATION: (9)..(9)
<223> OTHER INFORMATION: X at position 9 can be L or M
<220> FEATURE:
<221> NAME/KEY: MISC_FEATURE
<222> LOCATION: (10)..(10)
<223> OTHER INFORMATION: X at position 10 can be K, Q, N, E,
      g-glutamate, D, isoD, T, S, A, or G
<220> FEATURE:
<221> NAME/KEY: MISC_FEATURE
<222> LOCATION: (13)..(13)
<223> OTHER INFORMATION: X at position 13 can be E, g-glutamate, D,
      isoD, Q, N, T, S, A, or G
<220> FEATURE:
<221> NAME/KEY: MISC_FEATURE
<222> LOCATION: (14)..(14)
<223> OTHER INFORMATION: X at position 14 can be A, G, S, T, E,
      g-glutamate, D, isoD, Q, or N
<220> FEATURE:
<221> NAME/KEY: MISC_FEATURE
<222> LOCATION: (16)..(16)
<223> OTHER INFORMATION: V at position 16 is optional

<400> SEQUENCE: 17

Leu Xaa Xaa Val Leu Xaa Xaa Leu Xaa Xaa Ile Leu Xaa Xaa Leu Val
1               5                   10                  15

<210> SEQ ID NO 18
<211> LENGTH: 27
<212> TYPE: PRT
<213> ORGANISM: Artificial
<220> FEATURE:
<223> OTHER INFORMATION: P17/18 consensus
<220> FEATURE:
<221> NAME/KEY: MISC_FEATURE
<222> LOCATION: (1)..(1)
<223> OTHER INFORMATION: X at position 1 can be any amino acid, but
      preferably Q, S, E, g-glutamate, A, T, G, D, isoD, N, K, or R
<220> FEATURE:
<221> NAME/KEY: MISC_FEATURE
<222> LOCATION: (2)..(2)
<223> OTHER INFORMATION: X at position 2 can be any amino acid, but
      preferably Q, S, E, g-glutamate, A, T, G, D, isoD, N, K, or R
<220> FEATURE:
<221> NAME/KEY: MISC_FEATURE
<222> LOCATION: (3)..(3)
<223> OTHER INFORMATION: X at position 3 can be any amino acid, but
      preferably P, Q, S, E, g-glutamate, A, T, G, D, isoD, N, K, or R
<220> FEATURE:
<221> NAME/KEY: MISC_FEATURE
<222> LOCATION: (4)..(4)
<223> OTHER INFORMATION: X at position 4 can be any amino acid, but
      preferably I, Q, S, E, g-glutamate, A, T, G, D, N, isoD, K, or R
<220> FEATURE:
```

```
<221> NAME/KEY: MISC_FEATURE
<222> LOCATION: (5)..(5)
<223> OTHER INFORMATION: X at position 5 can be any amino acid, but
      preferably D, isoD, S, E, g-glutamate, A, T, G, N, Q, K, or R
<220> FEATURE:
<221> NAME/KEY: MISC_FEATURE
<222> LOCATION: (6)..(6)
<223> OTHER INFORMATION: X at position 6 can be any amino acid, but
      preferably R, Q, S, E, g-glutamate, A, T, G, D, isoD, N, or K
<220> FEATURE:
<221> NAME/KEY: MISC_FEATURE
<222> LOCATION: (7)..(7)
<223> OTHER INFORMATION: X of position 7 can be any amino acid, but
      preferably Q, S, E, g-glutamate, A, T, G, D, isoD, N, K, or R
<220> FEATURE:
<221> NAME/KEY: MISC_FEATURE
<222> LOCATION: (8)..(8)
<223> OTHER INFORMATION: X at position 8 can be any amino acid, but
      preferably T, Q, S, E, g-glutamate, A, G, D, isoD, N, K, or R
<220> FEATURE:
<221> NAME/KEY: MISC_FEATURE
<222> LOCATION: (9)..(9)
<223> OTHER INFORMATION: X at position 9 can be any amino acid, but
      preferably I, Q, S, E, g-glutamate, A, T, G, D, isoD, N, K, or R
<220> FEATURE:
<221> NAME/KEY: MISC_FEATURE
<222> LOCATION: (10)..(10)
<223> OTHER INFORMATION: X at position 10 can be any amino acid, but
      preferably E, g-glutamate, Q, S, A, T, G, D, isoD, N, K, or R
<220> FEATURE:
<221> NAME/KEY: MISC_FEATURE
<222> LOCATION: (11)..(11)
<223> OTHER INFORMATION: X at position 11 can be any amino acid, but
      preferably Q, S, E, g-glutamate, A, T, G, D, isoD, N, K, or R
<220> FEATURE:
<221> NAME/KEY: MISC_FEATURE
<222> LOCATION: (12)..(12)
<223> OTHER INFORMATION: X at position 12 can be L or M
<220> FEATURE:
<221> NAME/KEY: MISC_FEATURE
<222> LOCATION: (13)..(13)
<223> OTHER INFORMATION: X at position 13 can be any amino acid, but
      preferably A, S, T, G, D, isoD, E, g-glutamate, Q, N, K, or R
<220> FEATURE:
<221> NAME/KEY: MISC_FEATURE
<222> LOCATION: (14)..(14)
<223> OTHER INFORMATION: X at position 14 can be any amino acid, but
      preferably Q, A, S, T, G, D, isoD, E, g-glutamate, N, K, or R
<220> FEATURE:
<221> NAME/KEY: MISC_FEATURE
<222> LOCATION: (17)..(17)
<223> OTHER INFORMATION: X at position 17 can be any amino acid, but
      preferably A, S, T, G, D, isoD, E, g-glutamate, Q, N, K, or R
<220> FEATURE:
<221> NAME/KEY: MISC_FEATURE
<222> LOCATION: (18)..(18)
<223> OTHER INFORMATION: X at position 18 can be any amino acid, but
      preferably Q, A, S, T, G, D, isoD, E, g-glutamate, N, K, or R
<220> FEATURE:
<221> NAME/KEY: MISC_FEATURE
<222> LOCATION: (21)..(21)
<223> OTHER INFORMATION: X at position 21 can be any amino acid, but
      preferably K, A, S, T, G, D, isoD, E, g-glutamate, Q, N, or R
<220> FEATURE:
<221> NAME/KEY: MISC_FEATURE
<222> LOCATION: (22)..(22)
<223> OTHER INFORMATION: X at position 22 can be any amino acid, but
      preferably S, A, T, G, D, isoD, E, g-glutamate, Q, N, K, or R
<220> FEATURE:
<221> NAME/KEY: MISC_FEATURE
<222> LOCATION: (25)..(25)
<223> OTHER INFORMATION: X at position 25 can be any amino acid, but
      preferably S, A, T, G, D, isoD, E, g-glutamate, Q, N, K, or R
<220> FEATURE:
<221> NAME/KEY: MISC_FEATURE
<222> LOCATION: (26)..(26)
<223> OTHER INFORMATION: X at position 26 can be any amino acid, but
      preferably P, S, A, T, G, D, isoD, E, g-glutamate, Q, N, K, or R
<220> FEATURE:
```

```
<221> NAME/KEY: MISC_FEATURE
<222> LOCATION: (27)..(27)
<223> OTHER INFORMATION: X at position 27 can be any amino acid, but
      preferably Q, S, A, T, G, D, isoD, E, g-glutamate, N, K, or R

<400> SEQUENCE: 18

Xaa Xaa Xaa Xaa Xaa Xaa Xaa Xaa Xaa Xaa Xaa Xaa Xaa Xaa Leu Leu
1               5                   10                  15

Xaa Xaa Leu Leu Xaa Xaa Leu Leu Xaa Xaa Xaa
            20                  25

<210> SEQ ID NO 19
<211> LENGTH: 23
<212> TYPE: PRT
<213> ORGANISM: Artificial
<220> FEATURE:
<223> OTHER INFORMATION: synthetic peptide

<400> SEQUENCE: 19

Ser Gln Gly Ile Ser Glu Lys Gln Val Asp Gln Leu Leu Ser Gln Leu
1               5                   10                  15

Ile Gln Ala Leu Leu Gln Pro
            20

<210> SEQ ID NO 20
<211> LENGTH: 23
<212> TYPE: PRT
<213> ORGANISM: Artificial
<220> FEATURE:
<223> OTHER INFORMATION: synthetic peptide

<400> SEQUENCE: 20

Ser Gln Gly Ile Ser Glu Lys Gln Phe Asp Gln Leu Leu Ser Gln Leu
1               5                   10                  15

Ile Gln Ala Leu Leu Gln Pro
            20

<210> SEQ ID NO 21
<211> LENGTH: 27
<212> TYPE: PRT
<213> ORGANISM: Artificial
<220> FEATURE:
<223> OTHER INFORMATION: P17/18 consensus
<220> FEATURE:
<221> NAME/KEY: MISC_FEATURE
<222> LOCATION: (1)..(1)
<223> OTHER INFORMATION: X at position 1 can be any amino acid, but
      preferably Q, S, E, g-glutamate, A, T, G, D, isoD, N, K, or R
<220> FEATURE:
<221> NAME/KEY: MISC_FEATURE
<222> LOCATION: (2)..(2)
<223> OTHER INFORMATION: X at position 2 can be any amino acid, but
      preferably Q, S, E, g-glutamate, A, T, G, D, isoD, N, K, or R
<220> FEATURE:
<221> NAME/KEY: MISC_FEATURE
<222> LOCATION: (3)..(3)
<223> OTHER INFORMATION: X at position 3 can be any amino acid, but
      preferably P, Q, S, E, g-glutamate, A, T, G, D, isoD, N, K, or R
<220> FEATURE:
<221> NAME/KEY: MISC_FEATURE
<222> LOCATION: (4)..(4)
<223> OTHER INFORMATION: X at position 4 can be any amino acid, but
      preferably I, Q, S, E, g-glutamate, A, T, G, D, N, isoD, K, or R
<220> FEATURE:
<221> NAME/KEY: MISC_FEATURE
<222> LOCATION: (5)..(5)
<223> OTHER INFORMATION: X at position 5 can be any amino acid, but
      preferably D, isoD, S, E, g-glutamate, A, T, G, N, Q, K, or R
<220> FEATURE:
<221> NAME/KEY: MISC_FEATURE
```

```
<222> LOCATION: (6)..(6)
<223> OTHER INFORMATION: X at position 6 can be any amino acid, but
      preferably R, Q, S, E, g-glutamate, A, T, G, D, isoD, N, or K
<220> FEATURE:
<221> NAME/KEY: MISC_FEATURE
<222> LOCATION: (7)..(7)
<223> OTHER INFORMATION: X of position 7 can be any amino acid, but
      preferably Q, S, E, g-glutamate, A, T, G, D, isoD, N, K, or R
<220> FEATURE:
<221> NAME/KEY: MISC_FEATURE
<222> LOCATION: (8)..(8)
<223> OTHER INFORMATION: X at position 8 can be any amino acid, but
      preferably T, Q, S, E, g-glutamate, A, G, D, isoD, N, K, or R
<220> FEATURE:
<221> NAME/KEY: MISC_FEATURE
<222> LOCATION: (9)..(9)
<223> OTHER INFORMATION: X at position 9 can be any amino acid, but
      preferably I, Q, S, E, g-glutamate, A, T, G, D, isoD, N, K, or R
<220> FEATURE:
<221> NAME/KEY: MISC_FEATURE
<222> LOCATION: (10)..(10)
<223> OTHER INFORMATION: X at position 10 can be any amino acid, but
      preferably E, g-glutamate, Q, S, A, T, G, D, isoD, N, K, or R
<220> FEATURE:
<221> NAME/KEY: MISC_FEATURE
<222> LOCATION: (11)..(11)
<223> OTHER INFORMATION: X at position 11 can be any amino acid, but
      preferably Q, S, E, g-glutamate, A, T, G, D, isoD, N, K, or R
<220> FEATURE:
<221> NAME/KEY: MISC_FEATURE
<222> LOCATION: (12)..(12)
<223> OTHER INFORMATION: X at position 12 can be L or M
<220> FEATURE:
<221> NAME/KEY: MISC_FEATURE
<222> LOCATION: (13)..(13)
<223> OTHER INFORMATION: X at position 13 can be any amino acid, but
      preferably A, S, T, G, D, isoD, E, g-glutamate, Q, N, K, or R
<220> FEATURE:
<221> NAME/KEY: MISC_FEATURE
<222> LOCATION: (14)..(14)
<223> OTHER INFORMATION: X at position 14 can be any amino acid, but
      preferably Q, A, S, T, G, D, isoD, E, g-glutamate, N, K, or R
<220> FEATURE:
<221> NAME/KEY: MISC_FEATURE
<222> LOCATION: (17)..(17)
<223> OTHER INFORMATION: X at position 17 can be any amino acid, but
      preferably A, S, T, G, D, isoD, E, g-glutamate, Q, N, K, or R
<220> FEATURE:
<221> NAME/KEY: MISC_FEATURE
<222> LOCATION: (18)..(18)
<223> OTHER INFORMATION: X at position 18 can be any amino acid, but
      preferably Q, A, S, T, G, D, isoD, E, g-glutamate, N, K, or R
<220> FEATURE:
<221> NAME/KEY: MISC_FEATURE
<222> LOCATION: (21)..(21)
<223> OTHER INFORMATION: X at position 21 can be any amino acid, but
      preferably K, A, S, T, G, D, isoD, E, g-glutamate, Q, N, or R
<220> FEATURE:
<221> NAME/KEY: MISC_FEATURE
<222> LOCATION: (22)..(22)
<223> OTHER INFORMATION: X at position 22 can be any amino acid, but
      preferably S, A,T, G, D, isoD, E, g-glutamate, Q, N, K, or R
<220> FEATURE:
<221> NAME/KEY: MISC_FEATURE
<222> LOCATION: (25)..(25)
<223> OTHER INFORMATION: X at position 25 can be any amino acid, but
      preferably S, A, T, G, D, isoD, E, g-glutamate, Q, N, K, or R
<220> FEATURE:
<221> NAME/KEY: MISC_FEATURE
<222> LOCATION: (26)..(26)
<223> OTHER INFORMATION: X at position 26 can be any amino acid, but
      preferably P, S, A, T, G, D, isoD, E, g-glutamate, Q, N, K, or R
<220> FEATURE:
<221> NAME/KEY: MISC_FEATURE
<222> LOCATION: (27)..(27)
<223> OTHER INFORMATION: X at position 27 can be any amino acid, but
      preferably Q, S, A, T, G, D, isoD, E, g-glutamate, N, K, or R

<400> SEQUENCE: 21
```

```
Xaa Xaa Xaa Xaa Xaa Xaa Xaa Xaa Xaa Xaa Xaa Xaa Xaa Xaa Leu Leu
1               5                   10                  15

Xaa Xaa Leu Leu Xaa Xaa Leu Leu Xaa Xaa Xaa
            20                  25

<210> SEQ ID NO 22
<211> LENGTH: 23
<212> TYPE: PRT
<213> ORGANISM: Artificial
<220> FEATURE:
<223> OTHER INFORMATION: synthetic peptide

<400> SEQUENCE: 22

Ser Gln Gly Ile Ser Glu Lys Gln Leu Asp Gln Ile Leu Ser Gln Leu
1               5                   10                  15

Ile Gln Ala Leu Leu Gln Pro
            20

<210> SEQ ID NO 23
<211> LENGTH: 23
<212> TYPE: PRT
<213> ORGANISM: Artificial
<220> FEATURE:
<223> OTHER INFORMATION: synthetic peptide

<400> SEQUENCE: 23

Ser Gln Gly Ile Ser Glu Lys Gln Leu Asp Gln Phe Leu Ser Gln Leu
1               5                   10                  15

Ile Gln Ala Leu Leu Gln Pro
            20

<210> SEQ ID NO 24
<211> LENGTH: 23
<212> TYPE: PRT
<213> ORGANISM: Artificial
<220> FEATURE:
<223> OTHER INFORMATION: synthetic peptide

<400> SEQUENCE: 24

Ser Gln Gly Ile Ser Glu Lys Gln Leu Asp Gln Leu Ile Ser Gln Leu
1               5                   10                  15

Ile Gln Ala Leu Leu Gln Pro
            20

<210> SEQ ID NO 25
<211> LENGTH: 13
<212> TYPE: PRT
<213> ORGANISM: Artificial
<220> FEATURE:
<223> OTHER INFORMATION: P17/18 min consensus
<220> FEATURE:
<221> NAME/KEY: MISC_FEATURE
<222> LOCATION: (1)..(1)
<223> OTHER INFORMATION: X at position 1 can be L or M
<220> FEATURE:
<221> NAME/KEY: MISC_FEATURE
<222> LOCATION: (2)..(2)
<223> OTHER INFORMATION: X at position 2 can be any amino acid, but
      preferably A, S, T, G, D, isoD, E, g-glutamate, Q, N, K, or R
<220> FEATURE:
<221> NAME/KEY: MISC_FEATURE
<222> LOCATION: (3)..(3)
<223> OTHER INFORMATION: X at position 3 can be any amino acid, but
      preferably Q, A, S, T, G, D, isoD, E, g-glutamate, N, K, or R
<220> FEATURE:
<221> NAME/KEY: MISC_FEATURE
<222> LOCATION: (6)..(6)
```

```
<223> OTHER INFORMATION: X at position 6 can be any amino acid, but
      preferably A, S, T, G, D, isoD, E, g-gl

```
<210> SEQ ID NO 27
<211> LENGTH: 23
<212> TYPE: PRT
<213> ORGANISM: Artificial
<220> FEATURE:
<223> OTHER INFORMATION: synthetic peptide

<400> SEQUENCE: 27

Ser Gln Gly Ile Ser Glu Lys Gln Leu Asp Gln Leu Leu Ser Ala Leu
1               5                   10                  15

Ile Gln Ala Leu Leu Gln Pro
            20

<210> SEQ ID NO 28
<211> LENGTH: 23
<212> TYPE: PRT
<213> ORGANISM: Artificial
<220> FEATURE:
<223> OTHER INFORMATION: synthetic peptide

<400> SEQUENCE: 28

Ser Gln Gly Ile Ser Glu Lys Gln Leu Asp Gln Leu Leu Ser Lys Leu
1               5                   10                  15

Ile Gln Ala Leu Leu Gln Pro
            20

<210> SEQ ID NO 29
<211> LENGTH: 23
<212> TYPE: PRT
<213> ORGANISM: Artificial
<220> FEATURE:
<223> OTHER INFORMATION: synthetic peptide

<400> SEQUENCE: 29

Ser Gln Gly Ile Ser Glu Lys Gln Leu Asp Gln Leu Leu Ser Ser Leu
1               5                   10                  15

Ile Gln Ala Leu Leu Gln Pro
            20

<210> SEQ ID NO 30
<211> LENGTH: 23
<212> TYPE: PRT
<213> ORGANISM: Artificial
<220> FEATURE:
<223> OTHER INFORMATION: synthetic peptide

<400> SEQUENCE: 30

Ser Gln Gly Ile Ser Glu Lys Gln Leu Asp Gln Leu Leu Ser Ile Leu
1               5                   10                  15

Ile Gln Ala Leu Leu Gln Pro
            20

<210> SEQ ID NO 31
<211> LENGTH: 20
<212> TYPE: PRT
<213> ORGANISM: Artificial
<220> FEATURE:
<223> OTHER INFORMATION: synthetic peptide

<400> SEQUENCE: 31

Ser Glu Glu Glu Glu Glu Leu Asp Gln Leu Leu Ser Gln Leu Ile Gln
1               5                   10                  15

Ala Leu Leu Gln
            20
```

```
<210> SEQ ID NO 32
<211> LENGTH: 23
<212> TYPE: PRT
<213> ORGANISM: Artificial
<220> FEATURE:
<223> OTHER INFORMATION: synthetic peptide

<400> SEQUENCE: 32

Ser Gln Gly Ile Ser Glu Lys Gln Leu Asp Gln Leu Leu Ser Gln Ile
1               5                   10                  15

Ile Gln Ala Leu Leu Gln Pro
            20

<210> SEQ ID NO 33
<211> LENGTH: 19
<212> TYPE: PRT
<213> ORGANISM: Artificial
<220> FEATURE:
<223> OTHER INFORMATION: synthetic peptide

<400> SEQUENCE: 33

Ser Glu Glu Glu Glu Glu Leu Asp Gln Leu Leu Ser Gln Leu Ile Gln
1               5                   10                  15

Ala Leu Leu

<210> SEQ ID NO 34
<211> LENGTH: 23
<212> TYPE: PRT
<213> ORGANISM: Artificial
<220> FEATURE:
<223> OTHER INFORMATION: synthetic peptide

<400> SEQUENCE: 34

Ser Gln Gly Ile Ser Glu Lys Gln Leu Asp Gln Leu Leu Ser Gln Phe
1               5                   10                  15

Ile Gln Ala Leu Leu Gln Pro
            20

<210> SEQ ID NO 35
<211> LENGTH: 22
<212> TYPE: PRT
<213> ORGANISM: Artificial
<220> FEATURE:
<223> OTHER INFORMATION: synthetic peptide

<400> SEQUENCE: 35

Arg Arg Arg Arg Arg Gly Gly Leu Asp Gln Leu Leu Ser Gln Leu Ile
1               5                   10                  15

Gln Ala Leu Leu Gln Pro
            20

<210> SEQ ID NO 36
<211> LENGTH: 22
<212> TYPE: PRT
<213> ORGANISM: Artificial
<220> FEATURE:
<223> OTHER INFORMATION: synthetic peptide

<400> SEQUENCE: 36

Leu Asp Gln Leu Leu Ser Gln Leu Ile Gln Ala Leu Leu Gln Pro Gly
1               5                   10                  15

Gly Arg Arg Arg Arg Arg
            20
```

<210> SEQ ID NO 37
<211> LENGTH: 23
<212> TYPE: PRT
<213> ORGANISM: Artificial
<220> FEATURE:
<223> OTHER INFORMATION: synthetic peptide

<400> SEQUENCE: 37

Ser Gln Gly Ile Ser Glu Lys Gln Leu Asp Gln Leu Leu Ser Gln Leu
1               5                   10                  15

Ile Gln Ala Ile Leu Gln Pro
            20

<210> SEQ ID NO 38
<211> LENGTH: 22
<212> TYPE: PRT
<213> ORGANISM: Artificial
<220> FEATURE:
<223> OTHER INFORMATION: synthetic peptide

<400> SEQUENCE: 38

Lys Lys Lys Lys Lys Gly Gly Leu Asp Gln Leu Leu Ser Gln Leu Ile
1               5                   10                  15

Gln Ala Leu Leu Gln Pro
            20

<210> SEQ ID NO 39
<211> LENGTH: 22
<212> TYPE: PRT
<213> ORGANISM: Artificial
<220> FEATURE:
<223> OTHER INFORMATION: synthetic peptide

<400> SEQUENCE: 39

Leu Asp Gln Leu Leu Ser Gln Leu Ile Gln Ala Leu Leu Gln Pro Gly
1               5                   10                  15

Gly Lys Lys Lys Lys Lys
            20

<210> SEQ ID NO 40
<211> LENGTH: 23
<212> TYPE: PRT
<213> ORGANISM: Artificial
<220> FEATURE:
<223> OTHER INFORMATION: synthetic peptide

<400> SEQUENCE: 40

Ser Gln Gly Ile Ser Glu Lys Gln Leu Asp Gln Leu Leu Ser Gln Leu
1               5                   10                  15

Ile Gln Ala Leu Phe Gln Pro
            20

<210> SEQ ID NO 41
<211> LENGTH: 23
<212> TYPE: PRT
<213> ORGANISM: Artificial
<220> FEATURE:
<223> OTHER INFORMATION: synthetic peptide

<400> SEQUENCE: 41

Asn Glu Gly Ile Ser Glu Lys Gln Leu Asp Gln Leu Leu Thr Gln Leu
1               5                   10                  15

Ile Met Ala Leu Leu Gln Gln
            20

<210> SEQ ID NO 42
<211> LENGTH: 23
<212> TYPE: PRT
<213> ORGANISM: Artificial
<220> FEATURE:
<223> OTHER INFORMATION: synthetic peptide

<400> SEQUENCE: 42

Asn Gln Gly Ile Ser Glu Lys Gln Leu Asp Gln Leu Leu Thr Gln Leu
1               5                   10                  15

Ile Thr Ala Leu Leu Gln Gln
            20

<210> SEQ ID NO 43
<211> LENGTH: 23
<212> TYPE: PRT
<213> ORGANISM: Artificial
<220> FEATURE:
<223> OTHER INFORMATION: synthetic peptide

<400> SEQUENCE: 43

Asn Gln Gly Ile Ser Glu Lys Gln Leu Asp Gln Leu Leu Thr Gln Leu
1               5                   10                  15

Ile Glu Ala Leu Leu Gln Gln
            20

<210> SEQ ID NO 44
<211> LENGTH: 23
<212> TYPE: PRT
<213> ORGANISM: Artificial
<220> FEATURE:
<223> OTHER INFORMATION: synthetic peptide

<400> SEQUENCE: 44

Asn Gln Gly Ile Ser Glu Lys Gln Leu Asp Gln Leu Leu Thr Gln Leu
1               5                   10                  15

Ile Ala Ala Leu Leu Gln Gln
            20

<210> SEQ ID NO 45
<211> LENGTH: 23
<212> TYPE: PRT
<213> ORGANISM: Artificial
<220> FEATURE:
<223> OTHER INFORMATION: synthetic peptide

<400> SEQUENCE: 45

Asn Gln Gly Ile Ser Glu Lys Gln Leu Asp Gln Leu Leu Thr Gln Leu
1               5                   10                  15

Ile Lys Ala Leu Leu Gln Gln
            20

<210> SEQ ID NO 46
<211> LENGTH: 23
<212> TYPE: PRT
<213> ORGANISM: Artificial
<220> FEATURE:
<223> OTHER INFORMATION: synthetic peptide

<400> SEQUENCE: 46

Asn Glu Gly Ile Ser Glu Lys Glu Leu Asp Glu Leu Leu Thr Glu Leu
1               5                   10                  15

Ile Glu Ala Leu Leu Gln Gln

```
<210> SEQ ID NO 47
<211> LENGTH: 22
<212> TYPE: PRT
<213> ORGANISM: Artificial
<220> FEATURE:
<223> OTHER INFORMATION: P15b/P20 consensus
<220> FEATURE:
<221> NAME/KEY: MISC_FEATURE
<222> LOCATION: (3)..(3)
<223> OTHER INFORMATION: X at position 3 is N, D, or isoD
<220> FEATURE:
<221> NAME/KEY: MISC_FEATURE
<222> LOCATION: (6)..(6)
<223> OTHER INFORMATION: X at position 6 is Q, E, g-glutamate, G, A, or
      S
<220> FEATURE:
<221> NAME/KEY: MISC_FEATURE
<222> LOCATION: (8)..(8)
<223> OTHER INFORMATION: X at position 8 is N, D, or isoD
<220> FEATURE:
<221> NAME/KEY: MISC_FEATURE
<222> LOCATION: (15)..(15)
<223> OTHER INFORMATION: X at position 15 is optional and can be any
      amino acid
<220> FEATURE:
<221> NAME/KEY: MISC_FEATURE
<222> LOCATION: (18)..(18)
<223> OTHER INFORMATION: X at position 18 is M, E, g-glutamate, G, A, S,
      T, or K
<220> FEATURE:
<221> NAME/KEY: MISC_FEATURE
<222> LOCATION: (22)..(22)
<223> OTHER INFORMATION: X at position 22 is optional and can be Q, E,
      g-glutamate, G, A, or S

<400> SEQUENCE: 47

Lys Pro Xaa Asp Ser Xaa Ser Xaa Ile Ala Lys Leu Ile Ser Xaa Leu
1               5                   10                  15

Ile Xaa Ser Leu Leu Xaa
            20

<210> SEQ ID NO 48
<211> LENGTH: 45
<212> TYPE: PRT
<213> ORGANISM: Artificial
<220> FEATURE:
<223> OTHER INFORMATION: synthetic peptide

<400> SEQUENCE: 48

Gln Lys Asp Val Asn Phe Gly Thr Pro Asp Ser Thr Val Gln Asn Pro
1               5                   10                  15

Gln Asp Ala Ser Lys Pro Asn Asp Ser Gln Ser Asn Ile Ala Lys Leu
            20                  25                  30

Ile Ser Ala Leu Ile Met Ser Leu Leu Gln Met Leu Thr
        35                  40                  45

<210> SEQ ID NO 49
<211> LENGTH: 22
<212> TYPE: PRT
<213> ORGANISM: Artificial
<220> FEATURE:
<223> OTHER INFORMATION: synthetic peptide

<400> SEQUENCE: 49

Lys Pro Asn Asp Ser Gln Ser Asn Ile Ala Lys Leu Ile Ser Ala Leu
1               5                   10                  15

Ile Met Ser Leu Leu Gln
```

<210> SEQ ID NO 50
<211> LENGTH: 22
<212> TYPE: PRT
<213> ORGANISM: Artificial
<220> FEATURE:
<223> OTHER INFORMATION: synthetic peptide

<400> SEQUENCE: 50

Lys Pro Asn Asp Ser Gln Ser Asp Ile Ala Lys Leu Ile Ser Ala Leu
1               5                   10                  15

Ile Glu Ser Leu Leu Gln
            20

<210> SEQ ID NO 51
<211> LENGTH: 22
<212> TYPE: PRT
<213> ORGANISM: Artificial
<220> FEATURE:
<223> OTHER INFORMATION: synthetic peptide

<400> SEQUENCE: 51

Lys Pro Asn Asp Ser Gln Ser Asp Ile Ala Lys Leu Ile Ser Ala Leu
1               5                   10                  15

Ile Ala Ser Leu Leu Gln
            20

<210> SEQ ID NO 52
<211> LENGTH: 22
<212> TYPE: PRT
<213> ORGANISM: Artificial
<220> FEATURE:
<223> OTHER INFORMATION: synthetic peptide

<400> SEQUENCE: 52

Lys Pro Asn Asp Ser Gln Ser Asp Ile Ala Lys Leu Ile Ser Ala Leu
1               5                   10                  15

Ile Ser Ser Leu Leu Gln
            20

<210> SEQ ID NO 53
<211> LENGTH: 22
<212> TYPE: PRT
<213> ORGANISM: Artificial
<220> FEATURE:
<223> OTHER INFORMATION: synthetic peptide

<400> SEQUENCE: 53

Lys Pro Asn Asp Ser Gln Ser Asp Ile Ala Lys Leu Ile Ser Ala Leu
1               5                   10                  15

Ile Thr Ser Leu Leu Gln
            20

<210> SEQ ID NO 54
<211> LENGTH: 22
<212> TYPE: PRT
<213> ORGANISM: Artificial
<220> FEATURE:
<223> OTHER INFORMATION: synthetic peptide

<400> SEQUENCE: 54

Lys Pro Asn Asp Ser Gln Ser Asp Ile Ala Lys Leu Ile Ser Ala Leu
1               5                   10                  15

Ile Lys Ser Leu Leu Gln
            20

<210> SEQ ID NO 55
<211> LENGTH: 22
<212> TYPE: PRT
<213> ORGANISM: Artificial
<220> FEATURE:
<223> OTHER INFORMATION: synthetic peptide

<400> SEQUENCE: 55

Lys Pro Asn Asp Ser Glu Ser Asp Ile Ala Lys Leu Ile Ser Ala Leu
1               5                   10                  15

Ile Glu Ser Leu Leu Gln
            20

<210> SEQ ID NO 56
<211> LENGTH: 22
<212> TYPE: PRT
<213> ORGANISM: Artificial
<220> FEATURE:
<223> OTHER INFORMATION: synthetic peptide

<400> SEQUENCE: 56

Lys Pro Asp Asp Ser Gln Ser Asp Ile Ala Lys Leu Ile Ser Ala Leu
1               5                   10                  15

Ile Met Ser Leu Leu Gln
            20

<210> SEQ ID NO 57
<211> LENGTH: 22
<212> TYPE: PRT
<213> ORGANISM: Artificial
<220> FEATURE:
<223> OTHER INFORMATION: synthetic peptide

<400> SEQUENCE: 57

Lys Pro Asp Asp Ser Glu Ser Asp Ile Ala Lys Leu Ile Ser Ala Leu
1               5                   10                  15

Ile Met Ser Leu Leu Gln
            20

<210> SEQ ID NO 58
<211> LENGTH: 22
<212> TYPE: PRT
<213> ORGANISM: Artificial
<220> FEATURE:
<223> OTHER INFORMATION: synthetic peptide

<400> SEQUENCE: 58

Lys Pro Asp Asp Ser Gln Ser Asp Ile Ala Lys Leu Ile Ser Ala Leu
1               5                   10                  15

Ile Glu Ser Leu Leu Gln
            20

<210> SEQ ID NO 59
<211> LENGTH: 22
<212> TYPE: PRT
<213> ORGANISM: Artificial
<220> FEATURE:
<223> OTHER INFORMATION: synthetic peptide

<400> SEQUENCE: 59

Lys Pro Asp Asp Ser Glu Ser Asp Ile Ala Lys Leu Ile Ser Ala Leu
1               5                   10                  15

Ile Glu Ser Leu Leu Gln
            20

<210> SEQ ID NO 60
<211> LENGTH: 22
<212> TYPE: PRT
<213> ORGANISM: Artificial
<220> FEATURE:
<223> OTHER INFORMATION: synthetic peptide

<400> SEQUENCE: 60

Lys Pro Asp Asp Ser Glu Ser Asp Ile Ala Lys Leu Ile Ser Ala Leu
1               5                   10                  15

Ile Glu Ser Leu Leu Glu
            20

<210> SEQ ID NO 61
<211> LENGTH: 22
<212> TYPE: PRT
<213> ORGANISM: Artificial
<220> FEATURE:
<223> OTHER INFORMATION: synthetic peptide

<400> SEQUENCE: 61

Lys Pro Asn Asp Ser Glu Ser Asp Ile Ala Lys Leu Ile Ser Ala Leu
1               5                   10                  15

Ile Glu Ser Leu Leu Glu
            20

<210> SEQ ID NO 62
<211> LENGTH: 22
<212> TYPE: PRT
<213> ORGANISM: Artificial
<220> FEATURE:
<223> OTHER INFORMATION: synthetic peptide

<400> SEQUENCE: 62

Lys Pro Asp Asp Ser Glu Ser Asn Ile Ala Lys Leu Ile Ser Ala Leu
1               5                   10                  15

Ile Glu Ser Leu Leu Glu
            20

<210> SEQ ID NO 63
<211> LENGTH: 39
<212> TYPE: PRT
<213> ORGANISM: Artificial
<220> FEATURE:
<223> OTHER INFORMATION: synthetic peptide

<400> SEQUENCE: 63

Asn Phe Gly Thr Pro Asp Ser Thr Val Gln Asn Pro Gln Asp Ala Ser
1               5                   10                  15

Lys Pro Asn Asp Ser Gln Ser Asn Ile Ala Lys Leu Ile Ser Ala Leu
            20                  25                  30

Ile Met Ser Leu Leu Gln Met
        35

<210> SEQ ID NO 64
<211> LENGTH: 23
<212> TYPE: PRT
<213> ORGANISM: Artificial
<220> FEATURE:
<223> OTHER INFORMATION: synthetic peptide

```
<400> SEQUENCE: 64

Lys Pro Asn Asp Ser Gln Ser Asn Ile Ala Lys Leu Ile Ser Ala Leu
1               5                   10                  15

Ile Met Ser Leu Leu Gln Met
            20

<210> SEQ ID NO 65
<211> LENGTH: 34
<212> TYPE: PRT
<213> ORGANISM: Artificial
<220> FEATURE:
<223> OTHER INFORMATION: synthetic peptide

<400> SEQUENCE: 65

Gly Thr Pro Asp Ser Thr Val Gln Asn Pro Gln Asp Ala Ser Lys Pro
1               5                   10                  15

Asn Asp Ser Gln Ser Asn Ile Ala Lys Leu Ile Ser Leu Ile Met Ser
            20                  25                  30

Leu Leu

<210> SEQ ID NO 66
<211> LENGTH: 20
<212> TYPE: PRT
<213> ORGANISM: Artificial
<220> FEATURE:
<223> OTHER INFORMATION: P6/6a consensus
<220> FEATURE:
<221> NAME/KEY: MISC_FEATURE
<222> LOCATION: (4)..(4)
<223> OTHER INFORMATION: X at position 4 is F or Y
<220> FEATURE:
<221> NAME/KEY: MISC_FEATURE
<222> LOCATION: (6)..(6)
<223> OTHER INFORMATION: X at position 6 is Q, E, g-glutamate, G, A, or
      S
<220> FEATURE:
<221> NAME/KEY: MISC_FEATURE
<222> LOCATION: (7)..(7)
<223> OTHER INFORMATION: X at position 7 is optional and can be M, E,
      g-glutamate, G, A, S, T, or K or L
<220> FEATURE:
<221> NAME/KEY: MISC_FEATURE
<222> LOCATION: (9)..(9)
<223> OTHER INFORMATION: X at position 9 is M, E, g-glutamate, G, A, S,
      T, or K
<220> FEATURE:
<221> NAME/KEY: MISC_FEATURE
<222> LOCATION: (10)..(10)
<223> OTHER INFORMATION: X at position 10 is H or N
<220> FEATURE:
<221> NAME/KEY: MISC_FEATURE
<222> LOCATION: (14)..(14)
<223> OTHER INFORMATION: X at position 14 is E, g-glutamate, D, or isoD
<220> FEATURE:
<221> NAME/KEY: MISC_FEATURE
<222> LOCATION: (17)..(17)
<223> OTHER INFORMATION: X at position 17 is Q, E, g-glutamate, G, A, or
      S
<220> FEATURE:
<221> NAME/KEY: MISC_FEATURE
<222> LOCATION: (19)..(19)
<223> OTHER INFORMATION: X at position 19 is Q, E, g-glutamate, G, A, or
      S

<400> SEQUENCE: 66

Pro Ser Pro Xaa Thr Xaa Xaa Leu Xaa Xaa Ile Val Gly Xaa Ile Leu
1               5                   10                  15

Xaa Ala Xaa Asn
            20
```

<210> SEQ ID NO 67
<211> LENGTH: 20
<212> TYPE: PRT
<213> ORGANISM: Artificial
<220> FEATURE:
<223> OTHER INFORMATION: synthetic peptide

<400> SEQUENCE: 67

Pro Ser Pro Phe Thr Gln Met Leu Met His Ile Val Gly Glu Ile Leu
1               5                   10                  15

Gln Ala Gln Asn
            20

<210> SEQ ID NO 68
<211> LENGTH: 19
<212> TYPE: PRT
<213> ORGANISM: Artificial
<220> FEATURE:
<223> OTHER INFORMATION: synthetic peptide

<400> SEQUENCE: 68

Pro Ser Pro Phe Thr Gln Leu Met His Ile Val Gly Glu Ile Leu Gln
1               5                   10                  15

Ala Gln Asn

<210> SEQ ID NO 69
<211> LENGTH: 20
<212> TYPE: PRT
<213> ORGANISM: Artificial
<220> FEATURE:
<223> OTHER INFORMATION: synthetic peptide

<400> SEQUENCE: 69

Pro Ser Pro Phe Thr Gln Ala Leu Met His Ile Val Gly Glu Ile Leu
1               5                   10                  15

Gln Ala Gln Asn
            20

<210> SEQ ID NO 70
<211> LENGTH: 20
<212> TYPE: PRT
<213> ORGANISM: Artificial
<220> FEATURE:
<223> OTHER INFORMATION: synthetic peptide

<400> SEQUENCE: 70

Pro Ser Pro Phe Thr Gln Met Leu Met Asn Ile Val Gly Glu Ile Leu
1               5                   10                  15

Gln Ala Gln Asn
            20

<210> SEQ ID NO 71
<211> LENGTH: 20
<212> TYPE: PRT
<213> ORGANISM: Artificial
<220> FEATURE:
<223> OTHER INFORMATION: synthetic peptide

<400> SEQUENCE: 71

Pro Ser Pro Tyr Thr Gln Met Leu Met His Ile Val Gly Glu Ile Leu
1               5                   10                  15

Gln Ala Gln Asn
            20

<210> SEQ ID NO 72
<211> LENGTH: 20
<212> TYPE: PRT
<213> ORGANISM: Artificial
<220> FEATURE:
<223> OTHER INFORMATION: synthetic peptide

<400> SEQUENCE: 72

Pro Ser Pro Phe Thr Gln Met Leu Met His Ile Val Gly Asp Ile Leu
1               5                   10                  15

Gln Ala Gln Asn
            20

<210> SEQ ID NO 73
<211> LENGTH: 20
<212> TYPE: PRT
<213> ORGANISM: Artificial
<220> FEATURE:
<223> OTHER INFORMATION: synthetic peptide

<400> SEQUENCE: 73

Pro Ser Pro Phe Thr Gln Ala Leu Ala His Ile Val Gly Glu Ile Leu
1               5                   10                  15

Gln Ala Gln Asn
            20

<210> SEQ ID NO 74
<211> LENGTH: 20
<212> TYPE: PRT
<213> ORGANISM: Artificial
<220> FEATURE:
<223> OTHER INFORMATION: synthetic peptide

<400> SEQUENCE: 74

Pro Ser Pro Phe Thr Glu Ala Leu Met His Ile Val Gly Glu Ile Leu
1               5                   10                  15

Gln Ala Gln Asn
            20

<210> SEQ ID NO 75
<211> LENGTH: 20
<212> TYPE: PRT
<213> ORGANISM: Artificial
<220> FEATURE:
<223> OTHER INFORMATION: synthetic peptide

<400> SEQUENCE: 75

Pro Ser Pro Phe Thr Glu Ala Leu Met His Ile Val Gly Glu Ile Leu
1               5                   10                  15

Glu Ala Gln Asn
            20

<210> SEQ ID NO 76
<211> LENGTH: 20
<212> TYPE: PRT
<213> ORGANISM: Artificial
<220> FEATURE:
<223> OTHER INFORMATION: synthetic peptide

<400> SEQUENCE: 76

Pro Ser Pro Phe Thr Glu Ala Leu Met His Ile Val Gly Glu Ile Leu
1               5                   10                  15

Glu Ala Glu Asn
            20

<210> SEQ ID NO 77
<211> LENGTH: 20
<212> TYPE: PRT
<213> ORGANISM: Artificial
<220> FEATURE:
<223> OTHER INFORMATION: synthetic peptide

<400> SEQUENCE: 77

Pro Ser Pro Tyr Thr Glu Ala Leu Met His Ile Val Gly Glu Ile Leu
1               5                   10                  15

Glu Ala Glu Asn
            20

<210> SEQ ID NO 78
<211> LENGTH: 20
<212> TYPE: PRT
<213> ORGANISM: Artificial
<220> FEATURE:
<223> OTHER INFORMATION: synthetic peptide

<400> SEQUENCE: 78

Pro Ser Pro Phe Thr Glu Ala Leu Met Asn Ile Val Gly Glu Ile Leu
1               5                   10                  15

Glu Ala Glu Asn
            20

<210> SEQ ID NO 79
<211> LENGTH: 20
<212> TYPE: PRT
<213> ORGANISM: Artificial
<220> FEATURE:
<223> OTHER INFORMATION: synthetic peptide

<400> SEQUENCE: 79

Pro Ser Pro Phe Thr Glu Ala Leu Met His Ile Val Gly Asp Ile Leu
1               5                   10                  15

Glu Ala Glu Asn
            20

<210> SEQ ID NO 80
<211> LENGTH: 20
<212> TYPE: PRT
<213> ORGANISM: Artificial
<220> FEATURE:
<223> OTHER INFORMATION: synthetic peptide

<400> SEQUENCE: 80

Pro Ser Pro Tyr Thr Glu Ala Leu Met Asn Ile Val Gly Asp Ile Leu
1               5                   10                  15

Glu Ala Glu Asn
            20

<210> SEQ ID NO 81
<211> LENGTH: 50
<212> TYPE: PRT
<213> ORGANISM: Artificial
<220> FEATURE:
<223> OTHER INFORMATION: synthetic peptide

<400> SEQUENCE: 81

Thr Ser Ser Ser Pro Gly Leu Phe Gln Ser Gly Gly Asp Asn Gly Leu
1               5                   10                  15

Gly Gly His Asn Ala Asn Ser Ala Leu Gly Gln Gln Pro Ile Asp Arg

```
                20                  25                  30
Gln Thr Ile Glu Gln Met Ala Gln Leu Leu Ala Gln Leu Leu Lys Ser
            35                  40                  45
Leu Leu
    50

<210> SEQ ID NO 82
<211> LENGTH: 50
<212> TYPE: PRT
<213> ORGANISM: Artificial
<220> FEATURE:
<223> OTHER INFORMATION: synthetic peptide

<400> SEQUENCE: 82

Thr Ser Ser Ser Pro Gly Leu Phe Gln Ser Gly Gly Asp Asn Gly Leu
1               5                   10                  15

Gly Gly His Asn Ala Asn Ser Ala Leu Gly Gln Gln Pro Ile Asp Arg
                20                  25                  30

Gln Thr Ile Glu Gln Leu Ala Gln Leu Leu Ala Gln Leu Leu Lys Ser
            35                  40                  45

Leu Leu
    50

<210> SEQ ID NO 83
<211> LENGTH: 27
<212> TYPE: PRT
<213> ORGANISM: Artificial
<220> FEATURE:
<223> OTHER INFORMATION: synthetic peptide

<400> SEQUENCE: 83

Gln Gln Pro Ile Asp Arg Gln Thr Ile Glu Gln Met Ala Gln Leu Leu
1               5                   10                  15

Ala Gln Leu Leu Lys Ser Leu Leu Ser Pro Gln
                20                  25

<210> SEQ ID NO 84
<211> LENGTH: 27
<212> TYPE: PRT
<213> ORGANISM: Artificial
<220> FEATURE:
<223> OTHER INFORMATION: synthetic peptide

<400> SEQUENCE: 84

Gln Gln Pro Ile Asp Arg Gln Thr Ile Glu Gln Leu Ala Gln Leu Leu
1               5                   10                  15

Ala Gln Leu Leu Lys Ser Leu Leu Ser Pro Gln
                20                  25

<210> SEQ ID NO 85
<211> LENGTH: 16
<212> TYPE: PRT
<213> ORGANISM: Artificial
<220> FEATURE:
<223> OTHER INFORMATION: synthetic peptide

<400> SEQUENCE: 85

Ile Glu Gln Met Ala Gln Leu Leu Ala Gln Leu Leu Lys Ser Leu Leu
1               5                   10                  15

<210> SEQ ID NO 86
<211> LENGTH: 16
<212> TYPE: PRT
```

```
<213> ORGANISM: Artificial
<220> FEATURE:
<223> OTHER INFORMATION: synthetic peptide

<400> SEQUENCE: 86

Ile Glu Gln Leu Ala Gln Leu Leu Ala Gln Leu Leu Lys Ser Leu Leu
1               5                   10                  15

<210> SEQ ID NO 87
<211> LENGTH: 20
<212> TYPE: PRT
<213> ORGANISM: Artificial
<220> FEATURE:
<223> OTHER INFORMATION: synthetic peptide

<400> SEQUENCE: 87

Asp Arg Gln Thr Ile Glu Gln Met Ala Gln Leu Leu Ala Gln Leu Leu
1               5                   10                  15

Lys Ser Leu Leu
            20

<210> SEQ ID NO 88
<211> LENGTH: 20
<212> TYPE: PRT
<213> ORGANISM: Artificial
<220> FEATURE:
<223> OTHER INFORMATION: synthetic peptide

<400> SEQUENCE: 88

Asp Arg Gln Thr Ile Glu Gln Leu Ala Gln Leu Leu Ala Gln Leu Leu
1               5                   10                  15

Lys Ser Leu Leu
            20

<210> SEQ ID NO 89
<211> LENGTH: 25
<212> TYPE: PRT
<213> ORGANISM: Artificial
<220> FEATURE:
<223> OTHER INFORMATION: synthetic peptide of amino acids 116 to 140 of
      the full length Erwinia amylovora HrpW (P19)

<400> SEQUENCE: 89

Ile Thr Pro Asp Gly Gln Gly Gly Gly Gln Ile Gly Asp Asn Pro Leu
1               5                   10                  15

Leu Lys Ala Met Leu Lys Leu Ile Ala
            20                  25

<210> SEQ ID NO 90
<211> LENGTH: 25
<212> TYPE: PRT
<213> ORGANISM: Artificial
<220> FEATURE:
<223> OTHER INFORMATION: synthetic peptide

<400> SEQUENCE: 90

Ile Thr Pro Asp Gly Gln Gly Gly Gly Gln Ile Gly Asp Asn Pro Leu
1               5                   10                  15

Leu Lys Ala Leu Leu Lys Leu Ile Ala
            20                  25

<210> SEQ ID NO 91
<211> LENGTH: 30
<212> TYPE: PRT
<213> ORGANISM: Artificial
```

```
<220> FEATURE:
<223> OTHER INFORMATION: synthetic peptide

<400> SEQUENCE: 91

Ile Thr Pro Asp Gly Gln Gly Gly Gln Ile Gly Asp Asn Pro Leu
1               5                   10                  15

Leu Lys Ala Met Leu Lys Leu Ile Ala Arg Met Met Asp Gly
            20                  25                  30

<210> SEQ ID NO 92
<211> LENGTH: 30
<212> TYPE: PRT
<213> ORGANISM: Artificial
<220> FEATURE:
<223> OTHER INFORMATION: synthetic peptide

<400> SEQUENCE: 92

Ile Thr Pro Asp Gly Gln Gly Gly Gln Ile Gly Asp Asn Pro Leu
1               5                   10                  15

Leu Lys Ala Leu Leu Lys Leu Ile Ala Arg Leu Leu Asp Gly
            20                  25                  30

<210> SEQ ID NO 93
<211> LENGTH: 13
<212> TYPE: PRT
<213> ORGANISM: Artificial
<220> FEATURE:
<223> OTHER INFORMATION: HR Box Peptide Consensus
<220> FEATURE:
<221> NAME/KEY: MISC_FEATURE
<222> LOCATION: (1)..(1)
<223> OTHER INFORMATION: X at position 1 is L, I, V, or F
<220> FEATURE:
<221> NAME/KEY: MISC_FEATURE
<222> LOCATION: (2)..(2)
<223> OTHER INFORMATION: X at position 2 is optional and, when present,
      is any amino acid
<220> FEATURE:
<221> NAME/KEY: MISC_FEATURE
<222> LOCATION: (3)..(3)
<223> OTHER INFORMATION: X at position 3 is any amino acid
<220> FEATURE:
<221> NAME/KEY: MISC_FEATURE
<222> LOCATION: (4)..(4)
<223> OTHER INFORMATION: X at position 4 is L, I, V, or F
<220> FEATURE:
<221> NAME/KEY: MISC_FEATURE
<222> LOCATION: (5)..(5)
<223> OTHER INFORMATION: X at position 5 is L or I
<220> FEATURE:
<221> NAME/KEY: MISC_FEATURE
<222> LOCATION: (6)..(6)
<223> OTHER INFORMATION: X at position 6 is optional and, when present,
      is any amino acid
<220> FEATURE:
<221> NAME/KEY: MISC_FEATURE
<222> LOCATION: (7)..(7)
<223> OTHER INFORMATION: X at position 7 is any amino acid
<220> FEATURE:
<221> NAME/KEY: MISC_FEATURE
<222> LOCATION: (8)..(8)
<223> OTHER INFORMATION: X at position 8 is L, I, V, or F
<220> FEATURE:
<221> NAME/KEY: MISC_FEATURE
<222> LOCATION: (9)..(9)
<223> OTHER INFORMATION: X at position 9 is L, I, V, or A
<220> FEATURE:
<221> NAME/KEY: MISC_FEATURE
<222> LOCATION: (10)..(10)
<223> OTHER INFORMATION: X at position 10 is optional and, when present,
      is any amino acid
<220> FEATURE:
<221> NAME/KEY: MISC_FEATURE
```

```
<222> LOCATION: (11)..(11)
<223> OTHER INFORMATION: X at position 11 is any amino acid
<220> FEATURE:
<221> NAME/KEY: MISC_FEATURE
<222> LOCATION: (12)..(12)
<223> OTHER INFORMATION: X at position 12 is L or I
<220> FEATURE:
<221> NAME/KEY: MISC_FEATURE
<222> LOCATION: (13)..(13)
<223> OTHER INFORMATION: X at position 13 is L, I, V, or F

<400> SEQUENCE: 93

Xaa Xaa Xaa Xaa Xaa Xaa Xaa Xaa Xaa Xaa Xaa Xaa Xaa
 1               5                  10

<210> SEQ ID NO 94
<211> LENGTH: 17
<212> TYPE: PRT
<213> ORGANISM: Artificial
<220> FEATURE:
<223> OTHER INFORMATION: synthetic peptide

<400> SEQUENCE: 94

Lys Gln Leu Asp Gln Leu Leu Ser Gln Leu Ile Gln Ala Leu Leu Gln
 1               5                  10                  15

Pro

<210> SEQ ID NO 95
<211> LENGTH: 18
<212> TYPE: PRT
<213> ORGANISM: Artificial
<220> FEATURE:
<223> OTHER INFORMATION: synthetic peptide

<400> SEQUENCE: 95

Glu Lys Gln Leu Asp Gln Leu Leu Ser Gln Leu Ile Gln Ala Leu Leu
 1               5                  10                  15

Gln Pro

<210> SEQ ID NO 96
<211> LENGTH: 19
<212> TYPE: PRT
<213> ORGANISM: Artificial
<220> FEATURE:
<223> OTHER INFORMATION: synthetic peptide

<400> SEQUENCE: 96

Ser Glu Lys Gln Leu Asp Gln Leu Leu Ser Gln Leu Ile Gln Ala Leu
 1               5                  10                  15

Leu Gln Pro

<210> SEQ ID NO 97
<211> LENGTH: 21
<212> TYPE: PRT
<213> ORGANISM: Artificial
<220> FEATURE:
<223> OTHER INFORMATION: synthetic peptide

<400> SEQUENCE: 97

Gly Ile Ser Glu Lys Gln Leu Asp Gln Leu Leu Ser Gln Leu Ile Gln
 1               5                  10                  15

Ala Leu Leu Gln Pro
                20

<210> SEQ ID NO 98
```

```
<211> LENGTH: 23
<212> TYPE: PRT
<213> ORGANISM: Artificial
<220> FEATURE:
<223> OTHER INFORMATION: synthetic peptide

<400> SEQUENCE: 98

Ser Gln Glu Ile Ser Glu Lys Gln Leu Asp Gln Leu Leu Ser Gln Leu
1               5                   10                  15

Ile Gln Ala Leu Leu Gln Pro
            20

<210> SEQ ID NO 99
<211> LENGTH: 23
<212> TYPE: PRT
<213> ORGANISM: Artificial
<220> FEATURE:
<223> OTHER INFORMATION: synthetic peptide

<400> SEQUENCE: 99

Ser Gln Gly Leu Ser Glu Lys Gln Leu Asp Gln Leu Leu Ser Gln Leu
1               5                   10                  15

Ile Gln Ala Leu Leu Gln Pro
            20

<210> SEQ ID NO 100
<211> LENGTH: 23
<212> TYPE: PRT
<213> ORGANISM: Artificial
<220> FEATURE:
<223> OTHER INFORMATION: synthetic peptide

<400> SEQUENCE: 100

Ser Gln Gly Ala Ser Glu Lys Gln Leu Asp Gln Leu Leu Ser Gln Leu
1               5                   10                  15

Ile Gln Ala Leu Leu Gln Pro
            20

<210> SEQ ID NO 101
<211> LENGTH: 23
<212> TYPE: PRT
<213> ORGANISM: Artificial
<220> FEATURE:
<223> OTHER INFORMATION: synthetic peptide

<400> SEQUENCE: 101

Ser Gln Gly Asp Ser Glu Lys Gln Leu Asp Gln Leu Leu Ser Gln Leu
1               5                   10                  15

Ile Gln Ala Leu Leu Gln Pro
            20

<210> SEQ ID NO 102
<211> LENGTH: 23
<212> TYPE: PRT
<213> ORGANISM: Artificial
<220> FEATURE:
<223> OTHER INFORMATION: synthetic peptide

<400> SEQUENCE: 102

Ser Gln Gly Ile Val Glu Lys Gln Leu Asp Gln Leu Leu Ser Gln Leu
1               5                   10                  15

Ile Gln Ala Leu Leu Gln Pro
            20
```

```
<210> SEQ ID NO 103
<211> LENGTH: 23
<212> TYPE: PRT
<213> ORGANISM: Artificial
<220> FEATURE:
<223> OTHER INFORMATION: synthetic peptide

<400> SEQUENCE: 103

Ser Gln Gly Ile Ser Arg Lys Gln Leu Asp Gln Leu Leu Ser Gln Leu
1               5                   10                  15

Ile Gln Ala Leu Leu Gln Pro
            20

<210> SEQ ID NO 104
<211> LENGTH: 23
<212> TYPE: PRT
<213> ORGANISM: Artificial
<220> FEATURE:
<223> OTHER INFORMATION: synthetic peptide

<400> SEQUENCE: 104

Ser Gln Gly Ile Ser Val Lys Gln Leu Asp Gln Leu Leu Ser Gln Leu
1               5                   10                  15

Ile Gln Ala Leu Leu Gln Pro
            20

<210> SEQ ID NO 105
<211> LENGTH: 23
<212> TYPE: PRT
<213> ORGANISM: Artificial
<220> FEATURE:
<223> OTHER INFORMATION: synthetic peptide

<400> SEQUENCE: 105

Ser Gln Gly Ile Ser Glu Asp Gln Leu Asp Gln Leu Leu Ser Gln Leu
1               5                   10                  15

Ile Gln Ala Leu Leu Gln Pro
            20

<210> SEQ ID NO 106
<211> LENGTH: 23
<212> TYPE: PRT
<213> ORGANISM: Artificial
<220> FEATURE:
<223> OTHER INFORMATION: synthetic peptide

<400> SEQUENCE: 106

Ser Gln Gly Ile Ser Glu Val Gln Leu Asp Gln Leu Leu Ser Gln Leu
1               5                   10                  15

Ile Gln Ala Leu Leu Gln Pro
            20

<210> SEQ ID NO 107
<211> LENGTH: 23
<212> TYPE: PRT
<213> ORGANISM: Artificial
<220> FEATURE:
<223> OTHER INFORMATION: synthetic peptide

<400> SEQUENCE: 107

Ser Gln Gly Ile Ser Glu Lys Val Leu Asp Gln Leu Leu Ser Gln Leu
1               5                   10                  15

Ile Gln Ala Leu Leu Gln Pro
            20
```

```
<210> SEQ ID NO 108
<211> LENGTH: 23
<212> TYPE: PRT
<213> ORGANISM: Artificial
<220> FEATURE:
<223> OTHER INFORMATION: synthetic peptide

<400> SEQUENCE: 108

Ser Gln Gly Ile Ser Glu Lys Ser Leu Asp Gln Leu Leu Ser Gln Leu
1               5                   10                  15

Ile Gln Ala Leu Leu Gln Pro
            20

<210> SEQ ID NO 109
<211> LENGTH: 23
<212> TYPE: PRT
<213> ORGANISM: Artificial
<220> FEATURE:
<223> OTHER INFORMATION: synthetic peptide

<400> SEQUENCE: 109

Ser Gln Gly Ile Ser Glu Lys Gln Leu Asp Gln Leu Leu Thr Gln Leu
1               5                   10                  15

Ile Met Ala Leu Leu Gln Gln
            20

<210> SEQ ID NO 110
<211> LENGTH: 23
<212> TYPE: PRT
<213> ORGANISM: Artificial
<220> FEATURE:
<223> OTHER INFORMATION: synthetic peptide

<400> SEQUENCE: 110

Asn Gln Gly Ile Ser Glu Lys Gln Leu Asp Gln Leu Leu Ser Gln Leu
1               5                   10                  15

Ile Met Ala Leu Leu Gln Gln
            20

<210> SEQ ID NO 111
<211> LENGTH: 23
<212> TYPE: PRT
<213> ORGANISM: Artificial
<220> FEATURE:
<223> OTHER INFORMATION: synthetic peptide

<400> SEQUENCE: 111

Ser Gln Gly Ile Ser Glu Lys Gln Leu Val Gln Leu Leu Ser Gln Leu
1               5                   10                  15

Ile Gln Ala Leu Leu Gln Pro
            20

<210> SEQ ID NO 112
<211> LENGTH: 23
<212> TYPE: PRT
<213> ORGANISM: Artificial
<220> FEATURE:
<223> OTHER INFORMATION: synthetic peptide

<400> SEQUENCE: 112

Ser Gln Gly Ile Ser Glu Lys Gln Leu Asp Val Leu Leu Ser Gln Leu
1               5                   10                  15

Ile Gln Ala Leu Leu Gln Pro
            20
```

```
<210> SEQ ID NO 113
<211> LENGTH: 23
<212> TYPE: PRT
<213> ORGANISM: Artificial
<220> FEATURE:
<223> OTHER INFORMATION: synthetic peptide

<400> SEQUENCE: 113

Ser Gln Gly Ile Ser Glu Lys Gln Leu Asp Gln Val Leu Ser Gln Leu
1               5                   10                  15

Ile Gln Ala Leu Leu Gln Pro
            20

<210> SEQ ID NO 114
<211> LENGTH: 23
<212> TYPE: PRT
<213> ORGANISM: Artificial
<220> FEATURE:
<223> OTHER INFORMATION: synthetic peptide

<400> SEQUENCE: 114

Ser Gln Gly Ile Ser Glu Lys Gln Leu Asp Gln Ser Leu Ser Gln Leu
1               5                   10                  15

Ile Gln Ala Leu Leu Gln Pro
            20

<210> SEQ ID NO 115
<211> LENGTH: 23
<212> TYPE: PRT
<213> ORGANISM: Artificial
<220> FEATURE:
<223> OTHER INFORMATION: synthetic peptide

<400> SEQUENCE: 115

Asn Gln Gly Ile Ser Glu Lys Gln Leu Asp Gln Leu Leu Thr Gln Leu
1               5                   10                  15

Ile Gln Ala Leu Leu Gln Gln
            20

<210> SEQ ID NO 116
<211> LENGTH: 23
<212> TYPE: PRT
<213> ORGANISM: Artificial
<220> FEATURE:
<223> OTHER INFORMATION: synthetic peptide

<400> SEQUENCE: 116

Ser Gln Gly Ile Ser Glu Lys Gln Leu Asp Gln Leu Leu Val Gln Leu
1               5                   10                  15

Ile Gln Ala Leu Leu Gln Pro
            20

<210> SEQ ID NO 117
<211> LENGTH: 23
<212> TYPE: PRT
<213> ORGANISM: Artificial
<220> FEATURE:
<223> OTHER INFORMATION: synthetic peptide

<400> SEQUENCE: 117

Ser Gln Gly Ile Ser Glu Lys Gln Leu Asp Gln Leu Leu Ser Val Leu
1               5                   10                  15

Ile Gln Ala Leu Leu Gln Pro
```

```
                    20

<210> SEQ ID NO 118
<211> LENGTH: 23
<212> TYPE: PRT
<213> ORGANISM: Artificial
<220> FEATURE:
<223> OTHER INFORMATION: synthetic peptide

<400> SEQUENCE: 118

Asn Gln Gly Ile Ser Glu Lys Gln Leu Asp Gln Leu Leu Thr Gln Leu
1               5                  10                  15

Ile Met Ala Leu Leu Gln Pro
            20

<210> SEQ ID NO 119
<211> LENGTH: 23
<212> TYPE: PRT
<213> ORGANISM: Artificial
<220> FEATURE:
<223> OTHER INFORMATION: synthetic peptide

<400> SEQUENCE: 119

Ser Gln Gly Ile Ser Glu Lys Gln Leu Asp Gln Leu Leu Ser Gln Leu
1               5                  10                  15

Leu Gln Ala Leu Leu Gln Pro
            20

<210> SEQ ID NO 120
<211> LENGTH: 23
<212> TYPE: PRT
<213> ORGANISM: Artificial
<220> FEATURE:
<223> OTHER INFORMATION: synthetic peptide

<400> SEQUENCE: 120

Ser Gln Gly Ile Ser Glu Lys Gln Leu Asp Gln Leu Leu Ser Gln Leu
1               5                  10                  15

Ala Gln Ala Leu Leu Gln Pro
            20

<210> SEQ ID NO 121
<211> LENGTH: 23
<212> TYPE: PRT
<213> ORGANISM: Artificial
<220> FEATURE:
<223> OTHER INFORMATION: synthetic peptide

<400> SEQUENCE: 121

Ser Gln Gly Ile Ser Glu Lys Gln Leu Asp Gln Leu Leu Ser Gln Leu
1               5                  10                  15

Val Gln Ala Leu Leu Gln Pro
            20

<210> SEQ ID NO 122
<211> LENGTH: 23
<212> TYPE: PRT
<213> ORGANISM: Artificial
<220> FEATURE:
<223> OTHER INFORMATION: synthetic peptide

<400> SEQUENCE: 122

Ser Gln Gly Ile Ser Glu Lys Gln Leu Asp Gln Leu Leu Ser Gln Leu
1               5                  10                  15
```

-continued

Ile Val Ala Leu Leu Gln Pro
            20

<210> SEQ ID NO 123
<211> LENGTH: 23
<212> TYPE: PRT
<213> ORGANISM: Artificial
<220> FEATURE:
<223> OTHER INFORMATION: synthetic peptide

<400> SEQUENCE: 123

Ser Gln Gly Ile Ser Glu Lys Gln Leu Asp Gln Leu Leu Ser Gln Leu
1               5                   10                  15

Ile Gln Val Leu Leu Gln Pro
            20

<210> SEQ ID NO 124
<211> LENGTH: 23
<212> TYPE: PRT
<213> ORGANISM: Artificial
<220> FEATURE:
<223> OTHER INFORMATION: synthetic peptide

<400> SEQUENCE: 124

Ser Gln Gly Ile Ser Glu Lys Gln Leu Asp Gln Leu Leu Ser Gln Leu
1               5                   10                  15

Ile Gln Asp Leu Leu Gln Pro
            20

<210> SEQ ID NO 125
<211> LENGTH: 23
<212> TYPE: PRT
<213> ORGANISM: Artificial
<220> FEATURE:
<223> OTHER INFORMATION: synthetic peptide

<400> SEQUENCE: 125

Ser Gln Gly Ile Ser Glu Lys Gln Leu Asp Gln Leu Leu Ser Gln Leu
1               5                   10                  15

Ile Gln Ser Leu Leu Gln Pro
            20

<210> SEQ ID NO 126
<211> LENGTH: 21
<212> TYPE: PRT
<213> ORGANISM: Artificial
<220> FEATURE:
<223> OTHER INFORMATION: synthetic peptide

<400> SEQUENCE: 126

Ser Glu Glu Glu Glu Glu Leu Asp Gln Leu Leu Thr Gln Leu Ile Glu
1               5                   10                  15

Ala Leu Leu Gln Gln
            20

<210> SEQ ID NO 127
<211> LENGTH: 23
<212> TYPE: PRT
<213> ORGANISM: Artificial
<220> FEATURE:
<223> OTHER INFORMATION: synthetic peptide

<400> SEQUENCE: 127

Ser Gln Gly Ile Ser Glu Lys Gln Leu Asp Gln Leu Leu Ser Gln Leu
1               5                   10                  15

Ile Gln Ala Leu Ser Gln Pro
            20

<210> SEQ ID NO 128
<211> LENGTH: 23
<212> TYPE: PRT
<213> ORGANISM: Artificial
<220> FEATURE:
<223> OTHER INFORMATION: synthetic peptide

<400> SEQUENCE: 128

Ser Gln Gly Ile Ser Glu Lys Gln Leu Asp Gln Leu Leu Ser Gln Leu
1               5                   10                  15

Ile Gln Ala Leu Ile Gln Pro
            20

<210> SEQ ID NO 129
<211> LENGTH: 23
<212> TYPE: PRT
<213> ORGANISM: Artificial
<220> FEATURE:
<223> OTHER INFORMATION: synthetic peptide

<400> SEQUENCE: 129

Ser Gln Gly Ile Ser Glu Lys Gln Leu Asp Gln Leu Leu Ser Gln Leu
1               5                   10                  15

Ile Gln Ala Leu Val Gln Pro
            20

<210> SEQ ID NO 130
<211> LENGTH: 23
<212> TYPE: PRT
<213> ORGANISM: Artificial
<220> FEATURE:
<223> OTHER INFORMATION: synthetic peptide

<400> SEQUENCE: 130

Ser Gln Gly Ile Ser Glu Lys Gln Leu Asp Gln Leu Leu Ser Gln Leu
1               5                   10                  15

Ile Gln Ala Leu Leu Val Pro
            20

<210> SEQ ID NO 131
<211> LENGTH: 21
<212> TYPE: PRT
<213> ORGANISM: Artificial
<220> FEATURE:
<223> OTHER INFORMATION: synthetic peptide

<400> SEQUENCE: 131

Ser Gln Gly Ile Ser Glu Lys Gln Leu Asp Gln Leu Leu Ser Gln Leu
1               5                   10                  15

Ile Gln Ala Leu Leu
            20

<210> SEQ ID NO 132
<211> LENGTH: 22
<212> TYPE: PRT
<213> ORGANISM: Artificial
<220> FEATURE:
<223> OTHER INFORMATION: synthetic peptide

<400> SEQUENCE: 132

Ser Gln Gly Ile Ser Glu Lys Gln Leu Gln Leu Leu Ser Gln Leu Ile

```
                 1               5                  10                 15
Gln Ala Leu Leu Gln Pro
            20

<210> SEQ ID NO 133
<211> LENGTH: 22
<212> TYPE: PRT
<213> ORGANISM: Artificial
<220> FEATURE:
<223> OTHER INFORMATION: synthetic peptide

<400> SEQUENCE: 133

Ser Gln Gly Ile Ser Glu Lys Gln Leu Asp Gln Leu Leu Gln Leu Ile
1               5                   10                  15

Gln Ala Leu Leu Gln Pro
            20

<210> SEQ ID NO 134
<211> LENGTH: 20
<212> TYPE: PRT
<213> ORGANISM: Artificial
<220> FEATURE:
<223> OTHER INFORMATION: synthetic peptide

<400> SEQUENCE: 134

Ser Glu Glu Glu Glu Glu Leu Asp Gln Leu Leu Thr Gln Leu Ile Glu
1               5                   10                  15

Ala Leu Leu Gln
            20

<210> SEQ ID NO 135
<211> LENGTH: 13
<212> TYPE: PRT
<213> ORGANISM: Artificial
<220> FEATURE:
<223> OTHER INFORMATION: P6/6a min consensus
<220> FEATURE:
<221> NAME/KEY: MISC_FEATURE
<222> LOCATION: (1)..(1)
<223> OTHER INFORMATION: X at position 1 is F or Y
<220> FEATURE:
<221> NAME/KEY: MISC_FEATURE
<222> LOCATION: (3)..(3)
<223> OTHER INFORMATION: X at position 3 is Q, E, g-glutamate, G, A, or
      S
<220> FEATURE:
<221> NAME/KEY: MISC_FEATURE
<222> LOCATION: (4)..(4)
<223> OTHER INFORMATION: X at position 4 is optional and can be M, E,
      g-glutamate, G, A, S, T, or K, or L
<220> FEATURE:
<221> NAME/KEY: MISC_FEATURE
<222> LOCATION: (6)..(6)
<223> OTHER INFORMATION: X at position 6 is M, E, g-glutamate, G, A, S,
      T, or K
<220> FEATURE:
<221> NAME/KEY: MISC_FEATURE
<222> LOCATION: (7)..(7)
<223> OTHER INFORMATION: X at position 7 is H or N
<220> FEATURE:
<221> NAME/KEY: MISC_FEATURE
<222> LOCATION: (11)..(11)
<223> OTHER INFORMATION: X at position 11 is E, g-glutamate, D, or isoD

<400> SEQUENCE: 135

Xaa Thr Xaa Xaa Leu Xaa Xaa Ile Val Gly Xaa Ile Leu
1               5                   10

<210> SEQ ID NO 136
```

```
<211> LENGTH: 23
<212> TYPE: PRT
<213> ORGANISM: Artificial
<220> FEATURE:
<223> OTHER INFORMATION: synthetic peptide

<400> SEQUENCE: 136

Ser Gln Gly Ile Ser Glu Lys Gln Leu Asp Gln Leu Leu Ala Gln Leu
1               5                   10                  15

Ile Gln Ala Leu Leu Gln Pro
            20

<210> SEQ ID NO 137
<211> LENGTH: 23
<212> TYPE: PRT
<213> ORGANISM: Artificial
<220> FEATURE:
<223> OTHER INFORMATION: synthetic peptide

<400> SEQUENCE: 137

Ser Gln Gly Ile Ser Glu Lys Gln Leu Asp Gln Leu Leu Asp Gln Leu
1               5                   10                  15

Ile Gln Ala Leu Leu Gln Pro
            20

<210> SEQ ID NO 138
<211> LENGTH: 23
<212> TYPE: PRT
<213> ORGANISM: Artificial
<220> FEATURE:
<223> OTHER INFORMATION: synthetic peptide

<400> SEQUENCE: 138

Ser Gln Gly Ile Ser Glu Lys Gln Leu Asp Gln Leu Leu Lys Gln Leu
1               5                   10                  15

Ile Gln Ala Leu Leu Gln Pro
            20

<210> SEQ ID NO 139
<211> LENGTH: 23
<212> TYPE: PRT
<213> ORGANISM: Artificial
<220> FEATURE:
<223> OTHER INFORMATION: synthetic peptide

<400> SEQUENCE: 139

Ser Gln Gly Ile Ser Glu Lys Gln Leu Asp Gln Leu Leu Gln Gln Leu
1               5                   10                  15

Ile Gln Ala Leu Leu Gln Pro
            20

<210> SEQ ID NO 140
<211> LENGTH: 24
<212> TYPE: PRT
<213> ORGANISM: Artificial
<220> FEATURE:
<223> OTHER INFORMATION: synthetic peptide

<400> SEQUENCE: 140

Ser Gln Gly Ile Ser Glu Lys Gln Ala Leu Asp Gln Leu Leu Ser Gln
1               5                   10                  15

Leu Ile Gln Ala Leu Leu Gln Pro
            20
```

```
<210> SEQ ID NO 141
<211> LENGTH: 19
<212> TYPE: PRT
<213> ORGANISM: Artificial
<220> FEATURE:
<223> OTHER INFORMATION: synthetic peptide

<400> SEQUENCE: 141

Ser Glu Glu Glu Glu Glu Leu Asp Gln Leu Leu Thr Gln Leu Ile Glu
1               5                   10                  15

Ala Leu Leu

<210> SEQ ID NO 142
<211> LENGTH: 39
<212> TYPE: PRT
<213> ORGANISM: Artificial
<220> FEATURE:
<223> OTHER INFORMATION: synthetic peptide

<400> SEQUENCE: 142

Asn Phe Gly Thr Pro Asp Ser Thr Val Gln Asn Pro Gln Asp Ala Ser
1               5                   10                  15

Lys Pro Asn Asp Ser Gln Ser Asn Ile Ala Lys Leu Ile Ser Ala Leu
            20                  25                  30

Ile Gln Ser Leu Leu Gln Pro
            35

<210> SEQ ID NO 143
<211> LENGTH: 39
<212> TYPE: PRT
<213> ORGANISM: Artificial
<220> FEATURE:
<223> OTHER INFORMATION: synthetic peptide

<400> SEQUENCE: 143

Asn Phe Gly Thr Pro Asp Ser Thr Val Gln Asn Pro Gln Asp Ala Ser
1               5                   10                  15

Lys Pro Asn Asp Ser Gln Ser Asn Ile Ala Lys Leu Ile Ser Ala Leu
            20                  25                  30

Ile Met Ser Leu Leu Gln Pro
            35

<210> SEQ ID NO 144
<211> LENGTH: 39
<212> TYPE: PRT
<213> ORGANISM: Artificial
<220> FEATURE:
<223> OTHER INFORMATION: synthetic peptide

<400> SEQUENCE: 144

Asn Phe Gly Thr Pro Asp Ser Thr Val Gln Asn Pro Gln Asp Ala Ser
1               5                   10                  15

Lys Pro Asn Asp Ser Gln Ser Asn Ile Ala Lys Leu Ile Ser Ala Leu
            20                  25                  30

Ile Gln Ser Leu Leu Gln Met
            35

<210> SEQ ID NO 145
<211> LENGTH: 69
<212> TYPE: DNA
<213> ORGANISM: Artificial
<220> FEATURE:
<223> OTHER INFORMATION: synthetic fragment
```

<400> SEQUENCE: 145
tctcaaggaa tttctgaaaa gcaacttgat caacttcttt ctcaacttat tcaagctctt    60
cttcaacct                                                             69

<210> SEQ ID NO 146
<211> LENGTH: 69
<212> TYPE: DNA
<213> ORGANISM: Artificial
<220> FEATURE:
<223> OTHER INFORMATION: synthetic fragment

<400> SEQUENCE: 146
agccagggta ttagcgaaaa acagctggat cagctgctga gccagctgat tcaggcactg    60
ctgcagccg                                                             69

<210> SEQ ID NO 147
<211> LENGTH: 69
<212> TYPE: DNA
<213> ORGANISM: Artificial
<220> FEATURE:
<223> OTHER INFORMATION: synthetic fragment

<400> SEQUENCE: 147
aatgaaggaa tttctgaaaa ggaacttgat gaacttctta ctgaacttat tgaagctctt    60
cttcaacaa                                                             69

<210> SEQ ID NO 148
<211> LENGTH: 69
<212> TYPE: DNA
<213> ORGANISM: Artificial
<220> FEATURE:
<223> OTHER INFORMATION: synthetic fragment

<400> SEQUENCE: 148
aatgaaggta ttagcgaaaa agaactggat gaactgctga ccgaactgat tgaagcactg    60
ctgcagcag                                                             69

<210> SEQ ID NO 149
<211> LENGTH: 22
<212> TYPE: PRT
<213> ORGANISM: Artificial
<220> FEATURE:
<223> OTHER INFORMATION: synthetic peptide

<400> SEQUENCE: 149

Ser Glu Glu Glu Glu Glu Gly Gly Ile Ala Lys Leu Ile Ser Ala Leu
1               5                   10                  15

Ile Glu Ser Leu Leu Glu
            20

<210> SEQ ID NO 150
<211> LENGTH: 20
<212> TYPE: PRT
<213> ORGANISM: Artificial
<220> FEATURE:
<223> OTHER INFORMATION: synthetic peptide

<400> SEQUENCE: 150

Ser Glu Glu Glu Glu Glu Ile Ala Lys Leu Ile Ser Ala Leu Ile Glu
1               5                   10                  15

Ser Leu Leu Glu
            20

<210> SEQ ID NO 151
<211> LENGTH: 20
<212> TYPE: PRT
<213> ORGANISM: Artificial
<220> FEATURE:
<223> OTHER INFORMATION: synthetic peptide

<400> SEQUENCE: 151

Lys Pro Asn Asp Ser Gln Ser Asn Ile Ala Lys Leu Ile Ser Leu Ile
1               5                   10                  15

Met Ser Leu Leu
            20

<210> SEQ ID NO 152
<211> LENGTH: 20
<212> TYPE: PRT
<213> ORGANISM: Artificial
<220> FEATURE:
<223> OTHER INFORMATION: synthetic peptide

<400> SEQUENCE: 152

Lys Pro Asn Asp Ser Gln Ser Asn Ile Ala Lys Leu Ile Ser Leu Ile
1               5                   10                  15

Glu Ser Leu Leu
            20

<210> SEQ ID NO 153
<211> LENGTH: 21
<212> TYPE: PRT
<213> ORGANISM: Artificial
<220> FEATURE:
<223> OTHER INFORMATION: synthetic peptide of amino acids 85-103 of
      full-length harpin of Xanthomonas oryzae pv. Oryzae

<400> SEQUENCE: 153

Pro Ser P

```
<222> LOCATION: (13)..(13)
<223> OTHER INFORMATION: X at position 13 can be G or M
<220> FEATURE:
<221> NAME/KEY: MISC_FEATURE
<222> LOCATION: (14)..(14)
<223> OTHER INFORMATION: X at position 14 can be E, D, or Q

<400> SEQUENCE: 154

Xaa Ser Xaa Xaa Thr Gln Xaa Leu Met Xaa Ile Val Xaa Xaa
1               5                   10

<210> SEQ ID NO 155
<211> LENGTH: 17
<212> TYPE: PRT
<213> ORGANISM: Artificial
<220> FEATURE:
<223> OTHER INFORMATION: P6b

<400> SEQUENCE: 155

Phe Thr Gln Met Leu Met His Ile Val Gly Glu Ile Leu Gln Ala Gln
1               5                   10                  15

Asn

<210> SEQ ID NO 156
<211> LENGTH: 16
<212> TYPE: PRT
<213> ORGANISM: Artificial
<220> FEATURE:
<223> OTHER INFORMATION: synthetic peptide

<400> SEQUENCE: 156

Pro Ser Pro Phe Thr Gln Met Leu Met His Ile Val Gly Glu Ile Leu
1               5                   10                  15

<210> SEQ ID NO 157
<211> LENGTH: 20
<212> TYPE: PRT
<213> ORGANISM: Artificial
<220> FEATURE:
<223> OTHER INFORMATION: synthetic peptide

<400> SEQUENCE: 157

Pro Ser Pro Phe Thr Gln Leu Leu Met His Ile Val Gly Glu Ile Leu
1               5                   10                  15

Gln Ala Gln Asn
            20

<210> SEQ ID NO 158
<211> LENGTH: 20
<212> TYPE: PRT
<213> ORGANISM: Artificial
<220> FEATURE:
<223> OTHER INFORMATION: synthetic peptide

<400> SEQUENCE: 158

Pro Ser Pro Phe Thr Gln Met Leu Glu His Ile Val Gly Glu Ile Leu
1               5                   10                  15

Gln Ala Gln Asn
            20

<210> SEQ ID NO 159
<211> LENGTH: 20
<212> TYPE: PRT
<213> ORGANISM: Artificial
<220> FEATURE:
<223> OTHER INFORMATION: synthetic peptide
```

-continued

```
<400> SEQUENCE: 159

Pro Ser Pro Phe Thr Gln Leu Leu Glu His Ile Val Gly Glu Ile Leu
1               5                   10                  15

Gln Ala Gln Asn
            20

<210> SEQ ID NO 160
<211> LENGTH: 19
<212> TYPE: PRT
<213> ORGANISM: Artificial
<220> FEATURE:
<223> OTHER INFORMATION: synthetic peptide

<400> SEQUENCE: 160

Ser Glu Glu Glu Glu Glu Phe Thr Gln Met Leu Met His Ile Val Gly
1               5                   10                  15

Glu Ile Leu

<210> SEQ ID NO 161
<211> LENGTH: 19
<212> TYPE: PRT
<213> ORGANISM: Artificial
<220> FEATURE:
<223> OTHER INFORMATION: synthetic peptide

<400> SEQUENCE: 161

Ser Glu Glu Glu Glu Glu Phe Thr Gln Leu Leu Glu His Ile Val Gly
1               5                   10                  15

Glu Ile Leu

<210> SEQ ID NO 162
<211> LENGTH: 50
<212> TYPE: PRT
<213> ORGANISM: Artificial
<220> FEATURE:
<223> OTHER INFORMATION: synthetic peptide of amino acids 10 to 59 of
      the full length Erwinia amylovora HrpW

<400> SEQUENCE: 162

Thr Ser Ser Ser Pro Gly Leu Phe Gln Ser Gly Gly Asp Asn Gly Leu
1               5                   10                  15

Gly Gly His Asn Ala Asn Ser Ala Leu Gly Gln Gln Pro Ile Asp Arg
            20                  25                  30

Gln Thr Ile Glu Gln Met Ala Gln Leu Leu Ala Glu Leu Leu Lys Ser
        35                  40                  45

Leu Leu
    50

<210> SEQ ID NO 163
<211> LENGTH: 24
<212> TYPE: PRT
<213> ORGANISM: Artificial
<220> FEATURE:
<223> OTHER INFORMATION: synthetic peptide

<400> SEQUENCE: 163

Gln Gln Pro Ile Asp Arg Gln Thr Ile Glu Gln Met Ala Gln Leu Leu
1               5                   10                  15

Ala Gln Leu Leu Lys Ser Leu Leu
            20
```

```
<210> SEQ ID NO 164
<211> LENGTH: 22
<212> TYPE: PRT
<213> ORGANISM: Artificial
<220> FEATURE:
<223> OTHER INFORMATION: synthetic peptide

<400> SEQUENCE: 164

Asp Arg Gln Thr Ile Glu Gln Leu Ala Gln Leu Leu Ala Gln Leu Leu
1               5                   10                  15

Lys Ser Leu Leu Ser Pro
            20

<210> SEQ ID NO 165
<211> LENGTH: 20
<212> TYPE: PRT
<213> ORGANISM: Artificial
<220> FEATURE:
<223> OTHER INFORMATION: synthetic peptide

<400> SEQUENCE: 165

Gln Thr Ile Glu Gln Leu Ala Gln Leu Leu Ala Gln Leu Leu Lys Ser
1               5                   10                  15

Leu Leu Ser Pro
            20

<210> SEQ ID NO 166
<211> LENGTH: 22
<212> TYPE: PRT
<213> ORGANISM: Artificial
<220> FEATURE:
<223> OTHER INFORMATION: synthetic peptide

<400> SEQUENCE: 166

Ser Glu Glu Glu Glu Glu Ile Glu Gln Leu Ala Gln Leu Leu Ala Gln
1               5                   10                  15

Leu Leu Lys Ser Leu Leu
            20

<210> SEQ ID NO 167
<211> LENGTH: 19
<212> TYPE: PRT
<213> ORGANISM: Artificial
<220> FEATURE:
<223> OTHER INFORMATION: synthetic peptide

<400> SEQUENCE: 167

Ser Glu Glu Glu Glu Glu Leu Ala Gln Leu Leu Ala Gln Leu Leu Lys
1               5                   10                  15

Ser Leu Leu

<210> SEQ ID NO 168
<211> LENGTH: 26
<212> TYPE: PRT
<213> ORGANISM: Artificial
<220> FEATURE:
<223> OTHER INFORMATION: synthetic peptide

<400> SEQUENCE: 168

Ser Glu Glu Glu Glu Glu Ile Gly Asp Asn Pro Leu Leu Lys Ala Leu
1               5                   10                  15

Leu Lys Leu Ile Ala Arg Leu Leu Asp Gly
            20                  25
```

```
<210> SEQ ID NO 169
<211> LENGTH: 26
<212> TYPE: PRT
<213> ORGANISM: Artificial
<220> FEATURE:
<223> OTHER INFORMATION: synthetic peptide

<400> SEQUENCE: 169

Ser Glu Glu Glu Glu Glu Ile Gly Asp Asp Glu Leu Leu Lys Ala Leu
1               5                   10                  15

Leu Lys Leu Ile Ala Arg Leu Leu Asp Gly
            20                  25

<210> SEQ ID NO 170
<211> LENGTH: 21
<212> TYPE: PRT
<213> ORGANISM: Artificial
<220> FEATURE:
<223> OTHER INFORMATION: synthetic peptide

<400> SEQUENCE: 170

Ser Glu Glu Glu Glu Glu Leu Leu Lys Ala Leu Leu Lys Leu Ile Ala
1               5                   10                  15

Arg Leu Leu Asp Gly
            20

<210> SEQ ID NO 171
<211> LENGTH: 24
<212> TYPE: PRT
<213> ORGANISM: Artificial
<220> FEATURE:
<223> OTHER INFORMATION: synthetic peptide

<400> SEQUENCE: 171

Ser Glu Glu Glu Glu Glu Ile Gly Asp Asn Pro Leu Leu Lys Ala Leu
1               5                   10                  15

Leu Lys Leu Ile Ala Arg Leu Leu
            20

<210> SEQ ID NO 172
<211> LENGTH: 19
<212> TYPE: PRT
<213> ORGANISM: Artificial
<220> FEATURE:
<223> OTHER INFORMATION: synthetic peptide

<400> SEQUENCE: 172

Ser Glu Glu Glu Glu Glu Leu Leu Lys Ala Leu Leu Lys Leu Ile Ala
1               5                   10                  15

Arg Leu Leu

<210> SEQ ID NO 173
<211> LENGTH: 18
<212> TYPE: PRT
<213> ORGANISM: Artificial
<220> FEATURE:
<223> OTHER INFORMATION: synthetic peptide

<400> SEQUENCE: 173

Ser Glu Glu Glu Glu Glu Leu Lys Ala Leu Leu Lys Leu Ile Ala Arg
1               5                   10                  15

Leu Leu

<210> SEQ ID NO 174
```

```
<211> LENGTH: 34
<212> TYPE: PRT
<213> ORGANISM: Artificial
<220> FEATURE:
<223> OTHER INFORMATION: synthetic peptide of amino acids 92 to 125 of
      the Ralstonia solanacearum PopA

<400> SEQUENCE: 174

Gln Ala Pro Gln Ser Ala Asn Lys Thr Gly Asn Val Asp Asp Ala Asn
1               5                   10                  15

Asn Gln Asp Pro Met Gln Ala Leu Met Gln Leu Leu Glu Asp Leu Val
            20                  25                  30

Lys Leu

<210> SEQ ID NO 175
<211> LENGTH: 19
<212> TYPE: PRT
<213> ORGANISM: Artificial
<220> FEATURE:
<223> OTHER INFORMATION: synthetic peptide

<400> SEQUENCE: 175

Gln Asp Pro Met Gln Ala Leu Met Gln Leu Leu Glu Asp Leu Val Lys
1               5                   10                  15

Leu Leu Lys

<210> SEQ ID NO 176
<211> LENGTH: 19
<212> TYPE: PRT
<213> ORGANISM: Artificial
<220> FEATURE:
<223> OTHER INFORMATION: synthetic peptide

<400> SEQUENCE: 176

Gln Asp Pro Ala Gln Ala Leu Leu Gln Leu Leu Glu Asp Leu Val Lys
1               5                   10                  15

Leu Leu Lys

<210> SEQ ID NO 177
<211> LENGTH: 19
<212> TYPE: PRT
<213> ORGANISM: Artificial
<220> FEATURE:
<223> OTHER INFORMATION: synthetic peptide

<400> SEQUENCE: 177

Gln Asp Pro Ala Gln Ala Leu Glu Gln Leu Leu Glu Asp Leu Val Lys
1               5                   10                  15

Leu Leu Lys

<210> SEQ ID NO 178
<211> LENGTH: 20
<212> TYPE: PRT
<213> ORGANISM: Artificial
<220> FEATURE:
<223> OTHER INFORMATION: synthetic peptide

<400> SEQUENCE: 178

Ser Glu Glu Glu Glu Glu Ala Leu Glu Gln Leu Leu Glu Asp Leu Val
1               5                   10                  15

Lys Leu Leu Lys
            20
```

-continued

```
<210> SEQ ID NO 179
<211> LENGTH: 55
<212> TYPE: PRT
<213> ORGANISM: Artificial
<220> FEATURE:
<223> OTHER INFORMATION: synthetic peptide of amino acids 206 to 260 of
      the Ralstonia solanacearum  PopA

<400> SEQUENCE: 179

Asn Gly Ala Asp Gly Gly

-continued

Glu Asp Gln Gly Gly Leu Thr Leu Thr Gly Val Leu Gln Lys Leu Met
1               5                   10                  15

Lys Ile Leu Asn Ala Leu
            20

<210> SEQ ID NO 184
<211> LENGTH: 22
<212> TYPE: PRT
<213> ORGANISM: Artificial
<220> FEATURE:
<223> OTHER INFORMATION: synthetic peptide

<400> SEQUENCE: 184

Glu Asp Gln Gly Gly Leu Thr Leu Thr Gly Val Leu Gln Lys Leu Leu
1               5                   10                  15

Lys Ile Leu Asn Ala Leu
            20

<210> SEQ ID NO 185
<211> LENGTH: 22
<212> TYPE: PRT
<213> ORGANISM: Artificial
<220> FEATURE:
<223> OTHER INFORMATION: synthetic peptide

<400> SEQUENCE: 185

Glu Asp Gln Gly Gly Leu Thr Leu Thr Gly Val Leu Gln Glu Leu Met
1               5                   10                  15

Glu Ile Leu Asn Ala Leu
            20

<210> SEQ ID NO 186
<211> LENGTH: 24
<212> TYPE: PRT
<213> ORGANISM: Artificial
<220> FEATURE:
<223> OTHER INFORMATION: synthetic peptide

<400> SEQUENCE: 186

Glu Asp Gln Gly Gly Leu Thr Leu Thr Gly Val Leu Gln Lys Leu Leu
1               5                   10                  15

Lys Ile Leu Glu Ala Leu Val Gln
            20

<210> SEQ ID NO 187
<211> LENGTH: 22
<212> TYPE: PRT
<213> ORGANISM: Artificial
<220> FEATURE:
<223> OTHER INFORMATION: synthetic peptide

<400> SEQUENCE: 187

Ser Glu Glu Glu Glu Leu Thr Leu Thr Gly Val Leu Gln Lys Leu Leu
1               5                   10                  15

Lys Ile Leu Glu Ala Leu
            20

<210> SEQ ID NO 188
<211> LENGTH: 21
<212> TYPE: PRT
<213> ORGANISM: Artificial
<220> FEATURE:
<223> OTHER INFORMATION: synthetic peptide

<400> SEQUENCE: 188

Ser Glu Glu Glu Glu Glu Leu Thr Gly Val Leu Gln Lys Leu Leu Lys
1               5                   10                  15

Ile Leu Glu Ala Leu
            20

<210> SEQ ID NO 189
<211> LENGTH: 16
<212> TYPE: PRT
<213> ORGANISM: Artificial
<220> FEATURE:
<223> OTHER INFORMATION: synthetic peptide

<400> SEQUENCE: 189

Ser Glu Glu Leu Glu Glu Leu Leu Glu Glu Leu Ile Glu Glu Leu Leu
1               5                   10                  15

<210> SEQ ID NO 190
<211> LENGTH: 15
<212> TYPE: PRT
<213> ORGANISM: Artificial
<220> FEATURE:
<223> OTHER INFORMATION: synthetic peptide

<400> SEQUENCE: 190

Leu Glu Glu Leu Leu Glu Glu Leu Ile Glu Glu Leu Leu Glu Glu
1               5                   10                  15

<210> SEQ ID NO 191
<211> LENGTH: 23
<212> TYPE: PRT
<213> ORGANISM: Artificial
<220> FEATURE:
<223> OTHER INFORMATION: synthetic peptide

<400> SEQUENCE: 191

Ser Glu Gly Ile Ser Glu Lys Gln Leu Asp Gln Leu Leu Ser Gln Leu
1               5                   10                  15

Ile Glu Ala Leu Leu Gln Pro
            20

<210> SEQ ID NO 192
<211> LENGTH: 18
<212> TYPE: PRT
<213> ORGANISM: Artificial
<220> FEATURE:
<223> OTHER INFORMATION: synthetic peptide

<400> SEQUENCE: 192

Leu Asp Gln Leu Leu Ser Gln Leu Ile Gln Ala Leu Leu Glu Glu Glu
1               5                   10                  15

Glu Glu

<210> SEQ ID NO 193
<211> LENGTH: 18
<212> TYPE: PRT
<213> ORGANISM: Artificial
<220> FEATURE:
<223> OTHER INFORMATION: synthetic peptide

<400> SEQUENCE: 193

Ser Glu Glu Leu Asp Gln Leu Leu Ser Gln Leu Ile Gln Ala Leu Leu
1               5                   10                  15

Glu Glu

<210> SEQ ID NO 194
<211> LENGTH: 24
<212> TYPE: PRT
<213> ORGANISM: Artificial
<220> FEATURE:
<223> OTHER INFORMATION: synthetic peptide

<400> SEQUENCE: 194

Ser Gln Gly Ile Ser Glu Glu Gln Leu Asp Gln Leu Leu Ser Gln Leu
1               5                   10                  15

Ile Gln Ala Leu Leu Gln Pro Arg
            20

<210> SEQ ID NO 195
<211> LENGTH: 23
<212> TYPE: PRT
<213> ORGANISM: Artificial
<220> FEATURE:
<223> OTHER INFORMATION: synthetic peptide

<400> SEQUENCE: 195

Asn Glu Gly Ile Ser Glu Lys Glu Leu Asp Glu Leu Leu Thr Glu Leu
1               5                   10                  15

Ala Glu Ala Leu Leu Gln Gln
            20

<210> SEQ ID NO 196
<211> LENGTH: 23
<212> TYPE: PRT
<213> ORGANISM: Artificial
<220> FEATURE:
<223> OTHER INFORMATION: synthetic peptide

<400> SEQUENCE: 196

Ser Gln Gly Ile Ser Glu Lys Gln Ile Asp Gln Leu Leu Ser Gln Leu
1               5                   10                  15

Ile Gln Ala Leu Leu Gln Pro
            20

<210> SEQ ID NO 197
<211> LENGTH: 20
<212> TYPE: PRT
<213> ORGANISM: Artificial
<220> FEATURE:
<223> OTHER INFORMATION: synthetic peptide

<400> SEQUENCE: 197

Ser Glu Glu Phe Thr Gln Met Leu Met His Ile Val Gly Glu Ile Leu
1               5                   10                  15

Gln Ala Gln Asn
            20

<210> SEQ ID NO 198
<211> LENGTH: 20
<212> TYPE: PRT
<213> ORGANISM: Artificial
<220> FEATURE:
<223> OTHER INFORMATION: synthetic peptide

<400> SEQUENCE: 198

Ser Glu Glu Glu Pro Ser Pro Phe Thr Gln Met Leu Met His Ile Val
1               5                   10                  15

Gly Glu Ile Leu
            20

<210> SEQ ID NO 199
<211> LENGTH: 37
<212> TYPE: PRT
<213> ORGANISM: Artificial
<220> FEATURE:
<223> OTHER INFORMATION: synthetic peptide

<400> SEQUENCE: 199

Gln Ala Gly Pro Gln Ser Ala Asn Lys Thr Gly Asn Val Asp Ala
1               5                   10                  15

Asn Asn Gln Asp Pro Met Gln Ala Leu Met Gln Leu Leu Glu Asp Leu
            20                  25                  30

Val Lys Leu Leu Lys
        35

<210> SEQ ID NO 200
<211> LENGTH: 22
<212> TYPE: PRT
<213> ORGANISM: Artificial
<220> FEATURE:
<223> OTHER INFORMATION: synthetic peptide

<400> SEQUENCE: 200

Ser Glu Glu Glu Glu Glu Leu Thr Leu Thr Gly Val Leu Gln Lys Leu
1               5                   10                  15

Leu Lys Ile Leu Glu Ala
            20

<210> SEQ ID NO 201
<211> LENGTH: 19
<212> TYPE: PRT
<213> ORGANISM: Artificial
<220> FEATURE:
<223> OTHER INFORMATION: synthetic peptide

<400> SEQUENCE: 201

Ser Glu Glu Glu Glu Glu Val Leu Gln Lys Leu Leu Lys Ile Leu Glu
1               5                   10                  15

Ala Leu Val

<210> SEQ ID NO 202
<211> LENGTH: 19
<212> TYPE: PRT
<213> ORGANISM: Artificial
<220> FEATURE:
<223> OTHER INFORMATION: synthetic peptide

<400> SEQUENCE: 202

Ser Glu Glu Glu Glu Glu Leu Gln Lys Leu Leu Lys Ile Leu Glu Ala
1               5                   10                  15

Leu Val Gln

<210> SEQ ID NO 203
<211> LENGTH: 44
<212> TYPE: PRT
<213> ORGANISM: Artificial
<220> FEATURE:
<223> OTHER INFORMATION: synthetic peptide of amino acids 137 to 180 of
      Erwinia amylovora HrpN

<400> SEQUENCE: 203

Ser Thr Ser Gln Asn Asp Asp Ser Thr Ser Gly Thr Asp Ser Thr Ser
1               5                   10                  15

Asp Ser Ser Asp Pro Met Gln Gln Leu Leu Lys Met Phe Ser Glu Ile
            20                  25                  30

Met Gln Ser Leu Phe Gly Asp Gly Gln Asp Gly Thr
            35                  40

<210> SEQ ID NO 204
<211> LENGTH: 41
<212> TYPE: PRT
<213> ORGANISM: Artificial
<220> FEATURE:
<223> OTHER INFORMATION: synthetic peptide

<400> SEQUENCE: 204

Gln Asn Asp Asp Ser Thr Ser Gly Thr Asp Ser Thr Ser Asp Ser Ser
1               5                   10                  15

Asp Pro Met Gln Gln Leu Leu Lys Met Phe Ser Glu Ile Met Gln Ser
            20                  25                  30

Leu Phe Gly Asp Gly Gln Asp Gly Thr
            35                  40

<210> SEQ ID NO 205
<211> LENGTH: 19
<212> TYPE: PRT
<213> ORGANISM: Artificial
<220> FEATURE:
<223> OTHER INFORMATION: synthetic peptide

<400> SEQUENCE: 205

Ser Asp Pro Met Gln Gln Leu Leu Lys Met Phe Ser Glu Ile Met Gln
1               5                   10                  15

Ser Leu Phe

<210> SEQ ID NO 206
<211> LENGTH: 20
<212> TYPE: PRT
<213> ORGANISM: Artificial
<220> FEATURE:
<223> OTHER INFORMATION: synthetic peptide

<400> SEQUENCE: 206

Ser Glu Glu Glu Leu Gln Gln Leu Leu Lys Leu Phe Ser Glu Ile Leu
1               5                   10                  15

Gln Ser Leu Phe
            20

<210> SEQ ID NO 207
<211> LENGTH: 21
<212> TYPE: PRT
<213> ORGANISM: Artificial
<220> FEATURE:
<223> OTHER INFORMATION: synthetic peptide

<400> SEQUENCE: 207

Ser Glu Glu Glu Glu Glu Leu Gln Gln Leu Leu Lys Leu Phe Ser Glu
1               5                   10                  15

Ile Leu Gln Ser Leu
            20

<210> SEQ ID NO 208
<211> LENGTH: 20
<212> TYPE: PRT
<213> ORGANISM: Artificial
<220> FEATURE:

<223> OTHER INFORMATION: synthetic peptide

<400> SEQUENCE: 208

Ser Glu Glu Glu Glu Glu Leu Gln Gln Leu Leu Lys Leu Phe Ser Glu
1               5                   10                  15

Ile Leu Gln Ser
            20

<210> SEQ ID NO 209
<211> LENGTH: 20
<212> TYPE: PRT
<213> ORGANISM: Artificial
<220> FEATURE:
<223> OTHER INFORMATION: synthetic peptide

<400> SEQUENCE: 209

Leu Gln Gln Leu Leu Lys Leu Phe Ser Glu Ile Leu Gln Ser Leu Phe
1               5                   10                  15

Glu Glu Glu Glu
            20

<210> SEQ ID NO 210
<211> LENGTH: 13
<212> TYPE: PRT
<213> ORGANISM: Artificial
<220> FEATURE:
<223> OTHER INFORMATION: synthetic peptide

<400> SEQUENCE: 210

Leu Glu Glu Leu Leu Glu Glu Leu Ile Glu Glu Leu Leu
1               5                   10

<210> SEQ ID NO 211
<211> LENGTH: 16
<212> TYPE: PRT
<213> ORGANISM: Artificial
<220> FEATURE:
<223> OTHER INFORMATION: synthetic peptide

<400> SEQUENCE: 211

Arg Leu Arg Arg Leu Leu Arg Arg Leu Ile Arg Arg Leu Leu Arg Pro
1               5                   10                  15

<210> SEQ ID NO 212
<211> LENGTH: 15
<212> TYPE: PRT
<213> ORGANISM: Artificial
<220> FEATURE:
<223> OTHER INFORMATION: synthetic peptide

<400> SEQUENCE: 212

Leu Asp Asp Leu Leu Asp Asp Leu Ile Asp Asp Leu Leu Asp Asp
1               5                   10                  15

<210> SEQ ID NO 213
<211> LENGTH: 15
<212> TYPE: PRT
<213> ORGANISM: Artificial
<220> FEATURE:
<223> OTHER INFORMATION: synthetic peptide

<400> SEQUENCE: 213

Leu Glu Glu Leu Leu Glu Glu Leu Leu Glu Glu Leu Leu Glu Glu
1               5                   10                  15

```
<210> SEQ ID NO 214
<211> LENGTH: 15
<212> TYPE: PRT
<213> ORGANISM: Artificial
<220> FEATURE:
<223> OTHER INFORMATION: synthetic peptide

<400> SEQUENCE: 214

Leu Glu Gln Leu Leu Glu Asp Leu Val Lys Leu Leu Lys Glu Glu
1               5                   10                  15

<210> SEQ ID NO 215
<211> LENGTH: 15
<212> TYPE: PRT
<213> ORGANISM: Artificial
<220> FEATURE:
<223> OTHER INFORMATION: synthetic peptide

<400> SEQUENCE: 215

Leu Glu Gln Leu Leu Glu Asp Leu Val Glu Leu Leu Glu Glu Glu
1               5                   10                  15

<210> SEQ ID NO 216
<211> LENGTH: 15
<212> TYPE: PRT
<213> ORGANISM: Artificial
<220> FEATURE:
<223> OTHER INFORMATION: synthetic peptide

<400> SEQUENCE: 216

Leu Glu Glu Leu Leu Glu Asp Leu Val Glu Leu Leu Glu Glu Glu
1               5                   10                  15

<210> SEQ ID NO 217
<211> LENGTH: 15
<212> TYPE: PRT
<213> ORGANISM: Artificial
<220> FEATURE:
<223> OTHER INFORMATION: synthetic peptide

<400> SEQUENCE: 217

Leu Glu Glu Leu Leu Glu Glu Leu Val Glu Leu Leu Glu Glu Glu
1               5                   10                  15

<210> SEQ ID NO 218
<211> LENGTH: 18
<212> TYPE: PRT
<213> ORGANISM: Artificial
<220> FEATURE:
<223> OTHER INFORMATION: synthetic peptide

<400> SEQUENCE: 218

Leu Glu Glu Leu Leu Glu Leu Phe Glu Glu Ile Leu Glu Glu Leu Phe
1               5                   10                  15

Glu Glu

<210> SEQ ID NO 219
<211> LENGTH: 18
<212> TYPE: PRT
<213> ORGANISM: Artificial
<220> FEATURE:
<223> OTHER INFORMATION: synthetic peptide

<400> SEQUENCE: 219

Leu Glu Glu Leu Leu Lys Leu Phe Glu Glu Ile Leu Glu Glu Leu Phe
1               5                   10                  15
```

Glu Glu

<210> SEQ ID NO 220
<211> LENGTH: 14
<212> TYPE: PRT
<213> ORGANISM: Artificial
<220> FEATURE:
<223> OTHER INFORMATION: synthetic peptide

<400> SEQUENCE: 220

Ile Glu Glu Leu Ile Glu Leu Ile Glu Glu Leu Leu Glu Glu
1               5                   10

<210> SEQ ID NO 221
<211> LENGTH: 15
<212> TYPE: PRT
<213> ORGANISM: Artificial
<220> FEATURE:
<223> OTHER INFORMATION: synthetic peptide

<400> SEQUENCE: 221

Ile Glu Glu Leu Ile Glu Glu Leu Ile Glu Glu Leu Leu Glu Glu
1               5                   10                  15

<210> SEQ ID NO 222
<211> LENGTH: 14
<212> TYPE: PRT
<213> ORGANISM: Artificial
<220> FEATURE:
<223> OTHER INFORMATION: synthetic peptide

<400> SEQUENCE: 222

Leu Glu Glu Leu Leu Lys Leu Ile Glu Arg Leu Leu Glu Glu
1               5                   10

<210> SEQ ID NO 223
<211> LENGTH: 14
<212> TYPE: PRT
<213> ORGANISM: Artificial
<220> FEATURE:
<223> OTHER INFORMATION: synthetic peptide

<400> SEQUENCE: 223

Leu Glu Glu Leu Leu Glu Leu Ile Glu Arg Leu Leu Glu Glu
1               5                   10

<210> SEQ ID NO 224
<211> LENGTH: 14
<212> TYPE: PRT
<213> ORGANISM: Artificial
<220> FEATURE:
<223> OTHER INFORMATION: synthetic peptide

<400> SEQUENCE: 224

Leu Glu Glu Leu Leu Lys Leu Ile Glu Glu Leu Leu Glu Glu
1               5                   10

<210> SEQ ID NO 225
<211> LENGTH: 14
<212> TYPE: PRT
<213> ORGANISM: Artificial
<220> FEATURE:
<223> OTHER INFORMATION: synthetic peptide

<400> SEQUENCE: 225

Leu Glu Glu Leu Leu Glu Leu Ile Glu Glu Leu Leu Glu Glu
1               5                   10

<210> SEQ ID NO 226
<211> LENGTH: 25
<212> TYPE: PRT
<213> ORGANISM: Artificial
<220> FEATURE:
<223> OTHER INFORMATION: synthetic peptide

<400> SEQUENCE: 226

```
Gln Gly Gly Gly Gln Ile Gly Asp Asn Pro Leu Leu Lys Ala Met Leu
1               5                   10                  15

Lys Leu Ile Ala Arg Met Met Asp Gly
            20                  25
```

<210> SEQ ID NO 227
<211> LENGTH: 18
<212> TYPE: PRT
<213> ORGANISM: Artificial
<220> FEATURE:
<223> OTHER INFORMATION: synthetic peptide

<400> SEQUENCE: 227

```
Ser Gln Ser Asn Ile Ala Lys Leu Ile Ser Ala Leu Ile Met Ser Leu
1               5                   10                  15

Leu Gln
```

<210> SEQ ID NO 228
<211> LENGTH: 26
<212> TYPE: PRT
<213> ORGANISM: Artificial
<220> FEATURE:
<223> OTHER INFORMATION: synthetic peptide

<400> SEQUENCE: 228

```
Gln Gln Pro Ile Asp Arg Gln Thr Ile Glu Gln Leu Ala Gln Leu Leu
1               5                   10                  15

Ala Gln Leu Leu Lys Ser Leu Leu Ser Pro
            20                  25
```

<210> SEQ ID NO 229
<211> LENGTH: 24
<212> TYPE: PRT
<213> ORGANISM: Artificial
<220> FEATURE:
<223> OTHER INFORMATION: synthetic peptide

<400> SEQUENCE: 229

```
Gln Gln Pro Ile Asp Arg Gln Thr Ile Glu Gln Leu Ala Gln Leu Leu
1               5                   10                  15

Ala Gln Leu Leu Lys Ser Leu Leu
            20
```

<210> SEQ ID NO 230
<211> LENGTH: 44
<212> TYPE: PRT
<213> ORGANISM: Artificial
<220> FEATURE:
<223> OTHER INFORMATION: synthetic peptide of amino acids 137 to 180 of
      Erwinia amylovora HrpN

<400> SEQUENCE: 230

```
Ser Thr Ser Gln Asn Asp Asp Ser Thr Ser Gly Thr Asp Ser Thr Ser
1               5                   10                  15

Asp Ser Ser Asp Pro Met Gln Gln Leu Leu Lys Met Phe Ser Glu Ile
```

```
                20                  25                  30
Met Gln Ser Leu Phe Gly Asp Gly Gln Asp Gly Thr
            35                  40

<210> SEQ ID NO 231
<211> LENGTH: 19
<212> TYPE: PRT
<213> ORGANISM: Artificial
<220> FEATURE:
<223> OTHER INFORMATION: synthetic peptide

<400> SEQUENCE: 231

Ser Glu Glu Glu Glu Glu Leu Ala Glu Leu Leu Ala Glu Leu Leu Lys
1               5                   10                  15

Ser Leu Leu

<210> SEQ ID NO 232
<211> LENGTH: 21
<212> TYPE: PRT
<213> ORGANISM: Artificial
<220> FEATURE:
<223> OTHER INFORMATION: synthetic peptide

<400> SEQUENCE: 232

Ser Glu Glu Glu Glu Glu Leu Asp Gln Leu Leu Ser Gln Leu Ile Gln
1               5                   10                  15

Ala Leu Leu Gln Pro
            20
```